United States Patent [19]
Mittal et al.

[11] Patent Number: 5,820,868
[45] Date of Patent: Oct. 13, 1998

[54] RECOMBINANT PROTEIN PRODUCTION IN BOVINE ADENOVIRUS EXPRESSION VECTOR SYSTEM

[75] Inventors: Suresh K. Mittal, Saskatoon; Frank L. Graham, Hamilton; Ludvik Prevec, Burlington; Lorne A. Babiuk, Saskatoon, all of Canada

[73] Assignee: Veterinary Infectious Disease Organization, Saskatoon, Canada

[21] Appl. No.: 164,292

[22] Filed: Dec. 9, 1993

[51] Int. Cl.$^6$ .......................... A61K 39/235; C12N 7/01; C12N 15/00

[52] U.S. Cl. ................................. 424/199.1; 435/235.1; 435/320.1; 935/32; 935/65; 424/233.1

[58] Field of Search .................... 435/235.1, 320.1, 435/172.3, 69.1, 69.3; 935/32, 57, 65; 424/199.1, 233.1, 93.2; 536/23.72

[56] References Cited

U.S. PATENT DOCUMENTS

| | | | |
|---|---|---|---|
| 3,962,424 | 6/1976 | Zygraich et al. | 424/233.1 |
| 4,510,245 | 4/1985 | Cousens et al. | 435/172.3 |
| 4,920,209 | 4/1990 | Davis et al. | 435/235.1 |
| 5,024,939 | 6/1991 | Gorman | 435/69.1 |

FOREIGN PATENT DOCUMENTS

| | | |
|---|---|---|
| 2012895 | 9/1990 | Canada . |
| 185573 | 6/1986 | European Pat. Off. . |
| 389286 | 9/1990 | European Pat. Off. . |
| 2642797 | 8/1990 | France . |
| 2657880 | 8/1991 | France . |
| WO 86/06409 | 11/1986 | WIPO . |
| WO 91/11525 | 8/1991 | WIPO . |

OTHER PUBLICATIONS

Hu, S–L. et al. 1984. J. Virol. vol. 51 pp. 880–883.
Kaledin, A.S. 1988. "Cloning and sequencing of EIA gene of bovine adenovirus 3 genome" Sbornik Nauchnykh Trudov–Moskovskaya Veterinaria Akademiya vol. 159 pp. 78–82 (Translation provided).
Berkner, K.L. 1989. Biotechniques vol. 6 pp. 616–629.
Spibey, N. et al. 1989. Virus Research vol. 14 pp. 241–256.
Kruglyak, V.A. et al. 1987. Soviet Agricultural Sciences vol. 11 pp. 64–67.
Thomsen, D.R. et al. 1987. Gene vol. 57 pp. 261–265.
Tikoo, S.K. et al. 1990. J. Virol. vol. 64 pp. 5132–5142.
Boyle, D.B. 1989. Res. Virol. vol. 140 pp. 483–491.
Esposito, J.D. et al. 1989. Adv. Vet. Sci. Comp. Med. vol. 33 pp. 195–247.
Boyle, D.B. et al. 1992. In Animal Parasite Control Utilizing Biotechnology, ed. W.K. Yong CRC Press, Boca Raton, pp. 25–47.
Boyle, D.B. et al. 1993. Immunol. 611 Biol. vol. 71 pp. 391–397.
Moss, B. 1990. Semin. Immunol. vol. 2 pp. 317–327.
Bostock, C.J. 1990. Vet. Microbiol. vol. 23 pp. 55–71.
Kit. S. et al. 1991 Arch. Virol. vol. 120 pp. 1–17.
Belák et al., "Subtypes of bovine adenovirus type 2 exhibit major difference in region E3" *Virology* (1986) 153:262–271.
Benkö et al., "Molecular cloning and physical mapping of the DNA of bovine adenovirus serotype 4; study of the DNA homology among bovine, and porcine adenoviruses" *Journal of General Virology* (1990) 71:465–469.
Fejér et al., "Multiple enlargements in the right inverted terminal repeat of the DNA of canine adenovirus type 2" *Acta Microbiologica Hungarica* (1992) 39:159–168.
Hu et al., "Sequence homology between bovine and human adenoviruses" *Journal of Virology* (1984) 49:604–608.
Haj–Ahmad et al., "Development of a helper–independent human adenovirus vector and its use in the transfer of the herpes simplex virus thymidine kinase gene" *J. Virol.* (1986) 57:267–274.
Graham et al., "Cloning and expression of glycoprotein genes in human adenovirus vectors" *J. Cell. Biochem.*(1988) UCLA Symposium on Molecular and Cellular Biology, Suppl. 12B, abstract F109.
Prevec et al., "Use of human adenovirus–based vectors for antigen expression in animals" *J. Gen. Virol.*(1989) 70:429–434.
Mittal et al., "Sequence analysis of bovine adenovirus type 3 early region 3 and fibre protein gene" *J. Gen. Virol.*(1992) 73:3295–3300.

*Primary Examiner*—Mary E. Mosher
*Attorney, Agent, or Firm*—Morrison & Foerster LLP

[57] ABSTRACT

The present invention relates novel live bovine adenovirus (BAV) expression vector systems in which part or all of one or both of the early region 1 (E1) and early region 3 (E3) genes are deleted and replaced by a foreign gene or fragment thereof and novel recombinant mammalian cell lines stably transformed with BAV E1 sequences, and therefore, express E1 gene products capable of allowing replication therein of a bovine adenovirus having an E1 deletion replaced by a heterologous nucleotide sequence encoding a foreign gene or fragment thereof and their use in production of (antigenic) polypeptides or fragments thereof for the purpose of live recombinant virus or subunit vaccine or for other therapies.

5 Claims, 51 Drawing Sheets

```
         10         20         30         40         50         60
CATCATCAAT AATCTACAGT ACACTGATGG CAGCGGGTCCA ACTGCCAATC ATTTTTGCCA 70         80         90        100        110        120
CGTCATTTAT GACGCAACGA CGGCGAGCGT GGCGTGCTGA CGTAACTGTG GGGCGGAGCG 130        140        150        160        170        180
CGTCGCGGAG GCGGCGGGCGC TGGGCGGGGC TGAGGGGCGG GGGGCGGGCG CGCGGGGCGG 190        200        210        220        230        240
CGGCGCGGGGC GGGGCGAGGG GCGGAGTTCC GCACCCGCTA CGTCATTTTC AGACATTTT 250        260        270        280        290        300
TAGCAAATTT GCGCCTTTTG CAAGCATTTT TCTCACATTT CAGGTATTTA GAGGGCGGAT 310        320        330        340        350        360
TTTTGGTGTT CGTACTTCCG TGTCACATAG TTCACTGTCA ATCTTCATTA CGGCTTAGAC 370        380        390        400        410        420
AAATTTTCGG CGTCTTTTCC GGGTTTATGT CCCCGGTCAC CTTTATGACT GTGTGAAACA 430        440        450        460        470        480
CACCTGCCCA TTGTTTACCC TTGGTCAGTT TTTTCGTCTC CTAGGGTGGG AACATCAAGA
```

FIG. IA

```
         490         500         510         520         530         540
ACAAATTGC CGAGTAATTG TGCACCTTTT TCCGCGTTAG GACTGCGTTT CACACGTAGA 550         560         570         580         590         600
CAGACTTTTT CTCATTTCT CACACTCCGT CGTCCGCTTC AGAGCTCTGC GTCTTCGCTG 610         620         630         640         650
CCACC ATG AAG TAC CTG GTC CTC GTT CTC AAC GAC GGC ATG AGT CGA ATT GAA
      Met Lys Tyr Leu Val Leu Val Leu Asn Asp Gly Met Ser Arg Ile Glu 660         670         680         690         700
AAA GCT CTC CTG TGC AGC GAT GGT GAG GTG GAT TTA GAG TGT CAT GAG GTA
Lys Ala Leu Leu Cys Ser Asp Gly Glu Val Asp Leu Glu Cys His Glu Val 710         720         730         740         750
CTT CCC CCT TCT CCC GCG CCT GTC CCC GCT TCT GTG TCA CCC GTG AGG AGT
Leu Pro Pro Ser Pro Ala Pro Val Pro Ala Ser Val Ser Pro Val Arg Ser 760         770         780         790         800
CCT CCT CCT CTG TCT TCT CCG TTT CCT CCG TCT CCG CCA GCC CCG CTT GTG
Pro Pro Pro Leu Ser Ser Pro Val Phe Pro Pro Ser Pro Pro Ala Pro Leu Val 810         820         830         840         850
AAT CCA GAG GCG AGT TCG CTG CAG CAG TAT CGG AGA GAG CTG TTA GAG
Asn Pro Glu Ala Ser Ser Leu Gln Gln Tyr Arg Arg Glu Leu Leu Glu
```

FIG. 1B

```
860                 870                 880                 890                 900
AGG AGC CTG CTC CGA ACG GCC GAA GGT CAG CAG CGT GCA GTG TGT CCA TGT
Arg Ser Leu Leu Arg Thr Ala Glu Gly Gln Gln Arg Ala Val Cys Pro Cys 910                 920                 930                 940                 950
GAG CGG TTG CCC GTG GAA GAG GAT GAG TGT CTG AAT GCC GTA AAT TTG CTG
Glu Arg Leu Pro Val Glu Glu Asp Glu Cys Leu Asn Ala Val Asn Leu Leu 960                 970                 980                 990                 1000                1010
TTT CCT GAT CCC TGG CTA AAT GCA GCT GAA AAT GGG GGT GAT ATT TTT AAG
Phe Pro Asp Pro Trp Leu Asn Ala Ala Glu Asn Gly Gly Asp Ile Phe Lys 1020                1030                1040                1050                1060
TCT CCG GCT ATG TCT CCA GAA CCG TGG ATA GAT TTG TCT AGC TAC GAT AGC
Ser Pro Ala Met Ser Pro Glu Pro Trp Ile Asp Leu Ser Ser Tyr Asp Ser 1070                1080                1090                1100                1110
GAT GTA GAA GAG GTG ACT AGT CAC TTT TTT CTG GAT TGC CCT GAA GAC CCC
Asp Val Glu Glu Val Thr Ser His Phe Phe Leu Asp Cys Pro Glu Asp Pro 1120                1130                1140                1150                1160
AGT CGG GAG TGT TCA TCT TGT GGG TTT CAT CAG GCT CAA AGC GGA ATT CCA
Ser Arg Glu Cys Ser Ser Cys Gly Phe His Gln Ala Gln Ser Gly Ile Pro
```

FIG. IC

```
                1170        1180        1190        1200        1210
           GGC ATT ATG TGC AGT TTG TGC TAC ATG CGC CAA ACC TAC CAT TGC ATC TAT
           Gly Ile Met Cys Ser Leu Cys Tyr Met Arg Gln Thr Tyr His Cys Ile Tyr 1220        1230        1240        1250        1260        1270
           A[GTAAG TACATTCTGT AAAAGAACAT CTTGGTGATT TCTAGGTATT GTTAGGGAT
           s 1280        1290        1300        1310        1320        1330
           TAACTGGGTG GAGTGATCTT AATCCGGCAT AACCAAATAC ATGTTTTCAC AG]GT CCA GTT
                                                                      er Pro Val 1340        1350        1360        1370        1380        1390
           TCT GAG GAA ATG TGAGT CATGTTGACT TTGGCGCGC A AGAGGAAATG TGAGTCATGT
           Ser Glu Glu Met End 1400        1410        1420        1430        1440        1450
           TGACTTTGGC GCGCCCTACG GTGACTTTAA AGCAATTTGA GGATCACTTT TTTGTTAGTC 1460        1470        1480        1490        1500
           GCTATAAAGT AGTCACGGAG TCTTC ATG GAT CAC TTA AGC GTT CTT TTG GAT TTG
                                      Met Asp His Leu Ser Val Leu Leu Asp Leu 1510        1520        1530        1540        1550
           AAG CTG CTT CGC TCT ATC GTA GCG GGG GCT TCA AAT CGC ACT GGA GTG TGG
           Lys Leu Leu Arg Ser Ile Val Ala Gly Ala Ser Asn Arg Thr Gly Val Trp
```

FIG. ID

```
1560           1570            1580            1590            1600
AAG AGG CGG CTG TGG CTG GGA CGC CTG ACT CAA CTG GTC CAT GAT ACC TGC
Lys Arg Arg Leu Trp Leu Gly Arg Leu Thr Gln Leu Val His Asp Thr Cys 1610           1620            1630            1640            1650
GTA GAG AAC GAG AGC ATA TTT CTC AAT TCT CTG CCA GGG AAT GAA GCT TTT
Val Glu Asn Glu Ser Ile Phe Leu Asn Ser Leu Pro Gly Asn Glu Ala Phe 1660           1670            1680            1690            1700
TTA AGG TTG CTT CGG AGC GGC TAT TTT GAA GTG TTT GAC GTG TTT GTG GTG
Leu Arg Leu Leu Arg Ser Gly Tyr Phe Glu Val Phe Asp Val Phe Val Val 1710           1720            1730            1740            1750       1760
CCT GAG CTG CAT CTG GAC ACT CCG GGT CGA GTG GTC GCC GCT CTT GCT CTG
Pro Glu Leu His Leu Asp Thr Pro Gly Arg Val Val Ala Ala Leu Ala Leu 1770           1780            1790            1800            1810
CTG GTG TTC ATC CTC AAC GAT TTA GAC GCT AAT TCT GCT TCT TCA GGC TTT
Leu Val Phe Ile Leu Asn Asp Leu Asp Ala Asn Ser Ala Ser Ser Gly Phe 1820           1830            1840            1850            1860
GAT TCA GGT TTT CTC GTG GAC CGT CTC TGC GTG CCG CTA TGG CTG AAG GCC
Asp Ser Gly Phe Leu Val Asp Arg Leu Cys Val Pro Leu Trp Leu Lys Ala

Met Ala Glu Gly
```

FIG. IE

```
                                    1870                  1880                   1890                   1900                   1910
                               AGG GCG TTC AAG ATC ACC CAG AGC TCC AGG AGC ACT TCG CAG CCT TCC TCG
                               Arg Ala Phe Lys Ile Thr Gln Ser Ser Arg Ser Thr Ser Gln Pro Ser Ser
                               Gln Gly Val Gln Asp His Pro Glu Leu Gln Glu His Phe Ala Ala Phe Leu 1920                  1930                   1940                   1950                   1960
                               TCG CCC GAC AAG ACG ACC CAG ACT ACC AGC CAG TA GAC GGG GAC AGC CCA
                               Ser Pro Asp Lys Thr Thr Gln Thr Thr Ser Gln End
                               Val Ala Arg Gln Asp Asp Pro Asp Tyr Gln Pro Val Asp Gly Asp Ser Pro 1970                  1980                   1990                   2000                   2010
                               CCC CGG GCT AGC CTG GAG GAG GCT GAA CAG AGC ACT CGT TTC GAG CAC
                               Pro Arg Ala Ser Leu Glu Glu Ala Glu Gln Ser Ser Thr Arg Phe Glu His 2020                  2030                   2040                   2050                   2060
                               ATC AGT TAC CGA GAC GTG GTG GAT GAC TTC AAT AGA TGC CAT GAT GTT TTT
                               Ile Ser Tyr Arg Asp Val Val Asp Asp Phe Asn Arg Cys His Asp Val Phe 2070                  2080                   2090                   2100                   2110
                               TAT GAG AGG TAC AGT TTT GAG GAC ATA AAG AGC TAC GAG GCT TTG CCT GAG
                               Tyr Glu Arg Tyr Ser Phe Glu Asp Ile Lys Ser Tyr Glu Ala Leu Pro Glu
```

FIG. IF

```
     2120             2130             2140             2150             2160
GAC AAT TTG GAG CAG CTC ATA GCT ATG CAT GCT AAA ATC AAG CTG CCC
Asp Asn Leu Glu Gln Leu Ile Ala Met His Ala Lys Ile Lys Leu Pro 2170             2180             2190             2200             2210
GGT CGG GAG TAT GAG TTG ACT CAA CCT TTG AAC ATA ACA TCT TGC GCC TAT
Gly Arg Glu Tyr Glu Leu Thr Gln Pro Leu Asn Ile Thr Ser Cys Ala Tyr 2220             2230             2240             2250             2260
GTG CTC GGA AAT GGG GCT ACT ATT AGG GTA ACA GGG GAA GCC TCC CCG GCT
Val Leu Gly Asn Gly Ala Thr Ile Arg Val Thr Gly Glu Ala Ser Pro Ala 2270             2280             2290             2300             2310             2320
ATT AGA GTG GGG GCC ATG GCC GTG GGT CCG TGT GTA ACA GGA ATG ACT GGG
Ile Arg Val Gly Ala Met Ala Val Gly Pro Cys Val Thr Gly Met Thr Gly 2330             2340             2350             2360             2370
GTG ACT TTT GTG AAT TGT AGG TTT GAG AGA GAG TCA ACA ATT AGG GGG TCC
Val Thr Phe Val Asn Cys Arg Phe Glu Arg Glu Ser Thr Ile Arg Gly Ser 2380             2390             2400             2410             2420
CTG ATA CGA GCT TCA ACT CAC GTG CTG TTT CAT GGC TGT TAT TTT ATG GGA
Leu Ile Arg Ala Ser Thr His Val Leu Phe His Gly Cys Tyr Phe Met Gly
```

FIG. IG

```
       2430              2440              2450              2460              2470
ATT ATG GGC ACT TGT ATT GAG GTG GGG GCG GGA GCT TAC ATT CGG GGT TGT
Ile Met Gly Thr Cys Ile Glu Val Gly Ala Gly Ala Tyr Ile Arg Gly Cys 2480              2490              2500              2510              2520
GAG TTT GTG GGC TGT TAC CGG GGA ATC TGT TCT ACT TCT AAC AGA GAT ATT
Glu Phe Val Gly Cys Tyr Arg Gly Ile Cys Ser Thr Ser Asn Arg Asp Ile 2530              2540              2550              2560              2570
AAG GTG AGG CAG TGC AAC TTT GAC AAA TGC TTA CTG GGT ATT ACT TGT AAG
Lys Val Arg Gln Cys Asn Phe Asp Lys Cys Leu Leu Gly Ile Thr Cys Lys 2580              2590              2600              2610              2620
GGG GAC TAT CGT CTT TCG GGA AAT GTG TGT TCT GAG ACT TTC TGC TTT GCT
Gly Asp Tyr Arg Leu Ser Gly Asn Val Cys Ser Glu Thr Phe Cys Phe Ala 2630              2640              2650              2660              2670
CAT TTA GAG GGA GAG GGT TTG GTT AAA AAC ACA GTC AAG TCC CCT AGT
His Leu Glu Gly Glu Gly Leu Val Lys Asn Asn Thr Val Lys Ser Pro Ser 2680              2690              2700              2710              2720
CGC TGG ACC AGC GAG TCT GGC TTT TCC ATG ATA ACT TGT GCA GAC GGC AGG
Arg Trp Thr Ser Glu Ser Gly Phe Ser Met Ile Thr Cys Ala Asp Gly Arg
```

FIG. IH

```
2730            2740            2750            2760            2770
GTT ACG CCT TTG GGT TCC CTC CAC ATT GTG GGC AAC CGT TGT AGG CGT TGG
Val Thr Pro Leu Gly Ser Leu His Ile Val Gly Asn Arg Cys Arg Arg Trp 2780            2790            2800            2810            2820    2830
CCA ACC ATG CAG GGG AAT GTG TTT ATC ATG TCT AAA CTG TAT CTG GGC AAC
Pro Thr Met Gln Gly Asn Val Phe Ile Met Ser Lys Leu Tyr Leu Gly Asn 2840            2850            2860            2870    2880
AGA ATA GGG ACT GTA GCC CTG CCC CAG TGT GCT TTC TAC AAG TCC AGC ATT
Arg Ile Gly Thr Val Ala Leu Pro Gln Cys Ala Phe Tyr Lys Ser Ser Ile 2890            2900            2910            2920    2930
TGT TTG GAG GAG AGG GCG ACA AAC AAG CTG GTC TTG GCT TGT GCT TTT GAG
Cys Leu Glu Glu Arg Ala Thr Asn Lys Leu Val Leu Ala Cys Ala Phe Glu 2940            2950            2960            2970    2980
AAT AAT GTA CTG GTG TAC AAA GTG CTG AGA CGG GAG AGT CCC TCA ACC GTG
Asn Asn Val Leu Val Tyr Lys Val Leu Arg Arg Glu Ser Pro Ser Thr Val 2990            3000            3010            3020    3030
AAA ATG TGT GTT TGT TGG ACT TCT CAT TAT GCA AAG CCT TTG ACA CTG GCA
Lys Met Cys Val Cys Gly Thr Ser His Tyr Ala Lys Pro Leu Thr Leu Ala
```

FIG. 11

```
      3040                  3050                  3060                  3070                  3080
ATT ATT TCT TCA GAT ATT CGG GCT AAT CGA TAC ATG TAC ACT GTG GAC TCA
Ile Ile Ser Ser Asp Ile Arg Ala Asn Arg Tyr Met Tyr Thr Val Asp Ser 3090                  3100                  3110                  3120                  3130                 3140
ACA GAG TTC ACT TCT GAC GAG GAT T AAAAGTGGGC GGGGCCAAGA GGGGTATAAA
Thr Glu Phe Thr Ser Asp Glu Asp End 3150                  3160                  3170                  3180                  3190                  3200
TAGGTGGGGA GGTTGAGGGG AGCCGTAGTT TCTGTTTTTC CCAGACTGGG GGGGACAAC ATG
                                                                                                                    Met 3210                  3220                  3230                  3240                  3250
GCC GAG GAA GGG CGC ATT TAT GTG CCT TAT GTA ACT GCC CGC CTG CCC AAG
Ala Glu Glu Gly Arg Ile Tyr Val Pro Tyr Val Thr Ala Arg Leu Pro Lys 3260                  3270                  3280                  3290                  3300
TGG TCG GGT TCG GTG CAG GAT AAG ACG GGC TCG AAC ATG TTG GGG GGT GTG
Trp Ser Gly Ser Val Gln Asp Lys Thr Gly Ser Asn Met Leu Gly Gly Val 3310                  3320                  3330                  3340                  3350
GTA CTC CCT CCT AAT TCA CAG GCG CAC CGG ACG GAG ACC GTG GGC ACT GAG
Val Leu Pro Pro Asn Ser Gln Ala His Arg Thr Glu Thr Val Gly Thr Glu
```

FIG. 1J

```
       3360                    3370                     3380                     3390                     3400
GCC ACC AGA GAC AAC CTG CAC GCC GAG GGA GCG CGT CCT GAG GAT CAG
Ala Thr Arg Asp Asn Leu His Ala Glu Gly Ala Arg Arg Pro Glu Asp Gln 3410                    3420                     3430                     3440                     3450
ACG CCC TAC ATG ATC TTG GTG GAG GAC TCT CTG GGA GGT TTG AAG AGG CGA
Thr Pro Tyr Met Ile Leu Val Glu Asp Ser Leu Gly Gly Leu Lys Arg Arg 3460                    3470                     3480                     3490                     3500
ATG GAC TTG CTG GAA GAA TCT AAT CAG CAG CAG CTG CTG GCA ACT CTC AAC CGT
Met Asp Leu Leu Glu Glu Ser Asn Gln Gln Gln Leu Leu Ala Thr Leu Asn Arg 3510                    3520                     3530                     3540                     3550
CTC CGT ACA GGA CTC GCT GCC TAT GTG CAG GCT AAC CTT GTG GGC GGC CAA
Leu Arg Thr Gly Leu Ala Ala Tyr Val Gln Ala Asn Leu Val Gly Gly Gln 3560                    3570                     3580                     3590                     3600                     3610
GTT AAC CCC TTT GTT TAAAATA AAAATACACT CATACAGTTT ATTATGCTGT
Val Asn Pro Phe Val End 3620           3630           3640           3650           3660           3670
CAATAAAATT CTTTATTTTT CCTGTGATAA TACCGTGTCC AGCGTGCTCT GTCAATAAGG 3680           3690           3700           3710           3720           3730
GTCCTATGCA TCCTGAGAAG GGCCTCATAT ACCCATGGCA TGAATATTAA GATACATGGG
```

FIG. IK

```
3740        3750        3760        3770        3780        3790
CATAAGGCCC  TCAGAAGGGT  TGAGGTAGAG  CCACTGCAGA  CTTTCGTGGG  GAGGTAAGGT 3800        3810        3820        3830        3840        3850
GTTGTAAATA  ATCCAGTCAT  ACTGACTGTG  CTGGGCGTGG  AAGGAAAAGA  TGTCTTTTAG 3860        3870        3880        3890        3900        3910
AAGAAGGGTG  ATTGGCAAAG  GGAGGCTCTT  AGTGTAGGTA  TTGATAAATC  TGTTCAGTTG 3920        3930        3940        3950        3960        3970
GGAGGGATGC  ATTCGGGGGC  TAATAAGGTG  GAGTTTAGCC  TGAATCTTAA  GGTTGGCAAT 3980        3990        4000        4010        4020        4030
GTTGCCCCCT  AGTCTTTTGC  GAGGATTCAT  GTTGTGCAGT  ACCACAAAAA  CAGAGTAGCC 4040        4050        4060
TGTGCATTTG  GGGAATTTAT  CATGAAGCT T
```

ACTIVATION REGION

```
            140                      153
Ad5    GluGluPheValLeuAspTyr      ValGlu      HisProGlyHisGly
            | |      ::   |||||||    |   ::   |||||||
BAV3   GluGluValThrSerHisPhePheLeuAspCysProGluAspProSerArgGlu
            155                                             172
```

METAL BINDING REGION

```
            154                                              174
Ad5    CysArgSerCysHisTyrHisArgArgAsnThrGlyAspProAspIleMetCysSerLeuCys
            |||   ||| ::   |||   ::  ||| ::   ||||||||||||||
BAV3   CysSerSerCysGlyPheHisGlnAlaGlnSerGlyIleProGlyIleMetCysSerLeuCys
            173                                              193
```

PROMOTER BINDING REGION

```
            175                                  189
Ad5    TyrMetArgThrCys      GlyMetPheValTyrSerProValSerGluProGlu
            ||||||   :::        ::  |||||||||||||||
BAV3   TyrMetArgGlnThrTyrHisCys     IleTyrSerProValSerGluGluMetEnd
            194                                              208
```

```
                                              Rb BINDING SEQUENCE
Ad5      120                                                    132
         IleAspLeuThrCysHisGluAlaGlyPheProProSer
         :   |   |   |   |   |   |           |   |   |
         ValAspLeuGluCysHisGluVal         LeuProProSer
BAV3     26                                                37
```

FIG. 2B

```
Ad5    82                                                              100
       LeuAspPheSerThrProGlyArgAlaAlaAlaAlaValAlaPheLeuSerPheIle
       |   |       |   |   |   |       |   |       |       |   |   |
       LeuAsp      ThrProGlyArgValValAlaAlaLeuAlaLeuLeuValPheIle
BAV3   83                                                               99
```

FIG. 3A

```
Ad5    20              26
       GlnSerSerAsnSerThrSer
       |   |   |       |   |   |
       GlnSerSerArgSerThrSer
BAV3   136             142
```

FIG. 3B

```
Ad5  150  GlnLysTyrSerIleGluGlnLeuThrThrTyrTrpLeuGlnProGlyAspAspPheGlu
          : :           : :
BAV3  74  GluArgTyrLysPheGluAspIleLysSerTyrGluAlaLeuProGluAspAsnLeuGlu

170  GluAlaIleArgValTyrAlaLysValAlaAlaLeuArgProAspCysLysLysTyrIleSer
          :   : :             : :
      94  GlnLeuIleAlaMetHisAlaLysIleLeuLysLeuLeuProGlyArgGluTyrGluLeuThr

190  LysLeuValAsnIleArgAsnCysCysTyrIleSerGlyAsnGlyAlaGluValGluIle
                 : :               : :
     114  GlnProLeuAsnIleThrSerCysAlaTyrValLeuGlyAsnGlyAlaThrIleArgVal

210  AspThrGluAspArgValAlaPheArgCysSerMetIleAsnMetTrpProGlyValLeu
                    : :                 : :
     134  ThrGlyGluAlaSerProAlaIleArgValGlyAlaMetAlaValGlyProCysValThr

230  GlyMetAspGlyValValIleMetAsnValArgPheThr   GlyProAsnPheSerGly
          :     : :                           : :
     154  GlyMetThrGlyValThrPheValAsnCysArgPheGluArgSerThrIleArgGly

249  ThrValPheLeuAlaAsnThrAsnLeuIleLeuHisGlyValSerPheTyr   GlyPhe
                         : :                       : :
     174  SerLeuIleArgAlaSerThrHisValLeuPheHisGlyCys   TyrPheMetGlyIle

268  AsnAsnThrCysValGluAlaTrpThrAspValArgGlyAlaTyrIleArgGlyCysAlaPheTyrCys
                                       : :                       : :
     193  MetGlyThrCysIleGluValGlyAlaGlyAlaTyrIleArgGlyCysGluPheValGly
```

FIG. 4A

```
288  CysTrpLysGlyValValCysArgProLysSerArgAla    SerIleLysLysCysLeu
         ::                                         ::
213  CysTyrArgGlyIle    CysSerThrSerAsnArgAspIleLysValArgGlnCysAsn

307  PheGluArgCysThrLeuGlyIleIleLeuSerGluGlyAsnSerArgValArgHisAsnVal
       ::      ::   ::                              ::
232  PheAspLysCysLeuLeuGlyIleThrCysLysGlyAspTyrArgLeuSerGlyAsnVal

327  AlaSerAspCysGlyCysPheMetLeuValLysSerValAlaValIleLysHisAsnMet
        ::      ::  ::              ::
252  CysSerGluThrPheCysPheAlaHisLeuGluGlyLeuValLysAsnAsnThr

347  Val    CysGlyAsn    CysGluAspArgAlaSerGlnMetLeuThrCysSerAsp
                                       ::    ::      ::
272  ValLysSerProSerArgTrpThrSerGluSerGlyPheSerMetIleThrCysAlaAsp

364  GlyAsnCysHisLeuLeuLysThrIleHisVal    AlaSerHisSerArgLysAlaTrp
         ::         ::    ::                 ::           ::
292  GlyArgValThrProLeuGlySerLeuHisIleValGlyAsnArgCysArgArg    Trp

383  ProValPheGluHisAsnIleLeuThrArgCysSerLeuHisLeuGlyAsnArgArgGly
        ::                  ::                  ::
311  ProThrMetGlnGlyAsnValPheIleMetSerLysLeuTyrLeuGlyAsnArgIleGly

403  ValPheLeuProTyrGlnCysAsnLeuSerHisThrLysIleLeuLeuGluProGlu
        ::                                              ::
331  ThrValAlaLeuPro    GlnCysAlaPheTyrLysSerSerIleCysLeuGluGluArg
```

FIG. 4B

```
422  SerMetSerLysValAsnLeuAsnGlyValPheAspMetThrMetLysIleTrpLysVal
          :                    :           :   :    :
350  AlaThrAsnLysLeuValLeuValAlaCysAlaAlaPheGluAsnAsnValLeuValTyrLysVal

442  LeuArgTyrAspGluThrArgThrArgCysArgProCysGluCysGlyGlyLysHisIle
          :                    :                    :
370  LeuArgArgGluSerProSerThr    ValLysMetCysValCysGlyThrSerHisTyr

462  ArgAsnGlnProValMetLeuAspVal    ThrGluGluLeuArgProAspHisLeuVal
              :              :                    :
389       AlaLysProLeuThrLeuAlaAlaIleIleSerSerAspIleArgAlaAsnArgTyrMet

481  LeuAlaCysThrArgAlaGluPheGlySerSerAspGluAspThrAspEnd
          :
408       TyrThrValAspSerThrGluPhe   ThrSerAspGluAspEnd
```

FIG. 4C

```
Ad5   1   MetSerThrAsnSerPheAspGlySerIleValSerSerTyrLeuThrThrThrArgMetPro
                :          ::             :  ::           :
BAV3  1   MetAla       Glu       GluGlyArgIleTyrValProTyrValThrAlaArgLeuPro

21  ProTrpAlaGlyValArgGlnAsnValMetGlySerSerIleAspGlyArgProValLeu
                   :                                   :
      18           LysTrpSerGlyServalGlnAspLysThrGlySerAsnMetLeuGlyGlyValValLeu 41  ProAlaAsnSerThrThrLeuThrThrTyrGluThrValSerGlyThrProLeuGluThrAla
                                :
      38  ProProAsnSerGlnAlaHisArgThrGluThrVal    GlyThrGlu    AlaThr 61  AlaSerAlaAlaAlaSerAlaAlaAlaAlaThrAlaAlaArgGlyIleValThrAspPheAla 55  ArgAspAsnLeuHisAlaGluGlyAlaArg    ArgProGluAspGlnThr    Pro 81  PheLeuSerProLeuAlaSerSerAlaSerArgSerAlaAlaArgAspAspLysLeu
               :     :
      72       TyrMetIle    LeuValGluAspSerLeuGlyGlyLeuLysArgArgMetAspLeuLeu 101  ThrAlaLeuLeuAlaGlnLeu    AspSerLeuThrArgGluLeuAsnValValSerGln 91  GluGluSerAsnGlnGlnLeuLeuLeuAlaThrLeuAsnArg    LeuArgThr    Gly 120  GlnLeuLeuAspLeuArgGlnGlnValSerAlaLeuLysAlaSerSerProProAsnAla
                                 :
     108           LeuAlaAlaTyr    ValGln    AlaAsnLeuValGlyGlyGlnValAsnProPhe 140  ValEnd 125  ValEnd
```

FIG. 5

```
                                  10                    20                    30                    40                 50
            C CTC ATC AAA CAA CCC GTG GTG GGC ACC CAC GTG GAA ATG CCT CGC AAC
ORF 1         Leu Ile Lys Gln Pro Val Val Gly Thr His Val Glu Met Pro Arg Asn 60                    70                    80                    90                100
            GAA GTC CTA GAA CAA CAT CTG ACC TCA CAT GGC GCT CAA ATC GCG GGC GGA
              Glu Val Leu Glu Gln His Leu Thr Ser His Gly Ala Gln Ile Ala Gly Gly 110                   120                   130                   140                150
            GGC GCT GCG GGC GAT TAC TTT AAA AGC CCC ACT TCA GCT CGA ACC CTT ATC
              Gly Ala Ala Gly Asp Tyr Phe Lys Ser Pro Thr Ser Ala Arg Thr Leu Ile 160                   170                   180                   190                200
            CCG CTC ACC GCC TCC TGC TTA AGA CCA GAT GGA GTC TTT CAA CTA GGA GGA
              Pro Leu Thr Ala Ser Cys Leu Arg Pro Asp Gly Val Phe Gln Leu Gly Gly 210                   220                   230                   240                250
            GGC TCG CGT TCA TCT TTC AAC CCC CTG CAA ACA GAT TTT GCC TTC CAC GCC
              Gly Ser Arg Ser Ser Phe Asn Pro Leu Gln Thr Asp Phe Ala Phe His Ala 260                   270                   280                   290                300
            CTG CCC TCC AGA CCG CGC CAC GGG GGC ATA GGA TCC AGG CAG TTT GTA GAG
              Leu Pro Ser Arg Pro Arg His Gly Gly Ile Gly Ser Arg Gln Phe Val Glu
```

FIG. 7A

```
310                      320                      330                      340                      350
GAA TTT GTG CCC GCC GTC TAC CTC AAC CCC TAC TCG GGA CCG CCG GAC TCT
Glu Phe Val Pro Ala Val Tyr Leu Asn Pro Tyr Ser Gly Pro Pro Asp Ser 360                      370                      380                      390                      400
TAT CCG GAC CAG TTT ATA CGC CAC TAC AAC GTG TAC AGC AAC TCT GTG AGC
Tyr Pro Asp Gln Phe Ile Arg His Tyr Asn Val Tyr Ser Asn Ser Val Ser
                                                                ORF 2  Ala 410                      420                      430                      440                      450                   460
GGT TAT AGC T GAG ATT GTA AGA CTC TCC TAT CTG TCT CTG TGC TGC TTT TCC
Gly Tyr Ser
            Val Ile Ala  Glu Ile Val Arg Leu Ser Tyr Leu Ser Leu Cys Cys Phe Ser 470                      480                      490                      500                      510
GCT TCA AGC CCC ACA AGC ATG AAG GGG TTT CTG CTC ATC TTC AGC CTG CTT
Ala Ser Ser Pro Thr Ser Met Lys Gly Phe Leu Leu Ile Phe Ser Leu Leu 520                      530                      540                      550                      560
GTG CAT TGT CCC CTA ATT CAT GTT GGG ACC ATT AGC TTC TAT GCT GCA AGG
    ORF 3  Phe Leu Gly Pro Leu Ala Ser Met Leu Gln Gly
Val His Cys Pro Leu Ile His Val Gly Thr Ile Ser Phe Tyr Ala Ala Arg
```

FIG. 7B

```
                570                 580                 590                 600                 610
CCC GGG TCT GAG CCT AAC GCG ACT TAT GTT TGT GAC TAT GGA AGC GAG TCA
Pro Gly Leu Ser Leu Thr Arg Leu Met Phe Val Thr Met Glu Ala Ser Gln

Pro Gly Ser Glu Pro Asn Ala Thr Tyr Val Cys Asp Tyr Gly Ser Glu Ser 620                 630                 640                 650                 660
GAT TAC AAC CCC ACC ACG GTT CTG TGG TTG GCT CGA GAG ACC GAT GGC TCC
Ile Thr Thr Pro Pro Arg Phe Cys Gly Trp Leu Glu Arg Pro Met Ala Pro

Asp Tyr Asn Pro Thr Thr Val Leu Trp Leu Ala Arg Glu Thr Asp Gly Ser 670                 680                 690                 700                 710
TGG ATC TCT GTT CTT TTC CGT CAC AAC GGC TCC TCA ACT GCA GCC CCC GGG
Gly Ser Leu Phe Phe Ser Val Thr Thr Ala Pro Gln Leu Gln Pro Pro Gly

Trp Ile Ser Val Leu Phe Arg His Asn Gly Ser Ser Thr Ala Ala Pro Gly 720                 730                 740                 750                 760
GTC GTC GCG CAC TTT ACT GAC CAC AAC AGC AGC ATT GTG GTG CCC CAG TAT
Ser Ser Arg Thr Leu Leu Thr Thr Thr Ala Ala Leu Trp Cys Pro Ser Ile

Val Val Ala His Phe Thr Asp His Asn Ser Ser Ile Val Val Pro Gln Tyr 770                 780                 790                 800                 810
TAC CTC CTC AAC TCA CTC TCT AAG CTC TGC TGC TCA TAC CGG CAC AAC
Thr Ser Ser Thr His Ser Leu Ser Ser Ala Ala His Thr Gly Thr Thr

Tyr Leu Leu Asn Asn Ser Leu Ser Lys Cys Cys Ser Tyr Arg His Asn

FIG. 7C
```

```
820                830                840                850                860
GAG CGT TCT CAG TTT ACC TGC AAA CAA GCT GAC GTC CCT ACC TGT CAC GAG
Glu Arg Ser Gln Phe Thr Cys Lys Gln Ala Asp Val Pro Thr Cys His Glu
Ser Val Leu Ser Leu Pro Ala Asn Lys Leu Thr Ser Leu Pro Val Thr Ser 870                880                890                900                910                920
CCC GGC AAG CTC ACC CCG CTC CGC GTC TCC CCC GCG CTG GGA ACT GCC CAC
Pro Gly Lys Pro Leu Arg Val Ser Pro Ala Leu Gly Thr Ala His
Pro Ala Ser Arg Ser Pro Ser Ala Ser Pro Pro Arg Trp Glu Leu Pro Thr 930                940                950                960                970
CAA GCA GTC ACT TGG TTT TTT CAA AAT GTA CCC ATA GCT ACT GTT TAC CGA
Gln Ala Val Thr Trp Phe Phe Gln Asn Val Pro Ile Ala Thr Val Tyr Arg
Lys Gln Ser Leu Gly Phe Phe Lys Met Tyr Pro 980                990                1000               1010               1020
CCT TGG GGC AAT GTA ACT TGG TTT CCT CCC TTC ATG TGT ACC TTT AAT
Pro Trp Gly Asn Val Thr Trp Phe Pro Pro Phe Met Cys Thr Phe Asn 1030               1040               1050               1060               1070
GTC AGC CTG AAC TCC CTA CTT ATT TAC AAC TTT TCT GAC AAA ACC GGG GGG
Val Ser Leu Asn Ser Leu Leu Ile Tyr Asn Phe Ser Asp Lys Thr Gly Gly
```

FIG. 7D

```
      1080                1090                1100                1110                1120
CAA TAC ACA GCT CTC ATG CAC TCC GGA CCT GCT TCC CTC TTT CAG CTC TTT
Gln Tyr Thr Ala Leu Met His Ser Gly Pro Ala Ser Leu Phe Gln Leu Phe 1130                1140                1150                1160                1170
AAG CCA ACG ACT TGT GTC ACC AAG GTG GAG GAC CCG CCG TAT GCC AAC GAC
Lys Pro Thr Thr Cys Val Thr Lys Val Glu Asp Pro Pro Tyr Ala Asn Asp 1180                1190                1200                1210                1220
CCG GCC TCG CCT GTG TGG CGC CCA CTG CTT TTT GCC TTC GTC CTC TGC ACC
Pro Ala Ser Pro Val Trp Arg Pro Leu Leu Phe Ala Phe Val Leu Cys Thr 1230                1240        ORF 4    1250                1260                1270
GGC TGC GCG GTG TTG TTA ACC GCC TTC GGT CCA TCG ATT CTA TCC GGT ACC
Gly Cys Ala Val Leu Leu Thr Ala Phe Gly Pro Ser Ile Leu Ser Gly Thr

ORF 4    Pro Pro Ser Val His Arg Phe Tyr Pro Val Pro 1280                1290                1300                1310                1320
CGA AAG CTT ATC TCA GCC CGC TTT TGG AGT CCC GAG CCC TAT ACC ACC CTC
Glu Ser Leu Ser Gln Pro Ala Phe Gly Val Pro Ser Pro Ile Pro Pro Ser
Arg Lys Leu Ile Ser Ala Arg Phe Trp Ser Pro Glu Pro Tyr Thr Thr Leu
```

FIG. 7E

```
1330         1340         1350         1360         1370         1380
CAC T AAC AGT CCC ATG GAG CCA GAC GGA GTT CAT GCC GAG CAG CAG TTT
    Thr Asn Ser Pro Pro Met Glu Pro Asp Gly Val His Ala Glu Gln Gln Phe
    His 1390         1400         1410         1420         1430
ATC CTC AAT CAG ATT TCC TGC GCC AAC ACT GCC CTC CAG CGT CAA AGG GAG
Ile Leu Asn Gln Ile Ser Cys Ala Asn Thr Ala Leu Gln Arg Gln Arg Glu 1440         1450         1460         1470         1480
GAA CTA GCT TCC CTT GTC ATG TTG CAT GCC TGT AAG CGT GGC CTC TTT TGT
Glu Leu Ala Ser Leu Val Met Leu His Ala Cys Lys Arg Gly Leu Phe Cys
ORF 5   Leu Pro Leu Ser Cys Cys Met Pro Val Ser Val Ala Ser Phe Val 1490         1500         1510         1520         1530
CCA GTC AAA ACT TAC AAG CTC AGC CTC AAC GCC TCG GCC AGC GAG CAC AGC
Pro Val Lys Thr Tyr Lys Leu Ser Leu Asn Ala Ser Ala Ser Glu His Ser
Gln Ser Lys Leu Thr Ser Ser Ala Ser Thr Pro Arg Pro Ala Ser Thr Ala 1540         1550         1560         1570         1580
CTG CAC TTT GAA AAA ACT AGT CCC TCC CGA TTC ACC CTG GTC AAC ACT CAC GCC
Leu His Phe Glu Lys Thr Ser Pro Ser Arg Phe Thr Leu Val Asn Thr His Ala
Cys Thr Leu Lys Lys Val Pro Leu Pro Asp Ser Pro Trp Ser Pro Leu Thr Pro
```

FIG. 7F

```
         1590           1600           1610           1620           1630
GGA GCT TCT GTG CGA GTG GCC CTA CAC CAC CAG GGA GCT TCC GGC AGC ATC
Gly Ala Ser Val Arg Val Ala Leu His His Gln Gly Ala Ser Gly Ser Ile
Glu Leu Leu Cys Glu Trp Pro Tyr Thr Thr Arg Glu Leu Pro Ala Ala Ser 1640           1650           1660           1670           1680
CGC TGT TCC TGT TCC CAC GCC GAG TGC CTC CCC GTC CTC CTC AAG ACC CTC
Arg Cys Ser Cys Ser His Ala Glu Cys Leu Pro Val Leu Leu Lys Thr Leu
Ala Val Pro Val Pro Thr Pro Ser Ala Ser Pro Ser Ser Ser Arg Pro Ser 1690           1700           1710           1720           1730          1740
TGT GCC TTT AAC TTT TTA GAT TAG CTGAAAGCAA ATATAAAATG GTGTGCTTAC
Cys Ala Phe Asn Phe Leu Asp
Val Pro Leu Thr Phe 1750           1760           1770           1780           1790
CGTAATTCTG TTTTGACTTG TGTGCTTGA TTT CTC CCC CTG CGC CGT AAT CCA GTG 1800           1810           1820           1830           1840
CCC CTC TTC AAA ACT CTC GTA CCC TAT GCG ATT CGC ATA GGC ATA TTT TCT 1850           1860           1870           1880           1890
AAA AGC TCT GAA GTC AAC ATC ACT CTC AAA CAC TTC TCC GTT GTA GGT TAC
```

FIG. 7G

```
       1900          1910          1920          1930          1940          1950
       TTT CAT CTA CAG ATA AAG TCA TCC ACC GGT T AAC ATC ATG AAG AGA AGT GTG
                              ORF 6  Ser His Pro Pro Val  Asn Ile Met Lys Arg Ser Val 1960          1970          1980          1990          2000
       CCC CAG GAC TTT AAT CTT GTG TAT CCG TAC AAG GCT AAG AGG CCC AAC ATC
       Pro Gln Asp Phe Asn Leu Val Tyr Pro Tyr Lys Ala Lys Arg Pro Asn Ile 2010          2020          2030          2040          2050
       ATG CCG CCC TTT TTT TTT GAC CGC AAT GGC TTT GTT GAA AAC CAA GAA GCC ACG
       Met Pro Pro Phe Phe Phe Asp Arg Asn Gly Phe Val Glu Asn Gln Glu Ala Thr 2060          2070          2080          2090          2100
       CTA GCC ATG CTT GTG GAA AAG CCG CTC ACG TTC GAC AAG GAA GGT GCG CTG
       Leu Ala Met Leu Val Glu Lys Pro Leu Thr Phe Asp Lys Glu Gly Ala Leu 2110          2120          2130          2140          2150
       ACC CTG GGC GTC TCC GGA CGC GGC ATC CGC ATT AAC CCC GCG GGG CTT CTG GAG
       Thr Leu Gly Val Gly Arg Gly Ile Arg Ile Asn Pro Ala Gly Leu Leu Glu 2160          2170          2180          2190          2200
       ACA AAC GAC CTC GCG TCC GCT GTC TTC CCA CCG CTG GCC TCC GAT GAG GCC
       Thr Asn Asp Leu Ala Ser Ala Val Phe Pro Pro Leu Ala Ser Asp Glu Ala
```

FIG. 7H

```
       2210              2220              2230              2240              2250
GGC AAC GTC ACG CTC AAC ATG TCT GAC GGG CTA TAT ACT AAG GAC AAC AAG
Gly Asn Val Thr Leu Asn Met Ser Asp Gly Leu Tyr Thr Lys Asp Asn Lys 2260              2270              2280              2290              2300
CTA GCT GTC AAA GTA GGT CCC GGG CTG TCC CTC GAC TCC AAT AAT GCT CTC
Leu Ala Val Lys Val Gly Pro Gly Leu Ser Leu Asp Ser Asn Asn Ala Leu 2310              2320              2330              2340              2350
CAG GTC CAC ACA GGC GAC GGG CTC ACG GTA ACC GAT GAC AAG GTG TCT CTA
Gln Val His Thr Gly Asp Gly Leu Thr Val Thr Asp Asp Lys Val Ser Leu 2360              2370              2380              2390              2400
AAT ACC CAA GCT CCC CTC TCG ACC ACC AGC GCG GGC CTC TCC CTA CTT CTG
Asn Thr Gln Ala Pro Leu Ser Thr Thr Ser Ala Gly Leu Ser Leu Leu Leu 2410              2420              2430              2440              2450              2460
GGT CCC AGC CTC CAC TTA GGT GAG GAG GAA CGA CTA ACA GTA AAC ACC GGA
Gly Pro Ser Leu His Leu Gly Glu Glu Glu Arg Leu Thr Val Asn Thr Gly 2470              2480              2490              2500              2510
GCG GGC CTC CAA ATT AGC AAT AAC GCT CTG GCC GTA AAA GTA GGT TCA GGT
Ala Gly Leu Gln Ile Ser Asn Asn Ala Leu Ala Val Lys Val Gly Ser Gly
```

FIG. 7I

```
         2520                 2530                 2540                 2550                 2560
ATC ACC GTA GAT GCT CAA AAC CAG CTC GCT GCA TCC CTG GGG GAC GGT CTA
Ile Thr Val Asp Ala Gln Asn Gln Leu Ala Ala Ser Leu Gly Asp Gly Leu 2570                 2580                 2590                 2600                 2610
GAA AGC AGA GAT AAT AAA ACT GTC GTT AAG GCT GGG CCC GGA CTT ACA ATA
Glu Ser Arg Asp Asn Lys Thr Val Val Lys Ala Gly Pro Gly Leu Thr Ile 2620                 2630                 2640                 2650                 2660
ACT AAT CAA GCT CTT ACT GTT GCT ACC GGG AAC GGC CTT CAG GTC AAC CCG
Thr Asn Gln Ala Leu Thr Val Ala Thr Gly Asn Gly Leu Gln Val Asn Pro 2670                 2680                 2690                 2700                 2710
GAA GGG CAA CTG CAG CTA AAC ATT ACT GCC GGT CAG GGC CTC AAC TTT GCA
Glu Gly Gln Leu Gln Leu Asn Ile Thr Ala Gly Gln Gly Leu Asn Phe Ala 2720                 2730                 2740                 2750                 2760
AAC AAC AGC CTC GCC GTG GAG CTG GGC TCG GGC CTG CAT TTT CCC CCT GGC
Asn Asn Ser Leu Ala Val Glu Leu Gly Ser Gly Leu His Phe Pro Pro Gly 2770                 2780                 2790                 2800                 2810
CAA AAC CAA GTA AGC CTT TAT CCC GGA GAT GGA ATA GAC ATC CGA GAT AAT
Gln Asn Gln Val Ser Leu Tyr Pro Gly Asp Gly Ile Asp Ile Arg Asp Asn
```

FIG. 7J

```
        2820                    2830                    2840                    2850                    2860
        AGG GTG ACT GTG CCC GCT GGG CCA GGC CTG AGA ATG CTC AAC CAC CAA CTT
        Arg Val Thr Val Pro Ala Gly Pro Gly Leu Arg Met Leu Asn His Gln Leu 2870                    2880                    2890                    2900                    2910
GCC GTA GCT TCC GGA GAC GGT TTA GAA GTC CAC AGC GAC ACC CTC CGG TTA
Ala Val Ala Ser Gly Asp Gly Leu Glu Val His Ser Asp Thr Leu Arg Leu 2920                    2930                    2940                    2950                    2960                    2970
AAG CTC TCC CAC GGC CTG ACA TTT GAA AAT GGC GCC GTA CGA GCA AAA CTA
Lys Leu Ser His Gly Leu Thr Phe Glu Asn Gly Ala Val Arg Ala Lys Leu 2980                    2990                    3000                    3010                    3020
        GGA CCA GGA CTT GGC ACA GAC GAC TCT GGT CGG TCC GTG GTT CGC ACA GGT
        Gly Pro Gly Leu Gly Thr Asp Asp Ser Gly Arg Ser Val Val Arg Thr Gly 3030                    3040                    3050                    3060                    3070
        CGA GGA CTT AGA GTT GCA AAC GGC CAA GTC CAG ATC TTC AGC GGA AGA GGC
        Arg Gly Leu Arg Val Ala Asn Gly Gln Val Gln Ile Phe Ser Gly Arg Gly 3080                    3090                    3100                    3110                    3120
        ACC GCC ATC GGC ACT GAT AGC AGC AGC CTC ACT CTC AAC ATC CGG GCG CCC CTA
        Thr Ala Ile Gly Thr Asp Ser Ser Ser Leu Thr Leu Asn Ile Arg Ala Pro Leu
```

FIG. 7K

```
       3130             3140            3150              3160            3170
CAA TTT TCT GGA CCC GCC TTG ACT GCT AGT TTG CAA GGC AGT GGT CCG ATT
Gln Phe Ser Gly Pro Ala Leu Thr Ala Ser Leu Gln Gly Ser Gly Pro Ile 3180             3190            3200              3210            3220
ACT TAC AAC AGC AAC AAT GGC ACT TTC GGT CTC TCT ATA GGC CCC GGA ATG
Thr Tyr Asn Ser Asn Asn Gly Thr Phe Gly Leu Ser Ile Gly Pro Gly Met 3230             3240            3250              3260            3270
TGG GTA GAC CAA AAC AGA CTT CAG GTA AAC CCA GGC GCT GGT TTA GTC TTC
Trp Val Asp Gln Asn Arg Leu Gln Val Asn Pro Gly Ala Gly Leu Val Phe 3280             3290            3300              3310            3320
CAA GGA AAC AAC CTT GTC CCA AAC CTT GCG GAT CCG CTG GCT ATT TCC GAC
Gln Gly Asn Asn Leu Val Pro Asn Leu Ala Asp Pro Leu Ala Ile Ser Asp 3330             3340            3350              3360            3370
AGC AAA ATT AGT CTC AGT CTC GGT CCC GGC CTG ACC CAA GCT TCC AAC GCC
Ser Lys Ile Ser Leu Ser Leu Gly Pro Gly Leu Thr Gln Ala Ser Asn Ala 3380             3390            3400              3410            3420
CTG ACT TTA AGT TTA GGA AAC GGG CTT GAA TTC TCC AAT CAA GCC GTT GCT
Leu Thr Leu Ser Leu Gly Asn Gly Leu Glu Phe Ser Asn Gln Ala Val Ala
```

FIG. 7L

```
3430              3440                3450               3460              3470              3480
ATA AAA GCG GGC CGG GGC TTA CGC TTT GAG TCT TCC TCA CAA GCT TTA GAG
Ile Lys Ala Gly Arg Gly Leu Arg Phe Glu Ser Ser Ser Gln Ala Leu Glu 3490              3500                3510              3520              3530
AGC AGC CTC ACA GTC GGA AAT GGC TTA ACG CTT ACC GAT ACT GTG ATC CGC
Ser Ser Leu Thr Val Gly Asn Gly Leu Thr Leu Thr Asp Thr Val Ile Arg 3540              3550                3560              3570              3580
CCC AAC CTA GGG GAC GGC CTA GAG GTC AGA GAC AAT AAA ATC ATT GTT AAG
Pro Asn Leu Gly Asp Gly Leu Glu Val Arg Asp Asn Lys Ile Ile Val Lys 3590              3600                3610              3620              3630
CTG GGC GCG AAT CTT CGT TTT GAA AAC GGA GCC GTA ACC GCC GGC ACC GTT
Leu Gly Ala Asn Leu Arg Phe Glu Asn Gly Ala Val Thr Ala Gly Thr Val 3640              3650                3660              3670              3680
AAC CCT TCT GCG CCC GAG GCA CCA ACT CTC ACT GCA GAA CCA CCC CTC
Asn Pro Ser Ala Pro Glu Ala Pro Thr Leu Thr Ala Glu Pro Pro Leu 3690              3700                3710              3720              3730
CGA GCC TCC AAC TCC CAT CTT CAA CTG TCC CTA TCG GAG GGC TTG GTT GTG
Arg Ala Ser Asn Ser His Leu Gln Leu Ser Leu Ser Glu Gly Leu Val Val
```

FIG. 7M

```
       3740                      3750                      3760                      3770                      3780
CAT AAC AAC GCC CTT GCT CTC CAA CTG GGA GAC GGC ATG GAA GTA AAT CAG
His Asn Asn Ala Leu Ala Leu Gln Leu Gly Asp Gly Met Glu Val Asn Gln 3790                      3800                      3810                      3820                      3830
CAC GGA CTT ACT TTA AGA GTA GGC TCG GGT TTG CAA ATG CGT GAC GGC ATT
His Gly Leu Thr Leu Arg Val Gly Ser Gly Leu Gln Met Arg Asp Gly Ile 3840                      3850                      3860                      3870                      3880
TTA ACA GTT ACA CCC AGC ACT CCT ATT GAG CCC AGA CTG ACT GCC CCA
Leu Thr Val Thr Pro Ser Gly Thr Pro Ile Glu Pro Arg Leu Thr Ala Pro 3890                      3900                      3910                      3920                      3930
CTG ACT CAG ACA GAG AAT GGA ATC GGG CTC GCT CTC GGC GCC GGC TTG GAA
Leu Thr Gln Thr Glu Asn Gly Ile Gly Leu Ala Leu Gly Ala Gly Leu Glu 3940                      3950                      3960                      3970                      3980                      3990
TTA GAC GAG AGC GCG CTC CAA GTA AAA GTT GGG CCC GGC ATG CGC CTG AAC
Leu Asp Glu Ser Ala Leu Gln Val Lys Val Gly Pro Gly Met Arg Leu Asn 4000                      4010                      4020                      4030                      4040
CCT GTA GAA AAG TAT GTA ACC CTG CTC GGT CCT GGC CTT AGT TTT GGG
Pro Val Glu Lys Tyr Val Thr Leu Leu Gly Pro Gly Leu Ser Phe Gly
```

FIG. 7N

```
                    4050                 4060                 4070                 4080                 4090
CAG CCG GCC AAC AGG ACA AAT TAT GAT GTG CGC GTT TCT GTG GAG CCC CCC
Gln Pro Ala Asn Arg Thr Asn Tyr Asp Val Arg Val Ser Val Glu Pro Pro 4100                 4110                 4120                 4130                 4140
ATG GTT TTC GGA CAG CGT GGT CAG CTC ACA TTT TTA GTG GGT CAC GGA CTA
Met Val Phe Gly Gln Arg Gly Gln Leu Thr Phe Leu Val Gly His Gly Leu 4150                 4160                 4170                 4180                 4190
CAC ATT CAA AAT TCC AAA CTT CAG CTC AAT TTG GGA CAA GGC CTC AGA ACT
His Ile Gln Asn Ser Lys Leu Gln Leu Asn Leu Gly Gln Gly Leu Arg Thr 4200                 4210                 4220                 4230                 4240
GAC CCC GTC ACC AAC CAG CTG GAA GTG CCC CTC GGT CAA GGT TTG GAA ATT
Asp Pro Val Thr Asn Gln Leu Glu Val Pro Leu Gly Gln Gly Leu Glu Ile 4250                 4260                 4270                 4280                 4290
GCA GAC GAA TCC CAG GTT AGG GTT AAA TTG GGC GAT GGC CTG CAG TTT GAT
Ala Asp Glu Ser Gln Val Arg Val Lys Leu Gly Asp Gly Leu Gln Phe Asp 4300                 4310                 4320                 4330                 4340
TCA CAA GCT CGC ATC ACT ACC GCT CCT AAC ATG GTC ACT GAA ACT CTG TGG
Ser Gln Ala Arg Ile Thr Thr Ala Pro Asn Met Val Thr Glu Thr Leu Trp
```

FIG. 70

```
       4350                 4360                 4370                 4380                 4390
       ACC GGA ACA GGC AGT AAT GCT AAT GTT ACA TGG CGG GGC TAC ACT GCC CCC
       Thr Gly Thr Gly Ser Asn Ala Asn Val Thr Trp Arg Gly Tyr Thr Ala Pro 4400                 4410                 4420                 4430                 4440
       GGC AGC AAA CTC TTT TTG AGT CTC ACT CGG TTC AGC ACT GGT CTA GTT TTA
       Gly Ser Lys Leu Phe Leu Ser Leu Thr Arg Phe Ser Thr Gly Leu Val Leu 4450                 4460                 4470                 4480                 4490                 4500
       GGA AAC ATG ACT ATT GAC AGC AAT GCA TCC TTT GGG CAA TAC ATT AAC GCG
       Gly Asn Met Thr Ile Asp Ser Asn Ala Ser Phe Gly Gln Tyr Ile Asn Ala 4510                 4520                 4530                 4540                 4550
       GGA CAC GAA CAG ATC GAA TGC TTT ATA TTG TTG GAC AAT CAG GGT AAC CTA
       Gly His Glu Gln Ile Glu Cys Phe Ile Leu Leu Asp Asn Gln Gly Asn Leu 4560                 4570                 4580                 4590                 4600
       AAA GAA GGA TCT AAC TTG CAA GGC ACT TGG GAA GTG AAG AAC AAC CCC TCT
       Lys Glu Gly Ser Asn Leu Gln Gly Thr Trp Glu Val Lys Asn Asn Pro Ser 4610                 4620                 4630                 4640                 4650
       GCT TCC AAA GCT GCT TTT TTG CCT TCC ACC GCC CTA TAC CCC ATC CTC AAC
       Ala Ser Lys Ala Ala Phe Leu Pro Ser Thr Ala Leu Tyr Pro Ile Leu Asn
```

FIG. 7P

```
4660                4670                4680                4690                4700
GAA AGC CGA GGG AGT CTT CCT GGA AAA AAT CTT GTG GGC ATG CAA GCC ATA
Glu Ser Arg Gly Ser Leu Pro Gly Lys Asn Leu Val Gly Met Gln Ala Ile 4710                4720                4730                4740                4750
CTG GGA GGC GGG GGC ACT TGC ACT GTG ATA GCC ACC CTC AAT GGC AGA CGC
Leu Gly Gly Gly Gly Thr Cys Thr Val Ile Ala Thr Leu Asn Gly Arg Arg 4760                4770                4780                4790                4800
AGC AAC AAC TAT CCC GCG GGC CAG TCC ATA ATT TTC GTG TGG CAA GAA TTC
Ser Asn Asn Tyr Pro Ala Gly Gln Ser Ile Ile Phe Val Trp Gln Glu Phe 4810                4820                4830                4840                4850
AAC ACC ATA GCC CGC CAA CCT CTG AAC CAC TCT ACA CTT ACT TTT TCT TAC
Asn Thr Ile Ala Arg Gln Pro Leu Asn His Ser Thr Leu Thr Phe Ser Tyr 4860                4870                4880                4890                4900
TGG ACT TA AAT AAG TTG GAA ATA AAG AGT TAA ACT GAA TGT TTA AGT GCA
Trp Thr 4910                4920                4930                4940                4950
ACA GAC TTT TAT TGG TTT TGG CTC ACA ACA AAT TAC AAC AGC ATA GAC AAG 4960                4970                4980                4990                5000
TCA TAC CGG TCA AAC AAC ACA GGC TCT CGA AAA CGG GCT AAC CGC TCC AAG
```

FIG. 7Q

```
     5010          5020          5030          5040          5050          5060
      AAT CTG TCA CGC AGA CGA GCA AGT CCT AAA TGT TTT TTC ACT CTC TTC GGG
           5070          5080          5090          5100
      GCC AAG TTC AGC ATG TAT CGG ATT TTC TGC TTA CAC CTT T
```

FIG. 7R

```
Ad2    MSKEIPTPYMWSYQPQMGLAAGAAQDYSTRINYMSAGPHMISRVNGIRAH           50

BAV3         LIKQPVVGTTHV--------------------EMPRNEVLEQH           23
             .:  :  .::                        .::    :
Ad2    RNRILLEQAAITTTPRNNLNPRSWPAALVYQESPAPTTVVLPRDAQAEVQ          100

BAV3   LTSHGAQIAGGG-----AAGDYFKSPTSARTLIPLTASCL------RPDG           62
        .:  :::::.:::     . :            : :   .       ::::
Ad2    MTNSGAQLAGGFRHRVRSPGQGITHLKIRGRGIQLNDESVSSSLGLRPDG          150

BAV3   VFQLGGGSRSSFNPLQTDFAFHALPSRPRHGGIGSRQFVEEFVPAVYLNP          112
        ::.:: ::::  :  :.   .    :  ::  ::::. ::.::::.: ::
Ad2    TFQIGGAGRSSFTPRQAILTLQTSSSEPRSGGIGTLQFIEEFVPSVYFNP          200

BAV3   YSGPPDSYPDQFIRHYNVYSNSVSGYS                                 139
       .::::  :::::::  .     :  ::
Ad2    FSGPPGHYPDQFIPNFDAVKDSADGYD                                 227
```

FIG. 8A

```
BAV3   M------EPDGVHAEQQFILNQISCANTALQRQREELASLVMLHACKRGL           77
       :      : ::  .::   . :    :    ::   ::   .:  ::::.
Ad5    MTDTLDLEMDGIITEQRLL--ERRRAAAEQQRMNQELQDMVNLHQCKRGI           48

BAV3   FCPVKTYKLSLNASASEHSLHFEKSPSRFTLVNTHAGASVRVALHHQGAS          127
       :: :: :.     .. : :    ::  :   ::         ...  :
Ad5    FCLVKQAKVTYDSNTTGHRLSYKLPTKRQKLVVMVGEKPITITQHSVETE           98

BAV3   GSIRCSCSHAECLPVLLKTLCAFNFLD                                 154
       :  :  :    ::  :.:::::   :
Ad5    GCIHSPCQGPEDLCTLIKTLCGLKDLIPFN                              128
```

FIG. 8B

```
BAV3   - MKRSVPQD--FNLVYPYKAKR-----PNIMPPFFDRNGFVENQEATLAML  -43
         :::. : .  :: :::: .      : . :::  ::: :     :..
Ad2    - MKRARPSEDTFNPVYPYDTETGPPTVPFLTPPFVSPNGFQESPPGVLSLR  -50

BAV3   - VEKPLTFDKE-GALTLGVGRGIRINPAGLLETNDLASAVFPPLASDEAGN  -92
         : :: :    : :.: .: :. .  :: : .. ...
Ad2    - VSEPL--DTSHGMLALKMGSGLTLDKAGNLTSQNVTTV------------  -86

BAV3   - VTLNMSDGLYTKDNKLAVKVGPGLSLDSNNALQVHTGDGLTVTDDKVSLN  -142
            . :    ... :... . ::    : ::    .:..
Ad2    - -----TQPLKKTKSNISLDTSAPLTI-TSGALTVATTAPLIVTSGALSVQ  -130

BAV3   - TQAPLSTTSAGLSLLLGPSLHLGEEERLTVNTGAGLQISNNALAVKVGSG  -192
         .::::..         . .:.. :   . .:    :::.    .
Ad2    - SQAPLT---------------VQDSKLSIATKGPITVSDGKLALQTSAP  -164

BAV3   - ITVDAQNQLAASLGDGLESRDNKTVVKAGPGLTITNQALTVATGNGLQVN  -242
         ..       :. .                  .   :: :::    : ..:
Ad2    - LSGSDSDTLTVT--------------------ASPPLTTATGS-LGIN  -191

BAV3   - PEGQLQLNITAGQGLNFANNSLAVELGSGLHFPPGQNQVSLYPGDGIDIR  -292
         :   . .:         .   : . . . :
Ad2    - MEDPIYVN---------NGKIGIKISGPLQVAQ---------------  -215

BAV3   - DNRVTVPAGPGLRMLNHQLAVASGDGLEVHSDTLRLKLSHGLTFENGAVR  -342
                                       ::::  .   ...: :. ...
Ad2    - ------------------------------NSDTLTVVTGPGVTVEQNSLR  -236
```

FIG. 8C-1

```
BAV3  - AKLGPGLGTDDSGRSVVRTGRGLRVANGQVQIFSGRGTAIGTDSSLTLNI  -392
         .:.    .:   ..:: :..:.    ..  :  .    .. .:: .
Ad2   - TKVAGAIGYDSSNNMEIKTGGMRINNNL--LILDVDYPFDAQTKLRLKL  -284

BAV3  - RAPLQFSGPALTASLQGSGPITYNSNNGTFGLSIGPGMWVDQNRLQVNPG  -442
                          :  ::.  ::.
Ad2   - ---------------GQGPLYINASHN----------------LDINYN  -302

BAV3  - AGLVFQGNNLVPNLADPLAISDSKISLSLGPGLTQASNALTLSLGNGLEF  -492
         ::               :     :        ..         :: :
Ad2   - RGLYL------------FNASNNTKKLEVSIKKSS---------GLNF  -329

BAV3  - SNQAVAIKAGRGLRFESSSQALESSLTVGNGLTLTDTVIRPNLGDGLEVR  -542
          : :.::  ::..::  :...  .
Ad2   - DNTAIAINAGKGLEFDTNT-----------------------------  -348

BAV3  - DNKIIVKLGANLRFENGAVTAGTVNPSAPEAPPTLTAEPPLRASNSHLQL  -592
Ad2   - -------------------------------------------------  -348

BAV3  - SLSEGLVVHNNALALQLGDGMEVNQHGLTLRVGSGLQMRDGILTVTPSGT  -642
                          .   ..:  .   ..:::.            :..
Ad2   - ------------------SESPDIN--PIKTKIGSGID-------YNENGA  -372

BAV3  - PIEPRLTAPLTQTENGIGLALGAGLELDESALQVKVGPGMRLNPVEKYVT  -692
         :                     :::::  :  :
Ad2   - MIT--------------KLGAGLSFDNSG-------------------  -387
```

FIG. 8C-2

```
BAV3  - LLLGPGLSFGQPANRTNYDVRVSVEPPMVFGQRGQLTFLVGHGLHIQNSK  -742
         ..  :           :   ....                      :.  .
Ad2   - -----AITIG-----NKNDDKLTLWTTPDPSP---------------NCR  -412

BAV3  - LQLNLGQGLRTDPVTNQLEVPLGQGLEIADESQVRVKLGDGLQFDSQARI  -792
         .                              .    . :          ::
Ad2   - IHSD--------------------NDCKFTLVLT---KCGSQVLA  -434

BAV3  - TTAPNMVTETLWTGTGSNANVTWRGYTAPGSKLFLSLTRFSTGLVLGNMT  -842
         : :       :.   :    ::    :.         .::           :....  :.
Ad2   - TVAALAVSGDLSSMTGTVASVS---------IFLRFDQ--NGVLMENSS  -472

BAV3  - IDSNASFGQYINAGHEQIECFILLDNQGNLKEGSNLQGTWEVKNNPSASK  -892
           .                  . :                       :: .
Ad2   - LKKHY--------------------WNFRNGNS------TNANPYTNA  -494

BAV3  - AAFLPSTALYPILNESRGSLPGKNLVGMQAILGGGGTCTVIA-TLNGRRS  -941
         :.:   ::       .      :.:     . :          ... ::::
Ad2   - VGFMPNLLAYP---KTQSQTAKNNIVSQVYLHGDKTKPMILTITLNGTSE  -541

BAV3  - NNYPAGQSII---FVWQ-EFNTIARQPLNHSTLTFSYWT  -976
           .  :       :: :  .           . ::::  .
Ad2   - STETSEVSTYSMSFTWSWESGKYTTETFATNSYTFSYIAQE  -582
```

FIG. 8C-3

RECOMBINANT PROTEIN PRODUCTION IN BOVINE ADENOVIRUS EXPRESSION VECTOR SYSTEM

TECHNICAL FIELD

The present invention relates novel bovine adenovirus (BAV) expression vector systems in which one or both of the early region 1 (E1) and the early region 3 (E3) gene deletions are replaced by a foreign gene and novel recombinant mammalian cell lines stably transformed with BAV E1 sequences, and therefore, expresses E1 gene products, to allow a bovine adenovirus with an E1 gene deletion replaced by a foreign gene to replicate therein. These materials are used in production of recombinant BAV expressing heterologous (antigenic) polypeptides or fragments for the purpose of live recombinant virus or subunit vaccines or for other therapies.

BACKGROUND OF THE INVENTION

The adenoviruses cause enteric or respiratory infection in humans as well as in domestic and laboratory animals.

The bovine adenoviruses (BAVs) comprise at least nine serotypes divided into two subgroups. These subgroups have been characterized based on enzyme-linked immunoassays (ELISA), serologic studies with immunofluorescence assays, virus-neutralization tests, immunoelectron microscopy, by their host specificity and clinical syndromes. Subgroup 1 viruses include BAV 1, 2, 3 and 9 and grow relatively well in established bovine cells compared to subgroup 2 which includes BAV 4, 5, 6, 7 and 8.

BAV3 was first isolated in 1965 and is the best characterized of the BAV genotypes and contains a genome of approximately 35 kb (Kurokawa et al (1978) *J. Virol.* 28:212–218). The locations of hexon (Hu et al (1984) *J. Viol.* 49:604–608) and proteinase (Cai et al., (1990) *Nuc. Acids Res.*, 18:5568), genes in the BAV3 genome have been identified and sequenced. However, the location and sequences of other genes such as early region 1 (E1) and 3 (E3) in the BAV genome have not been reported.

In the human adenovirus (HAd) genome there are two important regions: E1 and E3 in which foreign genes can be inserted to generate recombinant adenoviruses (Berkner and Sharp (1984) *Nuc. Acid Res.*, 12:1925–1941 and Haj-Ahmad and Graham (1986) *J. Virol.*, 57:267–274). E1 proteins are essential for virus replication in tissue culture, however, conditional-helper adenovirus recombinants containing foreign DNA in the E1 region, can be generated in a cell line which constitutively expresses E1 (Graham et al., (1977) *J. Gen Virol.*, 36:59–72). In contrast, E3 gene products of HAd 2 and HAd 5 are not required for in vitro or in vivo infectious virion production, but have an important role in host immune responses to virus infection (Andersson et al (1985) *Cell* 43:215–222; Burgert et al (1987) *EMBO J.* 6:2019–2026; Carlin et al (1989) *Cell* 57:135–144; Ginsberg et al (1989) *PNAS, USA* 86:3823–3827; Gooding et al (1988) *Cell* 53:341–346; Tollefson et al (1991) *J. Virol.* 65:3095–3105; Wold and Gooding (1989) *Mol. Biol. Med.* 6:433–452 and Wold and Gooding (1991) *Virology* 184:1–8). The E3-19 kiloDalton (kDa) glycoprotein (gp19) of human adenovirus type 2 (HAd2) binds to the heavy chain of a number of class 1 major histocompatibility complex (MHC) antigens in the endoplasmic reticulum thus inhibiting their transport to the plasma membrane (Andersson et al. (1985) *Cell* 43:215–222; Burgert and Kvist, (1985) *Cell* 41:987–997; Burgert and Kvist, (1987) *EMBO J.* 6:2019–2026). The E3-14.7 kDa protein of HAd2 or HAd5 prevents lysis of virus-infected mouse cells by tumor necrosis factor (TNF) (Gooding et al. (1988) *Cell* 53:341–346). In addition, the E3-10.4 kDa and E3-14.5 kDa proteins form a complex to induce endosomal-mediated internalization and degradation of the epidermal growth factor receptor (EGF-R) in virus-infected cells (Carlin et al. *Cell* 57:135–144; Tollefson et al. (1991) *J. Virol.* 65:3095–3105). The helper-independent recombinant adenoviruses having foreign genes in the E3 region replicate and express very well in every permissive cell line (Chanda et al (1990) *Virology* 175:535–547; Dewar et al (1989) *J. Virol.* 63:129–136; Johnson et al (1988) *Virology* 164:1–14; Lubeck et al (1989) *PNAS, USA* 86:6763–6767; McDermott et al (1989) *Virology* 169:244–247; Mittal et al (1993) *Virus Res.* 28:67–90; Morin et al (1987) *PNAS. USA* 84:4626–4630; Prevec et al (1990) *J. Inf. Dis.* 161:27–30; Prevec et al (1989) *J. Gen Virol.* 70:429–434; Schneider et al (1989) *J. Gen Virol.* 70:417–427 and Yuasa et al (1991) *J. Gen Virol.* 72:1927–1934). Based on the above studies and the suggestion that adenoviruses can package approximately 105% of the wild-type (wt) adenovirus genome (Bett et al (1993) *J. Virol.* 67:5911–5921 and Ghosh-Choudhury et al (1987) *EMBO. J.* 6:1733–1739), an insertion of up to 1.8 kb foreign DNA can be packaged into adenovirus particles for use as an expression vector for foreign proteins without any compensating deletion.

It is assumed that an indigenous adenovirus vector would be better suited for use as a live recombinant virus vaccine in different animal species compared to an adenovirus of human origin. Non-human adenovirus-based expression vectors have not been reported so far. If like HAds E3, the E3 regions in other adenoviruses are not essential for virus replication in cultured cells, adenovirus recombinants containing foreign gene inserts in the E3 region could be generated.

BAV3 is a common pathogen of cattle usually resulting in subclinical infection though occasionally associated with a more serious respiratory tract infection (Darbyshire et al., 1966 *Res. Vet Sci* 7:81–93; Mattson et al., 1988 *J. Vet Res* 49:67–69). BAV3 can produce tumors when injected into hamsters (Darbyshire, 1966 *Nature* 211:102) and viral DNA can efficiently effect morphological transformation of mouse, hamster or rat cells in culture (Tsukamoto and Sugino, 1972 *J. Virol.* 9:465–473; Motoi et al., 1972 *Gann* 63:415–418; M. Hitt, personal communication). Cross hybridization was observed between BAV3 and human adenovirus type 2 (HAd2) (Hu et al., 1984 *J. Virol.* 49:604–608) in most regions of the genome including some regions near but not at the left end of the genome.

The E1A gene products of the group C human adenoviruses have been very extensively studied and shown to mediate transactivation of both viral and cellular genes (Berk et al., 1979 *Cell* 17:935–944; Jones and Shenk, 1979 *Cell* 16:683–689; Nevins, 1981 *Cell* 26:213–220; Nevins, 1982 *Cell* 29:913–919; reviewed in Berk, 1986 *Ann. Res. Genet* 20:45–79), to effect transformation of cells in culture (reviewed in Graham, F. L. (1984) "Transformation by and oncogenicity of human adenoviruses. In:The Adenoviruses." H. S. Ginsberg, Editor. Plenum Press, New York; Branton et al., 1985 *Biochim. Biophys. Acta* 780:67–94) and induce cell DNA synthesis and mitosis (Zerler et al., 1987 *Mol. Cell Biol.* 7:821–929; Bellet et al., 1989 *J. Virol.* 63:303–310; Howe et al., 1990 *PNAS, USA* 87:5883–5887; Howe and Bayley, 1992 *Virology* 186:15–24). The E1A transcription unit comprises two coding sequences separated by an intron region which is deleted from all processed E1A transcripts. In the two largest mRNA species produced from the E1A transcription unit, the first coding regions is further subdivided into exon 1, a sequence found in both the 12s and 13s mRNA species, and the unique region, which is found only in the 13s mRNA species. By comparisons between E1A proteins of human and simian adenoviruses three regions of somewhat conserved protein sequence (CR) have been defined (Kimelman et al., 1985 *J. Virol.* 53:399–409). CR1 and CR2 are encoded in exon 1, while CR3 is encoded in the unique sequence and a small portion of exon 2. Binding sites for a number of cellular proteins including the retinoblastoma protein Rb, cyclin A and an associated protein kinase p33$^{cdk2}$, and other, as yet unassigned, proteins have been defined in exon 1 encoded regions of E1A proteins (Yee and Branton, 1985 *Virology* 147:142–153; Harlow et al., 1986 *Mol. Cell Biol.* 6:1579–1589; Barbeau et al., 1992 *Biochem. Cell Biol.* 70:1123–1134). Interaction of E1A with these cellular proteins has been implicated as the mechanism through which E1A participates in immortalization and oncogenic transformation (Egan et al, 1989 *Oncogene* 4:383–388; Whyte et al., 1988 *Nature* 334:124–129; Whyte et al, 1988 *J. Virol.* 62:257–265). While E1A alone may transform or immortalize cells in culture, the coexpression of both E1A and either the E1-19k protein or the E1B-55k protein separately or together is usually required for high frequency transformation of rodent cells in culture (reviewed in Graham, 1984 supra; Branton et al., 1985 supra; McLorie et al., 1991 *J. Gen Virol.* 72:1467–1471).

Transactivation of other viral early genes in permissive infection of human cells is principally mediated by the amino acid sequence encoded in the CR3 region of E1A (Lillie et al., 1986 *Cell* 46:1043–1051). Conserved cysteine residues in a CysX$_2$CysX$_{13}$CysX$_2$Cys(SEQ ID NO:30) sequence motif in the unique region are associated with metal ion binding activity (Berg, 1986 supra) and are essential for transactivation activity (Jelsma et al., 1988 *Virology* 163:494–502; Culp et al., 1988 *PNAS. USA* 85:6450–6454). As well, the amino acids in CR3 which are immediately amino (N)-terminal to the metal binding domain have been shown to be important in transcription activation, while those immediately carboxy (C)-terminal to the metal binding domain are important in forming associations with the promoter region (Lillie and Green, 1989 *Nature* 338:39–44; see FIG. 3).

The application of genetic engineering has resulted in several attempts to prepare adenovirus expression systems for obtaining vaccines. Examples of such research include the disclosures in U.S. Pat. No. 4,510,245 on an adenovirus major late promoter for expression in a yeast host; U.S. Pat. No. 4,920,209 on a live recombinant adenovirus type 7 with a gene coding for hepatitis-B surface antigen located at a deleted early region 3; European patent 389 286 on a non-defective human adenovirus 5 recombinant expression system in human cells for HCMV major envelope glycoprotein; WO 91/11525 on live non-pathogenic immunogenic viable canine adenovirus in a cell expressing E1a proteins; French patent 2 642 767 on vectors containing a leader and/or promoter from the E3 of adenovirus 2.

The selection of a suitable virus to act as a vector for foreign gene expression, and the identification of a suitable non-essential region as a site for insertion of the gene pose a challenge. In particular, the insertion site must be non-essential for the viable replication of the virus and its effective operation in tissue culture and also in vivo. Moreover, the insertion site must be capable of accepting new genetic material, whilst ensuring that the virus continues to replicate. An essential region of a virus genome can also be utilized for foreign gene insertion if the recombinant virus is grown in a cell line which complements the function of that particular essential region in trans.

The present inventors have now identified suitable regions in the BAV genome and have succeeded in inserting foreign genes to generate BAV recombinants.

DISCLOSURE OF THE INVENTION

The present invention relates to novel bovine adenovirus expression vector systems in which part or all of one or both of the E1 and E3 gene regions are deleted and to recombinant mammalian cell lines of bovine origin transformed with the BAV E1 sequences, and thus, constitutively express the E1 gene products to allow bovine adenovirus, having a deletion of part or all of the E1 gene region replaced by a heterologous nucleotide sequence encoding a foreign gene or fragment thereof, to replicate therein and use of these materials in production of heterologous (antigenic) polypeptides or fragments thereof.

The invention also related to a method of preparing a live recombinant virus or subunit vaccines for producing antibodies or cell mediated immunity to an infectious organism in a mammal, such as bovine, which comprises inserting into the bovine adenovirus genome the gene or fragment coding for the antigen which corresponds to said antibodies or induces said cell mediated immunity, together with or without an effective promoter therefore, to produce BAV recombinants.

Generally, the foreign gene construct is cloned into a nucleotide sequence which represents only a part of the entire viral genome having one or more appropriate deletions. This chimeric DNA sequence is usually present in a plasmid which allows successful cloning to produce many copies of the sequence. The cloned foreign gene construct can then be included in the complete viral genome, for example, by in vivo recombination following a DNA-mediated cotransfection technique. Multiple copies of a coding sequence or more than one coding sequences can be inserted so that the recombinant vector can express more than one foreign protein. The foreign gene can have additions, deletions or substitutions to enhance expression and/or immunological effects of the expressed protein.

The invention also includes an expression system comprising an bovine adenovirus expression vector wherein heterologous nucleotide sequences with or without any exogenous regulatory elements, replace the E1 gene region and/or part or all of the E3 gene region.

The invention also includes (A) a recombinant vector system comprising the entire BAV DNA and a plasmid or two plasmids capable of generating a recombinant virus by in vivo recombination following cotransfection of a suitable cell line comprising BAV DNA representing the entire wild-type BAV genome and a plasmid comprising a bovine adenovirus left or right end sequences containing the E1 or E3 gene regions, respectively, with a heterologous nucleotide sequence encoding a foreign gene or fragment thereof substituted for part or all of the E1 or E3 gene regions; (B) a live recombinant bovine adenovirus vector (BAV) system selected from the group consisting of: (a) a system wherein part or all of the E1 gene region is replaced by a heterologous nucleotide sequence encoding a foreign gene or fragment thereof; (b) a system wherein a part or all of the E3 gene region is replaced by a heterologous nucleotide sequence encoding a foreign gene or fragment thereof; and (c) a system wherein part or all of the E1 gene region and part or all of the E3 gene region are deleted and a heterologous nucleotide sequence encoding a foreign gene or fragment thereof is inserted into at least one of the deletions; (C) a recombinant bovine adenovirus (BAV) comprising a deletion of part or all of E1 gene region, a deletion of part or all of E3 gene region or deletion of both, and inserted into at least one deletion a heterologous nucleotide sequence coding for an antigenic determinant of a disease causing organism; (D) a recombinant bovine adenovirus expression system comprising a deletion of part or all of E1, a deletion of part or all of E3, or both deletions, and inserted into at least one deletion a heterologous nucleotide sequence coding for a foreign gene or fragment thereof under control of an expression promoter: or (E) a recombinant bovine adenovirus (BAV) for producing an immune response in a mammalian host comprising: (1) BAV recombinant containing a heterologous nucleotide sequence coding for an antigenic determinant needed to obtain the desired immune response in association with or without (2) an effective promoter to provide expression of said antigenic determinant in immunogenic quantities for use as a live recombinant virus or recombinant protein or subunit vaccine; (F) a mutant bovine adenovirus (BAV) comprising a deletion of part or all of E1 and/or a deletion of part or all of E3.

Recombinant mammalian cell lines stably transformed with BAV E1 gene region sequences, said recombinant cell lines thereby capable of allowing replication therein of a bovine adenovirus comprising a deletion of part or all of the E1 or E3 gene regions replaced by a heterologous or homologous nucleotide sequence encoding a foreign gene or fragment thereof. The invention also includes production, isolation and purification of polypeptides or fragments thereof, such as growth factors, receptors and other cellular proteins from recombinant bovine cell lines expressing BAV E1 gene products.

The invention also includes a method for providing gene therapy to a mammal in need thereof to control a gene deficiency which comprises administering to said mammal a live recombinant bovine adenovirus containing a foreign nucleotide sequence encoding a non-defective form of said gene under conditions wherein the recombinant virus vector genome is incorporated into said mammalian genome or is maintained independently and extrachromosomally to provide expression of the required gene in a target organ or tissue.

Another aspect of the invention provides a virus vaccine composition which comprises the recombinant virus or recombinant protein in association with or without a pharmaceutically acceptable carrier. The recombinant virus vaccine can be formulated for administration by an oral dosage (e.g. as an enteric coated tablet), by injection or otherwise. More specifically, these include a vaccine for protecting a mammalian host against infection comprising a live recombinant adenovirus or recombinant protein produced by the recombinant adenovirus of the invention wherein the foreign gene or fragment encodes an antigen and formulated with or without a pharmaceutically acceptable carrier.

The invention also includes methods of producing antibodies or cell mediated immunity in a mammal including (1) a method for eliciting an immune response in a mammalian host against an infection comprising: administering a vaccine comprising a live BAV recombinant of the invention wherein the foreign gene or fragment encodes an antigen with or without a pharmaceutically acceptable carrier, and (2) a method for eliciting an immune response in a mammalian host against an infection comprising: administering a vaccine comprising a recombinant antigen prepared by culturing a BAV recombinant wherein the foreign gene or fragment encodes the desired antigen with or without a pharmaceutically acceptable carrier.

The following disclosure will render these and other embodiments of the present invention readily apparent to those of skill in the art. While the disclosure often refers to bovine adenovirus type 3 (BAV3), it should be understood that this is for the purpose of illustration and that the same features apply to bovine adenovirus of the other type, 1, 2, 4, 5, 6, 7 8, and 9 and the invention described and claimed herein is intended to cover all of these bovine adenovirus types.

BRIEF DESCRIPTION OF THE DRAWINGS

FIGS. 1A–1L. (SEQ ID NO: 1 through SEQ ID NO:87) Sequence and major open reading frames of the left 11% of the BAV3 genome. The region comprises the E1 and protein IX transcription region. The 195 nucleotide inverted terminal repeat sequence identified by Shinagawa et al., 1987 *Gene* 55:85–93 is shown in italics. The amino acid sequence for the largest E1A protein, two E1B proteins and protein IX are presented. The probable splice donor ([), splice acceptor (]) and intron sequence (underlined italics) within the E1A region are marked. A 35 base pair repeat sequence between E1A and E1B is indicated in bold underline. Possible transcription promoter TATA sequences and possible poly A addition sequences AATAA are also indicated.

FIGS. 2A–2B. Regions of homology in the E1A proteins of BAV3 and human adenovirus type 5 (HAd5). The amino acid residue of each serotype is indicated. A. Conserved region 3 (CR3) of HAd5 (SEQ ID NO:9) subdivided into three functional regions as defined by Lillie et al (1989) *Nature* 338:39–44 and described in the Background of the Invention. The intron sequence of BAV3 E1A (SEQ ID NO:33) occurs within the serine amino acid codon at position 204. B. A portion of conserved region 2 (CR2) of HAd5(SEQ ID NO:10), showing the residues thought to be important in the binding of retinoblastoma protein Rb (Dyson et al., 1990 *J. Virol.* 64:1353–1356), and the comparable sequence from BAV3(SEQ ID NO:34).

FIGS. 3A–3B. Homology regions between the HAd5 (SEQ ID NO:11 and SEQ ID NO:12) and E1B 19k (176R) protein and the corresponding BAV3 positions 83–99 of SEQ ID NO:4 and positions 136–142 of SEQ ID NO:4) (157R) protein. The amino acid residue number for each of the viruses is indicated.

FIGS. 4A–4C. The C-terminal 346R of HAd5 (SEQ ID NO:13) E1B 56k (496R) and the corresponding BAV3 (position 74–420 of SEQ ID NO:6) protein (420R). The HAd5 protein comparison begins at residue 150 and the BAV3 (in italics) at residue 74. The amino terminal regions of these proteins which are not presented show no significant homology.

FIG. 5. Homology comparison of the amino acid sequence of HAd5 (SEQ ID NO:14) protein IX and the corresponding protein of BAV3 (potition 1–125 of SEQ ID NO:8) (in italics).

FIGS. 7A–7R. Nucleotide sequence of BAV3 between 77 and 92 m.u. showing ORFs (SEQ ID NO:15 through SEQ ID NO:26) that have the potential to encode polypeptides of at least 50 amino acids after the initiating methionine. The nucleotide sequence was analyzed using the program DIS-PCOD (PC/GENE). Potential N-glycosylation sites (N-X-T/S) and polyadenylation signals are underlined and the first methionine of each ORF is shown in bold.

FIGS. 8(a), 8(b), 8(c)-1, and 8(c)-2, and 8(c)-3. Comparison between the predicted amino acid sequences for the ORFs of BAV3 and known proteins of HAd2 or −5 using the computer program PALIGN (PC/GENE), with comparison matrix structural-genetic matrix; open gap cost 6; unit gap cost 2. Identical residues are indicated by a colon and similar residues by a dot. (a) Comparison between the predicted amino acid sequence encoded by the 3' end of BAV3 ORF 1 end of BAV3 ORF 1 (positions 1–139 of SEQ ID NO:16) and the HAd2 (SEQ ID NO:27) hexon-associated pVIII precursor. (b) Comparison between the ORF 4 (positions 34–154 of SEQ ID NO:22) and the HAd5 14.7K E3 protein. (c) Comparison between the predicted amino acid sequence encoded by BAV3 ORF 6 (potitions 8–983 of SEQ ID NO:26) and the HAd2 (potitions 1–582 of SEQ ID NO:29) fibre protein.

Figure 6:
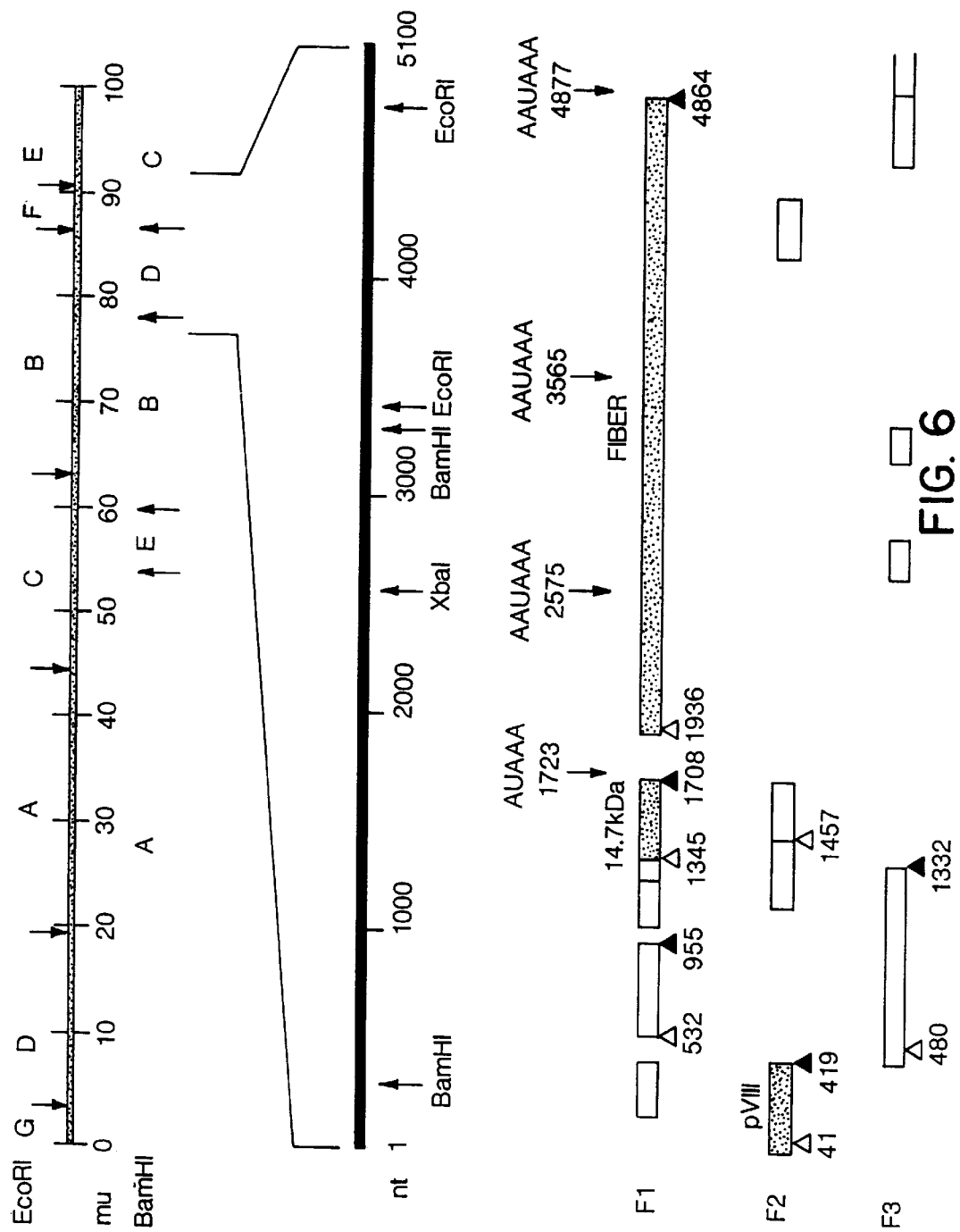
FIG. 6. The genome of BAV3 showing the location of EcoRI, XbaI and BAMHI sites and the structure of the 5100 bp segment from 77 to 92 m.u. ORFs for the upper strand which can encode 60 amino acids or more are represented by bars. Shaded portions indicate regions of similarity to pVIII, 14.7K E3 and fibre proteins of HAd2 or –5. The first methionine followed by a stretch of amino acids of at least 50 is shown by an open triangle. Termination codons for ORFs likely to code for viral proteins are shown by closed triangles.

The plasmid, pSM71 which contains the BAV3 genome between m.u. 0 and 24, was cleaved with ClaI and partially with AvrII to delete a 2.6 kb AvrII-ClaI fragment (between m.u. 1.3 and 8.7) which falls within the E1 region. A 0.5 kb fragment containing the SV40 promoter and polyadenylation sequences was obtained from pFG144K5-SV by digesting with XbaI and inserted into pSM71 to replace the 2.6 kb deletion to generate pSM71-dell-SV. A 3.26 kb fragment containing the bacterial beta-galactosidase gene was isolated from pDUC/Z (Liang et al (1993) *Virology* 195:42–50) after cleavage with NcoI and HindIII and cloned into pSM71-dell-SV at the BamHI site to put the beta-galactosidase gene under the control of the SV40 regulatory sequences to obtain pSM71-Z.

MODES OF CARRYING OUT THE INVENTION

The practice of the present invention will employ, unless otherwise indicated, conventional microbiology, immunology, virology, molecular biology, and recombinant DNA techniques which are within the skill of the art. These techniques are fully explained in the literature. See, e.g., Maniatis et al., *Molecular Cloning: A Laboratory Manual* (1982); *DNA Cloning: A Practical Approach*, vols. I & II (D. Glover, ed.); *Oligonucleotide Synthesis* (N. Gait, ed. (1984)); *Nucleic Acid Hybridization* (B. Hames & S. Higgins, eds. (1985)); *Transcription and Translation* (B. Hames & S. Higgins, eds. (1984)); *Animal Cell Culture* (R. Freshney, ed. (1986)); Perbal, *A Practical Guide to Molecular Cloning* (1984). Sambrook et al., *Molecular Cloning: A Laboratory Manual* (2nd Edition); vols. I, II & III (1989).

A. Definitions

In describing the present invention, the following terminology, as defined below, will be used.

A "replicon" is any genetic element (e.g., plasmid, chromosome, virus) that functions as an autonomous unit of DNA replication in vivo; i.e., is capable of replication under its own control.

A "vector" is a replicon, such as a plasmid, phage, cosmid or virus, to which another DNA segment may be attached so as to bring about the replication of the attached segment.

By "live virus" is meant, in contradistinction to "killed" virus, a virus which is capable of producing identical progeny in tissue culture and inoculated animals.

A "helper-free virus vector" is a vector that does not require a second virus or a cell line to supply something defective in the vector.

A "double-stranded DNA molecule" refers to the polymeric form of deoxyribonucleotides (adenine, guanine, thymine, or cytosine) in its normal, double-stranded helix. This term refers only to the primary and secondary structure of the molecule, and does not limit it to any particular tertiary forms. Thus, this term includes double-stranded DNA found, inter alia, in linear DNA molecules (e.g., restriction fragments of DNA from viruses, plasmids, and chromosomes). In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, viral DNA, and even synthetic DNA sequences. A polyadenylation signal and transcription termination sequence will usually be located 3' to the coding sequence.

A "transcriptional promoter sequence" is a DNA regulatory region capable of binding RNA polymerase in a cell and initiating transcription of a downstream (3' direction) coding sequence. For purposes of defining the present invention, the promoter sequence is bound at the 3' terminus by the translation start codon (ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eucaryotic promoters will often, but not always, contain "TATA" boxes and "CAAT" boxes. Procaryotic promoters contain Shine-Dalgarno sequences in addition to the −10 and −35 consensus sequences.

DNA "control sequences" refer collectively to promoter sequences, ribosome binding sites, polyadenylation signals, transcription termination sequences, upstream regulatory domains, enhancers, and the like, which collectively provide for the transcription and translation of a coding sequence in a host cell.

A coding sequence or sequence encoding is "operably linked to" or "under the control of" control sequences in a cell when RNA polymerase will bind the promoter sequence and transcribe the coding sequence into mRNA, which is then translated into the polypeptide encoded by the coding sequence.

A "host cell" is a cell which has been transformed, or is capable of transformation, by an exogenous DNA sequence.

A cell has been "transformed" by exogenous DNA when such exogenous DNA has been introduced inside the cell membrane. Exogenous DNA may or may not be integrated (covalently linked) to chromosomal DNA making up the genome of the cell. In procaryotes and yeasts, for example, the exogenous DNA may be maintained on an episomal element, such as a plasmid. A stably transformed cell is one in which the exogenous DNA has become integrated into the chromosome so that it is inherited by daughter cells through chromosome replication. For mammalian cells, this stability is demonstrated by the ability of the cell to establish cell lines or clones comprised of a population of daughter cell containing the exogenous DNA.

A "clone" is a population of daughter cells derived from a single cell or common ancestor. A "cell line" is a clone of a primary cell that is capable of stable growth in vitro for many generations.

Two polypeptide sequences are "substantially homologous" when at least about 80% (preferably at least about 90%, and most preferably at least about 95%) of the amino acids match over a defined length of the molecule.

Two DNA sequences are "substantially homologous" when they are identical to or not differing in more that 40% of the nucleotides, more preferably about 20% of the nucleotides, and most preferably about 10% of the nucleotides.

DNA sequences that are substantially homologous can be identified in a Southern hybridization experiment under, for example, stringent conditions, as defined for that particular system. Defining appropriate hybridization conditions is within the skill of the art. See, e.g., Maniatis et al., supra; *DNA Cloning*, vols. I & II, supra; *Nucleic Acid Hybridization*, supra.

A "heterologous" region of a DNA construct is an identifiable segment of DNA within or attached to another DNA molecule that is not found in association with the other molecule in nature. Thus, when the heterologous region encodes a viral gene, the gene will usually be flanked by DNA that does not flank the viral gene in the genome of the source virus or virus-infected cells. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

"Bovine host" refers to cattle of any breed, adult or infant.

The term "protein" is used herein to designate a polypeptide or glycosylated polypeptide, respectively, unless otherwise noted. The term "polypeptide" is used in its broadest sense, i.e., any polymer of amino acids (dipeptide or greater) linked through peptide bonds. Thus, the term "polypeptide" includes proteins, oligopeptides, protein fragments, analogs, muteins, fusion proteins and the like.

"Fusion protein" is usually defined as the expression product of a gene comprising a first region encoding a leader sequence or a stabilizing polypeptide, and a second region encoding a heterologous protein. It involves a polypeptide comprising an antigenic protein fragment or a full length BAV protein sequence as well as (a) heterologous sequence (s), typically a leader sequence functional for secretion in a recombinant host for intracellularly expressed polypeptide, or an N-terminal sequence that protects the protein from host cell proteases, such as SOD. An antigenic protein fragment is usually about 5–7 amino acids in length.

"Native" proteins or polypeptides refer to proteins or polypeptides recovered from BAV or BAV-infected cells. Thus, the term "native BAV polypeptide" would include naturally occurring BAV proteins and fragments thereof. "Non-native" polypeptides refer to polypeptides that have been produced by recombinant DNA methods or by direct synthesis. "Recombinant" polypeptides refers to polypeptides produced by recombinant DNA techniques; i.e., produced from cells transformed by an exogenous DNA construct encoding the desired polypeptide.

A "substantially pure" protein will be free of other proteins, preferably at least 10% homogeneous, more preferably 60% homogeneous, and most preferably 95% homogeneous.

An "antigen" refers to a molecule containing one or more epitopes that will stimulate a host's immune system to make a humoral and/or cellular antigen-specific response. The term is also used interchangeably with "immunogen."

A "hapten" is a molecule containing one or more epitopes that does not stimulate a host's immune system to make a humoral or cellular response unless linked to a carrier.

The term "epitope" refers to the site on an antigen or hapten to which a specific antibody molecule binds or is recognized by T cells. The term is also used interchangeably with "antigenic determinant" or "antigenic determinant site."

An "immunological response" to a composition or vaccine is the development in the host of a cellular and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

The terms "immunogenic polypeptide" and "immunogenic amino acid sequence" refer to a polypeptide or amino acid sequence, respectively, which elicit antibodies that neutralize viral infectivity, and/or mediate antibody-complement or antibody dependent cell cytotoxicity to provide protection of an immunized host. An "immunogenic polypeptide" as used herein, includes the full length (or near full length) sequence of the desired protein or an immunogenic fragment thereof.

By "immunogenic fragment" is meant a fragment of a polypeptide which includes one or more epitopes and thus elicits antibodies that neutralize viral infectivity, and/or mediates antibody-complement or antibody dependent cell cytotoxicity to provide protection of an immunized host. Such fragments will usually be at least about 5 amino acids in length, and preferably at least about 10 to 15 amino acids in length. There is no critical upper limit to the length of the fragment, which could comprise nearly the full length of the protein sequence, or even a fusion protein comprising fragments of two or more of the antigens. The term "treatment" as used herein refers to treatment of a mammal, such as bovine or the like, either (i) the prevention of infection or reinfection (prophylaxis), or (ii) the reduction or elimination of symptoms of an infection. The vaccine comprises the recombinant BAV itself or recombinant antigen produced by recombinant BAV.

By "infectious" is meant having the capacity to deliver the viral genome into cells.

B. General Method

The present invention identifies and provides a means of deleting part or all of the nucleotide sequence of bovine adenovirus E1 and/or E3 gene regions to provide sites into which heterologous or homologous nucleotide sequences encoding foreign genes or fragments thereof can be inserted to generate bovine adenovirus recombinants. By "deleting part of" the nucleotide sequence is meant using conventional genetic engineering techniques for deleting the nucleotide sequence of part of the E1 and/or E3 region.

Various foreign genes or coding sequences (prokaryotic, and eukaryotic) can be inserted in the bovine adenovirus nucleotide sequence, e.g., DNA, in accordance with the present invention, particularly to provide protection against a wide range of diseases and many such genes are already known in the art. The problem heretofore having been to provide a safe, convenient and effective vaccine vector for the genes or coding sequences.

It is also possible that only fragments of nucleotide sequences of genes can be used (where these are sufficient to generate a protective immune response) rather than the complete sequence as found in the wild-type organism. Where available, synthetic genes or fragments thereof can also be used. However, the present invention can be used with a wide variety of genes, fragment and the like, and is not limited to those set out above.

In some cases the gene for a particular antigen can contain a large number of introns or can be from an RNA virus, in these cases a complementary DNA copy (cDNA) can be used.

In order for successful expression of the gene to occur, it can be inserted into an expression vector together with a suitable promoter including enhancer elements and polyadenylation sequences. A number of eucaryotic promoter and polyadenylation sequences which provide successful expression of foreign genes in mammalian cells and how to construct expression cassettes, are known in the art, for example in U.S. Pat. No. 5,151,267, the disclosures of which are incorporated herein by reference. The promoter is selected to give optimal expression of immunogenic protein which in turn satisfactorily leads to humoral, cell mediated and mucosal immune responses according to known criteria.

The foreign protein produced by expression in vivo in a recombinant virus-infected cell may be itself immunogenic. More than one foreign gene can be inserted into the viral genome to obtain successful production of more than one effective protein.

Thus with the recombinant virus of the present invention, it is possible to provide protection against a wide variety of diseases affecting cattle. Any of the recombinant antigenic determinant or recombinant live virus of the invention can be formulated and used in substantially the same manner as described for the antigenic determinant vaccines or an live vaccine vectors.

The antigens used in the present invention can be either native or recombinant antigenic polypeptides or fragments. They can be partial sequences, full-length sequences, or even fusions (e.g., having appropriate leader sequences for the recombinant host, or with an additional antigen sequence for another pathogen). The preferred antigenic polypeptide to be expressed by the virus systems of the present invention contain full-length (or near full-length) sequences encoding antigens. Alternatively, shorter sequences that are antigenic (i.e., encode one or more epitopes) can be used. The shorter sequence can encode a "neutralizing epitope," which is defined as an epitope capable of eliciting antibodies that neutralize virus infectivity in an in vitro assay. Preferably the peptide should encode a "protective epitope" that is capable of raising in the host an "protective immune response;" i.e., an antibody- and/or a cell-mediated immune response that protects an immunized host from infection.

The antigens used in the present invention, particularly when comprised of short oligopeptides, can be conjugated to a vaccine carrier. Vaccine carriers are well known in the art: for example, bovine serum albumin (BSA), human serum albumin (HSA) and keyhole limpet hemocyanin (KLH). A preferred carrier protein, rotavirus VP6, is disclosed in EPO Pub. No. 0259149, the disclosure of which is incorporated by reference herein.

Genes for desired antigens or coding sequences thereof which can be inserted include those of organisms which cause disease in mammals, particularly bovine pathogens such as bovine rotavirus, bovine coronavirus, bovine herpes virus type 1, bovine respiratory syncytial virus, bovine para influenza virus type 3 (BPI-3), bovine diarrhea virus, *Pasteurella haemolytica, Haemophilus somnus* and the like. The vaccines of the invention carrying foreign genes or fragments can also be orally administered in a suitable oral carrier, such as in an enteric-coated dosage form. Oral formulations include such normally-employed excipients as, for example, pharmaceutical grades of mannitol, lactose, starch, magnesium stearate, sodium saccharin cellulose, magnesium carbonate, and the like. Oral vaccine compositions may be taken in the form of solutions, suspensions, tablets, pills, capsules, sustained release formulations, or powders, containing from about 10% to about 95% of the active ingredient, preferably about 25% to about 70%. An oral vaccine may be preferable to raise mucosal immunity in combination with systemic immunity, which plays an important role in protection against pathogens infecting the gastrointestinal tract.

In addition, the vaccine be formulated into a suppository. For suppositories, the vaccine composition will include traditional binders and carriers, such as polyalkaline glycols or triglycerides. Such suppositories may be formed from mixtures containing the active ingredient in the range of about 0.5% to about 10% (w/w), preferably about 1% to about 2%.

Protocols for administering to animals the vaccine composition(s) of the present invention are within the skill of the art in view of the present disclosure. Those skilled in the art will select a concentration of the vaccine composition in a dose effective to elicit an antibody and/or T-cell mediated immune response to the antigenic fragment. Within wide limits, the dosage is not believed to be critical. Typically, the vaccine composition is administered in a manner which will deliver between about 1 to about 1,000 micrograms of the subunit antigen in a convenient volume of vehicle, e.g., about 1–10 cc. Preferably, the dosage in a single immunization will deliver from about 1 to about 500 micrograms of subunit antigen, more preferably about 5–10 to about 100–200 micrograms (e.g., 5–200 micrograms).

The timing of administration may also be important. For example, a primary inoculation preferably may be followed by subsequent booster inoculations if needed. It may also be preferred, although optional, to administer a second, booster immunization to the animal several weeks to several months after the initial immunization. To insure sustained high levels of protection against disease, it may be helpful to readminister a booster immunization to the animals at regular intervals, for example once every several years. Alternatively, an initial dose may be administered orally followed by later inoculations, or vice versa. Preferred vaccination protocols can be established through routine vaccination protocol experiments.

The dosage for all routes of administration of in vivo recombinant virus vaccine depends on various factors including, the size of patient, nature of infection against which protection is needed, carrier and the like and can readily be determined by those of skill in the art. By way of non-limiting example, a dosage of between $10^3$ pfu and $10^8$ pfu and the like can be used. As with in vitro subunit vaccines, additional dosages can be given as determined by the clinical factors involved.

In one embodiment of the invention, a number of recombinant cell lines are produced according to the present invention by constructing an expression cassette comprising the BAV E1 region and transforming host cells therewith to provide cell lines or cultures expressing the E1 proteins. These recombinant cell lines are capable of allowing a recombinant BAV, having an E1 gene region deletion replaced by heterologous nucleotide sequence encoding for a foreign gene or fragment, to replicate and express the desired foreign gene or fragment thereof which is encoded within the recombinant BAV. These cell lines are also extremely useful in generating recombinant BAV, having an E3 gene deletion replaced by heterologous nucleotide sequence encoding for a foreign gene or fragment, by in vivo recombination following DNA-mediated cotransfection.

In one embodiment of the invention, the recombinant expression cassette can be obtained by cleaving the wild-type BAV genome with an appropriate restriction enzyme to produce a DNA fragment representing the left end or the right end of the genome comprising E1 or E3 gene region sequences, respectively and inserting the left or right end fragment into a cloning vehicle, such as plasmid and thereafter inserting at least one DNA sequence encoding a foreign protein, into E1 or E3 deletion with or without the control of an exogenous promoter. The recombinant expression cassette is contacted with the wild-type BAV DNA through homologous recombination or other conventional genetic engineering method within an E1 transformed cell line to obtain the desired recombinant.

The invention also includes an expression system comprising an bovine adenovirus expression vector wherein a heterologous nucleotide, e.g. DNA, replaces part or all of the E3 region and/or part or all of the E1 region. The expression system can be used wherein the foreign nucleotide sequences, e.g. DNA, is with or without the control of any other heterologous promoter.

The BAV E1 gene products of the adenovirus of the invention transactivate most of the cellular genes, and therefore, cell lines which constitutively express E1 proteins can express cellular polypeptides at a higher level than normal cell lines. The recombinant mammalian, particularly bovine, cell lines of the invention can be used to prepare and isolate polypeptides, including those such as (a) proteins associated with adenovirus E1A proteins: e.g. p300, retinoblastoma(Rb) protein, cyclins, kinases and the like.; (b) proteins associated with adenovirus E1B protein: e.g. p53 and the like.; (c) growth factors, such as epidermal growth factor (EGF), transforming growth factor (TGF) and the like; (d) receptors such as epidermal growth factor receptor (EGF-R), fibroblast growth factor receptor (FGF-R), tumor necrosis factor receptor (TNF-R), insulin-like growth factor receptor (IFG-R), major histocompatibility complex class I receptor and the like; (e) proteins encoded by proto-oncogenes such as protein kinases (tyrosine-specific protein kinases and protein kinases specific for serine or threonine), p21 proteins (guanine nucleotide-binding proteins with GTPase activity and the like; (f) other cellular proteins such as actins, collagens, fibronectins, integrins, phospholipids, proteoglycans, histones and the like, and (g) proteins involved in regulation of transcription such as TATA-box-binding protein (TBP), TBP-associated factors (TAFs). SP1 binding protein and the like.

The invention also includes a method for providing gene therapy to a mammal in need thereof to control a gene deficiency which comprises administering to said mammal a live recombinant bovine adenovirus containing a foreign nucleotide sequence encoding a non-defective form of said gene under conditions wherein the recombinant virus vector genome is incorporated into said mammalian genome or is maintained independently and extrachromosomally to provide expression of the required gene in the target organ or tissue. These kinds of techniques are recently being used by those of skill in the art to replace a defective gene or portion thereof. Examples of foreign genes nucleotide sequences or portions thereof that can be incorporated for use in a conventional gene therapy include, cystic fibrosis transmembrane conductance regulator gene, human minidystrophin gene, alphal-antitrypsin gene and the like.

EXAMPLES

Described below are examples of the present invention. These examples are provided only for illustrative purposes and are not intended to limit the scope of the present invention in any way. In light of the present disclosure, numerous embodiments within the scope of the claims will be apparent to those of ordinary skill in the art. The contents of the references cited in the specification are incorporated by reference herein.

Cells and viruses

Cell culture media and reagents were obtained from GIBCO/BRL Canada (Burlington, Ontario, Canada). Media were supplemented with 25 mM Hepes and 50 Ag/ml gentamicin. MDBK cells or MDBK cells transformed with a plasmid containing BAV3 E1 sequences were grown in MEM supplemented with 10% Fetal bovine serum. The wild-type BAV3 ((strain WBR-1) (Darbyshire et al, 1965 *J. Comparative Pathology* 75:327) was kindly provided by Dr. B. Darbyshire, University of Guelph, Guelph, Canada) and BAV3-luciferase recombinants working stocks and virus titrations were done in MDBK cells.

Enzymes, bacteria and plasmid

Restriction endonucleases, polymerase chain reaction (PAR) and other enzymes required for DNA manipulations were purchased from Pharmacies LKB Biotechnology (Canada) Ltd. (Dorval, Quebec, Canada), Boehringer-Mannheim, Inc. (Laval or Montreal, Quebec, Canada), New England BioLabs (Beverly, Mass.), or GIBCO/BRL Canada (Burlington, Ontario, Canada) and used as per manufacturer's instructions. Restriction enzyme fragments of BAV3 DNA were inserted into pUC18 or pUC19 (Yanich-Penon et al (1985) *Gene* 33:103–109) following standard procedures (Sambrook et al (1989) Molecular Cloning: A Laboratory Manual, 2nd ed. Cold Spring Harbour Laboratory, New York). *E. coli* strain DH5 (supE44 hsdR17 recA1 endA1 gyrA96 thi-1 relA1) was transformed with recombinant plasmids by electroporation (Dower et al. (1988) *Nuc. Acids Res.*, 16:6127–6145). Plasmid DNA was prepared using the alkaline lysis procedure (Bernboim and Doly (1978) *Nuc. Acids Res.*, 7:1513–1523). The plasmid, pSVOA/L containing the entire cDNA encoding firefly luciferase (de Wet et al (1987) *Mol. Cell. Biol.* 7:725–737), was a gift from D. R. Helinski, University of California, San Diego, La Jolla, Calif.

Construction of recombinant BAV3

MDBK cells transformed with a plasmid containing BAV3 E1 sequences were cotransfected with the wt BAV3 DNA digested with PvuI and the plasmid, pSM51-Luc (FIGS. 9 and 10) using the lipofection-mediated cotransfection protocol (GIBCO/BRL, Life Technologies, Inc., Grand Island, N.Y.). The virus plaques produced following cotransfection were isolated, plaque purified and the presence of the luciferase gene in the BAV3 genome was detected by agarose gel electrophoresis of recombinant virus DNA digested with appropriate restriction enzymes.

Southern blot and hybridization

Mock or virus-infected MDBK cells were harvested in lysis buffer (500 gg/ml pronase in 0.01M Tris, pH 7.4, 0.01M EDTA, 0.5% SDS) and DNA was extracted (Graham et al (1991) Manipulation of adenovirus vectors In: Methods and Molecular Biology, 7:Gene Transfer and Expression Techniques (Eds. Murray and Walker) Humana Press, Clifton, N.J. pp. 109–128). 100 ng DNA was digested either with BamHI, EcoRI or XbaI and resolved on a 1% agarose gel by electrophoresis. DNA bands from the agarose gel were transferred to a GeneScreenPlus™ membrane (Du Pont Canada Inc. (NEN Products), Lachine, Quebec, Canada) by the capillary blot procedure (Southern, E.M. (1975) *J. Mol. Biol.* 98:503–517). Probes were labeled with $^{32}$p using an Oligolabeling Kit (Pharmacia LKB Biotechnology (Canada) Ltd., Dorval, Quebec, Canada) and the unincorporated label was removed by passing the labeled probe through a sephadex G-50 column (Sambrook et al (1989) supra). Probes were kept in a boiling water bath for 2 min and used in hybridization experiments following GeneScreenPlus™ hybridization protocol. The DNA bands which hybridized with the probe were visualized by autoradiography.

Luciferase assays

The protocol was essentially the same as described (Mittal et al (1993) *Virus Res.* 28:67–90). Briefly, MDBK cell monolayers in 25 mm multi-well dishes (Corning Glass Works, Corning, N.Y.) were infected in duplicate either with BAV3-Luc (3.1) or BAV3-Luc (3.2) at a m.o.i. of 50 p.f.u. per cell. At indicated time points post-infection, recombinant virus-infected cell monolayers were washed once with PBS (0.137M NaCl, 2.7 mM KCl, 8 mM $Na_2HPO_4$, 1.5 mM $KH_2PO_4$) and harvested in 1 ml luciferase extraction buffer (100 mM potassium phosphate, pH 7.8, 1 mM dithiothreitol). The cell pellets were resuspended in 200 μl of luciferase extraction buffer and lysed by three cycles of freezing and thawing. The supernatants were assayed for luciferase activity. For the luciferase assay, 20 μl of undiluted or serially diluted cell extract was mixed with 350 μl of luciferase assay buffer (25 mM glycylglycine, pH 7.8, 15 mM $MgCl_2$, 5 mM ATP) in a 3.5 ml tube (Sarstedt Inc., St-Laurent, Quebec, Canada). Up to 48 tubes can be kept in the luminometer rack and the equipment was programed to inject 100 μl of luciferin solution (1 mM luciferin in 100 mM potassium phosphate buffer, pH 7.8) in the tube present in the luminometer chamber to start the enzyme reaction. The Luminometer (Packard Picolite Luminometer, Packard Instrument Canada, Ltd., Mississauga, Ontario, Canada) used in the present study produced 300 to 450 light units of background count in a 10 sec reaction time. Known amounts of the purified firefly luciferase were used in luciferase assays to calculate the amount of active luciferase present in each sample.

Western blotting

Mock or virus-infected MDBK cells were lysed in 1:2 diluted 2× loading buffer (80 mM Tris-HCl, pH 6.8, 0.67M urea, 25% glycerol, 2.5% SDS, 1M mercaptoethanol, 0.001% bromophenol blue), boiled for 3 min and then centrifuged to pellet cell debris. Proteins were separated by SDS-polyacrylamide gel electrophoresis (SDSPAGE) on 0.1% SDS-10% polyacrylamide gels (Laemmli, et al (1970) *Nature* 227:680–685). After the end of the run, polypeptide bands in the gel were electrophoretically transferred to a nitrocellulose membrane (Bio-Rad Laboratories, Richmond, Calif.). The membrane was incubated at room temperature for 2 h with 1:4000 diluted rabbit anti-luciferase antibody (Mittal et al (1993) supra). The binding of anti-luciferase antibody to the specific protein band/s on the membrane was detected with 1:5000 diluted horseradish peroxidase conjugated-goat antirabbit IgG (Bio-Rad Laboratories, Richmond, Calif.) and with an ECL Western blotting detection system (Amersham Canada Ltd., Oakville, Ontario).

Example 1

Cloning of BAV3 E1 Region DNA for sequencing

To complement the restriction site (Kurokawa et al, 1978 *J. Virol.*, 28:212–218; Hu et al, 1984 *J. Virol.* 49:604–608) other restriction enzyme sites in the BAV3 genome were defined. The 8.4 kilobase pair (kb) SalI B fragment which extends from the left end of the genome to approximately 24% was cloned into the SmaI-SalI sites of pUC18 essentially as described previously (Graham et al, 1989 *EMBO Journal* 8:2077–2085). Beginning at the left end of the BAV3 genome, the relevant restriction sites used for subsequent subcloning and their approximate positions are: SacI (2%), EcoRI (3.5%), HindIII (5%), SacI (5.5%), SmaI (5.6%) and HindIII (11%). Through the use of appropriate restriction enzymes, the original plasmid was collapsed to contain smaller inserts which could be sequenced using the pUC universal primers. Some fragments were also subcloned in both pUC18 and pUC19 to allow confirmational sequencing in both directions. These procedures, together with the use of twelve different oligonucleotide primers hybridizing with BAV3 sequences, allowed to sequence the BAV3 genome from its left end to the HindIII site at 11%.

To ensure that some features of the sequence obtained were not unique to the initial clone selected for sequencing, two more pUC19 clones were prepared containing the SalI fragment from a completely independent DNA preparation. These clones were used to confirm the original sequence for the region from approximately 3% to 5.5% of the BAV3 genome.

DNA sequencing reactions were based on the chain-termination method (Sanger et al. 1977 *PNAS, USA* 74:5463–5467) and manual sequencing followed the DNA sequencing protocol described in the Sequenase™ kit produced by US Biochemical. [α-$^{35}$S] dATPs was obtained from Amersham Canada Ltd. All oligonucleotides used as primers were synthesized by the Central Facility of the Molecular Biology and Biotechnology Institute (MOBIX) at McMaster University, Hamilton, Ontario. The entire region (0 to 11%) of the BAV3 genome was sequenced by at least two independent determinations for each position by automated sequencing on a 373A DNA Sequencer (Applied Biosystems) using Taq-Dye terminators. Over half of the region was further sequenced by manual procedures to confirm overlaps and other regions of interest.

DNA sequence analysis and protein comparisons were carried out on a MICROGENIE program.

Example 2

Coding Sequences of the BAV3 E1 Region

BAV3 genomic DNA, from the left end of the genome to the HindIII site at approximately 11%, was cloned into plasmids and sequenced by a combination of manual and automated sequencing. An examination of the resultant BAV3 E1 genomic sequence (FIG. 1) revealed a number of interesting features relevant both to trans activation and to other functions associated with adenovirus E1 proteins. On the basis of open reading frames (ORFS) it was possible to assign potential coding regions analogous to those defined in human Ad5 (HAd5). As shown in FIG. 1, ORFs corresponding roughly to the first exon and unique region of HAd5 E1A as well are ORFs corresponding to the 19k and 58K proteins of E1B and the ORF corresponding to protein IX were all defined in this sequence. The open reading frame defining the probable E1A coding region begins at the ATG at nt 606 and continues to a probable splice donor site at position 1215. The first consensus splice acceptor site after this is located after nt 1322 and defines an intron of 107 base pairs with an internal consensus splice branching site at position 1292. The putative BAV3 E1A polypeptide encoded by a message corresponding to these splice sites would have 211 amino acids and a unmodified molecular weight of 23,323. The major homology of the protein encoded by this ORF and HAd5 E1A is in the residues corresponding to CR3 (shown in FIG. 2). The homology of amino acid sequences on both sides of the putative intron strengthens the assignment of probable splice donor and acceptor sites. The CR3 has been shown to be of prime importance in the transactivation activity of HAd5 E1A gene products. As seen in FIG. 2A the homology of this sequence in the BAV3 protein to the corresponding region of the 289R E1A protein of HAd5 includes complete conservation of the CysX$_2$CysX$_{13}$CysX$_2$Cys (SEQ ID NO:30) sequence motif which defines the metal binding site of this protein (Berg, 1986 *Science* 232:485–487) as well as conservation of a number of amino acids within this region and within the promoter binding region as defined by Lillie and Green 1989 *Nature* 338:39–44).

The only other region of significant homology between the BAV3 E1A protein and that of HAd5 was a stretch of amino acids known to be important in binding of the cellular Rb protein to the HAd5 E1A protein (Dyson et al, 1990 *J. Virol.* 64:1353–1356). As shown in FIG. 2B, this sequence, which is located between amino acids 120 and 132 in the CR2 region of HAd5 E1A, is found near the amino (N-) terminus of the BAV3 protein between amino acids 26 and 37.

An open reading frame from the ATG at nt 1476 to the termination signal at 1947 defines a protein of 157 amino acids with two regions of major homology to the HAd5 E1B 19k protein. As shown in FIG. 3 both the BAV3 and the HAd5 proteins have a centrally located hydrophobic amino acid sequence. The sequence in BAV3, with substitutions of valine for alanine and leucine for valine, should result in a somewhat more hydrophobic pocket than the corresponding HAd5 region. The other portion of HAd5 19k that may be conserved in the BAV3 protein is the serine rich sequence found near the N-terminus (residues 20 to 26) in HAd5 19k and near the C-terminus (residues 136 to 142) in the BAV3 protein (also shown in FIG. 3).

On ORF beginning at the ATG at nt 1850 and terminating at nt 3110 overlaps the preceding BAV3 protein reading frame and thus has the same relationship to it as does the HAd5 E1B 56k protein to E1B 19k protein. As shown in FIG. 4 this BAV3 protein of 420R and the corresponding HAd5 E1B 56k protein of 496R show considerable sequence homology over their C-terminal 346 residues. The N-terminal regions of these proteins (not depicted in the figure) show no significant homology and differ in overall length.

Following the E1B ORFs, the open reading frame beginning at nt 3200 and ending at the translation terminator TAA at nt 3575 defines a protein of 125R with an unmodified molecular weight of 13,706. As seen in FIG. 5 this protein shares some homology with the structural protein IX of HAd5 particularly in N-terminal sequences.

Possible Transcription Control Regions in BAV3 E1

The inverted terminal repeats (ITR) at the ends of the BAV3 genome have been shown to extend to 195 nt (Shinagawa et al, 1987 *Gene* 55:85–93). The GC-rich 3' portion of the ITR contains a number of consensus binding sites for the transcription stimulating protein SR1 (Dynan and Tijan (1983) *Cell* 35:79–87) and possible consensus sites for the adenovirus transcription factor (ATF) (Lee et al. (1987) *Nature* 325:368–372) occur at nts 60 and 220. While there are no exact consensus sites for the factors EF-LA (Bruder and Healing (1989) *Mol. Cell Biol.* 9:5143–5153) or E2F (Kovesdi et al, 1987 *PNAS, USA* 84:2180–2184) upstream of the ATG at nt 606, there are numerous degenerate sequences which may define the enhancer region comparable to that seen in HAd5 (Hearing and Shenk, 1986 *Cell* 45:229–236).

The proposed BAV3 E1A coding sequence terminates at a TGA residue at nt 1346 which is located within a 35 base pair sequence which is immediately directly repeated (see FIG. 1). Two repeats of this sequence were detected in three independently derived clones for a plaque purified stock of BAV3. The number of direct repeats can vary in any BAV3 population though plaque purification allows for isolation of a relatively homogeneous population of viruses. That direct repeats in the sequences can function as promoter or enhancer elements for E1B transcription is being tested. There are no strong polyA addition consensus sites between the E1A and the E1B coding sequences and in fact no AATAA sequence is found until after the protein IX coding sequences following E1B. The TATAAA sequence beginning at nt 1453 could function as the proximal promoter for E1B but it is located closer to the ATG at 1476 than is considered usual (McKnight et al, 1982 *Science* 217:316–322). The TATA sequence located further upstream immediately before the proposed E1A intron sequence also seems inappropriately positioned to serve as a transcription box for the E1B proteins. There are clearly some unique features in this region of the BAV3 genome.

The transcriptional control elements for the protein IX transcription unit are conventional and well defined. Almost immediately following the open reading frame for the larger E1B protein there is, at nt 3117, a SR1 binding sequence. This is followed at 3135 by a TATAAAT sequence which could promote a transcript for the protein IX open reading frame beginning at the ATG at 3200 and ending with the TAA at 3575. One polyA addition sequence begins within the translation termination codon and four other AATAA sequences are located at nts 3612, 3664, 3796 and 3932.

In keeping with the general organization of the E1A region of other adenoviruses, the BAV3 E1A region contains an intron sequence with translation termination codons in all three reading frames and which is therefore probably deleted by splicing from all E1A mRNA transcripts. The largest possible protein produced from the BAV3 E1A region will have 211 amino acid residues and is the equivalent of the 289 amino acid protein translated from the 13s mRNA of HAd5. Two striking features in a comparison of these proteins are the high degree of homology in a region corresponding to CR3 and the absence in BAV3 of most of amino acids corresponding to the second exon of HAd5. In fact the only amino acids encoded in the second exon of BAV3 are, those which are considered to constitute part of CR3. A great deal of work carried out with HAd5 has identified the importance of the CR3 sequences in transactivation of other HAd5 genes. While a detailed analysis of the corresponding BAV3 region and its possible role in transactivation of BAV3 genes needs to be carried out, it is none-the-less interesting to note a couple of possibly pertinent features. The HAd5 CR3 region has been operationally subdivided into three regions (Lillie et al, 1989 *Nature* 338:39–44; see FIG. 8); an N-terminal region from 139 to 153 which has four acidic residues and is thought to be important in transcription activation, a central, metal binding, region defined by the Cys-$X_2$-Cys-$X_{13}$-Cys$X_2$-Cys (SEQ ID NO:30) sequence which is essential for both promoter binding and activation, and a C-terminal region (residues 175–189) which is essential for promoter binding. Since, in most instances, E1A protein is thought not to interact directly with DNA (Ferguson et al 1985), the promoter binding regions may be involved in forming associations with proteins which then allow association with DNA. In FIG. 2a the BAV3 E1A protein contains the central, metal binding domain and has considerable homology in the carboxy portion of this region. The BAV3 E1A protein also shows identity of sequence with HAd5 in the carboxy 6 amino acids of the promoter binding domain. These features may allow the BAV3 E1A protein to interact with the same transcription activating factors required for HAd5 E1A function. In contrast, except for a Glu-Glu pair there is little homology between the bovine and human viruses in the activation domain. The fact that this domain can be functionally substituted by a heterologous acidic activation sequence (Lillie et al, 1989 supra) suggests that protein specificity is not required in this region and this may allow the BAV3 E1A protein to function in the activation of BAV3 genes. The BAV3 E1A activation region contains six acidic residues in the 18 residues amino to the metal binding domain.

The other interesting feature of BAV3 E1A, which is undoubtedly relevant to the oncogenic potential of this virus, is the presence of the sequence Asp27-Leu-Glu-Cys-His-Glu which conforms to, a core sequence known to be important in the binding of cellular Rb and related proteins by the transforming proteins of a number of DNA tumor viruses (Dyson et al, 1990 supra). From deletion mutant analysis there is a clear association between the potential of HAd5 E1A proteins to bind Rb and the ability of the protein to induce morphological transformation in appropriate cells (see references in Dyson et al, 1990 supra). The BAV3 E1A protein is distinct from its HAd5 counterpart in the relative position of this Rb binding sequence which is in the CR2 of HAd5 E1A and near the N-terminus of the BAV3 E1A protein.

Through the use of alternative splice sites HAd5 E1A transcripts can give rise to at least 5 distinct mRNA species (Berk et al, 1978 *Cell* 14:695–711; Stephens et al, 1987 *EMBO Journal* 6:2027–2035). Whether BAV3, like HAd5, can generate a number of different mRNA species through the use of alternative splice sites in the E1A transcripts remains to be determined. For example a potential splice donor site which could delete the sequence equivalent to the unique sequence of HAd5 is present immediately after nt 1080 but it is not known if this site is actually used.

HAd5 E1B encodes two proteins (19k and 56k) either of which can cooperate with E1A, by pathways which are additive and therefore presumably independent (McLorie et al, 1991 *J. Gen Virol.* 72:1467–1471), to produce morphological transformation of cells in culture (see for example: Branton et al, 1985 supra; Graham, 1984 supra). The significance of the conservation of the hydrophobic stretch of amino acids in the central portion of the shorter E1B proteins of HAd5 and BAV3 is not clear as yet. A second short region of homology Gln-Ser-Ser-X-Ser-Thr-Ser (SEQ ID NO:31) at residue 136 near the C-terminus of the BAV3 protein is located near the N-terminus at residue 20 in the HAd5 19k protein. The major difference in both length and sequence of the larger (420R) E1B protein of BAV3 from the corresponding HAd5 protein (496R) is confined to the N-terminus of these proteins. The two proteins show considerable evolutionary homology in the 345 amino acids that extend to their C-termini. A similar degree of homology extends into the N-terminal halves of protein IX of BAV3 and HAd5. Taken together these analyses suggest that while BAV3 and the human adenoviruses have diverged by simple point mutational events in some regions, more dramatic genetic events such as deletion and recombination may have been operating in other regions particularly those defining the junction between E1A and E1B.

Example 3

Cloning and sequencing of the BAV3 E3 and fibre genes

The general organization of adenovirus genomes seems to be relatively well conserved so it was possible to predict, from the locations of a number of HAd E3 regions, that BAV E3 should lie between map units (m.u.) 77 to 86. To prepare DNA for cloning and sequencing, BAV3 (strain WBR-1) was grown in Madin-Darby bovine kidney (MDBK) cells, virions were purified and DNA was extracted (Graham, F. L. & Prevec, L. (1991) Methods in Molecular Biology, vol. 7, Gene Transfer and Expression Protocols, pp. 109–146. Edited by E. J. Murray, Clifton, N.J.; Humana Press.). Previously published restriction maps for EcoRI and BamHI (Kurokawa et al., 1978) were confirmed (FIG. 6). The BamHI D and EcoRI F fragments of BAV3 DNA were isolated and inserted into pUC18 and pUC19 vectors, and nested sets of deletions were made using exonuclease III and Si nuclease (Henikoff, S. (1984) *Gene*, 28:351–359). The resulting clones were sequenced by the dideoxynucleotide chain termination technique (Sanger, F., Nicklen, S. & Coulson, A. R. (1977) *Proceedings of the National Academy* of Sciences, U.S.A., 74:5463–5467). The nucleotide sequence from positions 1 to 287 was obtained from the right end of the BamHI B fragment (FIG. 6). The sequence of the regions spanning (i) the BamHI site at nucleotide 3306 and the EcoRI site at nucleotide 3406, and (ii) the EcoRI site at nucleotide 4801 and the nucleotide 5100 was obtained from a plasmid containing the XbaI C fragment (m.u. 83 to 100; not shown) using primers hybriding to BAV3 sequences. Analysis of the sequence was performed with the aid of the PC/GENE sequence analysis package developed by Amos Bairoch, Department of Medical Biochemistry, University of Geneva, Switzerland.

The 5100 nucleotide sequence which extends between 77 and 92 m.u. of the BAV3 genome is shown in FIG. 7. The upper strand contains 14 open reading frames (ORFs) which could encode polypeptides of 60 amino acid residues or more (FIGS. 6 and 7). The lower strand contains no ORF encoding a protein of longer than 50 amino acids after an initiation codon. The predicted amino acid sequence for each ORF on the upper strand was analyzed for homology with predicted amino acid sequences from several sequenced Ads: HAd2 (Hérissé, J., Courtois, G. & Galibert, F. (1980) *Nucleic Acids Research*, 8:2173–2192; Hérissé, J., Courtois, G. & Galibert, F. (1981) *Nucleic Acids Research*, 9:1229–1249), -3(Signas, C., Akusjarvi, G. & Pettersson, U. (1985) Journal of *Virology*, 53:672–678.), -5(Cladaras, C. & Wold, W. S. M. (1985) *Virology*, 140:28–43), -7 (Hong, J. S., Mullis, K. G. & Engler, J. A. (1988) *Virology*, 167:545–553) and -35(Flomenberg, P. R., Chen, M. & Horwitz, M. S. (1988) *Journal of Virology*, 62:4431–4437), and murine Adl (MAd1) (Raviprakash, K. S., Grunhaus, A., E1 Kholy, M. A. & Horwitz, M. S. (1989) *Journal of Virology*, 63:5455–5458) and canine Ad1 (CAd1) (Dragulev, B. P., Sira, S., Abouhaidar, M. G. & Campbell, J. B. (1991) *Virology*, 183:298–305). Three of the BAV3 ORFs exhibited homology with characterized HAd proteins pVIII, fibre and the 14.7K E3 protein. The amino acid sequence predicted from BAV3 ORF 1 shows overall identity of approximately 55% when compared to the C-terminal 75% of HAd2 pVIII (Cladaras & Wold, 1985, supra) (FIG. 8*a*), indicating that ORF 1 encodes the right end of BAd3 pVIII. Near the C-terminal end of BAd3 pVIII there is a 67 amino acid stretch (residues 59 to 125; FIG. 8*a*) which has 75% identity with HAd2 pVIII. This region has previously been shown to be highly conserved among different Ads (Cladaras & Wold, 1985, supra; Signas, C., Akusjarvi, G. & Pettersson, U. (1986) *Gene*, 50:173–184,; Raviprakash et al., 1989, supra; Dragulev et al., 1991, supra).

The fibre protein is present on the surface of the virion as long projections from each vertex of the icosahedral capsid and is involved in a number of Ad functions including attachment of the virus to the cell surface during infection, assembly of virions and antigenicity (Philipson, L. (1983) *Current Topics in Microbiology and Immunology*, 109:1–52). On the basis of the primary structure of HAd2 fibre protein, it has been proposed that the shaft region (between amino acid residues 40 and 400) is composed of a number of repeating structural motifs containing about 15 hydrophobic residues organized in two short β-sheets and two β-bends (Green, N. M., Wrigley, N. G., Russell, W. C., Martin, S. R. & McLachlan, A. D. (1983) *EMBO Journal*, 2:1357–1365). The amino acid sequences at the N terminus of the BAV3 ORF 6-encoded protein share about 60% identity with the HAd2 fibre protein tail, but there is little or no similarity in the knob region, and about 45% identity overall (FIG. 8*c*). The BAd3 fibre gene would encode a protein of 976 residues if no splicing occurs, i.e. 394 amino acid residues longer than the HAd2 fibre protein. The number of repeating motifs in the shaft region of the fibre protein from different Ads varies between 28 and 23 (Signas et al., 1985, supra; Chroboczek, J. & Jacrot, B. (1987) *Virology*, 161:549–554; Hong et al., 1988, supra; Raviprakash et al., 1989, supra; Dragulev et al., 1991, supra). The BAV3 fibre protein can be organized into 52 such repeats in this region (not shown), which would account for most of the difference in size compared to those of HAd2, HAd3, HAD5, HAd7, CAd1 and MAd1 (Signas et al., 1985,supra; Hérissé et al., 1980,supra; Herisse & Galibert, 1981, supra; Hong et al., 1988,supra; Raviprakash et al., 1989, supra; Dragulev et al., 1991, supra).

HAd2 and HAd5 E3 lies between the pVIII and the fibre genes an encodes at least 10 polypeptides (Cladaras & Wold, 1985,supra). The promoter for E3 of these two serotypes lies within the sequences encoding pVIII, about 320 bp 5' of the termination codon. No consensus TATA box is found in the corresponding region of the BAV3 sequences. A non-canonical polyadenylation signal (ATAAA) for E3 transcripts is located at position 1723, between the end of the putative E3 region and the beginning of ORF 6, encoding the fibre protein, and two consensus signals are located within ORF 6 at positions 2575 and 3565. The polyadenylation signal for the fibre protein is located at nucleotide 4877. Six ORFs were identified in the BAV3 genome between the pVIII and the fibre genes, but only four (ORFs 2, 3, 4 and 5) have the potential to encode polypeptides of at least 50 amino acids after an initiation codon (FIG. 7). The amino acid sequence predicted to be encoded by ORF 2 is 307 residues long and contains eight potential N-glycosylation sites (FIG. 7) as well as a hydrophobic sequence which may be a potential transmembrane domain (PLLFAFVLCTGCAVLLTAFGPSILSGT) (SEQ ID NO:32) between residues 262 and 289. This domain may be a part of the protein homologous to the HAd2 and HAd5 19K E3 glycoprotein (Cladaras & Wold, 1985, supra), and the proposed CAd1 22.2K protein (Dragulev et al., 1991, supra), but ORF 2 does not show appreciable homology with these proteins. The ORF 4 shows approximately 44% identity with the 14.7K E3 protein of HAd5 (FIG. 6 and 8*b*), which has been shown to prevent lysis of virus-infected mouse cells by tumour necrosis factor (Gooding, L. R., E1 more, L. W., Tollefson, A. E., Brody, H. A. & Wold, W. S. M. (1988) *Cell*, 53:341–346; Wold, W. S. M. & Gooding, L. R. (1989) *Molecular Biology and Medicine*, 6:433–452). Analysis of the 14.7K protein sequence from HAd2, -3, -5 and -7 has revealed a highly conserved domain, which in HAd5 lies between amino acid residues 41 and 56 (Horton, T. M., Tollefson, A. E., Wold, W. S. M. & Gooding, L. R. (1990) *Journal of Viroloqy*, 64:1250–1255). The corresponding region in the BAV3 ORF 4-encoded protein, between amino acids 70 and 85, contains 11 amino acids identical to those of the HAd5 14.7K protein conserved domain (FIG. 8*b*).

The BAV3 E3 region appears to be approximately 1.5 kbp long, about half the size of those of HAd2 and -5 (Cladaras & Wold, 1985, supra), and novel splicing events in BAV3 E3 would be required to generate more homologues to the HAd3 E3 proteins. A similarly short E3 region has been reported for MAd1 (RAviprakash et al., 1989, supra) and CAd1 (Dragulev et al., 1991, supra).

Example 4

Construction of BAV3-luciferase recombinants

Adenovirus-based mammalian cell expression vectors have gained tremendous importance in the last few years as a vehicle for recombinant vaccine delivery, and also in gene therapy. BAV3-based expression vectors have a greater potential for developing novel recombinant vaccines for veterinary use. To show that BAV3 E3 gene products are not essential for virus growth in cultured cells and this locus could be used to insert foreign DNA sequences, a 1.7 kb fragment containing the firefly luciferase gene was introduced in the 696 bp deletion of the E3 region of the BAV3 genome in the E3 parallel orientation to generate a BAV3 recombinant.

The rationale of using the luciferase gene is that it acted as a highly sensitive reporter gene when introduced in the E3 region of the HAd5 genome to generate HAd5-Luc recombinants (Mittal et al (1993) Virus Res. 28:67–90).

Figure 9:
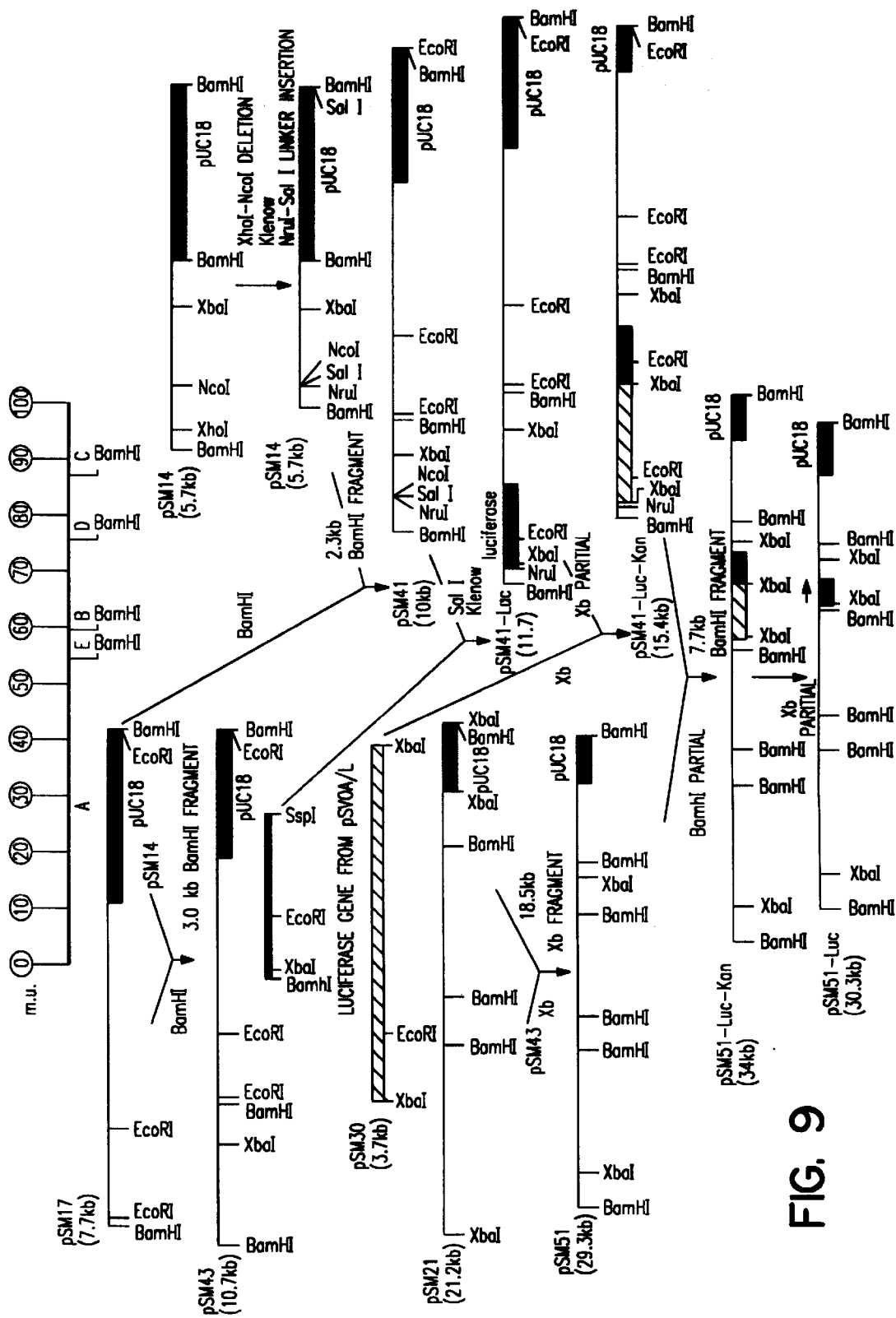
FIG. 9. Construction of BAV3 E3 transfer vector containing the firefly luciferase gene. The 3.0 kb BamHI 'D' fragment of the BAV3 genome which falls between m.u. 77.8 and 86.4, contains almost the entire E3 region (Mittal et al (1992) *J. Gen Virol.* 73:3295–3000). This 3.0 kb fragment was isolated by digesting BAV3 DNA with BamHI and cloned into pUC18 at the BamHI site to obtain pSM14. Similarly, the 4.8 kb BamHI 'C' fragment of BAV3 DNA which extends between m.u. 86.4 and 100 was isolated and inserted into pUC18 to produce pSM17. To delete a 696 bp XhoI-NcoI fragment, pSM14 was cleaved with XhoI and NcoI, the larger fragment was purified and the ends were made blunt with Klenow fragment of DNA polymerase I and a NruI-SalI linker was inserted to generate pSM14de12. A 2.3 kb BamHI fragment containing BAV3 sequences, an E3 deletion and NruI and SalI cloning sites, was inserted into pSM17 at the BamHI site to obtain pSM41, however, this step was not required for construction of a BAV3 E3 transfer vector. A 1716 bp fragment containing the firefly luciferase gene (de Wet et al (1987) *Mol. Cell. Biol.* 7:725–737) was isolated by digesting pSVOA/L (provided by D. R. Helinski, University of California at San Diego, Calif.) with BsmI and SspI as described (Mittal et al (1993) *Virus Res.* 28:67–90), and the ends were made blunt with Klenow. The luciferase gene was inserted into pSM41 at the SalI site by blunt end ligation. The resultant plasmid was named pSM41-Luc which contained the luciferase gene in the same orientation as the E3 transcription unit. The plasmid pKN30 was digested with XbaI and inserted into pSM41-Luc (partially cleaved with XbaI) at a XbaI site present within the luciferase gene to obtain pSM41-Luc-Kan. The plasmid pSM14 was digested with BamHI and a 3.0 kb fragment was isolated and inserted into pSM17 at the BamHI site to generate pSM43. The 18.5 kb XbaI 'A' fragment of the BAV3 genome which falls between m.u. 31.5 and 84.3 was cloned into pUC18 at the XbaI site to result pSM21. A 18.5 kb XbaI fragment was purified from pSM21 after cleavage with XbaI and inserted into pSM43 at the XbaI site and the resultant plasmid was named pSM51. A 7.7 kb BamHI fragment containing the luciferase gene and kanr gene was isolated after digesting pSM41-Luc-Kan with BamHI and ligated to pSM51, partially digested with BamHI, to isolate pSM51-Luc-Kan in the presence of ampicillin and kanamycin. Finally the kanr gene was deleted from pSM51-Luc-Kan by partial cleavage with XbaI and religation to obtain pSM51-Luc.

To facilitate the insertion of the firefly luciferase gene into the E3 region of the BAV3 genome, a BAV3 E3 transfer vector containing the luciferase gene was constructed (FIG. 9). The BAV3 E3 region falls approximately between m.u. 77 and 82. In our first series of vectors we replaced a 696 bp XhoI-NcoI E3 deletion (between m.u. 78.8 and 80.8) with a NruI-SalI cloning sites for insertion of foreign genes to obtain pSM14de12. A 1716 bp BsmI-SspI fragment containing the luciferase gene was isolated and first inserted into an intermediate plasmid, pSM41, in the E3 locus at the SalI site by blunt end ligation to generate pSM41-Luc. The luciferase gene without any exogenous regulatory sequences, was inserted into the E3 locus in the same orientation as the E3 transcription unit. The kan$^r$ gene was inserted into pSM41-Luc at the XbaI site present within the luciferase gene to generate an amp$^r$/kan$^r$ plasmid, pSM41-Luc-Kan. A 7.7 kb fragment containing the BAV3 sequences along with the luciferase gene and the kanr gene was obtained from pSM41-Luc-Kan by digestion with BamHI and inserted into an ampr plasmid, pSM51 partially digested with BamHI to replace a 3.0 kb BamHI fragment (lies between m.u. 77.8 and 86.4) to generate a doubly resistant (kan$^r$ & ampr) plasmid, pSM51-Luc-Kan. The kanr gene was deleted from pSM51-Luc-Kan by partial cleavage with XbaI to generate pSM51-Luc containing the luciferase gene in the E3-parallel orientation.

Figure 10:
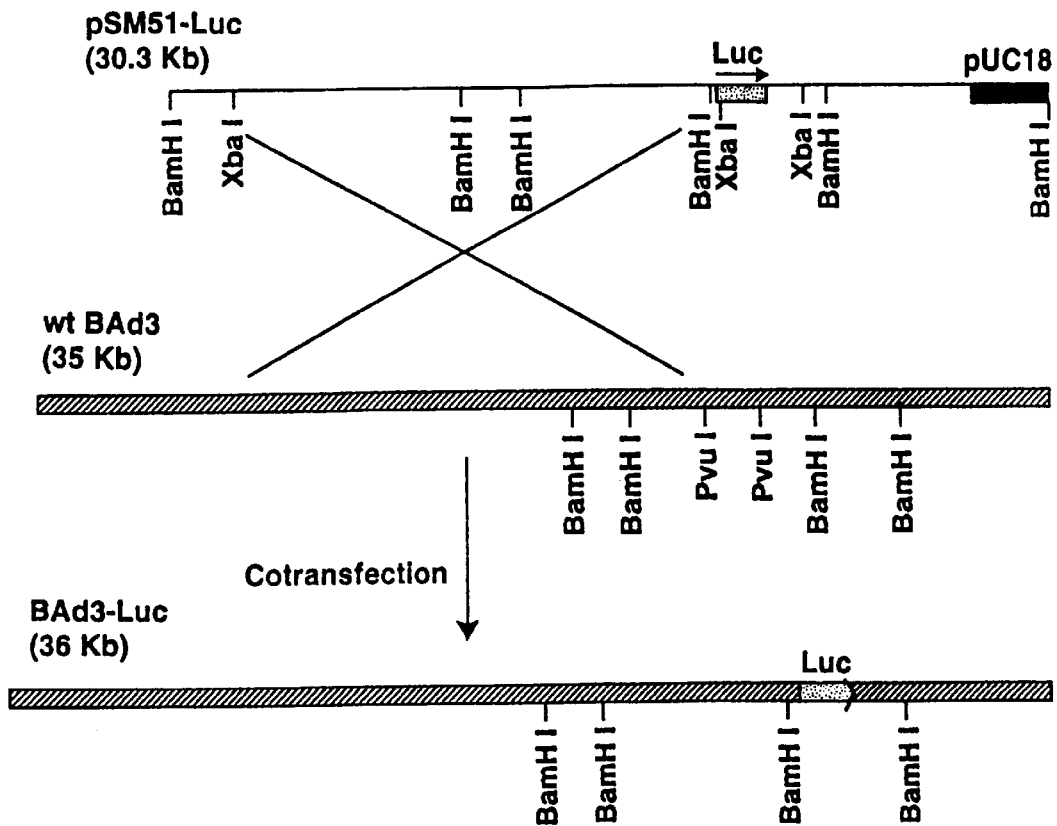
FIG. 10. Generation of BAV3 recombinants containing the firefly luciferase in the E3 region. The plasmid pSM51-Luc contains the BAV3 genome between m.u. 77.8–84.3 and 31.5–100, a 696 bp deletion in E3 and the luciferase gene in E3 in the E3 parallel orientation. The BAV3 genome digested with PvuI and uncut pSM51-Luc were used for cotransfection of MDBK cells transformed with a plasmid containing BAV3 E1 sequences to rescue the luciferase gene in E3 of the BAV3 genome by in vivo recombination. The resulting BAV3-luciferase recombinants (BAV3-Luc) isolated from two independent experiments were named BAV3-Luc (3.1) and BAV3-Luc (3.2). The BamHI restriction map of the BAV3-Luc genome is shown. The position and orientation of the firefly luciferase gene is shown as a hatched arrow.

MDBK cells transformed with a plasmid containing the BAV3 E1 sequences was cotransfected with the wt BAV3 DNA digested with PvuI, which make two cuts within the BAV3 genome at m.u 65.7 and 71.1, and the plasmid, pSM51-Luc to rescue the luciferase gene in E3 of the BAV3 genome by in vivo recombination (FIG. 10). The digestion of the wt BAV3 DNA with PvuI was helpful in minimizing the generation of the wt virus plaques following cotransfection. The left end of the wt BAV3 genome represented by PvuI 'A' fragment falls between m.u. 0 and 65.7, and pSM51-Luc which extends between m.u. 31.5 and 100 (except for E3 deletion replaced with the luciferase gene) have sufficient overlapping BAV3 DNA sequences to generate recombinant viruses.

Two virus plaques were obtained in two independent cotransfection experiments which were grown in MDBK cells. The viral DNA from both plaques was extracted and analyzed by agarose gel electrophoresis after digesting either with BamHI, EcoRI or XbaI to identify the presence and orientation of the luciferase gene in the viral genome (data not shown). In the genomes of both recombinants, the luciferase gene was present in the E3 region in the E3 parallel orientation. The BAV3-luciferase recombinants were plaque purified and named BAV3-Luc (3.1) and BAV3-Luc (3.2) to represent plaques obtained from two independent experiments. Since both recombinant virus isolates were identical they will be referred to as BAV3-Luc. The presence of the luciferase gene in BAV3-Luc isolates are further confirmed by Southern blot analyses and luciferase assays using extracts from recombinant virus-infected cells.

Characterization of BAV3-recombinants

Figure 11A:
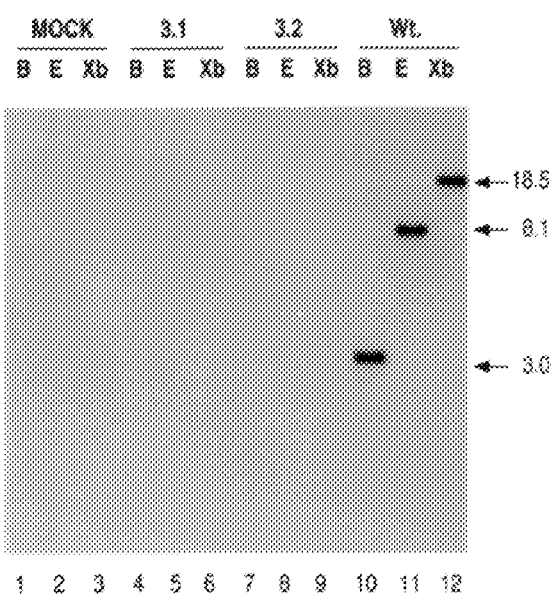
FIGS. 11A–11B. Southern blot analyses of restriction enzymes digested DNA fragments of the wt BAV3 or recombinant genomes by using a 696 bp XhoI-NcoI fragment from pSM14 (FIG. 9) and a DNA fragment containing the luciferase gene as probes. 100 ng DNA isolated from the mock (lanes 1, 2, 3), BAV3-Luc (3.1) (lanes 4, 5, 6), BAV3-Luc (3.2) (lanes 7, 8, 9) or wt BAV3 (lanes 10, 11 12)-infected MDBK cells were digested with BamHI (lanes 1, 4, 7, 10), EcoRI (lanes 2, 5, 8, 11) or XbaI (lanes 3, 6, 9, 12) and analyzed by agarose gel electrophoresis. The DNA fragments from the gel were transferred onto a GeneScreen-Plus™ membrane and hybridized with a 696 bp XhoI-NcoI fragment from pSM14 (FIG. 9) labeled with $^{32}$p using Pharmacia Oligolabeling Kit (panel A). Panel B blot represents duplicate samples as in panel A but was probed with a 1716 bp BsmI-SspI fragment containing the luciferase gene (FIG. 9). The sizes of bands visualized following hybridization are shown in kb on the right in panel A and on the left in panel B. B: BamHI, E: EcoRI, Xb: XbaI, 3.1: BAV3-Luc (3.1), 3.2: BAV3-Luc (3.2) and wt: wild-type BAV3.
Figure 11B:
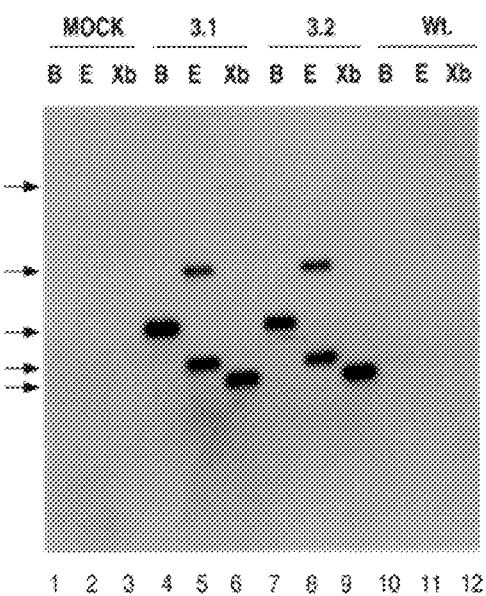

Southern blot analyses of the wt BAV3 and recombinants genomic DNA digested either with BamHI, EcoRI or XbaI, were carried out to confirm the presence and orientation of the luciferase gene in the E3 locus and the deletion of the 696 bp XhoI-NcoI fragment from E3 of the BAV3-Luc genome (FIG. 11). When the blot was probed with a 696 XhoI-NcoI fragment of E3 of the BAV3 genome (panel A, lanes 4 to 9) no hybridization signal was detected with the DNA fragments from the recombinant viruses, however, the expected bands (3.0 kb BamHI, 8.1 kb EcoRI, and 18.5 kb XbaI) of the wt BAV3 DNA fragments (panel A, lanes 10 to 12) showed hybridization, confirming that the 696 bp XhoI-NcoI fragment of the E3 region was indeed deleted in the BAV3-Luc genomic DNA. In panel B, when an identical blot was probed with the luciferase gene, there were strong hybridization signals with the DNA fragments from the recombinant viruses (4.0 kb BamHI (lane 4 & 7), 6.0 kb & 3.2 kb EcoRI (lanes 5 & 8), 16.7 kb & 2.9 kb XbaI (lanes p6 & 9)). These results confirmed that the BAV3-Luc contains the luciferase gene in the E3 parallel orientation with a 696 bp XhoI-NcoI E3 deletion.

Figure 12:
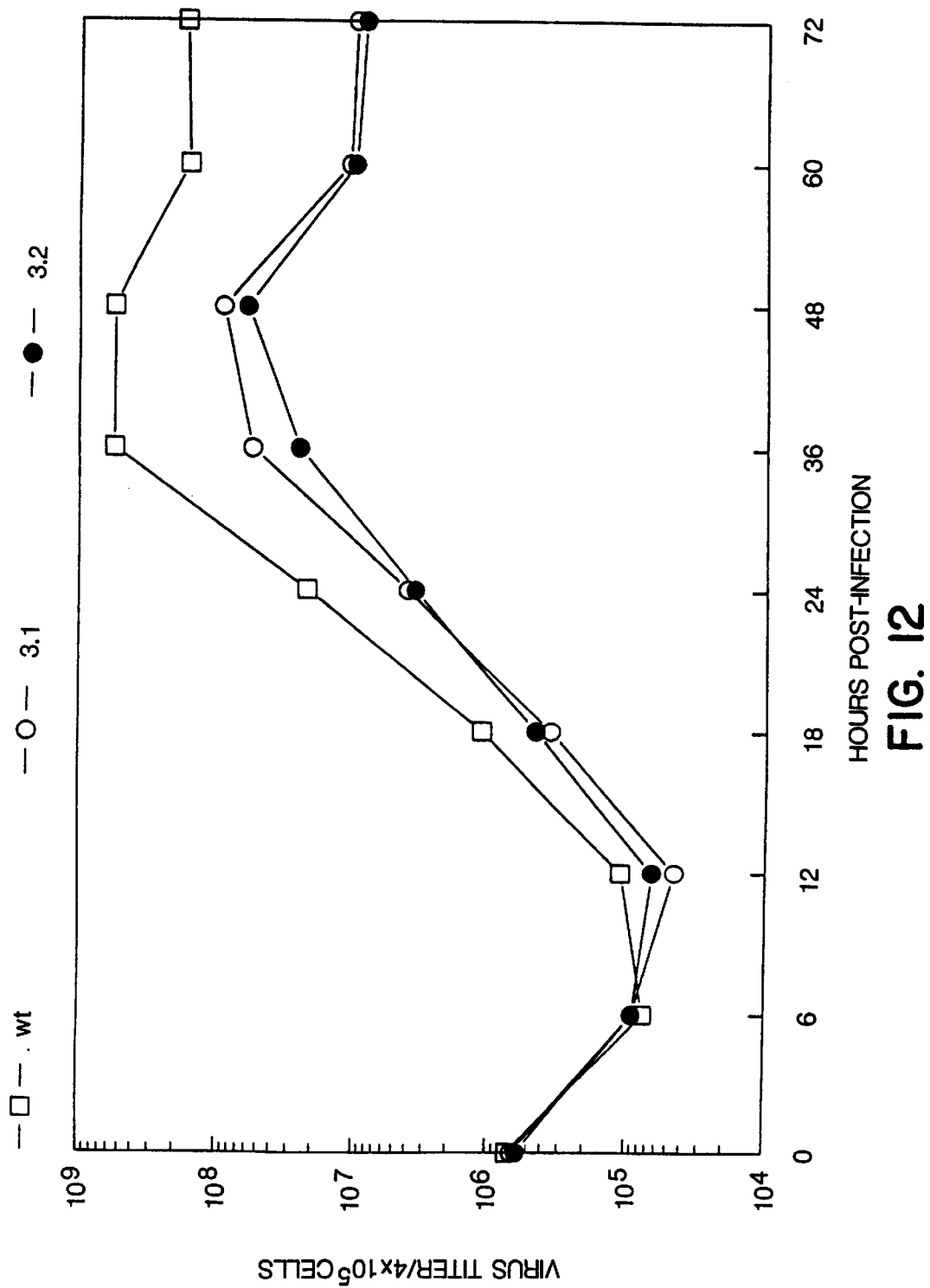
FIG. 12. Single step growth curve for wt BAV3 and BAV3-Luc. Confluent monolayers of MDBK cells in 25 mm multi-well culture plates were inoculated with the wt BAV3, BAV3-Luc (3.1) or BAV3-Luc (3.2) at a m.o.i. of 10 p.f.u. per cell. The virus was allowed to adsorb for 1 h at 37° C., cell monolayers were washed 3 times with PBS++ (0.137M NaCl, 2.7 mM KCl, 8 mM $Na_2HPO_4$, 1.5 mM $KH_2PO_4$, containing 0.01% $CaCl_2.2H_2$ & 0.01% $MgCl_2.6H_2$) and incubated at 37° C. in 1 ml maintenance medium containing 2% horse serum. At various times post-infection, cells were harvested along with the supernatant, frozen and thawed three times and titrated on MDBK cells by plaque assay. Results are the means of duplicate samples.

The growth characteristics of the recombinant viruses was compared with the wt BAV3 in a single step growth curve (FIG. 12). Virus titers in MDBK cells-infected with the wt BAV3 started increasing at 12 h post-infection reaching a maximum at 36–48 h post-infection and then declined thereafter. Virus titers of the recombinant viruses also started increasing at 12 h postinfection reaching a maximum at 48 h post-infection and then declined, however, the titers of recombinant viruses remained approximately one log lower than the wt virus. The plaque size of the recombinant viruses were also comparatively smaller than the wt virus (data not shown).

Kinetics of luciferase expression by BAV3-Luc

Figure 13:
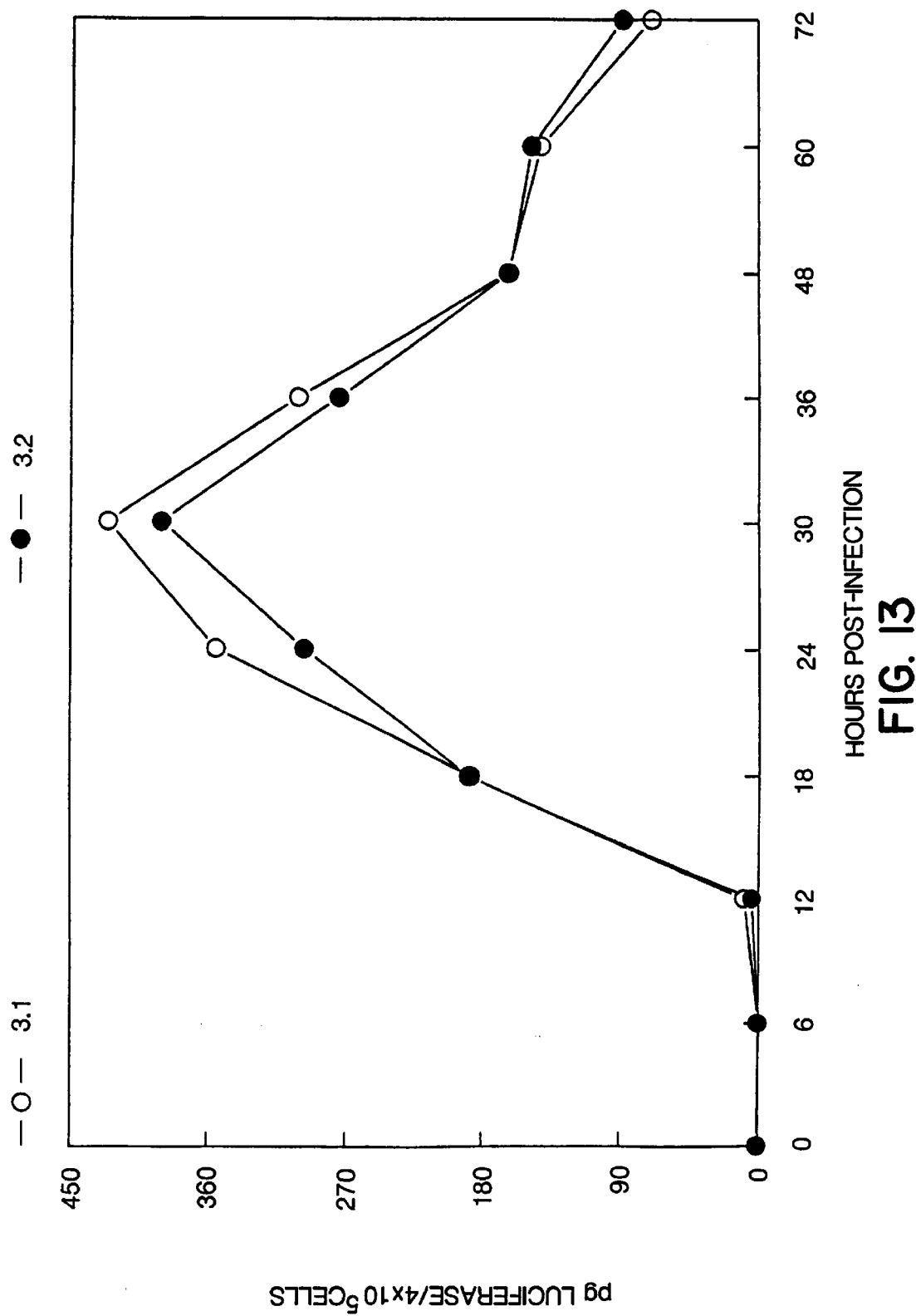
FIG. 13. Kinetics of luciferase expression in MDBK cells-infected with BAV3-Luc. Confluent MDBK cell monolayers in 25 mm multi-well culture plates were infected with BAV3-Luc (3.1) or BAV3-Luc (3.2) at a m.o.i. of 50 p.f.u. per cell. At indicated time points post-infection, virus-infected cells were harvested and assayed in duplicate for luciferase activity.
Figure 14A:
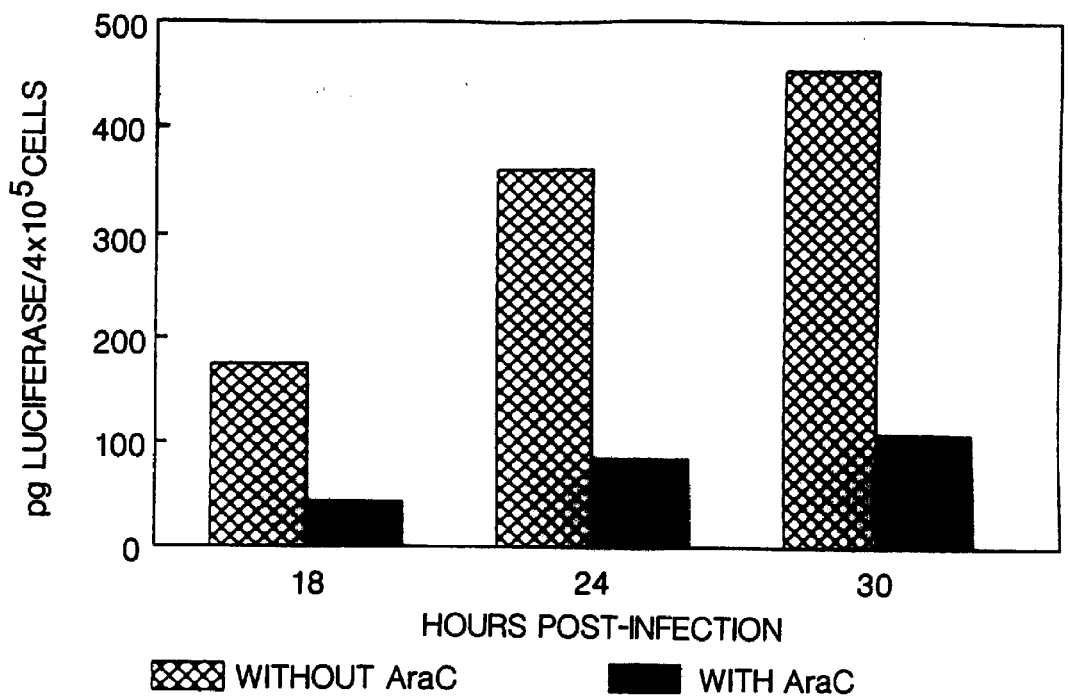
FIGS. 14A–14B. Luciferase expression in the presence of 1-β-D-arabinofluranosyl cytosine (AraC) in MDBK cells-infected with BAV3-Luc. Confluent MDBK cell monolayers in 25 mm multi-well culture plates were infected with A) BAV3-Luc (3.1) or B) BAV3-Luc (3.2) at a m.o.i. of 50 p.f.u. per cell and incubated in the absence or presence of 50 Ag AraC per ml of maintenance medium. At indicated time points post-infection, virus-infected cells were harvested and assayed in duplicate for luciferase activity.
Figure 14B:
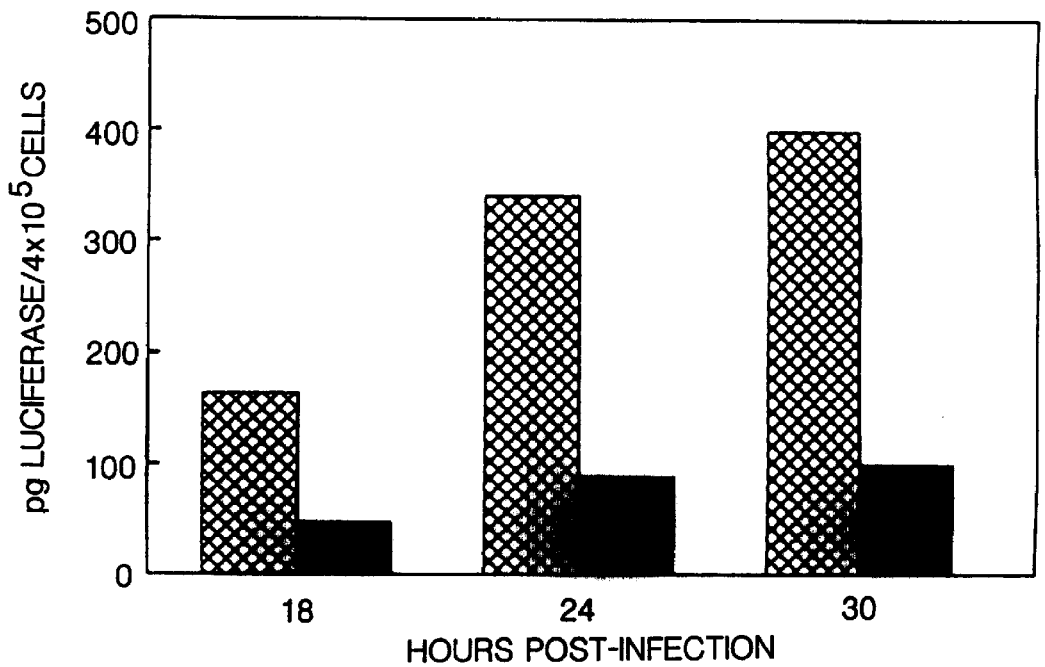
Figure 15A:
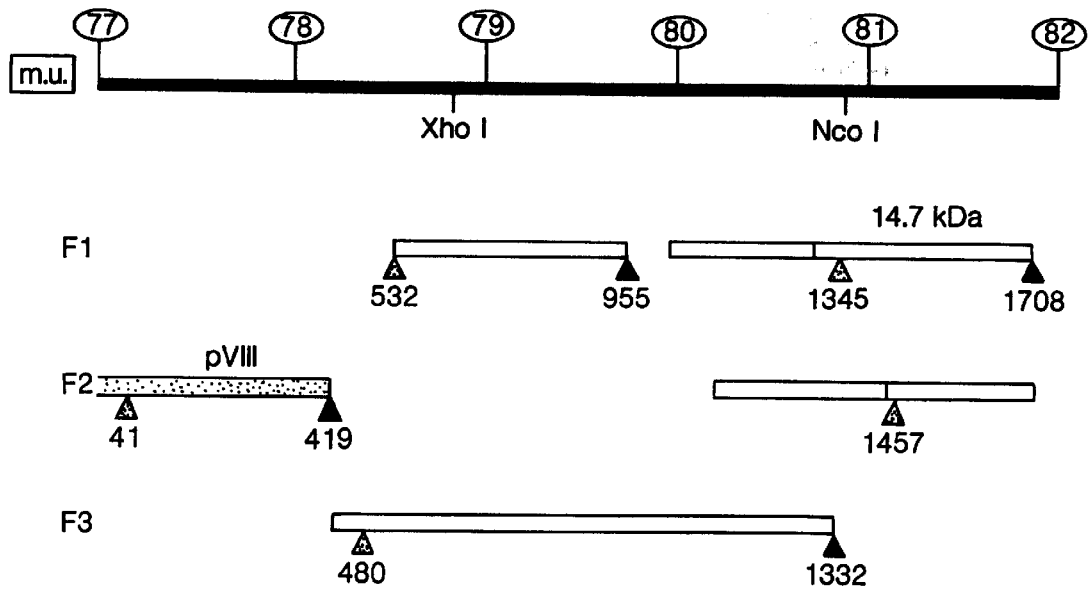
FIGS. 15A–15B. Transcription maps of the wt BAV3 and BAV3-Luc genomes in the E3 region. The genome of wt BAV3 between m.u. 77 and 82 is shown which represents the E3 region. The location of XhoI and NcoI sites which were used to make an E3 deletion are shown. (a) The three frames (F1, F2 and F3) representing the open reading frames (ORFS) in the upper strand of the wt BAV3 genome in the E3 region are represented by bars. The shaded portions indicate regions of similarities to pVIII and E3-14.7 kDa proteins of HAd5. The positions of the initiation and termination codons for ORFs likely to code for viral proteins are shown by open and closed triangles, respectively. (b) The predicted ORFs for the upper strand in E3 of the BAV3-Luc genome are shown after a 696 bp XhoI-NcoI E3 deletion replaced by the luciferase gene. The ORFs for pVIII and E3-14.7 kDa proteins are intact. The transcription map of the wt BAV3 E3 was adapted from the DNA sequence submitted to the GenBank database under accession number Dp16839.
Figure 15B:
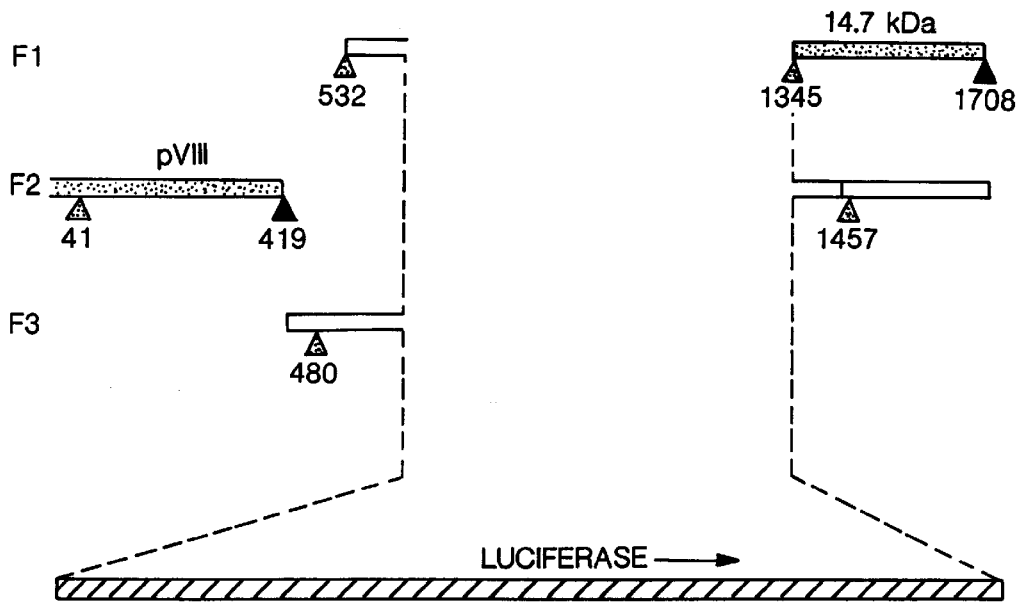
Figure 16:
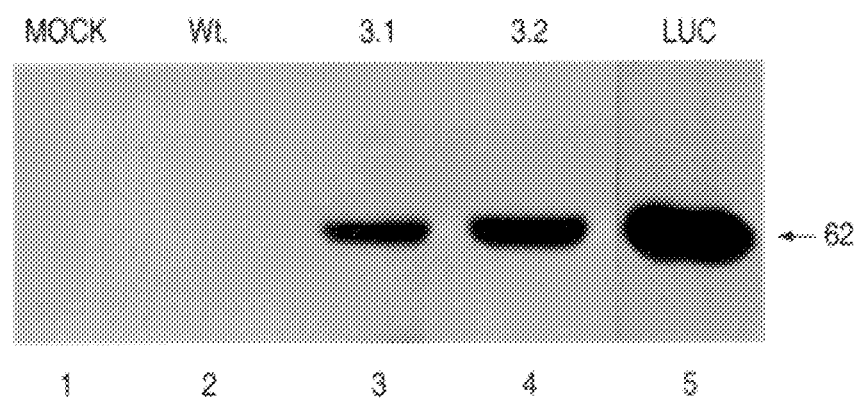
FIG. 16. Western blot analysis of virus-infected MDBK cells using an anti-luciferase antibody. Confluent monolayers of MDBK cells were mock-infected (lane 1) or infected with the wt BAV3 (lane 2), BAV3-Luc (3.1) (lane 3) and BAV3-Luc (3.2) (lane 4) at a m.o.i. of 50 p.f.u. per cell, harvested at 18 h post-infection, cell extracts prepared and analyzed by SDS-PAGE and Western blotting using a rabbit anti-luciferase antibody. Purified firefly luciferase was used as a positive control (lane 5). The lane 5 was excised to obtain a shorter exposure. The protein molecular weight markers in kDa are shown on the left. The arrow indicates the 62 kDa luciferase bands reacted with the anti-luciferase antibody. wt: wild-type BAV3, 3.1: BAV3-Luc (3.1) and 3.2: BAV3-Luc (3.2).
Figure 17:
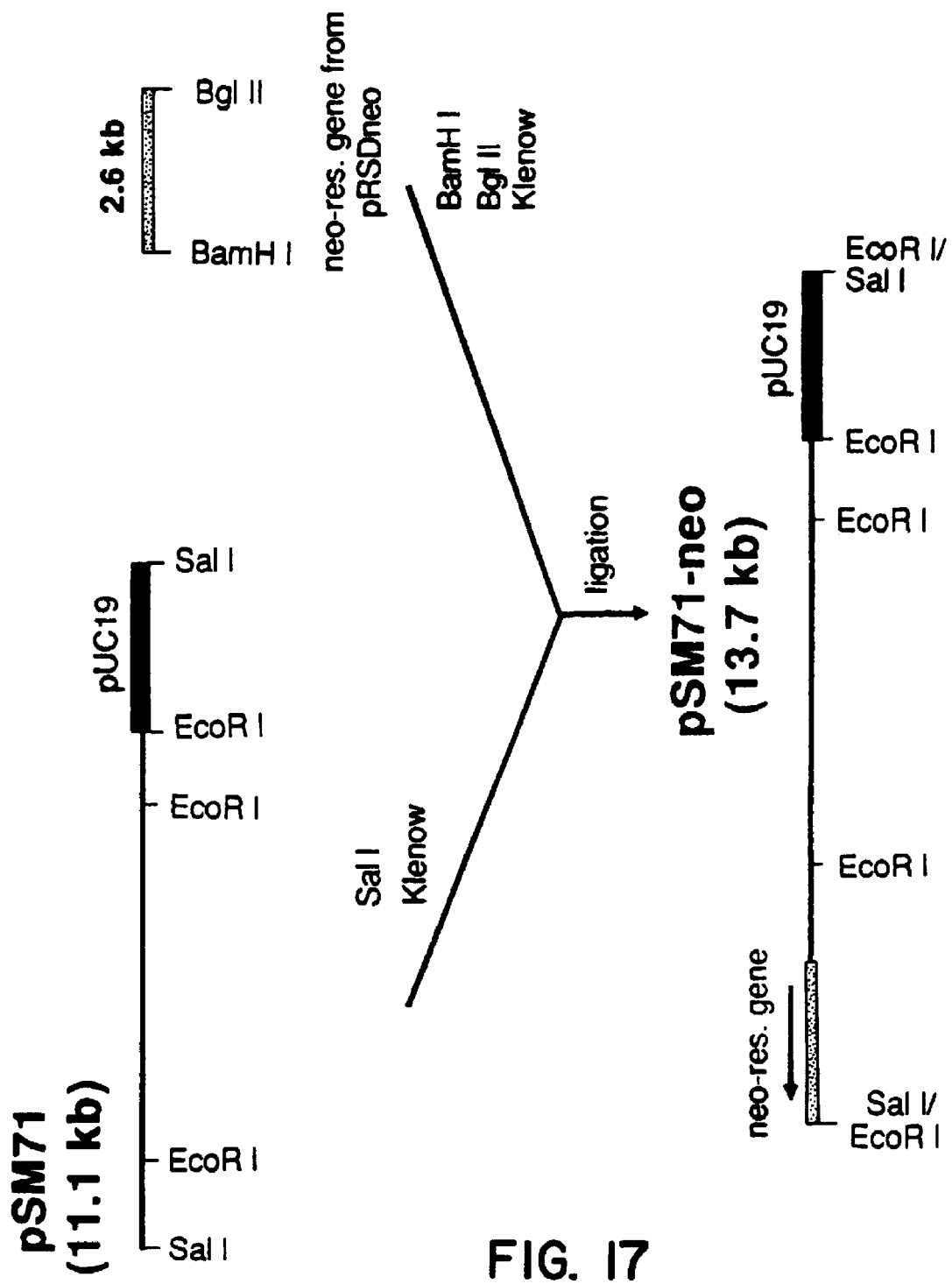
FIG. 17. Construction of pSM71-neo. A 8.4 kb SalI fragment of the BAV3 genome which falls between m.u. 0 and 24 was isolated and inserted into pUC19 at the SalI-SmaI site to generate pSM71. The plasmid, pRSDneo (Fitzpatrick et al (1990) *Virology* 176:145–157) contains the neomycin-resistant (neo$^r$ gene flanked with the simian virus 40 (SV40) regulatory sequences originally from the plasmid, pSV2neo (Southern et al (1982) *J. Mol. Appl. Genet* 1:327–341) after deleting a portion of the SV40 sequences upstream of the neo$^r$ gene to remove several false initiation codons. A 2.6 kb fragment containing the neo$^r$ gene under the control of the SV40 regulatory sequences, was obtained from the plasmid, pRSDneo after digestion with BamHI and BglII, and cloned into pSM71 at the SalI site by blunt end ligation to obtain pSM71-neo containing the neo$^r$ gene in the E1 parallel orientation.
Figure 18:
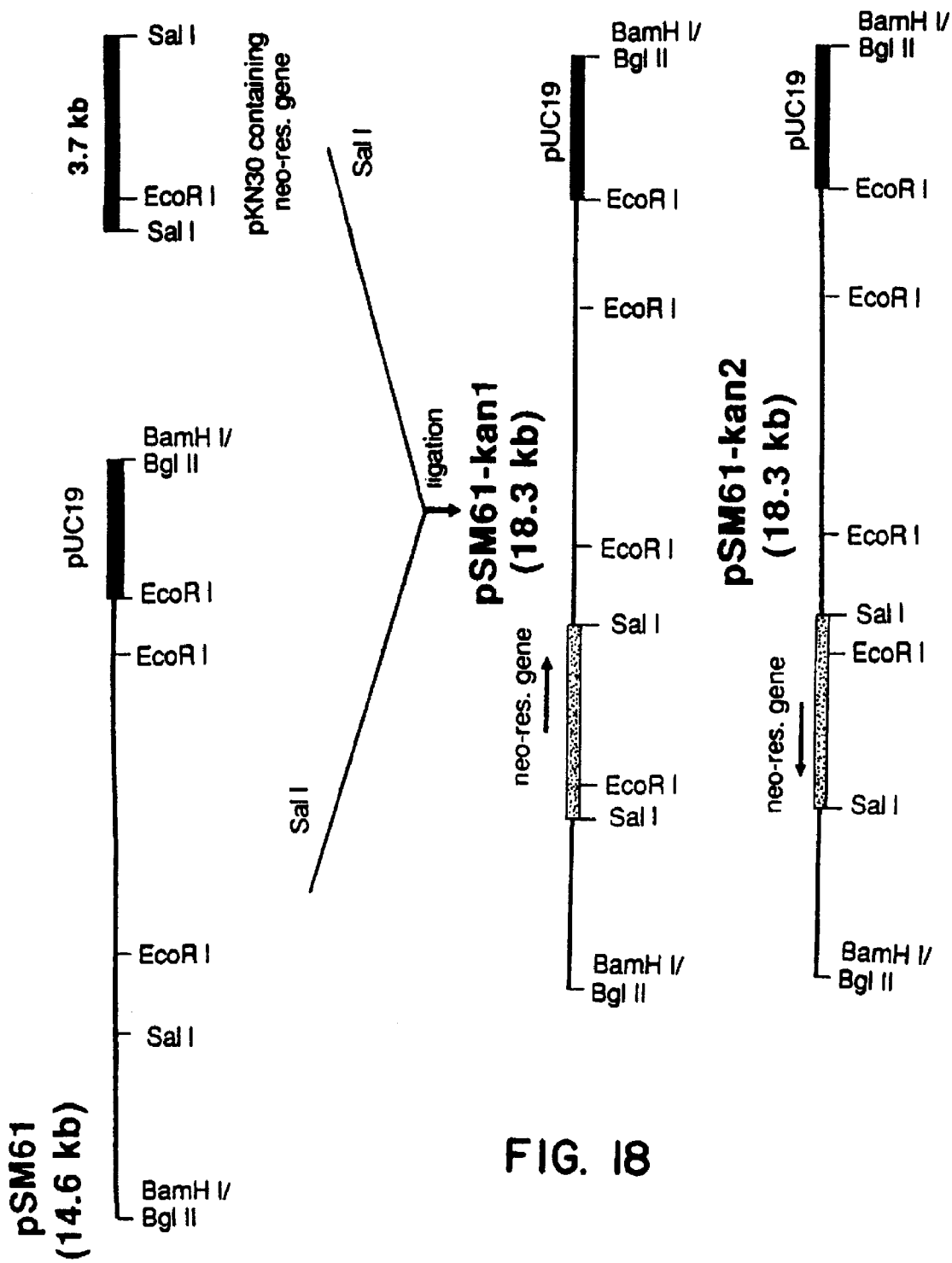
FIG. 18. Construction of pSM61-kan 1 and pSM61-kan2. A 11.9 kb BglII fragment of the BAV3 genome which extends between m.u. 0 and 34 was purified and introduced into pUC19 at the BamHI-HincII site to obtain pSM61. The plasmid, pKN30 contains the neo$^r$ gene along with SV40 promoter and polyadenylation sequences from the plasmid pSV2neo without any modification. The entire pKN30 plasmid was inserted into pSM61 at the SalI site to generate pSM61-kan1 having the neo$^r$ gene in the E1 anti-parallel orientation and pSM61-kan2 when the neo$^r$ gene is in the E1 parallel orientation.
Figure 19:
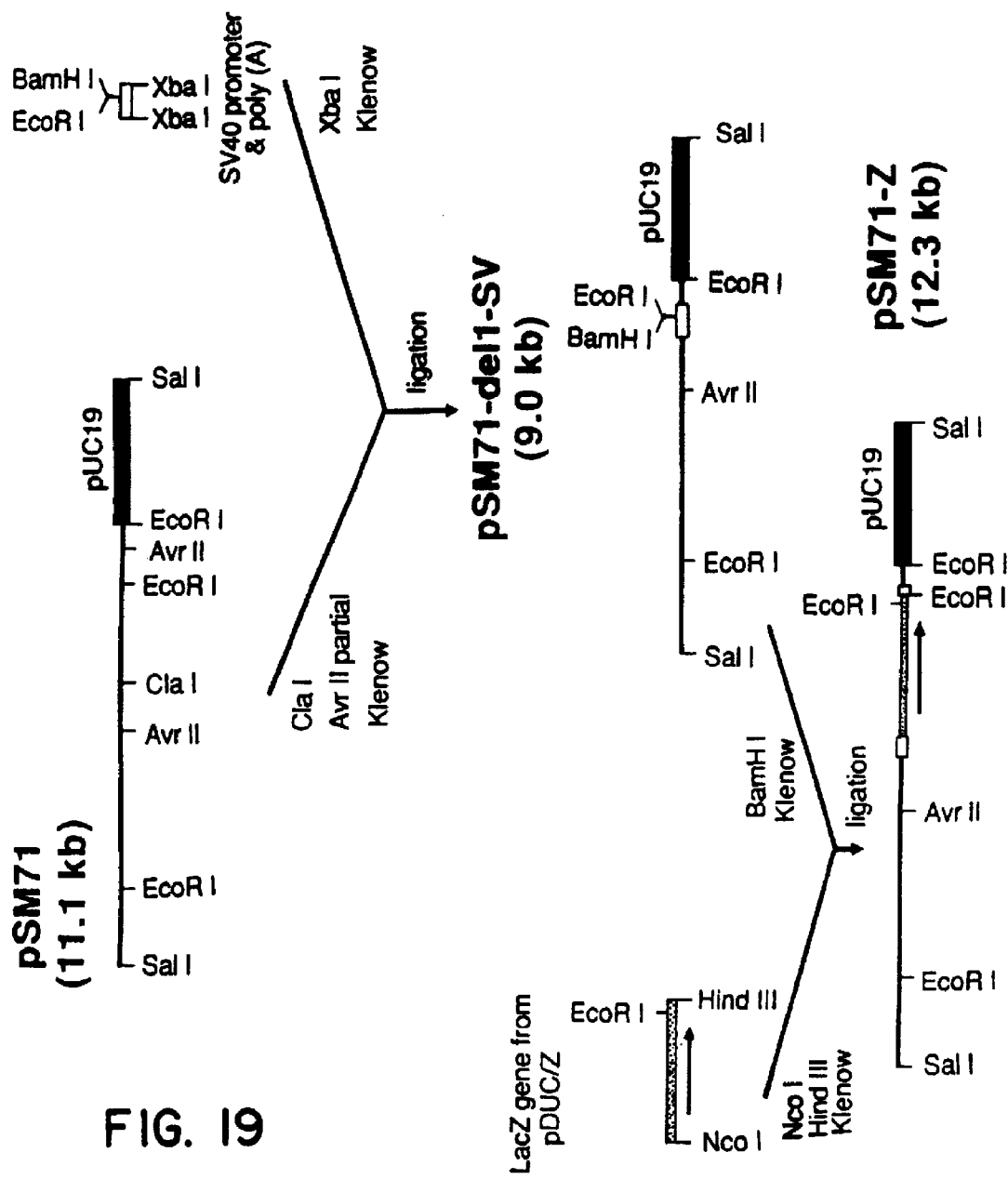
FIG. 19. Construction of an E1 transfer plasmid containing the beta-galactosidase gene.

Luciferase activity in BAV3-Luc-infected MDBK cells was monitored at different times post-infection by luciferase assays (FIG. 13). A low level of luciferase activity was first observed at 12 h post-infection reaching a peak at 30 h post-infection and then dropped subsequently. At 30 h post-infection, approximately 425 pg luciferase was detected in 4×10$^5$ BAV3-Luc (3.1)-infected MDBK cells. In MDBK cells-infected with the wt BAV3, luciferase expression was not detected (data not shown). The kinetics of luciferase expression by BAV3-Luc (3.1) and BAV3-Luc (3.2) appears very much similar. The kinetics of luciferase expression also showed that the majority of enzyme expression in virus-infected cells seemed to occur late in infection. To determine luciferase expression in the absence of viral DNA replication, BAV3-Luc-infected MDBK cells were incubated in the presence of an inhibitor of DNA synthesis, 1-β-D—arabinofuranosyl cytosine (AraC) and luciferase activity was measured in virus-infected cell extracts at various times post-infection and compared to luciferase expression obtained in the absence of AraC (FIG. 14). When the recombinant virus-infected cells were incubated in the presence of AraC, luciferase expression at 18, 24 and 30 h post-infection was approximately 20–30% of the value obtained in the absence of AraC. These results indicated that the majority of luciferase expression in MDBK cells infected with BAV3-Luc took place after the onset of viral DNA synthesis. To confirm this MDBK cells-infected with the BAV3-Luc were grown in the absence or presence of AraC, harvested at 18 h, 24 h, and 30 h post-infection, viral DNA extracted and analyzed by dot bot analysis using pSM51-Luc (see FIG. 9) as a probe (data not shown). In the presence of AraC, viral DNA synthesis was severely reduced compared to viral DNA synthesis in the absence of AraC. Western blot analysis of BAV3-Luc-infected cells Luciferase was expressed as an active enzyme as determined by luciferase assays using extracts from MDBK cells-infected with BAV3-Luc (see FIG. 13). The luciferase gene without any exogenous regulatory sequences was inserted into E3 of the BAV3 genome, therefore, there was a possibility of luciferase expression as a fusion protein with part of an E3 protein if the luciferase gene was in the same frame, Such as, F1 and F3 which represent open reading frames (ORFs) for E3 proteins (FIG. 15) or the fusion protein may arise due to recognition of an upstream initiation codon in the luciferase ORF. To explore this possibility we sequenced the DNA at the junction of the luciferase gene and the BAV3 sequences with the help of a plasmid, pSM51-Luc and a synthetic primer design to bind luciferase coding sequences near the initiation codon (data not shown). The luciferase coding region fell in frame F2. The luciferase initiation codon was the first start codon in this frame, however, the ORF started at 84 nucleotides upstream of the luciferase start codon. To further confirm that luciferase protein is of the same molecular weight as purified firefly luciferase, unlabeled mock infected, wt BAV3-infected or BAV3-Luc-infected MDBK cell extracts were reacted with an anti-luciferase antibody in a Western blot (FIG. 16). A 62 kDa polypeptide band was visible in the BAV3-Luc (lane 3 and 4)-infected cell extracts which were of the same molecular weight as pure firefly luciferase (lane 5). We are not sure whether a band of approximately 30 kDa which also reacted with the anti-luciferase antibody in lanes 3 and 4 represented a degraded luciferase protein.

The majority of luciferase expression is probably driven from the major late promoter (MLP) to provide expression paralleling viral late gene expression, moreover, the enzyme expression seen in the presence of AraC may be taking place from the E3 promoter. In HAd5 vectors, foreign genes without any exogenous regulatory sequences when inserted in E3 also displayed late kinetics and were inhibited by AraC. The BAV3 recombinant virus replicated relatively well in cultured cells but not as good as the wt BAV3. This is not surprising as infectious virus titers of a number of HAd5 recombinants were slightly lower than the wt HAd5 (Bett et al (1993) *J. Virol.* 67:5911–5921). This may be because of reduced expression of fiber protein in recombinant adenoviruses having inserts in the E3 region compared to the wt virus (Bett et al, supra and Mittal et al (1993) *Virus Res.* 28:67–90).

The E3 of BAV3 is approximately half the size of the E3 region of HAd2 or HAd5 and thus has the coding potential for only half the number of proteins compared to E3 of HAd2 or HAdS (Cladaras et al (1985) *Virology* 140:28–43: Herisse et al (1980) *Nuc. Acids Res.* 8:2173–2192; Herisse et al (1981) *Nuc. Acids Res.* 9:1229–1249 and Mittal et al (1993 *J. Gen Virol.* 73:3295–3000). BAV3 E3 gene products have been shown to be not required for virus growth in tissue culture. However, presently it is known that BAV3 E3 gene products also evade immune surveillance in vivo like HAds E3 proteins. One of the BAV3 E3 open reading frames (ORFs) has been shown to have amino acid homology with the 14.7 kDa E3 protein of HAds (Mittal et al (1993) supra). The 14.7 kDa E3 protein of HAds prevents lysis of virus-infected mouse cells by tumour necrosis factor (Gooding et al (1988) *Cell* 53:341–346 and Horton et al (1990) *J. Virol.* 64:1250–1255). The study of pathogenesis and immune responses of a series of BAV3 E3 deletion mutants in cattle provides very useful information regarding the role of E3 gene products in modulating immune responses in their natural host.

The BAV3-based vector has a 0.7 kb E3 deletion which can hold an insert up to 2.5 kb in size. The BAV3 E3 deletion can extend probably up to 1.4 kb which in turn would also increase the insertion capacity of this system. The role of the MLP and the E3 promoter is examined to determine their ability to drive expression of a foreign gene inserted into E3 when a proper polyadenylation signal is provided. Exogenous promoters, such as, the simian virus 40 (SV40) promoter (Subramant et al (1983) *Anal. Biochem.* 135:1–15), the human cytomegalovirus immediate early promoter (Boshart et al (1985) *Cell* 43:215–222), and the human beta-actin promoter (Gunning et al (1987) *PNAS, USA* 84:4831–4835) are tested to evaluate their ability to facilitate expression of foreign genes when introduced into E3 of the BAV3 genome.

Recently HAd-based expression vectors are under close scrutiny for their potential use in human gene therapy (Ragot et al (1993) *Nature* 361:647–650; Rosenfeld et al (1991) *Science* 252:431–434; Rosenfeld et al (1992) *Cell* 68:141–155 and Stratford-Perricaudet et al (1990) *Hum. Gene. Ther.* 1:241–256). A preferable adenovirus vector for gene therapy would be one which maintains expression of the required gene for indefinite or for a long period in the target organ or tissue. It may be obtained if the recombinant virus vector genome is incorporate into the host genome or maintained its independent existence extrachromosomally without active virus replication. HAds replicate very well in human, being their natural host. HAds can be made defective in replication by deleting the E1 region, however, how such vectors would maintain the expression of the target gene in a required fashion is not very clear. Moreover, the presence of anti-HAds antibodies in almost every human being may create some problems with the HAd-based delivery system. The adenovirus genomes have a tendency to form circles in non-permissive cells. BAV-based vectors could provide a possible alternative to HAd-based vectors for human gene therapy. As BAV3 does not replicate in human, the recombinant BAV3 genomes may be maintained as independent circles in human cells providing expression of the essential protein for a long period of time.

The foreign gene insertion in animal adenoviruses is much more difficult than HAds because it is hard to develop a cell line which is also good for adenovirus DNA-mediated transfection. This may be one of the major reasons that the development of an animal adenovirus-based expression system has not been reported so far. It took us more than a year to isolate a cell line suitable for BAV3 DNA-mediated transfection. However, the rapid implementation of BAV-based expression vectors for the production of live virus recombinant vaccines for farm animals, is very promising. BAVs grow in the respiratory and gastrointestinal tracts of cattle, therefore, recombinant BAV-based vaccines have use to provide a protective mucosal immune response, in addition to humoral and cellular immune responses, against pathogens where mucosal immunity plays a major role in protection.

Example 5

Generation of cell lines transformed with the BAV3 E1 sequences

MDBK cells in monolayer cultures were transfected with pSM71-neo, pSM61-kanl or pSM61-kan2 by a lipofection-mediated transfection technique (GIBCO/BRL, Life Technologies, Inc., Grand Island, N.Y.). At 48 h after transfection, cells were maintained in the MEM supplemented with 5% fetal bovine serum and 700 µg/ml G418. The medium was changed every 3rd day. In the presence of G418, only those cells would grow which have stably incorporated the plasmid DNA used in transfection experiments into their genomes and are expressing the neo$^r$ gene. The cells which have incorporated the neo$^r$ gene might also have taken up the BAV3 E1 sequences and thus expressing BAV3 E1 protein/s. A number of neo$^r$ (i.e., G418-resistant) colonies were isolated, expended and tested for the presence of BAV3 E1 message/s by Northern blot analyses using a DNA probe containing only the BAV3 E1 sequences. Expression of BAV3 E1 protein/s were confirmed by a complimentation assay using a HAd5 deletion mutant defective in E1 function due to an E1 deletion.

Fetal bovine kidney cells in monolayers were also transfected with pSM71-neo, pSM61kan-1 or pSM61-kan2 by the lipofection-mediated transfection technique, electroporation (Chu et al (1987) *Nucl. Acids Res.* 15:1311–1326), or calcium phosphate precipitation technique (Graham et al (1973) *Virology* 52:456–467). Similarly, a number of G418-resistant colonies were isolated, expended and tested for the presence of BAV3 E1 gene products as mentioned above.

Example 6

Generation of a BAV3 recombinant containing the beta-galactosidase gene as an E1 insert As E1 gene products are essential for virus replication, adenovirus recombinants containing E1 inserts will grow only in a cell line which is transformed with the adenovirus E1 sequences and expresses E1. A number of cell line which are transformed with the BAV3 E1 sequences were isolated as described earlier. The technique of foreign gene insertions into the E1 regions is similar to the gene insertion into the E3 region of the BAV3 genome, however, for insertion into E1 there is a need of an E1 transfer plasmid which contains DNA sequences from the left end of the BAV3 genome, an appropriate deletion and a cloning site for the insertion of foreign DNA sequences. G418-resistant MDBK cell monolayers were cotransfected with the wild-type (wt) BAV3 DNA and pSM71-Z following the lipofection-mediated transfection procedure (GIBCO/BRL, Life Technologies, Inc., Grand Island, N.Y.). The monolayers were incubated at 37° C. under an agarose overlay. After a week post-incubation an another layer of overlay containing 300 ug/ml Blu-gal™ (GIBCO/BRL Canada, Burlington, Ontario, Canada) was put onto each monolayer. The blue plaques were isolated, plaque purified and the presence of the beta-galactosidase gene in the BAV3 genome was identified by agarose gel electrophoresis of recombinant virus DNA digested with suitable restriction enzymes and confirmed by beta-galactosidase assays using extracts from recombinant virus infected cells.

Deposit of Biological Materials

The following materials were deposited and are maintained with the Veterinary Infectious Disease Organization (VIDO), Saskatoon, Saskatchewan, Canada.

The nucleotide sequences of the deposited materials are incorporated by reference herein, as well as the sequences of the polypeptides encoded thereby. In the event of any discrepancy between a sequence expressly disclosed herein and a deposited sequence, the deposited sequence is controlling.

| Material | Internal Accession No. | Deposit Date |
|---|---|---|
| Recombinant plasmids | | |
| pSM51 | pSM51 | Dec 6, 1993 |
| pSM71 | pSM71 | Dec 6, 1993 |
| Recombinant cell lines | | |
| MDBK cells transformed with BAV3 E1 sequences (MDBK-BAVE1) | | Dec 6, 1993 |
| Fetal bovine kidney cells transformed with BAV3 E1 sequences (FBK-BAV-E1) | | Dec 6, 1993 |

While the present invention has been illustrated above by certain specific embodiments, the specific examples are not intended to limit the scope of the invention as described in the appended claims.

We claim:

1. A live recombinant bovine adenovirus vector (BAV) wherein a part or all of the E3 multiple gene coding region is replaced by a heterologous nucleotide sequence encoding a foreign gene or fragment thereof.

2. A live recombinant bovine adenovirus vector (BAV) wherein part or all of the E3 multiple gene coding region is replaced by a heterologous nucleotide sequence encoding a foreign gene or fragment thereof and wherein said heterologous nucleotide sequence is optionally under the control of a promoter not normally associated with either said foreign gene or the bovine adenovirus genome.

3. A live viable recombinant bovine adenovirus (BAV) for producing an immune response in a mammalian host comprising a bovine adenovirus (BAV) subgroup I genome modified in the E3 multiple gene coding region to contain a heterologous nucleotide sequence coding for a polypeptide or an antigenic determinant capable of eliciting a desired immune response, in association with an effective promoter for said nucleotide sequence.

4. A method for eliciting an immune response in a mammalian host comprising administering an immunogenic composition comprising:

a live recombinant BAV of claim 3 wherein the heterologous nucleotide sequence encodes an antigen; and a pharmaceutically acceptable excipient.

5. An immunogenic composition comprising:

a live recombinant adenovirus of claim 3 wherein the heterologous nucleotide sequence encodes an antigen; and a pharmaceutically acceptable excipient.

\* \* \* \* \*

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 4060 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: join(606..1215, 1323..1345)

( x i ) SEQUENCE DESCRIPTION: SEQ ID NO:1:

```
CATCATCAAT    AATCTACAGT    ACACTGATGG    CAGCGGTCCA    ACTGCCAATC    ATTTTTGCCA    6 0
```

-continued

```
CGTCATTTAT GACGCAACGA CGGCGAGCGT GGCGTGCTGA CGTAACTGTG GGGCGGAGCG      120

CGTCGCGGAG GCGGCGGCGC TGGGCGGGGC TGAGGCGGC GGGGGCGGCG CGCGGGGCGG       180

CGCGCGGGGC GGGGCGAGGG GCGGAGTTCC GCACCCGCTA CGTCATTTTC AGACATTTTT      240

TAGCAAATTT GCGCCTTTTG CAAGCATTTT TCTCACATTT CAGGTATTTA GAGGGCGGAT      300

TTTTGGTGTT CGTACTTCCG TGTCACATAG TTCACTGTCA ATCTTCATTA CGGCTTAGAC      360

AAATTTTCGG CGTCTTTTCC GGGTTTATGT CCCCGGTCAC CTTTATGACT GTGTGAAACA      420

CACCTGCCCA TTGTTTACCC TTGGTCAGTT TTTTCGTCTC CTAGGGTGGG AACATCAAGA      480

ACAAATTTGC CGAGTAATTG TGCACCTTTT TCCGCGTTAG GACTGCGTTT CACACGTAGA      540

CAGACTTTTT CTCATTTTCT CACACTCCGT CGTCCGCTTC AGAGCTCTGC GTCTTCGCTG      600

CCACC ATG AAG TAC CTG GTC CTC GTT CTC AAC GAC GGC ATG AGT CGA          647
      Met Lys Tyr Leu Val Leu Val Leu Asn Asp Gly Met Ser Arg
        1               5                      10

ATT GAA AAA GCT CTC CTG TGC AGC GAT GGT GAG GTG GAT TTA GAG TGT        695
Ile Glu Lys Ala Leu Leu Cys Ser Asp Gly Glu Val Asp Leu Glu Cys
 15              20                  25                      30

CAT GAG GTA CTT CCC CCT TCT CCC GCG CCT GTC CCC GCT TCT GTG TCA        743
His Glu Val Leu Pro Pro Ser Pro Ala Pro Val Pro Ala Ser Val Ser
                 35                  40                  45

CCC GTG AGG AGT CCT CCT CCT CTG TCT CCG GTG TTT CCT CCG TCT CCG        791
Pro Val Arg Ser Pro Pro Pro Leu Ser Pro Val Phe Pro Pro Ser Pro
             50                  55                  60

CCA GCC CCG CTT GTG AAT CCA GAG GCG AGT TCG CTG CTG CAG CAG TAT        839
Pro Ala Pro Leu Val Asn Pro Glu Ala Ser Ser Leu Leu Gln Gln Tyr
         65                  70                  75

CGG AGA GAG CTG TTA GAG AGG AGC CTG CTC CGA ACG GCC GAA GGT CAG        887
Arg Arg Glu Leu Leu Glu Arg Ser Leu Leu Arg Thr Ala Glu Gly Gln
     80                  85                  90

CAG CGT GCA GTG TGT CCA TGT GAG CGG TTG CCC GTG GAA GAG GAT GAG        935
Gln Arg Ala Val Cys Pro Cys Glu Arg Leu Pro Val Glu Glu Asp Glu
 95                 100                 105                 110

TGT CTG AAT GCC GTA AAT TTG CTG TTT CCT GAT CCC TGG CTA AAT GCA        983
Cys Leu Asn Ala Val Asn Leu Leu Phe Pro Asp Pro Trp Leu Asn Ala
                115                 120                 125

GCT GAA AAT GGG GGT GAT ATT TTT AAG TCT CCG GCT ATG TCT CCA GAA       1031
Ala Glu Asn Gly Gly Asp Ile Phe Lys Ser Pro Ala Met Ser Pro Glu
            130                 135                 140

CCG TGG ATA GAT TTG TCT AGC TAC GAT AGC GAT GTA GAA GAG GTG ACT       1079
Pro Trp Ile Asp Leu Ser Ser Tyr Asp Ser Asp Val Glu Glu Val Thr
        145                 150                 155

AGT CAC TTT TTT CTG GAT TGC CCT GAA GAC CCC AGT CGG GAG TGT TCA       1127
Ser His Phe Phe Leu Asp Cys Pro Glu Asp Pro Ser Arg Glu Cys Ser
    160                 165                 170

TCT TGT GGG TTT CAT CAG GCT CAA AGC GGA ATT CCA GGC ATT ATG TGC       1175
Ser Cys Gly Phe His Gln Ala Gln Ser Gly Ile Pro Gly Ile Met Cys
175                 180                 185                 190

AGT TTG TGC TAC ATG CGC CAA ACC TAC CAT TGC ATC TAT A                 1215
Ser Leu Cys Tyr Met Arg Gln Thr Tyr His Cys Ile Tyr
                195                 200

GTAAGTACAT TCTGTAAAAG AACATCTTGG TGATTTCTAG GTATTGTTTA GGGATTAACT     1275

GGGTGGAGTG ATCTTAATCC GGCATAACCA AATACATGTT TTCACAG  GT CCA GTT      1330
                                                       Ser Pro Val
                                                              205

TCT GAA GAG GAA ATG TGAGTCATGT TGACTTTGGC GCGCAAGAGG AAATGTGAGT      1385
Ser Glu Glu Glu Met
                210
```

-continued

```
CATGTTGACT TTGGCGCGCC CTACGGTGAC TTTAAAGCAA TTTGAGGATC ACTTTTTTGT   1445
TAGTCGCTAT AAAGTAGTCA CGGAGTCTTC ATGGATCACT TAAGCGTTCT TTTGGATTTG   1505
AAGCTGCTTC GCTCTATCGT AGCGGGGGCT TCAAATCGCA CTGGAGTGTG GAAGAGGCGG   1565
CTGTGGCTGG GACGCCTGAC TCAACTGGTC CATGATACCT GCGTAGAGAA CGAGAGCATA   1625
TTTCTCAATT CTCTGCCAGG GAATGAAGCT TTTTTAAGGT TGCTTCGGAG CGGCTATTTT   1685
GAAGTGTTTG ACGTGTTTGT GGTGCCTGAG CTGCATCTGG ACACTCCGGG TCGAGTGGTC   1745
GCCGCTCTTG CTCTGCTGGT GTTCATCCTC AACGATTTAG ACGCTAATTC TGCTTCTTCA   1805
GGCTTTGATT CAGGTTTTCT CGTGGACCGT CTCTGCGTGC CGCTATGGCT GAAGGCCAGG   1865
GCGTTCAAGA TCACCCAGAG CTCCAGGAGC ACTTCGCAGC CTTCCTCGTC GCCCGACAAG   1925
ACGACCCAGA CTACCAGCCA GTAGACGGGG ACAGCCCACC CCGGGCTAGC CTGGAGGAGG   1985
CTGAACAGAG CAGCACTCGT TTCGAGCACA TCAGTTACCG AGACGTGGTG GATGACTTCA   2045
ATAGATGCCA TGATGTTTTT TATGAGAGGT ACAGTTTTGA GGACATAAAG AGCTACGAGG   2105
CTTTGCCTGA GGACAATTTG GAGCAGCTCA TAGCTATGCA TGCTAAAATC AAGCTGCTGC   2165
CCGGTCGGGA GTATGAGTTG ACTCAACCTT TGAACATAAC ATCTTGCGCC TATGTGCTCG   2225
GAAATGGGGC TACTATTAGG GTAACAGGGG AAGCCTCCCC GGCTATTAGA GTGGGGGCCA   2285
TGGCCGTGGG TCCGTGTGTA ACAGGAATGA CTGGGGTGAC TTTTGTGAAT TGTAGGTTTG   2345
AGAGAGAGTC AACAATTAGG GGGTCCCTGA TACGAGCTTC AACTCACGTG CTGTTTCATG   2405
GCTGTTATTT TATGGGAATT ATGGGCACTT GTATTGAGGT GGGGGCGGGA GCTTACATTC   2465
GGGGTTGTGA GTTTGTGGGC TGTTACCGGG GAATCTGTTC TACTTCTAAC AGAGATATTA   2525
AGGTGAGGCA GTGCAACTTT GACAAATGCT TACTGGGTAT TACTTGTAAG GGGGACTATC   2585
GTCTTTCGGG AAATGTGTGT TCTGAGACTT TCTGCTTTGC TCATTTAGAG GGAGAGGGTT   2645
TGGTTAAAAA CAACACAGTC AAGTCCCCTA GTCGCTGGAC CAGCGAGTCT GGCTTTTCCA   2705
TGATAACTTG TGCAGACGGC AGGGTTACGC CTTTGGGTTC CCTCCACATT GTGGGCAACC   2765
GTTGTAGGCG TTGGCCAACC ATGCAGGGGA ATGTGTTTAT CATGTCTAAA CTGTATCTGG   2825
GCAACAGAAT AGGGACTGTA GCCCTGCCCC AGTGTGCTTT CTACAAGTCC AGCATTTGTT   2885
TGGAGGAGAG GGCGACAAAC AAGCTGGTCT TGGCTTGTGC TTTTGAGAAT AATGTACTGG   2945
TGTACAAAGT GCTGAGACGG GAGAGTCCCT CAACCGTGAA AATGTGTGTT TGTGGGACTT   3005
CTCATTATGC AAAGCCTTTG ACACTGGCAA TTATTCTTC AGATATTCGG GCTAATCGAT   3065
ACATGTACAC TGTGGACTCA ACAGAGTTCA CTTCTGACGA GGATTAAAAG TGGGCGGGGC   3125
CAAGAGGGGT ATAAATAGGT GGGGAGGTTG AGGGGAGCCG TAGTTTCTGT TTTTCCCAGA   3185
CTGGGGGGGA CAACATGGCC GAGGAAGGGC GCATTTATGT GCCTTATGTA ACTGCCCGCC   3245
TGCCCAAGTG GTCGGGTTCG GTGCAGGATA AGACGGGCTC GAACATGTTG GGGGTGTGG   3305
TACTCCCTCC TAATTCACAG GCGCACCGGA CGGAGACCGT GGGCACTGAG GCCACCAGAG   3365
ACAACCTGCA CGCCGAGGGA GCGCGTCGTC CTGAGGATCA GACGCCCTAC ATGATCTTGG   3425
TGGAGGACTC TCTGGGAGGT TTGAAGAGGC GAATGGACTT GCTGGAAGAA TCTAATCAGC   3485
AGCTGCTGGC AACTCTCAAC CGTCTCCGTA CAGGACTCGC TGCCTATGTG CAGGCTAACC   3545
TTGTGGGCGG CCAAGTTAAC CCCTTTGTTT AAATAAAAAT ACACTCATAC AGTTTATTAT   3605
GCTGTCAATA AAATTCTTTA TTTTTCCTGT GATAATACCG TGTCCAGCGT GCTCTGTCAA   3665
TAAGGGTCCT ATGCATCCTG AGAAGGGCCT CATATACCCA TGGCATGAAT ATTAAGATAC   3725
ATGGGCATAA GGCCCTCAGA AGGGTTGAGG TAGAGCCACT GCAGACTTTC GTGGGGAGGT   3785
```

| | | | | | |
|---|---|---|---|---|---|
| AAGGTGTTGT | AAATAATCCA | GTCATACTGA | CTGTGCTGGG | CGTGGAAGGA | AAAGATGTCT | 3845 |
| TTTAGAAGAA | GGGTGATTGG | CAAAGGGAGG | CTCTTAGTGT | AGGTATTGAT | AAATCTGTTC | 3905 |
| AGTTGGGAGG | GATGCATTCG | GGGGCTAATA | AGGTGGAGTT | TAGCCTGAAT | CTTAAGGTTG | 3965 |
| GCAATGTTGC | CCCCTAGGTC | TTTGCGAGGA | TTCATGTTGT | GCAGTACCAC | AAAAACAGAG | 4025 |
| TAGCCTGTGC | ATTTGGGGAA | TTTATCATGA | AGCTT | | | 4060 |

( 2 ) INFORMATION FOR SEQ ID NO:2:

( i ) SEQUENCE CHARACTERISTICS:
        ( A ) LENGTH: 211 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Lys Tyr Leu Val Leu Val Leu Asn Asp Gly Met Ser Arg Ile Glu
 1               5                  10                  15

Lys Ala Leu Leu Cys Ser Asp Gly Glu Val Asp Leu Glu Cys His Glu
            20                  25                  30

Val Leu Pro Pro Ser Pro Ala Pro Val Pro Ala Ser Val Ser Pro Val
        35                  40                  45

Arg Ser Pro Pro Pro Leu Ser Pro Val Phe Pro Pro Ser Pro Pro Ala
    50                  55                  60

Pro Leu Val Asn Pro Glu Ala Ser Ser Leu Leu Gln Gln Tyr Arg Arg
65                  70                  75                  80

Glu Leu Leu Glu Arg Ser Leu Leu Arg Thr Ala Glu Gly Gln Gln Arg
                85                  90                  95

Ala Val Cys Pro Cys Glu Arg Leu Pro Val Glu Glu Asp Glu Cys Leu
           100                 105                 110

Asn Ala Val Asn Leu Leu Phe Pro Asp Pro Trp Leu Asn Ala Ala Glu
           115                 120                 125

Asn Gly Gly Asp Ile Phe Lys Ser Pro Ala Met Ser Pro Glu Pro Trp
       130                 135                 140

Ile Asp Leu Ser Ser Tyr Asp Ser Asp Val Glu Glu Val Thr Ser His
145                 150                 155                 160

Phe Phe Leu Asp Cys Pro Glu Asp Pro Ser Arg Glu Cys Ser Ser Cys
                165                 170                 175

Gly Phe His Gln Ala Gln Ser Gly Ile Pro Gly Ile Met Cys Ser Leu
           180                 185                 190

Cys Tyr Met Arg Gln Thr Tyr His Cys Ile Tyr Ser Pro Val Ser Glu
           195                 200                 205

Glu Glu Met
210
```

( 2 ) INFORMATION FOR SEQ ID NO:3:

( i ) SEQUENCE CHARACTERISTICS:
        ( A ) LENGTH: 4060 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1476..1946

( x i ) SEQUENCE DESCRIPTION: SEQ ID NO:3:

-continued

| | | | | | |
|---|---|---|---|---|---|
| CATCATCAAT | AATCTACAGT | ACACTGATGG | CAGCGGTCCA | ACTGCCAATC | ATTTTTGCCA | 60 |
| CGTCATTTAT | GACGCAACGA | CGGCGAGCGT | GGCGTGCTGA | CGTAACTGTG | GGGCGGAGCG | 120 |
| CGTCGCGGAG | GCGGCGGCGC | TGGGCGGGGC | TGAGGGCGGC | GGGGGCGGCG | CGCGGGGCGG | 180 |
| CGCGCGGGGC | GGGGCGAGGG | GCGGAGTTCC | GCACCCGCTA | CGTCATTTTC | AGACATTTTT | 240 |
| TAGCAAATTT | GCGCCTTTTG | CAAGCATTTT | TCTCACATTT | CAGGTATTTA | GAGGGCGGAT | 300 |
| TTTTGGTGTT | CGTACTTCCG | TGTCACATAG | TTCACTGTCA | ATCTTCATTA | CGGCTTAGAC | 360 |
| AAATTTTCGG | CGTCTTTTCC | GGGTTTATGT | CCCCGGTCAC | CTTTATGACT | GTGTGAAACA | 420 |
| CACCTGCCCA | TTGTTTACCC | TTGGTCAGTT | TTTTCGTCTC | CTAGGGTGGG | AACATCAAGA | 480 |
| ACAAATTTGC | CGAGTAATTG | TGCACCTTTT | TCCGCGTTAG | GACTGCGTTT | CACACGTAGA | 540 |
| CAGACTTTTT | CTCATTTTCT | CACACTCCGT | CGTCCGCTTC | AGAGCTCTGC | GTCTTCGCTG | 600 |
| CCACCATGAA | GTACCTGGTC | CTCGTTCTCA | ACGACGGCAT | GAGTCGAATT | GAAAAAGCTC | 660 |
| TCCTGTGCAG | CGATGGTGAG | GTGGATTTAG | AGTGTCATGA | GGTACTTCCC | CCTTCTCCCG | 720 |
| CGCCTGTCCC | CGCTTCTGTG | TCACCCGTGA | GGAGTCCTCC | TCCTCTGTCT | CCGGTGTTTC | 780 |
| CTCCGTCTCC | GCCAGCCCCG | CTTGTGAATC | AGAGGCGAG | TTCGCTGCTG | CAGCAGTATC | 840 |
| GGAGAGAGCT | GTTAGAGAGG | AGCCTGCTCC | GAACGGCCGA | AGGTCAGCAG | CGTGCAGTGT | 900 |
| GTCCATGTGA | GCGGTTGCCC | GTGGAAGAGG | ATGAGTGTCT | GAATGCCGTA | AATTTGCTGT | 960 |
| TTCCTGATCC | CTGGCTAAAT | GCAGCTGAAA | ATGGGGGTGA | TATTTTTAAG | TCTCCGGCTA | 1020 |
| TGTCTCCAGA | ACCGTGGATA | GATTTGTCTA | GCTACGATAG | CGATGTAGAA | GAGGTGACTA | 1080 |
| GTCACTTTTT | TCTGGATTGC | CCTGAAGACC | CCAGTCGGGA | GTGTTCATCT | TGTGGGTTTC | 1140 |
| ATCAGGCTCA | AAGCGGAATT | CCAGGCATTA | TGTGCAGTTT | GTGCTACATG | CGCCAAACCT | 1200 |
| ACCATTGCAT | CTATAGTAAG | TACATTCTGT | AAAAGAACAT | CTTGGTGATT | TCTAGGTATT | 1260 |
| GTTTAGGGAT | TAACTGGGTG | GAGTGATCTT | AATCCGGCAT | AACCAAATAC | ATGTTTTCAC | 1320 |
| AGGTCCAGTT | TCTGAAGAGG | AAATGTGAGT | CATGTTGACT | TGGCGCGCA | AGAGGAAATG | 1380 |
| TGAGTCATGT | TGACTTTGGC | GCGCCCTACG | GTGACTTTAA | AGCAATTTGA | GGATCACTTT | 1440 |

```
TTTGTTAGTC GCTATAAAGT AGTCACGGAG TCTTC ATG GAT CAC TTA AGC GTT   1493
                                       Met Asp His Leu Ser Val
                                                        215

CTT TTG GAT TTG AAG CTG CTT CGC TCT ATC GTA GCG GGG GCT TCA AAT  1541
Leu Leu Asp Leu Lys Leu Leu Arg Ser Ile Val Ala Gly Ala Ser Asn
    220                 225                 230

CGC ACT GGA GTG TGG AAG AGG CGG CTG TGG CTG GGA CGC CTG ACT CAA  1589
Arg Thr Gly Val Trp Lys Arg Arg Leu Trp Leu Gly Arg Leu Thr Gln
235                 240                 245

CTG GTC CAT GAT ACC TGC GTA GAG AAC GAG AGC ATA TTT CTC AAT TCT  1637
Leu Val His Asp Thr Cys Val Glu Asn Glu Ser Ile Phe Leu Asn Ser
250                 255                 260                 265

CTG CCA GGG AAT GAA GCT TTT TTA AGG TTG CTT CGG AGC GGC TAT TTT  1685
Leu Pro Gly Asn Glu Ala Phe Leu Arg Leu Leu Arg Ser Gly Tyr Phe
        270                 275                 280

GAA GTG TTT GAC GTG TTT GTG GTG CCT GAG CTG CAT CTG GAC ACT CCG  1733
Glu Val Phe Asp Val Phe Val Val Pro Glu Leu His Leu Asp Thr Pro
        285                 290                 295

GGT CGA GTG GTC GCC GCT CTT GCT CTG CTG GTG TTC ATC CTC AAC GAT  1781
Gly Arg Val Val Ala Ala Leu Ala Leu Leu Val Phe Ile Leu Asn Asp
        300                 305                 310

TTA GAC GCT AAT TCT GCT TCT TCA GGC TTT GAT TCA GGT TTT CTC GTG  1829
Leu Asp Ala Asn Ser Ala Ser Ser Gly Phe Asp Ser Gly Phe Leu Val
        315                 320                 325
```

| | | | | | | | | | | | | | | | | |
|---|---|---|---|---|---|---|---|---|---|---|---|---|---|---|---|---|
|GAC|CGT|CTC|TGC|GTG|CCG|CTA|TGG|CTG|AAG|GCC|AGG|GCG|TTC|AAG|ATC|1877|
|Asp|Arg|Leu|Cys|Val|Pro|Leu|Trp|Leu|Lys|Ala|Arg|Ala|Phe|Lys|Ile||
|330| | | | |335| | | | |340| | | | |345||
|ACC|CAG|AGC|TCC|AGG|AGC|ACT|TCG|CAG|CCT|TCC|TCG|TCG|CCC|GAC|AAG|1925|
|Thr|Gln|Ser|Ser|Arg|Ser|Thr|Ser|Gln|Pro|Ser|Ser|Ser|Pro|Asp|Lys||
| | | | |350| | | | |355| | | | |360| |

| | | | | | | |
|---|---|---|---|---|---|---|
|ACG|ACC|CAG|ACT|ACC|AGC|CAG TAGACGGGA CAGCCCACCC CGGGCTAGCC|1976|
|Thr|Thr|Gln|Thr|Thr|Ser|Gln|
| | | |365| | | |

| | | | | |
|---|---|---|---|---|---|
|TGGAGGAGGC|TGAACAGAGC|AGCACTCGTT|TCGAGCACAT|CAGTTACCGA GACGTGGTGG|2036|
|ATGACTTCAA|TAGATGCCAT|GATGTTTTTT|ATGAGAGGTA|CAGTTTTGAG GACATAAAGA|2096|
|GCTACGAGGC|TTTGCCTGAG|GACAATTTGG|AGCAGCTCAT|AGCTATGCAT GCTAAAATCA|2156|
|AGCTGCTGCC|CGGTCGGGAG|TATGAGTTGA|CTCAACCTTT|GAACATAACA TCTTGCGCCT|2216|
|ATGTGCTCGG|AAATGGGGCT|ACTATTAGGG|TAACAGGGGA|AGCCTCCCCG GCTATTAGAG|2276|
|TGGGGGCCAT|GGCCGTGGGT|CCGTGTGTAA|CAGGAATGAC|TGGGGTGACT TTTGTGAATT|2336|
|GTAGGTTTGA|GAGAGAGTCA|ACAATTAGGG|GGTCCCTGAT|ACGAGCTTCA ACTCACGTGC|2396|
|TGTTTCATGG|CTGTTATTTT|ATGGGAATTA|TGGGCACTTG|TATTGAGGTG GGGGCGGGAG|2456|
|CTTACATTCG|GGGTTGTGAG|TTTGTGGGCT|GTTACCGGGG|AATCTGTTCT ACTTCTAACA|2516|
|GAGATATTAA|GGTGAGGCAG|TGCAACTTTG|ACAAATGCTT|ACTGGGTATT ACTTGTAAGG|2576|
|GGGACTATCG|TCTTTCGGGA|AATGTGTGTT|CTGAGACTTT|CTGCTTGCT CATTTAGAGG|2636|
|GAGAGGGTTT|GGTTAAAAAC|AACACAGTCA|AGTCCCTAG|TCGCTGGACC AGCGAGTCTG|2696|
|GCTTTTCCAT|GATAACTTGT|GCAGACGGCA|GGGTTACGCC|TTTGGGTTCC CTCCACATTG|2756|
|TGGGCAACCG|TTGTAGGCGT|TGGCCAACCA|TGCAGGGAA|TGTGTTTATC ATGTCTAAAC|2816|
|TGTATCTGGG|CAACAGAATA|GGGACTGTAG|CCCTGCCCCA|GTGTGCTTTC TACAAGTCCA|2876|
|GCATTTGTTT|GGAGGAGAGG|GCGACAAACA|AGCTGGTCTT|GGCTTGTGCT TTTGAGAATA|2936|
|ATGTACTGGT|GTACAAAGTG|CTGAGACGGG|AGAGTCCCTC|AACCGTGAAA ATGTGTGTTT|2996|
|GTGGGACTTC|TCATTATGCA|AAGCCTTTGA|CACTGGCAAT|TATTTCTTCA GATATTCGGG|3056|
|CTAATCGATA|CATGTACACT|GTGGACTCAA|CAGAGTTCAC|TTCTGACGAG GATTAAAAGT|3116|
|GGGCGGGGCC|AAGAGGGGTA|TAAATAGGTG|GGGAGGTTGA|GGGGAGCCGT AGTTTCTGTT|3176|
|TTTCCCAGAC|TGGGGGGGAC|AACATGGCCG|AGGAAGGGCG|CATTTATGTG CCTTATGTAA|3236|
|CTGCCCGCCT|GCCCAAGTGG|TCGGGTTCGG|TGCAGGATAA|GACGGGCTCG AACATGTTGG|3296|
|GGGGTGTGGT|ACTCCCTCCT|AATTCACAGG|CGCACCGGAC|GGAGACCGTG GCACTGAGG|3356|
|CCACCAGAGA|CAACCTGCAC|GCCGAGGGAG|CGCGTCGTCC|TGAGGATCAG ACGCCCTACA|3416|
|TGATCTTGGT|GGAGGACTCT|CTGGGAGGTT|TGAAGAGGCG|AATGGACTTG CTGGAAGAAT|3476|
|CTAATCAGCA|GCTGCTGGCA|ACTCTCAACC|GTCTCCGTAC|AGGACTCGCT GCCTATGTGC|3536|
|AGGCTAACCT|TGTGGGCGGC|CAAGTTAACC|CCTTTGTTTA|AATAAAAATA CACTCATACA|3596|
|GTTTATTATG|CTGTCAATAA|AATTCTTTAT|TTTTCCTGTG|ATAATACCGT GTCCAGCGTG|3656|
|CTCTGTCAAT|AAGGGTCCTA|TGCATCCTGA|GAAGGGCCTC|ATATACCCAT GGCATGAATA|3716|
|TTAAGATACA|TGGGCATAAG|GCCCTCAGAA|GGGTTGAGGT|AGAGCCACTG CAGACTTTCG|3776|
|TGGGGAGGTA|AGGTGTTGTA|ATAATCCAG|TCATACTGAC|TGTGCTGGGC GTGGAAGGAA|3836|
|AAGATGTCTT|TTAGAAGAAG|GGTGATTGGC|AAAGGGAGGC|TCTTAGTGTA GGTATTGATA|3896|
|AATCTGTTCA|GTTGGGAGGG|ATGCATTCGG|GGGCTAATAA|GGTGGAGTTT AGCCTGAATC|3956|
|TTAAGGTTGG|CAATGTTGCC|CCCTAGGTCT|TTGCGAGGAT|TCATGTTGTG CAGTACCACA|4016|

AAAACAGAGT AGCCTGTGCA TTTGGGGAAT TTATCATGAA GCTT        4060

(2) INFORMATION FOR SEQ ID NO:4:

(i) SEQUENCE CHARACTERISTICS:
        (A) LENGTH: 157 amino acids
        (B) TYPE: amino acid
        (D) TOPOLOGY: linear (ii) MOLECULE TYPE: protein (xi) SEQUENCE DESCRIPTION: SEQ ID NO:4:

```
Met Asp His Leu Ser Val Leu Leu Asp Leu Lys Leu Leu Arg Ser Ile
 1               5                  10                  15
Val Ala Gly Ala Ser Asn Arg Thr Gly Val Trp Lys Arg Arg Leu Trp
            20                  25                  30
Leu Gly Arg Leu Thr Gln Leu Val His Asp Thr Cys Val Glu Asn Glu
        35                  40                  45
Ser Ile Phe Leu Asn Ser Leu Pro Gly Asn Glu Ala Phe Leu Arg Leu
    50                  55                  60
Leu Arg Ser Gly Tyr Phe Glu Val Phe Asp Val Phe Val Val Pro Glu
65                  70                  75                  80
Leu His Leu Asp Thr Pro Gly Arg Val Val Ala Ala Leu Ala Leu Leu
                85                  90                  95
Val Phe Ile Leu Asn Asp Leu Asp Ala Asn Ser Ala Ser Ser Gly Phe
            100                 105                 110
Asp Ser Gly Phe Leu Val Asp Arg Leu Cys Val Pro Leu Trp Leu Lys
        115                 120                 125
Ala Arg Ala Phe Lys Ile Thr Gln Ser Ser Arg Ser Thr Ser Gln Pro
    130                 135                 140
Ser Ser Ser Pro Asp Lys Thr Thr Gln Thr Thr Ser Gln
145                 150                 155
```

(2) INFORMATION FOR SEQ ID NO:5:

(i) SEQUENCE CHARACTERISTICS:
        (A) LENGTH: 4060 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1850..3109

(xi) SEQUENCE DESCRIPTION: SEQ ID NO:5:

CATCATCAAT AATCTACAGT ACACTGATGG CAGCGGTCCA ACTGCCAATC ATTTTTGCCA        60
CGTCATTTAT GACGCAACGA CGGCGAGCGT GGCGTGCTGA CGTAACTGTG GGGCGGAGCG        120
CGTCGCGGAG GCGGCGGCGC TGGGCGGGGC TGAGGGCGGC GGGGGCGGCG CGCGGGGCGG        180
CGCGCGGGGC GGGGCGAGGG GCGGAGTTCC GCACCCGCTA CGTCATTTTC AGACATTTTT        240
TAGCAAATTT GCGCCTTTTG CAAGCATTTT TCTCACATTT CAGGTATTTA GAGGGCGGAT        300
TTTTGGTGTT CGTACTTCCG TGTCACATAG TTCACTGTCA ATCTTCATTA CGGCTTAGAC        360
AAATTTTCGG CGTCTTTTCC GGGTTTATGT CCCCGGTCAC CTTTATGACT GTGTGAAACA        420
CACCTGCCCA TTGTTTACCC TTGGTCAGTT TTTTCGTCTC CTAGGGTGGG AACATCAAGA        480
ACAAATTTGC CGAGTAATTG TGCACCTTTT TCCGCGTTAG GACTGCGTTT CACACGTAGA        540

-continued

| | | | | | |
|---|---|---|---|---|---|
| CAGACTTTTT | CTCATTTTCT | CACACTCCGT | CGTCCGCTTC | AGAGCTCTGC | GTCTTCGCTG | 600 |
| CCACCATGAA | GTACCTGGTC | CTCGTTCTCA | ACGACGGCAT | GAGTCGAATT | GAAAAAGCTC | 660 |
| TCCTGTGCAG | CGATGGTGAG | GTGGATTTAG | AGTGTCATGA | GGTACTTCCC | CCTTCTCCCG | 720 |
| CGCCTGTCCC | CGCTTCTGTG | TCACCCGTGA | GGAGTCCTCC | TCCTCTGTCT | CCGGTGTTTC | 780 |
| CTCCGTCTCC | GCCAGCCCCG | CTTGTGAATC | CAGAGGCGAG | TTCGCTGCTG | CAGCAGTATC | 840 |
| GGAGAGAGCT | GTTAGAGAGG | AGCCTGCTCC | GAACGGCCGA | AGGTCAGCAG | CGTGCAGTGT | 900 |
| GTCCATGTGA | GCGGTTGCCC | GTGGAAGAGG | ATGAGTGTCT | GAATGCCGTA | AATTTGCTGT | 960 |
| TTCCTGATCC | CTGGCTAAAT | GCAGCTGAAA | ATGGGGGTGA | TATTTTAAG | TCTCCGGCTA | 1020 |
| TGTCTCCAGA | ACCGTGGATA | GATTTGTCTA | GCTACGATAG | CGATGTAGAA | GAGGTGACTA | 1080 |
| GTCACTTTTT | TCTGGATTGC | CCTGAAGACC | CCAGTCGGGA | GTGTTCATCT | TGTGGGTTTC | 1140 |
| ATCAGGCTCA | AAGCGGAATT | CCAGGCATTA | TGTGCAGTTT | GTGCTACATG | CGCCAAACCT | 1200 |
| ACCATTGCAT | CTATAGTAAG | TACATTCTGT | AAAAGAACAT | CTTGGTGATT | TCTAGGTATT | 1260 |
| GTTAGGGAT | TAACTGGGTG | GAGTGATCTT | AATCCGGCAT | AACCAAATAC | ATGTTTTCAC | 1320 |
| AGGTCCAGTT | TCTGAAGAGG | AAATGTGAGT | CATGTTGACT | TGGCGCGCA | AGAGGAAATG | 1380 |
| TGAGTCATGT | TGACTTTGGC | GCGCCCTACG | GTGACTTTAA | AGCAATTTGA | GGATCACTTT | 1440 |
| TTTGTTAGTC | GCTATAAAGT | AGTCACGGAG | TCTTCATGGA | TCACTTAAGC | GTTCTTTTGG | 1500 |
| ATTTGAAGCT | GCTTCGCTCT | ATCGTAGCGG | GGGCTTCAAA | TCGCACTGGA | GTGTGGAAGA | 1560 |
| GGCGGCTGTG | GCTGGGACGC | CTGACTCAAC | TGGTCCATGA | TACCTGCGTA | GAGAACGAGA | 1620 |
| GCATATTTCT | CAATTCTCTG | CCAGGGAATG | AAGCTTTTT | AAGGTTGCTT | CGGAGCGGCT | 1680 |
| ATTTTGAAGT | GTTTGACGTG | TTTGTGGTGC | CTGAGCTGCA | TCTGGACACT | CCGGGTCGAG | 1740 |
| TGGTCGCCGC | TCTTGCTCTG | CTGGTGTTCA | TCCTCAACGA | TTTAGACGCT | AATTCTGCTT | 1800 |
| CTTCAGGCTT | TGATTCAGGT | TTTCTCGTGG | ACCGTCTCTG | CGTGCCGCT | ATG GCT | 1855 |
| | | | | | Met Ala | |

```
GAA GGC CAG GGC GTT CAA GAT CAC CCA GAG CTC CAG GAG CAC TTC GCA        1903
Glu Gly Gln Gly Val Gln Asp His Pro Glu Leu Gln Glu His Phe Ala
160             165                 170                 175

GCC TTC CTC GTC GCC CGA CAA GAC GAC CCA GAC TAC CAG CCA GTA GAC        1951
Ala Phe Leu Val Ala Arg Gln Asp Asp Pro Asp Tyr Gln Pro Val Asp
        180                 185                 190

GGG GAC AGC CCA CCC CGG GCT AGC CTG GAG GAG GCT GAA CAG AGC AGC        1999
Gly Asp Ser Pro Pro Arg Ala Ser Leu Glu Glu Ala Glu Gln Ser Ser
                195                 200                 205

ACT CGT TTC GAG CAC ATC AGT TAC CGA GAC GTG GTG GAT GAC TTC AAT        2047
Thr Arg Phe Glu His Ile Ser Tyr Arg Asp Val Val Asp Asp Phe Asn
            210                 215                 220

AGA TGC CAT GAT GTT TTT TAT GAG AGG TAC AGT TTT GAG GAC ATA AAG        2095
Arg Cys His Asp Val Phe Tyr Glu Arg Tyr Ser Phe Glu Asp Ile Lys
    225                 230                 235

AGC TAC GAG GCT TTG CCT GAG GAC AAT TTG GAG CAG CTC ATA GCT ATG        2143
Ser Tyr Glu Ala Leu Pro Glu Asp Asn Leu Glu Gln Leu Ile Ala Met
240                 245                 250                 255

CAT GCT AAA ATC AAG CTG CTG CCC GGT CGG GAG TAT GAG TTG ACT CAA        2191
His Ala Lys Ile Lys Leu Leu Pro Gly Arg Glu Tyr Glu Leu Thr Gln
                260                 265                 270

CCT TTG AAC ATA ACA TCT TGC GCC TAT GTG CTC GGA AAT GGG GCT ACT        2239
Pro Leu Asn Ile Thr Ser Cys Ala Tyr Val Leu Gly Asn Gly Ala Thr
            275                 280                 285

ATT AGG GTA ACA GGG GAA GCC TCC CCG GCT ATT AGA GTG GGG GCC ATG        2287
Ile Arg Val Thr Gly Glu Ala Ser Pro Ala Ile Arg Val Gly Ala Met
    290                 295                 300
```

| | | | | | | | | | | | | | | | | |
|---|---|---|---|---|---|---|---|---|---|---|---|---|---|---|---|---|
| GCC | GTG | GGT | CCG | TGT | GTA | ACA | GGA | ATG | ACT | GGG | GTG | ACT | TTT | GTG | AAT | 2335 |
| Ala | Val | Gly | Pro | Cys | Val | Thr | Gly | Met | Thr | Gly | Val | Thr | Phe | Val | Asn | |
| | 305 | | | | 310 | | | | | | 315 | | | | | |
| TGT | AGG | TTT | GAG | AGA | GAG | TCA | ACA | ATT | AGG | GGG | TCC | CTG | ATA | CGA | GCT | 2383 |
| Cys | Arg | Phe | Glu | Arg | Glu | Ser | Thr | Ile | Arg | Gly | Ser | Leu | Ile | Arg | Ala | |
| 320 | | | | | 325 | | | | | 330 | | | | | 335 | |
| TCA | ACT | CAC | GTG | CTG | TTT | CAT | GGC | TGT | TAT | TTT | ATG | GGA | ATT | ATG | GGC | 2431 |
| Ser | Thr | His | Val | Leu | Phe | His | Gly | Cys | Tyr | Phe | Met | Gly | Ile | Met | Gly | |
| | | | | 340 | | | | | 345 | | | | | 350 | | |
| ACT | TGT | ATT | GAG | GTG | GGG | GCG | GGA | GCT | TAC | ATT | CGG | GGT | TGT | GAG | TTT | 2479 |
| Thr | Cys | Ile | Glu | Val | Gly | Ala | Gly | Ala | Tyr | Ile | Arg | Gly | Cys | Glu | Phe | |
| | | | 355 | | | | | 360 | | | | | 365 | | | |
| GTG | GGC | TGT | TAC | CGG | GGA | ATC | TGT | TCT | ACT | TCT | AAC | AGA | GAT | ATT | AAG | 2527 |
| Val | Gly | Cys | Tyr | Arg | Gly | Ile | Cys | Ser | Thr | Ser | Asn | Arg | Asp | Ile | Lys | |
| | | 370 | | | | | 375 | | | | | 380 | | | | |
| GTG | AGG | CAG | TGC | AAC | TTT | GAC | AAA | TGC | TTA | CTG | GGT | ATT | ACT | TGT | AAG | 2575 |
| Val | Arg | Gln | Cys | Asn | Phe | Asp | Lys | Cys | Leu | Leu | Gly | Ile | Thr | Cys | Lys | |
| 385 | | | | | 390 | | | | | 395 | | | | | | |
| GGG | GAC | TAT | CGT | CTT | TCG | GGA | AAT | GTG | TGT | TCT | GAG | ACT | TTC | TGC | TTT | 2623 |
| Gly | Asp | Tyr | Arg | Leu | Ser | Gly | Asn | Val | Cys | Ser | Glu | Thr | Phe | Cys | Phe | |
| 400 | | | | | 405 | | | | | 410 | | | | | 415 | |
| GCT | CAT | TTA | GAG | GGA | GAG | GGT | TTG | GTT | AAA | AAC | AAC | ACA | GTC | AAG | TCC | 2671 |
| Ala | His | Leu | Glu | Gly | Glu | Gly | Leu | Val | Lys | Asn | Asn | Thr | Val | Lys | Ser | |
| | | | | 420 | | | | | 425 | | | | | 430 | | |
| CCT | AGT | CGC | TGG | ACC | AGC | GAG | TCT | GGC | TTT | TCC | ATG | ATA | ACT | TGT | GCA | 2719 |
| Pro | Ser | Arg | Trp | Thr | Ser | Glu | Ser | Gly | Phe | Ser | Met | Ile | Thr | Cys | Ala | |
| | | | 435 | | | | | 440 | | | | | 445 | | | |
| GAC | GGC | AGG | GTT | ACG | CCT | TTG | GGT | TCC | CTC | CAC | ATT | GTG | GGC | AAC | CGT | 2767 |
| Asp | Gly | Arg | Val | Thr | Pro | Leu | Gly | Ser | Leu | His | Ile | Val | Gly | Asn | Arg | |
| | | 450 | | | | | 455 | | | | | 460 | | | | |
| TGT | AGG | CGT | TGG | CCA | ACC | ATG | CAG | GGG | AAT | GTG | TTT | ATC | ATG | TCT | AAA | 2815 |
| Cys | Arg | Arg | Trp | Pro | Thr | Met | Gln | Gly | Asn | Val | Phe | Ile | Met | Ser | Lys | |
| 465 | | | | | 470 | | | | | 475 | | | | | | |
| CTG | TAT | CTG | GGC | AAC | AGA | ATA | GGG | ACT | GTA | GCC | CTG | CCC | CAG | TGT | GCT | 2863 |
| Leu | Tyr | Leu | Gly | Asn | Arg | Ile | Gly | Thr | Val | Ala | Leu | Pro | Gln | Cys | Ala | |
| 480 | | | | | 485 | | | | | 490 | | | | | 495 | |
| TTC | TAC | AAG | TCC | AGC | ATT | TGT | TTG | GAG | GAG | AGG | GCG | ACA | AAC | AAG | CTG | 2911 |
| Phe | Tyr | Lys | Ser | Ser | Ile | Cys | Leu | Glu | Glu | Arg | Ala | Thr | Asn | Lys | Leu | |
| | | | | 500 | | | | | 505 | | | | | 510 | | |
| GTC | TTG | GCT | TGT | GCT | TTT | GAG | AAT | AAT | GTA | CTG | GTG | TAC | AAA | GTG | CTG | 2959 |
| Val | Leu | Ala | Cys | Ala | Phe | Glu | Asn | Asn | Val | Leu | Val | Tyr | Lys | Val | Leu | |
| | | | 515 | | | | | 520 | | | | | 525 | | | |
| AGA | CGG | GAG | AGT | CCC | TCA | ACC | GTG | AAA | ATG | TGT | GTT | TGT | GGG | ACT | TCT | 3007 |
| Arg | Arg | Glu | Ser | Pro | Ser | Thr | Val | Lys | Met | Cys | Val | Cys | Gly | Thr | Ser | |
| | | 530 | | | | | 535 | | | | | 540 | | | | |
| CAT | TAT | GCA | AAG | CCT | TTG | ACA | CTG | GCA | ATT | ATT | TCT | TCA | GAT | ATT | CGG | 3055 |
| His | Tyr | Ala | Lys | Pro | Leu | Thr | Leu | Ala | Ile | Ile | Ser | Ser | Asp | Ile | Arg | |
| 545 | | | | | 550 | | | | | 555 | | | | | | |
| GCT | AAT | CGA | TAC | ATG | TAC | ACT | GTG | GAC | TCA | ACA | GAG | TTC | ACT | TCT | GAC | 3103 |
| Ala | Asn | Arg | Tyr | Met | Tyr | Thr | Val | Asp | Ser | Thr | Glu | Phe | Thr | Ser | Asp | |
| 560 | | | | | 565 | | | | | 570 | | | | | 575 | |
| GAG | GAT | TAAAAGTGGG | CGGGGCCAAG | AGGGGTATAA | ATAGGTGGGG | AGGTTGAGGG | | | | | | | | | | 3159 |
| Glu | Asp | | | | | | | | | | | | | | | |

```
GAGCCGTAGT TTCTGTTTTT CCCAGACTGG GGGGGACAAC ATGGCCGAGG AAGGGCGCAT    3219

TTATGTGCCT TATGTAACTG CCCGCCTGCC CAAGTGGTCG GGTTCGGTGC AGGATAAGAC    3279

GGGCTCGAAC ATGTTGGGGG GTGTGGTACT CCCTCCTAAT TCACAGGCGC ACCGGACGGA    3339

GACCGTGGGC ACTGAGGCCA CCAGAGACAA CCTGCACGCC GAGGGAGCGC GTCGTCCTGA    3399
```

```
GGATCAGACG CCCTACATGA TCTTGGTGGA GGACTCTCTG GGAGGTTTGA AGAGGCGAAT    3459

GGACTTGCTG GAAGAATCTA ATCAGCAGCT GCTGGCAACT CTCAACCGTC TCCGTACAGG    3519

ACTCGCTGCC TATGTGCAGG CTAACCTTGT GGGCGGCCAA GTTAACCCCT TTGTTTAAAT    3579

AAAAATACAC TCATACAGTT TATTATGCTG TCAATAAAAT TCTTTATTTT TCCTGTGATA    3639

ATACCGTGTC CAGCGTGCTC TGTCAATAAG GGTCCTATGC ATCCTGAGAA GGGCCTCATA    3699

TACCCATGGC ATGAATATTA AGATACATGG GCATAAGGCC CTCAGAAGGG TTGAGGTAGA    3759

GCCACTGCAG ACTTTCGTGG GGAGGTAAGG TGTTGTAAAT AATCCAGTCA TACTGACTGT    3819

GCTGGGCGTG GAAGGAAAAG ATGTCTTTTA GAAGAAGGGT GATTGGCAAA GGGAGGCTCT    3879

TAGTGTAGGT ATTGATAAAT CTGTTCAGTT GGGAGGGATG CATTCGGGGG CTAATAAGGT    3939

GGAGTTTAGC CTGAATCTTA AGGTTGGCAA TGTTGCCCCC TAGGTCTTTG CGAGGATTCA    3999

TGTTGTGCAG TACCACAAAA ACAGAGTAGC CTGTGCATTT GGGGAATTTA TCATGAAGCT    4059

T                                                                    4060
```

( 2 ) INFORMATION FOR SEQ ID NO:6:

( i ) SEQUENCE CHARACTERISTICS:
       ( A ) LENGTH: 420 amino acids
       ( B ) TYPE: amino acid
       ( D ) TOPOLOGY: linear ( i i ) MOLECULE TYPE: protein ( x i ) SEQUENCE DESCRIPTION: SEQ ID NO:6:

```
Met  Ala  Glu  Gly  Gln  Gly  Val  Gln  Asp  His  Pro  Glu  Leu  Gln  Glu  His
 1                  5                      10                      15

Phe  Ala  Ala  Phe  Leu  Val  Ala  Arg  Gln  Asp  Pro  Asp  Tyr  Gln  Pro
             20                      25                      30

Val  Asp  Gly  Asp  Ser  Pro  Pro  Arg  Ala  Ser  Leu  Glu  Glu  Ala  Glu  Gln
             35                      40                      45

Ser  Ser  Thr  Arg  Phe  Glu  His  Ile  Ser  Tyr  Arg  Asp  Val  Val  Asp  Asp
       50                      55                      60

Phe  Asn  Arg  Cys  His  Asp  Val  Phe  Tyr  Glu  Arg  Tyr  Ser  Phe  Glu  Asp
 65                      70                      75                      80

Ile  Lys  Ser  Tyr  Glu  Ala  Leu  Pro  Glu  Asp  Asn  Leu  Glu  Gln  Leu  Ile
                85                      90                      95

Ala  Met  His  Ala  Lys  Ile  Lys  Leu  Leu  Pro  Gly  Arg  Glu  Tyr  Glu  Leu
               100                     105                     110

Thr  Gln  Pro  Leu  Asn  Ile  Thr  Ser  Cys  Ala  Tyr  Val  Leu  Gly  Asn  Gly
          115                     120                     125

Ala  Thr  Ile  Arg  Val  Thr  Gly  Glu  Ala  Ser  Pro  Ala  Ile  Arg  Val  Gly
     130                     135                     140

Ala  Met  Ala  Val  Gly  Pro  Cys  Val  Thr  Gly  Met  Thr  Gly  Val  Thr  Phe
145                     150                     155                     160

Val  Asn  Cys  Arg  Phe  Glu  Arg  Glu  Ser  Thr  Ile  Arg  Gly  Ser  Leu  Ile
                165                     170                     175

Arg  Ala  Ser  Thr  His  Val  Leu  Phe  His  Gly  Cys  Tyr  Phe  Met  Gly  Ile
               180                     185                     190

Met  Gly  Thr  Cys  Ile  Glu  Val  Gly  Ala  Gly  Ala  Tyr  Ile  Arg  Gly  Cys
          195                     200                     205

Glu  Phe  Val  Gly  Cys  Tyr  Arg  Gly  Ile  Cys  Ser  Thr  Ser  Asn  Arg  Asp
     210                     215                     220

Ile  Lys  Val  Arg  Gln  Cys  Asn  Phe  Asp  Lys  Cys  Leu  Leu  Gly  Ile  Thr
225                     230                     235                     240
```

| | | | | | | | | | | | | | | |
|---|---|---|---|---|---|---|---|---|---|---|---|---|---|---|
| Cys | Lys | Gly | Asp | Tyr 245 | Arg | Leu | Ser | Gly | Asn 250 | Val | Cys | Ser | Glu | Thr 255 | Phe |
| Cys | Phe | Ala | His 260 | Leu | Glu | Gly | Glu | Gly 265 | Leu | Val | Lys | Asn | Asn 270 | Thr | Val |
| Lys | Ser | Pro 275 | Ser | Arg | Trp | Thr | Ser 280 | Glu | Ser | Gly | Phe | Ser 285 | Met | Ile | Thr |
| Cys | Ala 290 | Asp | Gly | Arg | Val | Thr 295 | Pro | Leu | Gly | Ser | Leu 300 | His | Ile | Val | Gly |
| Asn 305 | Arg | Cys | Arg | Arg | Trp 310 | Pro | Thr | Met | Gln | Gly 315 | Asn | Val | Phe | Ile | Met 320 |
| Ser | Lys | Leu | Tyr | Leu 325 | Gly | Asn | Arg | Ile | Gly 330 | Thr | Val | Ala | Leu | Pro 335 | Gln |
| Cys | Ala | Phe | Tyr 340 | Lys | Ser | Ser | Ile | Cys 345 | Leu | Glu | Glu | Arg | Ala 350 | Thr | Asn |
| Lys | Leu | Val 355 | Leu | Ala | Cys | Ala | Phe 360 | Glu | Asn | Asn | Val | Leu 365 | Val | Tyr | Lys |
| Val | Leu 370 | Arg | Arg | Glu | Ser | Pro 375 | Ser | Thr | Val | Lys | Met 380 | Cys | Val | Cys | Gly |
| Thr 385 | Ser | His | Tyr | Ala | Lys 390 | Pro | Leu | Thr | Leu | Ala 395 | Ile | Ile | Ser | Ser | Asp 400 |
| Ile | Arg | Ala | Asn | Arg 405 | Tyr | Met | Tyr | Thr | Val 410 | Asp | Ser | Thr | Glu | Phe 415 | Thr |
| Ser | Asp | Glu | Asp 420 | | | | | | | | | | | | |

( 2 ) INFORMATION FOR SEQ ID NO:7:

( i ) SEQUENCE CHARACTERISTICS:
        ( A ) LENGTH: 4060 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 3200..3574

( x i ) SEQUENCE DESCRIPTION: SEQ ID NO:7:

| | | | | | | |
|---|---|---|---|---|---|---|
| CATCATCAAT | AATCTACAGT | ACACTGATGG | CAGCGGTCCA | ACTGCCAATC | ATTTTTGCCA | 60 |
| CGTCATTTAT | GACGCAACGA | CGGCGAGCGT | GGCGTGCTGA | CGTAACTGTG | GGGCGGAGCG | 120 |
| CGTCGCGGAG | GCGGCGGCGC | TGGGCGGGGC | TGAGGGCGGC | GGGGGCGGCG | CGCGGGGCGG | 180 |
| CGCGCGGGGC | GGGGCGAGGG | GCGGAGTTCC | GCACCCGCTA | CGTCATTTTC | AGACATTTTT | 240 |
| TAGCAAATTT | GCGCCTTTTG | CAAGCATTTT | TCTCACATTT | CAGGTATTTA | GAGGGCGGAT | 300 |
| TTTTGGTGTT | CGTACTTCCG | TGTCACATAG | TTCACTGTCA | ATCTTCATTA | CGGCTTAGAC | 360 |
| AAATTTTCGG | CGTCTTTTCC | GGGTTTATGT | CCCCGGTCAC | CTTTATGACT | GTGTGAAACA | 420 |
| CACCTGCCCA | TTGTTTACCC | TTGGTCAGTT | TTTTCGTCTC | CTAGGGTGGG | AACATCAAGA | 480 |
| ACAAATTTGC | CGAGTAATTG | TGCACCTTTT | TCCGCGTTAG | GACTGCGTTT | CACACGTAGA | 540 |
| CAGACTTTTT | CTCATTTTCT | CACACTCCGT | CGTCCGCTTC | AGAGCTCTGC | GTCTTCGCTG | 600 |
| CCACCATGAA | GTACCTGGTC | CTCGTTCTCA | ACGACGGCAT | GAGTCGAATT | GAAAAAGCTC | 660 |
| TCCTGTGCAG | CGATGGTGAG | GTGGATTTAG | AGTGTCATGA | GGTACTTCCC | CCTTCTCCCG | 720 |
| CGCCTGTCCC | CGCTTCTGTG | TCACCCGTGA | GGAGTCCTCC | TCCTCTGTCT | CCGGTGTTTC | 780 |

-continued

| | | | | | | |
|---|---|---|---|---|---|---|
| CTCCGTCTCC | GCCAGCCCCG | CTTGTGAATC | CAGAGGCGAG | TTCGCTGCTG | CAGCAGTATC | 840 |
| GGAGAGAGCT | GTTAGAGAGG | AGCCTGCTCC | GAACGGCCGA | AGGTCAGCAG | CGTGCAGTGT | 900 |
| GTCCATGTGA | GCGGTTGCCC | GTGGAAGAGG | ATGAGTGTCT | GAATGCCGTA | AATTTGCTGT | 960 |
| TTCCTGATCC | CTGGCTAAAT | GCAGCTGAAA | ATGGGGGTGA | TATTTTAAG | TCTCCGGCTA | 1020 |
| TGTCTCCAGA | ACCGTGGATA | GATTTGTCTA | GCTACGATAG | CGATGTAGAA | GAGGTGACTA | 1080 |
| GTCACTTTTT | TCTGGATTGC | CCTGAAGACC | CCAGTCGGGA | GTGTTCATCT | TGTGGGTTTC | 1140 |
| ATCAGGCTCA | AAGCGGAATT | CCAGGCATTA | TGTGCAGTTT | GTGCTACATG | CGCCAAACCT | 1200 |
| ACCATTGCAT | CTATAGTAAG | TACATTCTGT | AAAAGAACAT | CTTGGTGATT | TCTAGGTATT | 1260 |
| GTTAGGGAT | TAACTGGGTG | GAGTGATCTT | AATCCGGCAT | AACCAAATAC | ATGTTTTCAC | 1320 |
| AGGTCCAGTT | TCTGAAGAGG | AAATGTGAGT | CATGTTGACT | TTGGCGCGCA | AGAGGAAATG | 1380 |
| TGAGTCATGT | TGACTTTGGC | GCGCCCTACG | GTGACTTTAA | AGCAATTTGA | GGATCACTTT | 1440 |
| TTTGTTAGTC | GCTATAAAGT | AGTCACGGAG | TCTTCATGGA | TCACTTAAGC | GTTCTTTTGG | 1500 |
| ATTTGAAGCT | GCTTCGCTCT | ATCGTAGCGG | GGGCTTCAAA | TCGCACTGGA | GTGTGGAAGA | 1560 |
| GGCGGCTGTG | GCTGGGACGC | CTGACTCAAC | TGGTCCATGA | TACCTGCGTA | GAGAACGAGA | 1620 |
| GCATATTTCT | CAATTCTCTG | CCAGGGAATG | AAGCTTTTTT | AAGGTTGCTT | CGGAGCGGCT | 1680 |
| ATTTGAAGT | GTTTGACGTG | TTTGTGGTGC | CTGAGCTGCA | TCTGGACACT | CCGGGTCGAG | 1740 |
| TGGTCGCCGC | TCTTGCTCTG | CTGGTGTTCA | TCCTCAACGA | TTTAGACGCT | AATTCTGCTT | 1800 |
| CTTCAGGCTT | TGATTCAGGT | TTTCTCGTGG | ACCGTCTCTG | CGTGCCGCTA | TGGCTGAAGG | 1860 |
| CCAGGGCGTT | CAAGATCACC | CAGAGCTCCA | GGAGCACTTC | GCAGCCTTCC | TCGTCGCCCG | 1920 |
| ACAAGACGAC | CCAGACTACC | AGCCAGTAGA | CGGGGACAGC | CCACCCCGGG | CTAGCCTGGA | 1980 |
| GGAGGCTGAA | CAGAGCAGCA | CTCGTTTCGA | GCACATCAGT | TACCGAGACG | TGGTGGATGA | 2040 |
| CTTCAATAGA | TGCCATGATG | TTTTTTATGA | GAGGTACAGT | TTTGAGGACA | TAAAGAGCTA | 2100 |
| CGAGGCTTTG | CCTGAGGACA | ATTTGGAGCA | GCTCATAGCT | ATGCATGCTA | AAATCAAGCT | 2160 |
| GCTGCCCGGT | CGGGAGTATG | AGTTGACTCA | ACCTTTGAAC | ATAACATCTT | GCGCCTATGT | 2220 |
| GCTCGGAAAT | GGGGCTACTA | TTAGGGTAAC | AGGGGAAGCC | TCCCCGGCTA | TTAGAGTGGG | 2280 |
| GGCCATGGCC | GTGGGTCCGT | GTGTAACAGG | AATGACTGGG | GTGACTTTTG | TGAATTGTAG | 2340 |
| GTTTGAGAGA | GAGTCAACAA | TTAGGGGGTC | CCTGATACGA | GCTTCAACTC | ACGTGCTGTT | 2400 |
| TCATGGCTGT | TATTTTATGG | GAATTATGGG | CACTTGTATT | GAGGTGGGGG | CGGGAGCTTA | 2460 |
| CATTCGGGGT | TGTGAGTTTG | TGGGCTGTTA | CCGGGGAATC | TGTTCTACTT | CTAACAGAGA | 2520 |
| TATTAAGGTG | AGGCAGTGCA | ACTTTGACAA | ATGCTTACTG | GGTATTACTT | GTAAGGGGA | 2580 |
| CTATCGTCTT | TCGGGAAATG | TGTGTTCTGA | GACTTTCTGC | TTTGCTCATT | TAGAGGGAGA | 2640 |
| GGGTTTGGTT | AAAAACAACA | CAGTCAAGTC | CCCTAGTCGC | TGGACCAGCG | AGTCTGGCTT | 2700 |
| TTCCATGATA | ACTTGTGCAG | ACGGCAGGGT | TACGCCTTTG | GGTTCCCTCC | ACATTGTGGG | 2760 |
| CAACCGTTGT | AGGCGTTGGC | CAACCATGCA | GGGGAATGTG | TTTATCATGT | CTAAACTGTA | 2820 |
| TCTGGGCAAC | AGAATAGGGA | CTGTAGCCCT | GCCCCAGTGT | GCTTTCTACA | AGTCCAGCAT | 2880 |
| TTGTTTGGAG | GAGAGGGCGA | CAAACAAGCT | GGTCTTGGCT | TGTGCTTTTG | AGAATAATGT | 2940 |
| ACTGGTGTAC | AAAGTGCTGA | GACGGGAGAG | TCCCTCAACC | GTGAAAATGT | GTGTTTGTGG | 3000 |
| GACTTCTCAT | TATGCAAAGC | CTTTGACACT | GGCAATTATT | TCTTCAGATA | TTCGGGCTAA | 3060 |
| TCGATACATG | TACACTGTGG | ACTCAACAGA | GTTCACTTCT | GACGAGGATT | AAAAGTGGGC | 3120 |
| GGGGCCAAGA | GGGGTATAAA | TAGGTGGGGA | GGTTGAGGGG | AGCCGTAGTT | TCTGTTTTTC | 3180 |

-continued

```
CCAGACTGGG GGGGACAAC ATG GCC GAG GAA GGG CGC ATT TAT GTG CCT TAT        3232
                    Met Ala Glu Glu Gly Arg Ile Tyr Val Pro Tyr
                                    425                 430

GTA ACT GCC CGC CTG CCC AAG TGG TCG GGT TCG GTG CAG GAT AAG ACG        3280
Val Thr Ala Arg Leu Pro Lys Trp Ser Gly Ser Val Gln Asp Lys Thr
            435             440                 445

GGC TCG AAC ATG TTG GGG GGT GTG GTA CTC CCT CCT AAT TCA CAG GCG        3328
Gly Ser Asn Met Leu Gly Gly Val Val Leu Pro Pro Asn Ser Gln Ala
        450             455                 460

CAC CGG ACG GAG ACC GTG GGC ACT GAG GCC ACC AGA GAC AAC CTG CAC        3376
His Arg Thr Glu Thr Val Gly Thr Glu Ala Thr Arg Asp Asn Leu His
    465             470                 475

GCC GAG GGA GCG CGT CGT CCT GAG GAT CAG ACG CCC TAC ATG ATC TTG        3424
Ala Glu Gly Ala Arg Arg Pro Glu Asp Gln Thr Pro Tyr Met Ile Leu
480             485                 490                 495

GTG GAG GAC TCT CTG GGA GGT TTG AAG AGG CGA ATG GAC TTG CTG GAA        3472
Val Glu Asp Ser Leu Gly Gly Leu Lys Arg Arg Met Asp Leu Leu Glu
                500             505                 510

GAA TCT AAT CAG CAG CTG CTG GCA ACT CTC AAC CGT CTC CGT ACA GGA        3520
Glu Ser Asn Gln Gln Leu Leu Ala Thr Leu Asn Arg Leu Arg Thr Gly
            515             520                 525

CTC GCT GCC TAT GTG CAG GCT AAC CTT GTG GGC GGC CAA GTT AAC CCC        3568
Leu Ala Ala Tyr Val Gln Ala Asn Leu Val Gly Gly Gln Val Asn Pro
        530             535                 540

TTT GTT TAAATAAAAA TACACTCATA CAGTTTATTA TGCTGTCAAT AAAATTCTTT        3624
Phe Val
    545

ATTTTTCCTG TGATAATACC GTGTCCAGCG TGCTCTGTCA ATAAGGGTCC TATGCATCCT        3684
GAGAAGGGCC TCATATACCC ATGGCATGAA TATTAAGATA CATGGGCATA AGCCCTCAG         3744
AAGGGTTGAG GTAGAGCCAC TGCAGACTTT CGTGGGGAGG TAAGGTGTTG TAAATAATCC        3804
AGTCATACTG ACTGTGCTGG GCGTGGAAGG AAAAGATGTC TTTTAGAAGA AGGGTGATTG        3864
GCAAAGGGAG GCTCTTAGTG TAGGTATTGA TAAATCTGTT CAGTTGGGAG GGATGCATTC        3924
GGGGGCTAAT AAGGTGGAGT TTAGCCTGAA TCTTAAGGTT GGCAATGTTG CCCCCTAGGT        3984
CTTTGCGAGG ATTCATGTTG TGCAGTACCA CAAAAACAGA GTAGCCTGTG CATTTGGGGA        4044
ATTTATCATG AAGCTT                                                      4060
```

( 2 ) INFORMATION FOR SEQ ID NO:8:

( i ) SEQUENCE CHARACTERISTICS:
        ( A ) LENGTH: 125 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Ala Glu Glu Gly Arg Ile Tyr Val Pro Tyr Val Thr Ala Arg Leu
 1               5                  10                  15

Pro Lys Trp Ser Gly Ser Val Gln Asp Lys Thr Gly Ser Asn Met Leu
             20                  25                  30

Gly Gly Val Val Leu Pro Pro Asn Ser Gln Ala His Arg Thr Glu Thr
         35                  40                  45

Val Gly Thr Glu Ala Thr Arg Asp Asn Leu His Ala Glu Gly Ala Arg
     50                  55                  60

Arg Pro Glu Asp Gln Thr Pro Tyr Met Ile Leu Val Glu Asp Ser Leu
 65                  70                  75                  80
```

Gly Gly Leu Lys Arg Arg Met Asp Leu Leu Glu Glu Ser Asn Gln Gln
              85                      90                    95

Leu Leu Ala Thr Leu Asn Arg Leu Arg Thr Gly Leu Ala Ala Tyr Val
            100                 105                 110

Gln Ala Asn Leu Val Gly Gly Gln Val Asn Pro Phe Val
            115             120             125

(2) INFORMATION FOR SEQ ID NO:9:

(i) SEQUENCE CHARACTERISTICS:
        (A) LENGTH: 54 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Glu Glu Phe Val Leu Asp Tyr Val Glu His Pro Gly His Gly Cys Arg
1               5                   10                  15

Ser Cys His Tyr His Arg Arg Asn Thr Gly Asp Pro Asp Ile Met Cys
            20              25                  30

Ser Leu Cys Tyr Met Arg Thr Cys Gly Met Phe Val Tyr Ser Pro Val
            35              40                  45

Ser Glu Pro Glu Pro Glu
            50

(2) INFORMATION FOR SEQ ID NO:10:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Ile Asp Leu Thr Cys His Glu Ala Gly Phe Pro Pro Ser
1               5                   10

(2) INFORMATION FOR SEQ ID NO:11:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Leu Asp Phe Ser Thr Pro Gly Arg Ala Ala Ala Ala Val Ala Phe Leu
1               5                   10                  15

Ser Phe Ile (2) INFORMATION FOR SEQ ID NO:12:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Gln  Ser  Ser  Asn  Ser  Thr  Ser
 1              5
```

(2) INFORMATION FOR SEQ ID NO:13:

(i) SEQUENCE CHARACTERISTICS:
        (A) LENGTH: 347 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

```
Gln  Lys  Tyr  Ser  Ile  Glu  Gln  Leu  Thr  Thr  Tyr  Trp  Leu  Gln  Pro  Gly
 1              5                        10                       15

Asp  Asp  Phe  Glu  Glu  Ala  Ile  Arg  Val  Tyr  Ala  Lys  Val  Ala  Leu  Arg
               20                       25                       30

Pro  Asp  Cys  Lys  Tyr  Lys  Ile  Ser  Lys  Leu  Val  Asn  Ile  Arg  Asn  Cys
               35                       40                       45

Cys  Tyr  Ile  Ser  Gly  Asn  Gly  Ala  Glu  Val  Glu  Ile  Asp  Thr  Glu  Asp
     50                       55                       60

Arg  Val  Ala  Phe  Arg  Cys  Ser  Met  Ile  Asn  Met  Trp  Pro  Gly  Val  Leu
 65                  70                       75                            80

Gly  Met  Asp  Gly  Val  Val  Ile  Met  Asn  Val  Arg  Phe  Thr  Gly  Pro  Asn
                     85                       90                       95

Phe  Ser  Gly  Thr  Val  Phe  Leu  Ala  Asn  Thr  Asn  Leu  Ile  Leu  His  Gly
               100                      105                      110

Val  Ser  Phe  Tyr  Gly  Phe  Asn  Asn  Thr  Cys  Val  Glu  Ala  Trp  Thr  Asp
               115                      120                      125

Val  Arg  Val  Arg  Gly  Cys  Ala  Phe  Tyr  Cys  Cys  Trp  Lys  Gly  Val  Val
          130                      135                      140

Cys  Arg  Pro  Lys  Ser  Arg  Ala  Ser  Ile  Lys  Lys  Cys  Leu  Phe  Glu  Arg
145                      150                      155                      160

Cys  Thr  Leu  Gly  Ile  Leu  Ser  Glu  Gly  Asn  Ser  Arg  Val  Arg  His  Asn
                    165                      170                      175

Val  Ala  Ser  Asp  Cys  Gly  Cys  Phe  Met  Leu  Val  Lys  Ser  Val  Ala  Val
               180                      185                      190

Ile  Lys  His  Asn  Met  Val  Cys  Gly  Asn  Cys  Glu  Asp  Arg  Ala  Ser  Gln
          195                      200                      205

Met  Leu  Thr  Cys  Ser  Asp  Gly  Asn  Cys  His  Leu  Leu  Lys  Thr  Ile  His
     210                      215                      220

Val  Ala  Ser  His  Ser  Arg  Lys  Ala  Trp  Pro  Val  Phe  Glu  His  Asn  Ile
225                      230                      235                      240

Leu  His  Arg  Cys  Ser  Leu  His  Leu  Gly  Asn  Arg  Arg  Gly  Val  Phe  Leu
                    245                      250                      255

Pro  Tyr  Gln  Cys  Asn  Leu  Ser  His  Thr  Lys  Ile  Leu  Leu  Glu  Pro  Glu
               260                      265                      270

Ser  Met  Ser  Lys  Val  Asn  Leu  Asn  Gly  Val  Phe  Asp  Met  Thr  Met  Lys
               275                      280                      285

Ile  Trp  Lys  Val  Leu  Arg  Tyr  Asp  Glu  Thr  Arg  Thr  Arg  Cys  Arg  Pro
     290                      295                      300

Cys  Glu  Cys  Gly  Gly  Lys  His  Ile  Arg  Asn  Gln  Pro  Val  Met  Leu  Asp
305                      310                      315                      320

Val  Thr  Glu  Glu  Leu  Arg  Pro  Asp  His  Leu  Val  Leu  Ala  Cys  His  Arg
                    325                      330                      335
```

```
                Ala  Glu  Phe  Gly  Ser  Ser  Asp  Glu  Asp  Thr  Asp
                              340                     345
```

( 2 ) INFORMATION FOR SEQ ID NO:14:

( i ) SEQUENCE CHARACTERISTICS:
        ( A ) LENGTH: 140 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:14:

```
        Met  Ser  Thr  Asn  Ser  Phe  Asp  Gly  Ser  Ile  Val  Ser  Ser  Tyr  Leu  Thr
        1                   5                        10                       15

Thr  Arg  Met  Pro  Pro  Trp  Ala  Gly  Val  Arg  Gln  Asn  Val  Met  Gly  Ser
                       20                        25                       30

Ser  Ile  Asp  Gly  Arg  Pro  Val  Leu  Pro  Ala  Asn  Ser  Thr  Thr  Leu  Thr
                       35                        40                       45

Tyr  Glu  Thr  Val  Ser  Gly  Thr  Pro  Leu  Glu  Thr  Ala  Ala  Ser  Ala  Ala
                  50                        55                        60

Ala  Ser  Ala  Ala  Ala  Ala  Thr  Ala  Arg  Gly  Ile  Val  Thr  Asp  Phe  Ala
        65                        70                        75                       80

Phe  Leu  Ser  Pro  Leu  Ala  Ser  Ser  Ala  Ala  Ser  Arg  Ser  Ser  Ala  Arg
                            85                        90                       95

Asp  Asp  Lys  Leu  Thr  Ala  Leu  Leu  Ala  Gln  Leu  Asp  Ser  Leu  Thr  Arg
                            100                      105                      110

Glu  Leu  Asn  Val  Val  Ser  Gln  Gln  Leu  Leu  Asp  Leu  Arg  Gln  Gln  Val
                       115                       120                      125

Ser  Ala  Leu  Lys  Ala  Ser  Ser  Pro  Pro  Asn  Ala  Val
                  130                      135                      140
```

( 2 ) INFORMATION FOR SEQ ID NO:15:

( i ) SEQUENCE CHARACTERISTICS:
        ( A ) LENGTH: 5100 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 2..418

( x i ) SEQUENCE DESCRIPTION: SEQ ID NO:15:

```
C  CTC  ATC  AAA  CAA  CCC  GTG  GTG  GGC  ACC  ACC  CAC  GTG  GAA  ATG  CCT           46
   Leu  Ile  Lys  Gln  Pro  Val  Val  Gly  Thr  Thr  His  Val  Glu  Met  Pro
                  130                      135                      140

CGC  AAC  GAA  GTC  CTA  GAA  CAA  CAT  CTG  ACC  TCA  CAT  GGC  GCT  CAA  ATC          94
Arg  Asn  Glu  Val  Leu  Glu  Gln  His  Leu  Thr  Ser  His  Gly  Ala  Gln  Ile
                  145                      150                      155

GCG  GGC  GGA  GGC  GCT  GCG  GGC  GAT  TAC  TTT  AAA  AGC  CCC  ACT  TCA  GCT         142
Ala  Gly  Gly  Gly  Ala  Ala  Gly  Asp  Tyr  Phe  Lys  Ser  Pro  Thr  Ser  Ala
                  160                      165                      170

CGA  ACC  CTT  ATC  CCG  CTC  ACC  GCC  TCC  TGC  TTA  AGA  CCA  GAT  GGA  GTC         190
Arg  Thr  Leu  Ile  Pro  Leu  Thr  Ala  Ser  Cys  Leu  Arg  Pro  Asp  Gly  Val
                  175                      180                      185

TTT  CAA  CTA  GGA  GGA  GGC  TCG  CGT  TCA  TCT  TTC  AAC  CCC  CTG  CAA  ACA         238
Phe  Gln  Leu  Gly  Gly  Gly  Ser  Arg  Ser  Ser  Phe  Asn  Pro  Leu  Gln  Thr
190                      195                      200
```

```
GAT TTT GCC TTC CAC GCC CTG CCC TCC AGA CCG CGC CAC GGG GGC ATA      286
Asp Phe Ala Phe His Ala Leu Pro Ser Arg Pro Arg His Gly Gly Ile
205             210             215             220

GGA TCC AGG CAG TTT GTA GAG GAA TTT GTG CCC GCC GTC TAC CTC AAC      334
Gly Ser Arg Gln Phe Val Glu Glu Phe Val Pro Ala Val Tyr Leu Asn
            225             230             235

CCC TAC TCG GGA CCG CCG GAC TCT TAT CCG GAC CAG TTT ATA CGC CAC      382
Pro Tyr Ser Gly Pro Pro Asp Ser Tyr Pro Asp Gln Phe Ile Arg His
            240             245             250

TAC AAC GTG TAC AGC AAC TCT GTG AGC GGT TAT AGC TGAGATTGTA           428
Tyr Asn Val Tyr Ser Asn Ser Val Ser Gly Tyr Ser
        255             260

AGACTCTCCT ATCTGTCTCT GTGCTGCTTT TCCGCTTCAA GCCCCACAAG CATGAAGGGG    488
TTTCTGCTCA TCTTCAGCCT GCTTGTGCAT TGTCCCCTAA TTCATGTTGG GACCATTAGC    548
TTCTATGCTG CAAGGCCCGG GTCTGAGCCT AACGCGACTT ATGTTTGTGA CTATGGAAGC    608
GAGTCAGATT ACAACCCCAC CACGGTTCTG TGGTTGGCTC GAGAGACCGA TGGCTCCTGG    668
ATCTCTGTTC TTTTCCGTCA CAACGGCTCC TCAACTGCAG CCCCGGGGT CGTCGCGCAC     728
TTTACTGACC ACAACAGCAG CATTGTGGTG CCCCAGTATT ACCTCCTCAA CAACTCACTC    788
TCTAAGCTCT GCTGCTCATA CCGGCACAAC GAGCGTTCTC AGTTTACCTG CAAACAAGCT    848
GACGTCCCTA CCTGTCACGA GCCCGGCAAG CCGCTCACCC TCCGCGTCTC CCCCGCGCTG    908
GGAACTGCCC ACCAAGCAGT CACTTGGTTT TTTCAAAATG TACCCATAGC TACTGTTTAC    968
CGACCTTGGG GCAATGTAAC TTGGTTTTGT CCTCCCTTCA TGTGTACCTT TAATGTCAGC   1028
CTGAACTCCC TACTTATTTA CAACTTTTCT GACAAAACCG GGGGCAATA CACAGCTCTC    1088
ATGCACTCCG GACCTGCTTC CCTCTTTCAG CTCTTTAAGC CAACGACTTG TGTCACCAAG   1148
GTGGAGGACC CGCCGTATGC CAACGACCCG GCCTCGCCTG TGTGGCGCCC ACTGCTTTTT   1208
GCCTTCGTCC TCTGCACCGG CTGCGCGGTG TTGTTAACCG CCTTCGGTCC ATCGATTCTA   1268
TCCGGTACCC GAAAGCTTAT CTCAGCCCGC TTTTGGAGTC CCGAGCCCTA TACCACCCTC   1328
CACTAACAGT CCCCCCATGG AGCCAGACGG AGTTCATGCC GAGCAGCAGT TTATCCTCAA   1388
TCAGATTTCC TGCGCCAACA CTGCCCTCCA GCGTCAAAGG GAGGAACTAG CTTCCCTTGT   1448
CATGTTGCAT GCCTGTAAGC GTGGCCTCTT TTGTCCAGTC AAAACTTACA AGCTCAGCCT   1508
CAACGCCTCG GCCAGCGAGC ACAGCCTGCA CTTTGAAAAA AGTCCCTCCC GATTCACCCT   1568
GGTCAACACT CACGCCGGAG CTTCTGTGCG AGTGGCCCTA CACCACCAGG GAGCTTCCGG   1628
CAGCATCCGC TGTTCCTGTT CCCACGCCGA GTGCCTCCCC GTCCTCCTCA AGACCCTCTG   1688
TGCCTTTAAC TTTTTAGATT AGCTGAAAGC AAATATAAAA TGGTGTGCTT ACCGTAATTC   1748
TGTTTTGACT TGTGTGCTTG ATTTCTCCCC CTGCGCCGTA ATCCAGTGCC CCTCTTCAAA   1808
ACTCTCGTAC CCTATGCGAT TCGCATAGGC ATATTTTCTA AAAGCTCTGA AGTCAACATC   1868
ACTCTCAAAC ACTTCTCCGT TGTAGGTTAC TTTCATCTAC AGATAAAGTC ATCCACCGGT   1928
TAACATCATG AAGAGAAGTG TGCCCCAGGA CTTTAATCTT GTGTATCCGT ACAAGGCTAA   1988
GAGGCCCAAC ATCATGCCGC CCTTTTTTGA CCGCAATGGC TTTGTTGAAA ACCAAGAAGC   2048
CACGCTAGCC ATGCTTGTGG AAAAGCCGCT CACGTTCGAC AAGGAAGGTG CGCTGACCCT   2108
GGGCGTCGGA CGCGGCATCC GCATTAACCC CGCGGGGCTT CTGGAGACAA CGACCTCGC   2168
GTCCGCTGTC TTCCCACCGC TGGCCTCCGA TGAGGCCGGC AACGTCACGC TCAACATGTC   2228
TGACGGGCTA TATACTAAGG ACAACAAGCT AGCTGTCAAA GTAGGTCCCG GCTGTCCCT   2288
CGACTCCAAT AATGCTCTCC AGGTCCACAC AGGCGACGGG CTCACGGTAA CCGATGACAA   2348
```

| | | | | | | |
|---|---|---|---|---|---|---|
| GGTGTCTCTA | AATACCCAAG | CTCCCCTCTC | GACCACCAGC | GCGGGCCTCT | CCCTACTTCT | 2408 |
| GGGTCCCAGC | CTCCACTTAG | GTGAGGAGGA | ACGACTAACA | GTAAACACCG | GAGCGGGCCT | 2468 |
| CCAAATTAGC | AATAACGCTC | TGGCCGTAAA | AGTAGGTTCA | GGTATCACCG | TAGATGCTCA | 2528 |
| AAACCAGCTC | GCTGCATCCC | TGGGGACGG | TCTAGAAAGC | AGAGATAATA | AAACTGTCGT | 2588 |
| TAAGGCTGGG | CCCGGACTTA | CAATAACTAA | TCAAGCTCTT | ACTGTTGCTA | CCGGGAACGG | 2648 |
| CCTTCAGGTC | AACCCGGAAG | GGCAACTGCA | GCTAAACATT | ACTGCCGGTC | AGGGCCTCAA | 2708 |
| CTTTGCAAAC | AACAGCCTCG | CCGTGGAGCT | GGGCTCGGGC | CTGCATTTTC | CCCCTGGCCA | 2768 |
| AAACCAAGTA | AGCCTTTATC | CCGGAGATGG | AATAGACATC | CGAGATAATA | GGGTGACTGT | 2828 |
| GCCCGCTGGG | CCAGGCCTGA | GAATGCTCAA | CCACCAACTT | GCCGTAGCTT | CCGGAGACGG | 2888 |
| TTTAGAAGTC | CACAGCGACA | CCCTCCGGTT | AAAGCTCTCC | CACGGCCTGA | CATTTGAAAA | 2948 |
| TGGCGCCGTA | CGAGCAAAAC | TAGGACCAGG | ACTTGGCACA | GACGACTCTG | GTCGGTCCGT | 3008 |
| GGTTCGCACA | GGTCGAGGAC | TTAGAGTTGC | AAACGGCCAA | GTCCAGATCT | TCAGCGGAAG | 3068 |
| AGGCACCGCC | ATCGGCACTG | ATAGCAGCCT | CACTCTCAAC | ATCCGGGCGC | CCCTACAATT | 3128 |
| TTCTGGACCC | GCCTTGACTG | CTAGTTTGCA | AGGCAGTGGT | CCGATTACTT | ACAACAGCAA | 3188 |
| CAATGGCACT | TTCGGTCTCT | CTATAGGCCC | CGGAATGTGG | GTAGACCAAA | ACAGACTTCA | 3248 |
| GGTAAACCCA | GGCGCTGGTT | TAGTCTTCCA | AGGAAACAAC | CTTGTCCCAA | ACCTTGCGGA | 3308 |
| TCCGCTGGCT | ATTTCCGACA | GCAAAATTAG | TCTCAGTCTC | GGTCCCGGCC | TGACCCAAGC | 3368 |
| TTCCAACGCC | CTGACTTTAA | GTTAGGAAA | CGGGCTTGAA | TTCTCCAATC | AAGCCGTTGC | 3428 |
| TATAAAAGCG | GGCCGGGGCT | TACGCTTTGA | GTCTTCCTCA | CAAGCTTTAG | AGAGCAGCCT | 3488 |
| CACAGTCGGA | AATGGCTTAA | CGCTTACCGA | TACTGTGATC | CGCCCCAACC | TAGGGGACGG | 3548 |
| CCTAGAGGTC | AGAGACAATA | AAATCATTGT | TAAGCTGGGC | GCGAATCTTC | GTTTTGAAAA | 3608 |
| CGGAGCCGTA | ACCGCCGGCA | CCGTTAACCC | TTCTGCGCCC | GAGGCACCAC | CAACTCTCAC | 3668 |
| TGCAGAACCA | CCCCTCCGAG | CCTCCAACTC | CCATCTTCAA | CTGTCCCTAT | CGGAGGGCTT | 3728 |
| GGTTGTGCAT | AACAACGCCC | TTGCTCTCCA | ACTGGGAGAC | GGCATGGAAG | TAAATCAGCA | 3788 |
| CGGACTTACT | TTAAGAGTAG | GCTCGGGTTT | GCAAATGCGT | GACGGCATTT | TAACAGTTAC | 3848 |
| ACCCAGCGGC | ACTCCTATTG | AGCCCAGACT | GACTGCCCCA | CTGACTCAGA | CAGAGAATGG | 3908 |
| AATCGGGCTC | GCTCTCGGCG | CCGGCTTGGA | ATTAGACGAG | AGCGCGCTCC | AAGTAAAAGT | 3968 |
| TGGGCCCGGC | ATGCGCCTGA | ACCCTGTAGA | AAAGTATGTA | ACCCTGCTCC | TGGGTCCTGG | 4028 |
| CCTTAGTTTT | GGGCAGCCGG | CCAACAGGAC | AAATTATGAT | GTGCGCGTTT | CTGTGGAGCC | 4088 |
| CCCCATGGTT | TTCGGACAGC | GTGGTCAGCT | CACATTTTA | GTGGGTCACG | GACTACACAT | 4148 |
| TCAAAATTCC | AAACTTCAGC | TCAATTTGGG | ACAAGGCCTC | AGAACTGACC | CCGTCACCAA | 4208 |
| CCAGCTGGAA | GTGCCCCTCG | GTCAAGGTTT | GGAAATTGCA | GACGAATCCC | AGGTTAGGGT | 4268 |
| TAAATTGGGC | GATGGCCTGC | AGTTTGATTC | ACAAGCTCGC | ATCACTACCG | CTCCTAACAT | 4328 |
| GGTCACTGAA | ACTCTGTGGA | CCGGAACAGG | CAGTAATGCT | AATGTTACAT | GGCGGGGCTA | 4388 |
| CACTGCCCCC | GGCAGCAAAC | TCTTTTTGAG | TCTCACTCGG | TTCAGCACTG | GTCTAGTTTT | 4448 |
| AGGAAACATG | ACTATTGACA | GCAATGCATC | CTTTGGGCAA | TACATTAACG | CGGGACACGA | 4508 |
| ACAGATCGAA | TGCTTTATAT | TGTTGGACAA | TCAGGGTAAC | CTAAAAGAAG | GATCTAACTT | 4568 |
| GCAAGGCACT | TGGGAAGTGA | AGAACAACCC | CTCTGCTTCC | AAAGCTGCTT | TTTTGCCTTC | 4628 |
| CACCGCCCTA | TACCCCATCC | TCAACGAAAG | CCGAGGGAGT | CTTCCTGGAA | AAAATCTTGT | 4688 |
| GGGCATGCAA | GCCATACTGG | GAGGCGGGGG | CACTTGCACT | GTGATAGCCA | CCCTCAATGG | 4748 |

```
CAGACGCAGC  AACAACTATC  CCGCGGGCCA  GTCCATAATT  TTCGTGTGGC  AAGAATTCAA    4808

CACCATAGCC  CGCCAACCTC  TGAACCACTC  TACACTTACT  TTTTCTTACT  GGACTTAAAT    4868

AAGTTGGAAA  TAAAGAGTTA  AACTGAATGT  TTAAGTGCAA  CAGACTTTTA  TTGGTTTTGG    4928

CTCACAACAA  ATTACAACAG  CATAGACAAG  TCATACCGGT  CAAACAACAC  AGGCTCTCGA    4988

AAACGGGCTA  ACCGCTCCAA  GAATCTGTCA  CGCAGACGAG  CAAGTCCTAA  ATGTTTTTC     5048

ACTCTCTTCG  GGGCCAAGTT  CAGCATGTAT  CGGATTTTCT  GCTTACACCT  TT            5100
```

( 2 ) INFORMATION FOR SEQ ID NO:16:

( i ) SEQUENCE CHARACTERISTICS:
        ( A ) LENGTH: 139 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Leu  Ile  Lys  Gln  Pro  Val  Val  Gly  Thr  Thr  His  Val  Glu  Met  Pro  Arg
 1              5                        10                       15

Asn  Glu  Val  Leu  Glu  Gln  His  Leu  Thr  Ser  His  Gly  Ala  Gln  Ile  Ala
              20                        25                       30

Gly  Gly  Gly  Ala  Ala  Gly  Asp  Tyr  Phe  Lys  Ser  Pro  Thr  Ser  Ala  Arg
         35                        40                       45

Thr  Leu  Ile  Pro  Leu  Thr  Ala  Ser  Cys  Leu  Arg  Pro  Asp  Gly  Val  Phe
     50                       55                  60

Gln  Leu  Gly  Gly  Gly  Ser  Arg  Ser  Ser  Phe  Asn  Pro  Leu  Gln  Thr  Asp
 65                       70                       75                       80

Phe  Ala  Phe  His  Ala  Leu  Pro  Ser  Arg  Pro  Arg  His  Gly  Gly  Ile  Gly
                    85                       90                       95

Ser  Arg  Gln  Phe  Val  Glu  Glu  Phe  Val  Pro  Ala  Val  Tyr  Leu  Asn  Pro
               100                      105                      110

Tyr  Ser  Gly  Pro  Pro  Asp  Ser  Tyr  Pro  Asp  Gln  Phe  Ile  Arg  His  Tyr
          115                      120                      125

Asn  Val  Tyr  Ser  Asn  Ser  Val  Ser  Gly  Tyr  Ser
     130                      135
```

( 2 ) INFORMATION FOR SEQ ID NO:17:

( i ) SEQUENCE CHARACTERISTICS:
        ( A ) LENGTH: 5100 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 408..1331

( x i ) SEQUENCE DESCRIPTION: SEQ ID NO:17:

```
CCTCATCAAA  CAACCCGTGG  TGGGCACCAC  CCACGTGGAA  ATGCCTCGCA  ACGAAGTCCT      60

AGAACAACAT  CTGACCTCAC  ATGGCGCTCA  AATCGCGGGC  GGAGGCGCTG  CGGGCGATTA     120

CTTTAAAAGC  CCCACTTCAG  CTCGAACCCT  TATCCCGCTC  ACCGCCTCCT  GCTTAAGACC     180

AGATGGAGTC  TTTCAACTAG  GAGGAGGCTC  GCGTTCATCT  TTCAACCCCC  TGCAAACAGA     240

TTTTGCCTTC  CACGCCCTGC  CCTCCAGACC  GCGCCACGGG  GGCATAGGAT  CCAGGCAGTT     300

TGTAGAGGAA  TTTGTGCCCG  CCGTCTACCT  CAACCCCTAC  TCGGACCGC   CGGACTCTTA     360
```

| | | | | | | | | | | | | | | | | |
|---|---|---|---|---|---|---|---|---|---|---|---|---|---|---|---|---|
| TCCGGACCAG | | TTTATACGCC | | ACTACAACGT | | GTACAGCAAC | | TCTGTGA | GCG | GTT | ATA | | | | | 416 |
| | | | | | | | | | Ala | Val | Ile | | | | | |
| | | | | | | | | | | | 140 | | | | | |
| GCT | GAG | ATT | GTA | AGA | CTC | TCC | TAT | CTG | TCT | CTG | TGC | TGC | TTT | TCC | GCT | 464 |
| Ala | Glu | Ile | Val | Arg | Leu | Ser | Tyr | Leu | Ser | Leu | Cys | Cys | Phe | Ser | Ala | |
| | | 145 | | | | | 150 | | | | 155 | | | | | |
| TCA | AGC | CCC | ACA | AGC | ATG | AAG | GGG | TTT | CTG | CTC | ATC | TTC | AGC | CTG | CTT | 512 |
| Ser | Ser | Pro | Thr | Ser | Met | Lys | Gly | Phe | Leu | Leu | Ile | Phe | Ser | Leu | Leu | |
| | 160 | | | | | 165 | | | | | 170 | | | | | |
| GTG | CAT | TGT | CCC | CTA | ATT | CAT | GTT | GGG | ACC | ATT | AGC | TTC | TAT | GCT | GCA | 560 |
| Val | His | Cys | Pro | Leu | Ile | His | Val | Gly | Thr | Ile | Ser | Phe | Tyr | Ala | Ala | |
| 175 | | | | | 180 | | | | | 185 | | | | | 190 | |
| AGG | CCC | GGG | TCT | GAG | CCT | AAC | GCG | ACT | TAT | GTT | TGT | GAC | TAT | GGA | AGC | 608 |
| Arg | Pro | Gly | Ser | Glu | Pro | Asn | Ala | Thr | Tyr | Val | Cys | Asp | Tyr | Gly | Ser | |
| | | | | 195 | | | | | 200 | | | | | 205 | | |
| GAG | TCA | GAT | TAC | AAC | CCC | ACC | ACG | GTT | CTG | TGG | TTG | GCT | CGA | GAG | ACC | 656 |
| Glu | Ser | Asp | Tyr | Asn | Pro | Thr | Thr | Val | Leu | Trp | Leu | Ala | Arg | Glu | Thr | |
| | | | 210 | | | | | 215 | | | | | 220 | | | |
| GAT | GGC | TCC | TGG | ATC | TCT | GTT | CTT | TTC | CGT | CAC | AAC | GGC | TCC | TCA | ACT | 704 |
| Asp | Gly | Ser | Trp | Ile | Ser | Val | Leu | Phe | Arg | His | Asn | Gly | Ser | Ser | Thr | |
| | | 225 | | | | | 230 | | | | | 235 | | | | |
| GCA | GCC | CCC | GGG | GTC | GTC | GCG | CAC | TTT | ACT | GAC | CAC | AAC | AGC | AGC | ATT | 752 |
| Ala | Ala | Pro | Gly | Val | Val | Ala | His | Phe | Thr | Asp | His | Asn | Ser | Ser | Ile | |
| | 240 | | | | | 245 | | | | | 250 | | | | | |
| GTG | GTG | CCC | CAG | TAT | TAC | CTC | CTC | AAC | AAC | TCA | CTC | TCT | AAG | CTC | TGC | 800 |
| Val | Val | Pro | Gln | Tyr | Tyr | Leu | Leu | Asn | Asn | Ser | Leu | Ser | Lys | Leu | Cys | |
| 255 | | | | | 260 | | | | | 265 | | | | | 270 | |
| TGC | TCA | TAC | CGG | CAC | AAC | GAG | CGT | TCT | CAG | TTT | ACC | TGC | AAA | CAA | GCT | 848 |
| Cys | Ser | Tyr | Arg | His | Asn | Glu | Arg | Ser | Gln | Phe | Thr | Cys | Lys | Gln | Ala | |
| | | | | 275 | | | | | 280 | | | | | 285 | | |
| GAC | GTC | CCT | ACC | TGT | CAC | GAG | CCC | GGC | AAG | CCG | CTC | ACC | CTC | CGC | GTC | 896 |
| Asp | Val | Pro | Thr | Cys | His | Glu | Pro | Gly | Lys | Pro | Leu | Thr | Leu | Arg | Val | |
| | | | 290 | | | | | 295 | | | | | 300 | | | |
| TCC | CCC | GCG | CTG | GGA | ACT | GCC | CAC | CAA | GCA | GTC | ACT | TGG | TTT | TTT | CAA | 944 |
| Ser | Pro | Ala | Leu | Gly | Thr | Ala | His | Gln | Ala | Val | Thr | Trp | Phe | Phe | Gln | |
| | | 305 | | | | | 310 | | | | | 315 | | | | |
| AAT | GTA | CCC | ATA | GCT | ACT | GTT | TAC | CGA | CCT | TGG | GGC | AAT | GTA | ACT | TGG | 992 |
| Asn | Val | Pro | Ile | Ala | Thr | Val | Tyr | Arg | Pro | Trp | Gly | Asn | Val | Thr | Trp | |
| | 320 | | | | | 325 | | | | | 330 | | | | | |
| TTT | TGT | CCT | CCC | TTC | ATG | TGT | ACC | TTT | AAT | GTC | AGC | CTG | AAC | TCC | CTA | 1040 |
| Phe | Cys | Pro | Pro | Phe | Met | Cys | Thr | Phe | Asn | Val | Ser | Leu | Asn | Ser | Leu | |
| 335 | | | | | 340 | | | | | 345 | | | | | 350 | |
| CTT | ATT | TAC | AAC | TTT | TCT | GAC | AAA | ACC | GGG | GGG | CAA | TAC | ACA | GCT | CTC | 1088 |
| Leu | Ile | Tyr | Asn | Phe | Ser | Asp | Lys | Thr | Gly | Gly | Gln | Tyr | Thr | Ala | Leu | |
| | | | | 355 | | | | | 360 | | | | | 365 | | |
| ATG | CAC | TCC | GGA | CCT | GCT | TCC | CTC | TTT | CAG | CTC | TTT | AAG | CCA | ACG | ACT | 1136 |
| Met | His | Ser | Gly | Pro | Ala | Ser | Leu | Phe | Gln | Leu | Phe | Lys | Pro | Thr | Thr | |
| | | | 370 | | | | | 375 | | | | | 380 | | | |
| TGT | GTC | ACC | AAG | GTG | GAG | GAC | CCG | CCG | TAT | GCC | AAC | GAC | CCG | GCC | TCG | 1184 |
| Cys | Val | Thr | Lys | Val | Glu | Asp | Pro | Pro | Tyr | Ala | Asn | Asp | Pro | Ala | Ser | |
| | | 385 | | | | | 390 | | | | | 395 | | | | |
| CCT | GTG | TGG | CGC | CCA | CTG | CTT | TTT | GCC | TTC | GTC | CTC | TGC | ACC | GGC | TGC | 1232 |
| Pro | Val | Trp | Arg | Pro | Leu | Leu | Phe | Ala | Phe | Val | Leu | Cys | Thr | Gly | Cys | |
| | | 400 | | | | 405 | | | | | 410 | | | | | |
| GCG | GTG | TTG | TTA | ACC | GCC | TTC | GGT | CCA | TCG | ATT | CTA | TCC | GGT | ACC | CGA | 1280 |
| Ala | Val | Leu | Leu | Thr | Ala | Phe | Gly | Pro | Ser | Ile | Leu | Ser | Gly | Thr | Arg | |
| 415 | | | | | 420 | | | | | 425 | | | | | 430 | |
| AAG | CTT | ATC | TCA | GCC | CGC | TTT | TGG | AGT | CCC | GAG | CCC | TAT | ACC | ACC | CTC | 1328 |
| Lys | Leu | Ile | Ser | Ala | Arg | Phe | Trp | Ser | Pro | Glu | Pro | Tyr | Thr | Thr | Leu | |
| | | | | 435 | | | | | 440 | | | | | 445 | | |

```
CAC TAACAGTCCC CCCATGGAGC CAGACGGAGT TCATGCCGAG CAGCAGTTTA    1381
His
TCCTCAATCA GATTTCCTGC GCCAACACTG CCCTCCAGCG TCAAAGGGAG GAACTAGCTT    1441
CCCTTGTCAT GTTGCATGCC TGTAAGCGTG GCCTCTTTTG TCCAGTCAAA ACTTACAAGC    1501
TCAGCCTCAA CGCCTCGGCC AGCGAGCACA GCCTGCACTT TGAAAAAGT CCCTCCCGAT    1561
TCACCCTGGT CAACACTCAC GCCGGAGCTT CTGTGCGAGT GGCCCTACAC CACCAGGGAG    1621
CTTCCGGCAG CATCCGCTGT TCCTGTTCCC ACGCCGAGTG CCTCCCCGTC CTCCTCAAGA    1681
CCCTCTGTGC CTTTAACTTT TTAGATTAGC TGAAAGCAAA TATAAATGG TGTGCTTACC    1741
GTAATTCTGT TTTGACTTGT GTGCTTGATT CTCCCCCTG CGCCGTAATC CAGTGCCCCT    1801
CTTCAAAACT CTCGTACCCT ATGCGATTCG CATAGGCATA TTTTCTAAAA GCTCTGAAGT    1861
CAACATCACT CTCAAACACT TCTCCGTTGT AGGTTACTTT CATCTACAGA TAAAGTCATC    1921
CACCGGTTAA CATCATGAAG AGAAGTGTGC CCCAGGACTT TAATCTTGTG TATCCGTACA    1981
AGGCTAAGAG GCCCAACATC ATGCCGCCCT TTTTGACCG CAATGGCTTT GTTGAAAACC    2041
AAGAAGCCAC GCTAGCCATG CTTGTGGAAA AGCCGCTCAC GTTCGACAAG GAAGGTGCGC    2101
TGACCCTGGG CGTCGGACGC GGCATCCGCA TTAACCCCGC GGGGCTTCTG GAGACAAACG    2161
ACCTCGCGTC CGCTGTCTTC CCACCGCTGG CCTCCGATGA GGCCGGCAAC GTCACGCTCA    2221
ACATGTCTGA CGGGCTATAT ACTAAGGACA ACAAGCTAGC TGTCAAAGTA GGTCCCGGGC    2281
TGTCCCTCGA CTCCAATAAT GCTCTCCAGG TCCACACAGG CGACGGGCTC ACGGTAACCG    2341
ATGACAAGGT GTCTCTAAAT ACCCAAGCTC CCCTCTCGAC CACCAGCGCG GGCCTCTCCC    2401
TACTTCTGGG TCCCAGCCTC CACTTAGGTG AGGAGGAACG ACTAACAGTA AACACCGGAG    2461
CGGGCCTCCA AATTAGCAAT AACGCTCTGG CCGTAAAAGT AGGTTCAGGT ATCACCGTAG    2521
ATGCTCAAAA CCAGCTCGCT GCATCCCTGG GGACGGTCT AGAAAGCAGA GATAATAAAA    2581
CTGTCGTTAA GGCTGGGCCC GGACTTACAA TAACTAATCA AGCTCTTACT GTTGCTACCG    2641
GGAACGGCCT TCAGGTCAAC CCGGAAGGGC AACTGCAGCT AAACATTACT GCCGGTCAGG    2701
GCCTCAACTT TGCAAACAAC AGCCTCGCCG TGGAGCTGGG CTCGGGCCTG CATTTTCCCC    2761
CTGGCCAAAA CCAAGTAAGC CTTTATCCCG GAGATGGAAT AGACATCCGA GATAATAGGG    2821
TGACTGTGCC CGCTGGGCCA GGCCTGAGAA TGCTCAACCA CCAACTTGCC GTAGCTTCCG    2881
GAGACGGTTT AGAAGTCCAC AGCGACACCC TCCGGTTAAA GCTCTCCCAC GGCCTGACAT    2941
TTGAAAATGG CGCCGTACGA GCAAAACTAG GACCAGGACT TGGCACAGAC GACTCTGGTC    3001
GGTCCGTGGT TCGCACAGGT CGAGGACTTA GAGTTGCAAA CGGCCAAGTC CAGATCTTCA    3061
GCGGAAGAGG CACCGCCATC GGCACTGATA GCAGCCTCAC TCTCAACATC CGGGCGCCCC    3121
TACAATTTTC TGGACCCGCC TTGACTGCTA GTTTGCAAGG CAGTGGTCCG ATTACTTACA    3181
ACAGCAACAA TGGCACTTTC GGTCTCTCTA TAGGCCCCGG AATGTGGGTA GACCAAAACA    3241
GACTTCAGGT AAACCCAGGC GCTGGTTTAG TCTTCCAAGG AAACAACCTT GTCCCAAACC    3301
TTGCGGATCC GCTGGCTATT TCCGACAGCA AAATTAGTCT CAGTCTCGGT CCCGGCCTGA    3361
CCCAAGCTTC CAACGCCCTG ACTTTAAGTT TAGGAAACGG GCTTGAATTC TCCAATCAAG    3421
CCGTTGCTAT AAAAGCGGGC CGGGGCTTAC GCTTTGAGTC TTCCTCACAA GCTTTAGAGA    3481
GCAGCCTCAC AGTCGGAAAT GGCTTAACGC TTACCGATAC TGTGATCCGC CCCAACCTAG    3541
GGGACGGCCT AGAGGTCAGA GACAATAAAA TCATTGTTAA GCTGGGCGCG AATCTTCGTT    3601
TTGAAAACGG AGCCGTAACC GCCGGCACCG TTAACCCTTC TGCGCCCGAG GCACCACCAA    3661
CTCTCACTGC AGAACCACCC CTCCGAGCCT CCAACTCCCA TCTTCAACTG TCCCTATCGG    3721
```

-continued

```
AGGGCTTGGT TGTGCATAAC AACGCCCTTG CTCTCCAACT GGGAGACGGC ATGGAAGTAA    3781
ATCAGCACGG ACTTACTTTA AGAGTAGGCT CGGGTTTGCA AATGCGTGAC GGCATTTTAA    3841
CAGTTACACC CAGCGGCACT CCTATTGAGC CCAGACTGAC TGCCCCACTG ACTCAGACAG    3901
AGAATGGAAT CGGGCTCGCT CTCGGCGCCG GCTTGGAATT AGACGAGAGC GCGCTCCAAG    3961
TAAAAGTTGG GCCCGGCATG CGCCTGAACC CTGTAGAAAA GTATGTAACC CTGCTCCTGG    4021
GTCCTGGCCT TAGTTTTGGG CAGCCGGCCA ACAGGACAAA TTATGATGTG CGCGTTTCTG    4081
TGGAGCCCCC CATGGTTTTC GGACAGCGTG GTCAGCTCAC ATTTTAGTG GGTCACGGAC     4141
TACACATTCA AAATTCCAAA CTTCAGCTCA ATTTGGGACA AGGCCTCAGA ACTGACCCCG    4201
TCACCAACCA GCTGGAAGTG CCCCTCGGTC AAGGTTTGGA AATTGCAGAC GAATCCCAGG    4261
TTAGGGTTAA ATTGGGCGAT GGCCTGCAGT TTGATTCACA AGCTCGCATC ACTACCGCTC    4321
CTAACATGGT CACTGAAACT CTGTGGACCG GAACAGGCAG TAATGCTAAT GTTACATGGC    4381
GGGGCTACAC TGCCCCCGGC AGCAAACTCT TTTTGAGTCT CACTCGGTTC AGCACTGGTC    4441
TAGTTTTAGG AAACATGACT ATTGACAGCA ATGCATCCTT TGGGCAATAC ATTAACGCGG    4501
GACACGAACA GATCGAATGC TTTATATTGT TGGACAATCA GGGTAACCTA AAAGAAGGAT    4561
CTAACTTGCA AGGCACTTGG GAAGTGAAGA ACAACCCCTC TGCTTCCAAA GCTGCTTTTT    4621
TGCCTTCCAC CGCCCTATAC CCCATCCTCA ACGAAAGCCG AGGGAGTCTT CCTGGAAAAA    4681
ATCTTGTGGG CATGCAAGCC ATACTGGGAG GCGGGGGCAC TTGCACTGTG ATAGCCACCC    4741
TCAATGGCAG ACGCAGCAAC AACTATCCCG CGGGCCAGTC CATAATTTTC GTGTGGCAAG    4801
AATTCAACAC CATAGCCCGC CAACCTCTGA ACCACTCTAC ACTTACTTTT TCTTACTGGA    4861
CTTAAATAAG TTGGAAATAA AGAGTTAAAC TGAATGTTTA AGTGCAACAG ACTTTTATTG    4921
GTTTTGGCTC ACAACAAATT ACAACAGCAT AGACAAGTCA TACCGGTCAA ACAACACAGG    4981
CTCTCGAAAA CGGGCTAACC GCTCCAAGAA TCTGTCACGC AGACGAGCAA GTCCTAAATG    5041
TTTTTTCACT CTCTTCGGGG CCAAGTTCAG CATGTATCGG ATTTCTGCT TACACCTTT     5100
```

(2) INFORMATION FOR SEQ ID NO:18:

(i) SEQUENCE CHARACTERISTICS:
        (A) LENGTH: 308 amino acids
        (B) TYPE: amino acid
        (D) TOPOLOGY: linear (ii) MOLECULE TYPE: protein (xi) SEQUENCE DESCRIPTION: SEQ ID NO:18:

```
Ala Val Ile Ala Glu Ile Val Arg Leu Ser Tyr Leu Ser Leu Cys Cys
 1               5                  10                  15

Phe Ser Ala Ser Ser Pro Thr Ser Met Lys Gly Phe Leu Leu Ile Phe
                20                  25                  30

Ser Leu Leu Val His Cys Pro Leu Ile His Val Gly Thr Ile Ser Phe
                35                  40                  45

Tyr Ala Ala Arg Pro Gly Ser Glu Pro Asn Ala Thr Tyr Val Cys Asp
            50                  55                  60

Tyr Gly Ser Glu Ser Asp Tyr Asn Pro Thr Thr Val Leu Trp Leu Ala
 65                 70                  75                  80

Arg Glu Thr Asp Gly Ser Trp Ile Ser Val Leu Phe Arg His Asn Gly
                85                  90                  95

Ser Ser Thr Ala Ala Pro Gly Val Val Ala His Phe Thr Asp His Asn
                100                 105                 110
```

| | | | | | | | | | | | | | |
|---|---|---|---|---|---|---|---|---|---|---|---|---|---|
| Ser | Ser | Ile | Val | Val | Pro | Gln | Tyr | Tyr | Leu | Leu | Asn | Asn | Ser | Leu | Ser |
| | | 115 | | | | 120 | | | | | 125 | | | | |
| Lys | Leu | Cys | Cys | Ser | Tyr | Arg | His | Asn | Glu | Arg | Ser | Gln | Phe | Thr | Cys |
| | 130 | | | | | 135 | | | | | 140 | | | | |
| Lys | Gln | Ala | Asp | Val | Pro | Thr | Cys | His | Glu | Pro | Gly | Lys | Pro | Leu | Thr |
| 145 | | | | | 150 | | | | | 155 | | | | | 160 |
| Leu | Arg | Val | Ser | Pro | Ala | Leu | Gly | Thr | Ala | His | Gln | Ala | Val | Thr | Trp |
| | | | | 165 | | | | | 170 | | | | | 175 | |
| Phe | Phe | Gln | Asn | Val | Pro | Ile | Ala | Thr | Val | Tyr | Arg | Pro | Trp | Gly | Asn |
| | | | 180 | | | | | 185 | | | | | 190 | | |
| Val | Thr | Trp | Phe | Cys | Pro | Pro | Phe | Met | Cys | Thr | Phe | Asn | Val | Ser | Leu |
| | | 195 | | | | | 200 | | | | | 205 | | | |
| Asn | Ser | Leu | Leu | Ile | Tyr | Asn | Phe | Ser | Asp | Lys | Thr | Gly | Gly | Gln | Tyr |
| | 210 | | | | | 215 | | | | | 220 | | | | |
| Thr | Ala | Leu | Met | His | Ser | Gly | Pro | Ala | Ser | Leu | Phe | Gln | Leu | Phe | Lys |
| 225 | | | | | 230 | | | | | 235 | | | | | 240 |
| Pro | Thr | Thr | Cys | Val | Thr | Lys | Val | Glu | Asp | Pro | Pro | Tyr | Ala | Asn | Asp |
| | | | | 245 | | | | | 250 | | | | | 255 | |
| Pro | Ala | Ser | Pro | Val | Trp | Arg | Pro | Leu | Leu | Phe | Ala | Phe | Val | Leu | Cys |
| | | | 260 | | | | | 265 | | | | | 270 | | |
| Thr | Gly | Cys | Ala | Val | Leu | Leu | Thr | Ala | Phe | Gly | Pro | Ser | Ile | Leu | Ser |
| | | 275 | | | | | 280 | | | | | 285 | | | |
| Gly | Thr | Arg | Lys | Leu | Ile | Ser | Ala | Arg | Phe | Trp | Ser | Pro | Glu | Pro | Tyr |
| | 290 | | | | | 295 | | | | | 300 | | | | |
| Thr | Thr | Leu | His | | | | | | | | | | | | |
| 305 | | | | | | | | | | | | | | | |

( 2 ) INFORMATION FOR SEQ ID NO:19:

( i ) SEQUENCE CHARACTERISTICS:
        ( A ) LENGTH: 5100 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 529..954

( x i ) SEQUENCE DESCRIPTION: SEQ ID NO:19:

```
CCTCATCAAA  CAACCCGTGG  TGGGCACCAC  CCACGTGGAA  ATGCCTCGCA  ACGAAGTCCT      60

AGAACAACAT  CTGACCTCAC  ATGGCGCTCA  AATCGCGGGC  GGAGGCGCTG  CGGGCGATTA     120

CTTTAAAAGC  CCCACTTCAG  CTCGAACCCT  TATCCCGCTC  ACCGCCTCCT  GCTTAAGACC     180

AGATGGAGTC  TTTCAACTAG  GAGGAGGCTC  GCGTTCATCT  TCAACCCCC   TGCAAACAGA     240

TTTTGCCTTC  CACGCCCTGC  CCTCCAGACC  GCGCCACGGG  GGCATAGGAT  CCAGGCAGTT     300

TGTAGAGGAA  TTTGTGCCCG  CCGTCTACCT  CAACCCCTAC  TCGGGACCGC  CGGACTCTTA     360

TCCGGACCAG  TTTATACGCC  ACTACAACGT  GTACAGCAAC  TCTGTGAGCG  GTTATAGCTG     420

AGATTGTAAG  ACTCTCCTAT  CTGTCTCTGT  GCTGCTTTTC  CGCTTCAAGC  CCCACAAGCA     480

TGAAGGGGTT  TCTGCTCATC  TTCAGCCTGC  TTGTGCATTG  TCCCCTAA    TTC ATG TTG    537
                                                            Phe Met Leu
                                                                310

GGA  CCA  TTA  GCT  TCT  ATG  CTG  CAA  GGC  CCG  GGT  CTG  AGC  CTA  ACG  CGA     585
Gly  Pro  Leu  Ala  Ser  Met  Leu  Gln  Gly  Pro  Gly  Leu  Ser  Leu  Thr  Arg
               315                    320                    325
```

```
CTT ATG TTT GTG ACT ATG GAA GCG AGT CAG ATT ACA ACC CCA CCA CGG        633
Leu Met Phe Val Thr Met Glu Ala Ser Gln Ile Thr Thr Pro Pro Arg
    330                 335                 340

TTC TGT GGT TGG CTC GAG AGA CCG ATG GCT CCT GGA TCT CTG TTC TTT        681
Phe Cys Gly Trp Leu Glu Arg Pro Met Ala Pro Gly Ser Leu Phe Phe
345                 350                 355

TCC GTC ACA ACG GCT CCT CAA CTG CAG CCC CCG GGG TCG TCG CGC ACT        729
Ser Val Thr Thr Ala Pro Gln Leu Gln Pro Pro Gly Ser Ser Arg Thr
360                 365                 370                 375

TTA CTG ACC ACA ACA GCA GCA TTG TGG TGC CCC AGT ATT ACC TCC TCA        777
Leu Leu Thr Thr Thr Ala Ala Leu Trp Cys Pro Ser Ile Thr Ser Ser
                380                 385                 390

ACA ACT CAC TCT CTA AGC TCT GCT GCT CAT ACC GGC ACA ACG AGC GTT        825
Thr Thr His Ser Leu Ser Ser Ala Ala His Thr Gly Thr Thr Ser Val
            395                 400                 405

CTC AGT TTA CCT GCA AAC AAG CTG ACG TCC CTA CCT GTC ACG AGC CCG        873
Leu Ser Leu Pro Ala Asn Lys Leu Thr Ser Leu Pro Val Thr Ser Pro
        410                 415                 420

GCA AGC CGC TCA CCC TCC GCG TCT CCC CCG CGC TGG GAA CTG CCC ACC        921
Ala Ser Arg Ser Pro Ser Ala Ser Pro Pro Arg Trp Glu Leu Pro Thr
    425                 430                 435

AAG CAG TCA CTT GGT TTT TTC AAA ATG TAC CCA TAGCTACTGT TTACCGACCT      974
Lys Gln Ser Leu Gly Phe Phe Lys Met Tyr Pro
440                 445                 450

TGGGGCAATG TAACTTGGTT TTGTCCTCCC TTCATGTGTA CCTTTAATGT CAGCCTGAAC     1034
TCCCTACTTA TTTACAACTT TTCTGACAAA ACCGGGGGGC AATACACAGC TCTCATGCAC     1094
TCCGGACCTG CTTCCCTCTT TCAGCTCTTT AAGCCAACGA CTTGTGTCAC CAAGGTGGAG     1154
GACCCGCCGT ATGCCAACGA CCCGGCCTCG CCTGTGTGGC GCCCACTGCT TTTTGCCTTC     1214
GTCCTCTGCA CCGGCTGCGC GGTGTTGTTA ACCGCCTTCG GTCCATCGAT TCTATCCGGT     1274
ACCCGAAAGC TTATCTCAGC CCGCTTTTGG AGTCCCGAGC CCTATACCAC CCTCCACTAA     1334
CAGTCCCCCC ATGGAGCCAG ACGGAGTTCA TGCCGAGCAG CAGTTTATCC TCAATCAGAT     1394
TTCCTGCGCC AACACTGCCC TCCAGCGTCA AGGGAGGAA CTAGCTTCCC TTGTCATGTT     1454
GCATGCCTGT AAGCGTGGCC TCTTTTGTCC AGTCAAAACT TACAAGCTCA GCCTCAACGC     1514
CTCGGCCAGC GAGCACAGCC TGCACTTTGA AAAAGTCCC TCCCGATTCA CCCTGGTCAA     1574
CACTCACGCC GGAGCTTCTG TGCGAGTGGC CCTACACCAC CAGGGAGCTT CCGGCAGCAT     1634
CCGCTGTTCC TGTTCCCACG CCGAGTGCCT CCCCGTCCTC CTCAAGACCC TCTGTGCCTT     1694
TAACTTTTTA GATTAGCTGA AAGCAAATAT AAAATGGTGT GCTTACCGTA ATTCTGTTTT     1754
GACTTGTGTG CTTGATTTCT CCCCCTGCGC CGTAATCCAG TGCCCCTCTT CAAAACTCTC     1814
GTACCCTATG CGATTCGCAT AGGCATATTT TCTAAAAGCT CTGAAGTCAA CATCACTCTC     1874
AAACACTTCT CCGTTGTAGG TTACTTTCAT CTACAGATAA AGTCATCCAC CGGTTAACAT     1934
CATGAAGAGA AGTGTGCCCC AGGACTTTAA TCTTGTGTAT CCGTACAAGG CTAAGAGGCC     1994
CAACATCATG CCGCCCTTTT TTGACCGCAA TGGCTTTGTT GAAAACCAAG AAGCCACGCT     2054
AGCCATGCTT GTGGAAAAGC CGCTCACGTT CGACAAGGAA GGTGCGCTGA CCCTGGGCGT     2114
CGGACGCGGC ATCCGCATTA ACCCCGCGGG GCTTCTGGAG ACAAACGACC TCGCGTCCGC     2174
TGTCTTCCCA CCGCTGGCCT CCGATGAGGC CGGCAACGTC ACGCTCAACA TGTCTGACGG     2234
GCTATATACT AAGGACAACA AGCTAGCTGT CAAAGTAGGT CCCGGGCTGT CCCTCGACTC     2294
CAATAATGCT CTCCAGGTCC ACACAGGCGA CGGGCTCACG GTAACCGATG ACAAGGTGTC     2354
TCTAAATACC CAAGCTCCCC TCTCGACCAC CAGCGCGGGC CTCTCCCTAC TTCTGGGTCC     2414
```

| | | | | | | |
|---|---|---|---|---|---|---|
| CAGCCTCCAC | TTAGGTGAGG | AGGAACGACT | AACAGTAAAC | ACCGGAGCGG | GCCTCCAAAT | 2474 |
| TAGCAATAAC | GCTCTGGCCG | TAAAAGTAGG | TTCAGGTATC | ACCGTAGATG | CTCAAAACCA | 2534 |
| GCTCGCTGCA | TCCCTGGGGG | ACGGTCTAGA | AAGCAGAGAT | AATAAAACTG | TCGTTAAGGC | 2594 |
| TGGGCCCGGA | CTTACAATAA | CTAATCAAGC | TCTTACTGTT | GCTACCGGGA | ACGGCTTCA | 2654 |
| GGTCAACCCG | GAAGGGCAAC | TGCAGCTAAA | CATTACTGCC | GGTCAGGGCC | TCAACTTTGC | 2714 |
| AAACAACAGC | CTCGCCGTGG | AGCTGGGCTC | GGGCCTGCAT | TTTCCCCCTG | GCCAAAACCA | 2774 |
| AGTAAGCCTT | TATCCCGGAG | ATGGAATAGA | CATCCGAGAT | AATAGGGTGA | CTGTGCCCGC | 2834 |
| TGGGCCAGGC | CTGAGAATGC | TCAACCACCA | ACTTGCCGTA | GCTTCCGGAG | ACGGTTTAGA | 2894 |
| AGTCCACAGC | GACACCCTCC | GGTTAAAGCT | CTCCACGGC | CTGACATTTG | AAAATGGCGC | 2954 |
| CGTACGAGCA | AAACTAGGAC | CAGGACTTGG | CACAGACGAC | TCTGGTCGGT | CCGTGGTTCG | 3014 |
| CACAGGTCGA | GGACTTAGAG | TTGCAAACGG | CCAAGTCCAG | ATCTTCAGCG | GAAGAGGCAC | 3074 |
| CGCCATCGGC | ACTGATAGCA | GCCTCACTCT | CAACATCCGG | GCGCCCTAC | AATTTCTGG | 3134 |
| ACCCGCCTTG | ACTGCTAGTT | TGCAAGGCAG | TGGTCCGATT | ACTTACAACA | GCAACAATGG | 3194 |
| CACTTTCGGT | CTCTCTATAG | GCCCCGGAAT | GTGGGTAGAC | CAAAACAGAC | TTCAGGTAAA | 3254 |
| CCCAGGCGCT | GGTTTAGTCT | TCCAAGGAAA | CAACCTTGTC | CCAAACCTTG | CGGATCCGCT | 3314 |
| GGCTATTTCC | GACAGCAAAA | TTAGTCTCAG | TCTCGGTCCC | GGCCTGACCC | AAGCTTCCAA | 3374 |
| CGCCCTGACT | TTAAGTTTAG | GAAACGGGCT | TGAATTCTCC | AATCAAGCCG | TTGCTATAAA | 3434 |
| AGCGGGCCGG | GGCTTACGCT | TTGAGTCTTC | CTCACAAGCT | TTAGAGAGCA | GCCTCACAGT | 3494 |
| CGGAAATGGC | TTAACGCTTA | CCGATACTGT | GATCCGCCCC | AACCTAGGGG | ACGGCCTAGA | 3554 |
| GGTCAGAGAC | AATAAAATCA | TTGTTAAGCT | GGGCGCGAAT | CTTCGTTTTG | AAAACGGAGC | 3614 |
| CGTAACCGCC | GGCACCGTTA | ACCCTTCTGC | GCCCGAGGCA | CCACCAACTC | TCACTGCAGA | 3674 |
| ACCACCCTC | CGAGCCTCCA | ACTCCATCT | TCAACTGTCC | CTATCGGAGG | GCTTGGTTGT | 3734 |
| GCATAACAAC | GCCCTTGCTC | TCCAACTGGG | AGACGGCATG | GAAGTAAATC | AGCACGGACT | 3794 |
| TACTTTAAGA | GTAGGCTCGG | GTTTGCAAAT | GCGTGACGGC | ATTTAACAG | TTACACCCAG | 3854 |
| CGGCACTCCT | ATTGAGCCCA | GACTGACTGC | CCCACTGACT | CAGACAGAGA | ATGGAATCGG | 3914 |
| GCTCGCTCTC | GGCGCCGGCT | TGGAATTAGA | CGAGAGCGCG | CTCCAAGTAA | AAGTTGGGCC | 3974 |
| CGGCATGCGC | CTGAACCCTG | TAGAAAAGTA | TGTAACCCTG | CTCCTGGGTC | CTGGCCTTAG | 4034 |
| TTTTGGGCAG | CCGGCCAACA | GGACAAATTA | TGATGTGCGC | GTTTCTGTGG | AGCCCCCAT | 4094 |
| GGTTTTCGGA | CAGCGTGGTC | AGCTCACATT | TTTAGTGGGT | CACGGACTAC | ACATTCAAAA | 4154 |
| TTCCAAACTT | CAGCTCAATT | TGGGACAAGG | CCTCAGAACT | GACCCCGTCA | CCAACCAGCT | 4214 |
| GGAAGTGCCC | CTCGGTCAAG | GTTTGGAAAT | TGCAGACGAA | TCCCAGGTTA | GGGTTAAATT | 4274 |
| GGGCGATGGC | CTGCAGTTTG | ATTCACAAGC | TCGCATCACT | ACCGCTCCTA | ACATGGTCAC | 4334 |
| TGAAACTCTG | TGGACCGGAA | CAGGCAGTAA | TGCTAATGTT | ACATGGCGGG | GCTACACTGC | 4394 |
| CCCCGGCAGC | AAACTCTTTT | TGAGTCTCAC | TCGGTTCAGC | ACTGGTCTAG | TTTTAGGAAA | 4454 |
| CATGACTATT | GACAGCAATG | CATCCTTTGG | GCAATACATT | AACGCGGGAC | ACGAACAGAT | 4514 |
| CGAATGCTTT | ATATTGTTGG | ACAATCAGGG | TAACCTAAAA | GAAGGATCTA | ACTTGCAAGG | 4574 |
| CACTTGGGAA | GTGAAGAACA | ACCCCTCTGC | TTCCAAAGCT | GCTTTTTTGC | CTTCCACCGC | 4634 |
| CCTATACCCC | ATCCTCAACG | AAAGCCGAGG | GAGTCTTCCT | GGAAAAAATC | TTGTGGGCAT | 4694 |
| GCAAGCCATA | CTGGGAGGCG | GGGGCACTTG | CACTGTGATA | GCCACCCTCA | ATGGCAGACG | 4754 |
| CAGCAACAAC | TATCCCGCGG | GCCAGTCCAT | AATTTTCGTG | TGGCAAGAAT | TCAACACCAT | 4814 |

| | | | | | |
|---|---|---|---|---|---|
| AGCCCGCCAA | CCTCTGAACC | ACTCTACACT | TACTTTTTCT | TACTGGACTT | AAATAAGTTG | 4874 |
| GAAATAAAGA | GTTAAACTGA | ATGTTTAAGT | GCAACAGACT | TTTATTGGTT | TTGGCTCACA | 4934 |
| ACAAATTACA | ACAGCATAGA | CAAGTCATAC | CGGTCAAACA | ACACAGGCTC | TCGAAAACGG | 4994 |
| GCTAACCGCT | CCAAGAATCT | GTCACGCAGA | CGAGCAAGTC | CTAAATGTTT | TTTCACTCTC | 5054 |
| TTCGGGGCCA | AGTTCAGCAT | GTATCGGATT | TTCTGCTTAC | ACCTTT | | 5100 |

( 2 ) INFORMATION FOR SEQ ID NO:20:

( i ) SEQUENCE CHARACTERISTICS:
        ( A ) LENGTH: 142 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

```
Phe Met Leu Gly Pro Leu Ala Ser Met Leu Gln Gly Pro Gly Leu Ser
 1               5                  10                 15
Leu Thr Arg Leu Met Phe Val Thr Met Glu Ala Ser Gln Ile Thr Thr
             20                  25                  30
Pro Pro Arg Phe Cys Gly Trp Leu Glu Arg Pro Met Ala Pro Gly Ser
             35                  40                  45
Leu Phe Phe Ser Val Thr Thr Ala Pro Gln Leu Gln Pro Pro Gly Ser
     50                  55                  60
Ser Arg Thr Leu Leu Thr Thr Ala Ala Leu Trp Cys Pro Ser Ile
 65                  70                  75                  80
Thr Ser Ser Thr Thr His Ser Leu Ser Ser Ala Ala His Thr Gly Thr
                 85                  90                  95
Thr Ser Val Leu Ser Leu Pro Ala Asn Lys Leu Thr Ser Leu Pro Val
             100                 105                 110
Thr Ser Pro Ala Ser Arg Ser Pro Ser Ala Ser Pro Pro Arg Trp Glu
             115                 120                 125
Leu Pro Thr Lys Gln Ser Leu Gly Phe Phe Lys Met Tyr Pro
     130                 135                 140
```

( 2 ) INFORMATION FOR SEQ ID NO:21:

( i ) SEQUENCE CHARACTERISTICS:
        ( A ) LENGTH: 5100 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1246..1707

( x i ) SEQUENCE DESCRIPTION: SEQ ID NO:21:

| | | | | | |
|---|---|---|---|---|---|
| CCTCATCAAA | CAACCCGTGG | TGGGCACCAC | CCACGTGGAA | ATGCCTCGCA | ACGAAGTCCT | 60 |
| AGAACAACAT | CTGACCTCAC | ATGGCGCTCA | AATCGCGGGC | GGAGGCGCTG | CGGGCGATTA | 120 |
| CTTTAAAAGC | CCCACTTCAG | CTCGAACCCT | TATCCCGCTC | ACCGCCTCCT | GCTTAAGACC | 180 |
| AGATGGAGTC | TTTCAACTAG | GAGGAGGCTC | GCGTTCATCT | TTCAACCCCC | TGCAAACAGA | 240 |
| TTTTGCCTTC | CACGCCCTGC | CCTCCAGACC | GCGCCACGGG | GGCATAGGAT | CCAGGCAGTT | 300 |
| TGTAGAGGAA | TTTGTGCCCG | CCGTCTACCT | CAACCCCTAC | TCGGGACCGC | CGGACTCTTA | 360 |
| TCCGGACCAG | TTTATACGCC | ACTACAACGT | GTACAGCAAC | TCTGTGAGCG | GTTATAGCTG | 420 |

```
AGATTGTAAG  ACTCTCCTAT  CTGTCTCTGT  GCTGCTTTTC  CGCTTCAAGC  CCCACAAGCA          480

TGAAGGGGTT  TCTGCTCATC  TTCAGCCTGC  TTGTGCATTG  TCCCCTAATT  CATGTTGGGA          540

CCATTAGCTT  CTATGCTGCA  AGGCCCGGGT  CTGAGCCTAA  CGCGACTTAT  GTTTGTGACT          600

ATGGAAGCGA  GTCAGATTAC  AACCCCACCA  CGGTTCTGTG  GTTGGCTCGA  GAGACCGATG          660

GCTCCTGGAT  CTCTGTTCTT  TTCCGTCACA  ACGGCTCCTC  AACTGCAGCC  CCCGGGGTCG          720

TCGCGCACTT  TACTGACCAC  AACAGCAGCA  TTGTGGTGCC  CCAGTATTAC  CTCCTCAACA          780

ACTCACTCTC  TAAGCTCTGC  TGCTCATACC  GGCACAACGA  GCGTTCTCAG  TTTACCTGCA          840

AACAAGCTGA  CGTCCCTACC  TGTCACGAGC  CCGGCAAGCC  GCTCACCCTC  CGCGTCTCCC          900

CCGCGCTGGG  AACTGCCCAC  CAAGCAGTCA  CTTGGTTTTT  TCAAAATGTA  CCCATAGCTA          960

CTGTTTACCG  ACCTTGGGGC  AATGTAACTT  GGTTTTGTCC  TCCCTTCATG  TGTACCTTTA         1020

ATGTCAGCCT  GAACTCCCTA  CTTATTTACA  ACTTTTCTGA  CAAAACGGG   GGGCAATACA         1080

CAGCTCTCAT  GCACTCCGGA  CCTGCTTCCC  TCTTTCAGCT  CTTTAAGCCA  ACGACTTGTG         1140

TCACCAAGGT  GGAGGACCCG  CCGTATGCCA  ACGACCCGGC  CTCGCCTGTG  TGGCGCCCAC         1200

TGCTTTTTGC  CTTCGTCCTC  TGCACCGGCT  GCGCGGTGTT  GTTAA CCG CCT TCG              1254
                                                 Pro Pro Ser
                                                       145

GTC CAT CGA TTC TAT CCG GTA CCC GAA AGC TTA TCT CAG CCC GCT TTT                1302
Val His Arg Phe Tyr Pro Val Pro Glu Ser Leu Ser Gln Pro Ala Phe
            150                 155                 160

GGA GTC CCG AGC CCT ATA CCA CCC TCC ACT AAC AGT CCC CCC ATG GAG                1350
Gly Val Pro Ser Pro Ile Pro Pro Ser Thr Asn Ser Pro Pro Met Glu
            165                 170                 175

CCA GAC GGA GTT CAT GCC GAG CAG CAG TTT ATC CTC AAT CAG ATT TCC                1398
Pro Asp Gly Val His Ala Glu Gln Gln Phe Ile Leu Asn Gln Ile Ser
        180                 185                 190

TGC GCC AAC ACT GCC CTC CAG CGT CAA AGG GAG GAA CTA GCT TCC CTT                1446
Cys Ala Asn Thr Ala Leu Gln Arg Gln Arg Glu Glu Leu Ala Ser Leu
        195                 200                 205

GTC ATG TTG CAT GCC TGT AAG CGT GGC CTC TTT TGT CCA GTC AAA ACT                1494
Val Met Leu His Ala Cys Lys Arg Gly Leu Phe Cys Pro Val Lys Thr
210                 215                 220                 225

TAC AAG CTC AGC CTC AAC GCC TCG GCC AGC GAG CAC AGC CTG CAC TTT                1542
Tyr Lys Leu Ser Leu Asn Ala Ser Ala Ser Glu His Ser Leu His Phe
                230                 235                 240

GAA AAA AGT CCC TCC CGA TTC ACC CTG GTC AAC ACT CAC GCC GGA GCT                1590
Glu Lys Ser Pro Ser Arg Phe Thr Leu Val Asn Thr His Ala Gly Ala
            245                 250                 255

TCT GTG CGA GTG GCC CTA CAC CAC CAG GGA GCT TCC GGC AGC ATC CGC                1638
Ser Val Arg Val Ala Leu His His Gln Gly Ala Ser Gly Ser Ile Arg
        260                 265                 270

TGT TCC TGT TCC CAC GCC GAG TGC CTC CCC GTC CTC CTC AAG ACC CTC                1686
Cys Ser Cys Ser His Ala Glu Cys Leu Pro Val Leu Leu Lys Thr Leu
275                 280                 285

TGT GCC TTT AAC TTT TTA GAT TAGCTGAAAG CAAATATAAA ATGGTGTGCT                   1737
Cys Ala Phe Asn Phe Leu Asp
290                 295

TACCGTAATT  CTGTTTTGAC  TTGTGTGCTT  GATTTCTCCC  CCTGCGCCGT  AATCCAGTGC         1797

CCCTCTTCAA  AACTCTCGTA  CCCTATGCGA  TTCGCATAGG  CATATTTTCT  AAAAGCTCTG         1857

AAGTCAACAT  CACTCTCAAA  CACTTCTCCG  TTGTAGGTTA  CTTTCATCTA  CAGATAAAGT         1917

CATCCACCGG  TTAACATCAT  GAAGAGAAGT  GTGCCCCAGG  ACTTTAATCT  TGTGTATCCG         1977

TACAAGGCTA  AGAGGCCCAA  CATCATGCCG  CCCTTTTTTG  ACCGCAATGG  CTTTGTTGAA         2037
```

| | | | | | | |
|---|---|---|---|---|---|---|
| AACCAAGAAG | CCACGCTAGC | CATGCTTGTG | GAAAAGCCGC | TCACGTTCGA | CAAGGAAGGT | 2097 |
| GCGCTGACCC | TGGGCGTCGG | ACGCGGCATC | CGCATTAACC | CCGCGGGGCT | TCTGGAGACA | 2157 |
| AACGACCTCG | CGTCCGCTGT | CTTCCCACCG | CTGGCCTCCG | ATGAGGCCGG | CAACGTCACG | 2217 |
| CTCAACATGT | CTGACGGGCT | ATATACTAAG | GACAACAAGC | TAGCTGTCAA | AGTAGGTCCC | 2277 |
| GGGCTGTCCC | TCGACTCCAA | TAATGCTCTC | CAGGTCCACA | CAGGCGACGG | GCTCACGGTA | 2337 |
| ACCGATGACA | AGGTGTCTCT | AAATACCCAA | GCTCCCTCT | CGACCACCAG | CGCGGGCCTC | 2397 |
| TCCCTACTTC | TGGGTCCAG | CCTCCACTTA | GGTGAGGAGG | AACGACTAAC | AGTAAACACC | 2457 |
| GGAGCGGGCC | TCCAAATTAG | CAATAACGCT | CTGGCCGTAA | AAGTAGGTTC | AGGTATCACC | 2517 |
| GTAGATGCTC | AAAACCAGCT | CGCTGCATCC | CTGGGGACG | GTCTAGAAAG | CAGAGATAAT | 2577 |
| AAAACTGTCG | TTAAGGCTGG | GCCCGGACTT | ACAATAACTA | ATCAAGCTCT | TACTGTTGCT | 2637 |
| ACCGGGAACG | GCCTTCAGGT | CAACCCGGAA | GGGCAACTGC | AGCTAAACAT | TACTGCCGGT | 2697 |
| CAGGGCCTCA | ACTTTGCAAA | CAACAGCCTC | GCCGTGGAGC | TGGGCTCGGG | CCTGCATTTT | 2757 |
| CCCCCTGGCC | AAAACCAAGT | AAGCCTTTAT | CCCGGAGATG | GAATAGACAT | CCGAGATAAT | 2817 |
| AGGGTGACTG | TGCCCGCTGG | GCCAGGCCTG | AGAATGCTCA | ACCACCAACT | TGCCGTAGCT | 2877 |
| TCCGGAGACG | GTTTAGAAGT | CCACAGCGAC | ACCCTCCGGT | TAAAGCTCTC | CCACGGCCTG | 2937 |
| ACATTTGAAA | ATGGCGCCGT | ACGAGCAAAA | CTAGGACCAG | GACTTGGCAC | AGACGACTCT | 2997 |
| GGTCGGTCCG | TGGTTCGCAC | AGGTCGAGGA | CTTAGAGTTG | CAAACGGCCA | AGTCCAGATC | 3057 |
| TTCAGCGGAA | GAGGCACCGC | CATCGGCACT | GATAGCAGCC | TCACTCTCAA | CATCCGGGCG | 3117 |
| CCCCTACAAT | TTTCTGGACC | CGCCTTGACT | GCTAGTTTGC | AAGGCAGTGG | TCCGATTACT | 3177 |
| TACAACAGCA | ACAATGGCAC | TTTCGGTCTC | TCTATAGGCC | CCGGAATGTG | GGTAGACCAA | 3237 |
| AACAGACTTC | AGGTAAACCC | AGGCGCTGGT | TTAGTCTTCC | AAGGAAACAA | CCTTGTCCCA | 3297 |
| AACCTTGCGG | ATCCGCTGGC | TATTTCCGAC | AGCAAAATTA | GTCTCAGTCT | CGGTCCCGGC | 3357 |
| CTGACCCAAG | CTTCCAACGC | CCTGACTTTA | AGTTTAGGAA | ACGGGCTTGA | ATTCTCCAAT | 3417 |
| CAAGCCGTTG | CTATAAAAGC | GGGCCGGGGC | TTACGCTTTG | AGTCTTCCTC | ACAAGCTTTA | 3477 |
| GAGAGCAGCC | TCACAGTCGG | AAATGGCTTA | ACGCTTACCG | ATACTGTGAT | CCGCCCCAAC | 3537 |
| CTAGGGACG | GCCTAGAGGT | CAGAGACAAT | AAAATCATTG | TTAAGCTGGG | CGCGAATCTT | 3597 |
| CGTTTTGAAA | ACGGAGCCGT | AACCGCCGGC | ACCGTTAACC | CTTCTGCGCC | CGAGGCACCA | 3657 |
| CCAACTCTCA | CTGCAGAACC | ACCCCTCCGA | GCCTCCAACT | CCCATCTTCA | ACTGTCCCTA | 3717 |
| TCGGAGGGCT | TGGTTGTGCA | TAACAACGCC | CTTGCTCTCC | AACTGGGAGA | CGGCATGGAA | 3777 |
| GTAAATCAGC | ACGGACTTAC | TTTAAGAGTA | GGCTCGGGTT | TGCAAATGCG | TGACGGCATT | 3837 |
| TTAACAGTTA | CACCCAGCGG | CACTCCTATT | GAGCCCAGAC | TGACTGCCCC | ACTGACTCAG | 3897 |
| ACAGAGAATG | GAATCGGGCT | CGCTCTCGGC | GCCGGCTTGG | AATTAGACGA | GAGCGCGCTC | 3957 |
| CAAGTAAAAG | TTGGGCCCGG | CATGCGCCTG | AACCCTGTAG | AAAAGTATGT | AACCCTGCTC | 4017 |
| CTGGGTCCTG | GCCTTAGTTT | TGGGCAGCCG | GCCAACAGGA | CAAATTATGA | TGTGCGCGTT | 4077 |
| TCTGTGGAGC | CCCCCATGGT | TTTCGGACAG | CGTGGTCAGC | TCACATTTTT | AGTGGGTCAC | 4137 |
| GGACTACACA | TTCAAAATTC | CAAACTTCAG | CTCAATTTGG | GACAAGGCCT | CAGAACTGAC | 4197 |
| CCCGTCACCA | ACCAGCTGGA | AGTGCCCCTC | GGTCAAGGTT | TGGAAATTGC | AGACGAATCC | 4257 |
| CAGGTTAGGG | TTAAATTGGG | CGATGGCCTG | CAGTTTGATT | CACAAGCTCG | CATCACTACC | 4317 |
| GCTCCTAACA | TGGTCACTGA | AACTCTGTGG | ACCGGAACAG | GCAGTAATGC | TAATGTTACA | 4377 |
| TGGCGGGGCT | ACACTGCCCC | CGGCAGCAAA | CTCTTTTTGA | GTCTCACTCG | GTTCAGCACT | 4437 |

-continued

```
GGTCTAGTTT TAGGAAACAT GACTATTGAC AGCAATGCAT CCTTTGGGCA ATACATTAAC    4497

GCGGGACACG AACAGATCGA ATGCTTTATA TTGTTGGACA ATCAGGGTAA CCTAAAAGAA    4557

GGATCTAACT TGCAAGGCAC TTGGGAAGTG AAGAACAACC CCTCTGCTTC CAAAGCTGCT    4617

TTTTTGCCTT CCACCGCCCT ATACCCCATC CTCAACGAAA GCCGAGGGAG TCTTCCTGGA    4677

AAAAATCTTG TGGGCATGCA AGCCATACTG GGAGGCGGGG GCACTTGCAC TGTGATAGCC    4737

ACCCTCAATG GCAGACGCAG CAACAACTAT CCCGCGGGCC AGTCCATAAT TTTCGTGTGG    4797

CAAGAATTCA ACACCATAGC CCGCCAACCT CTGAACCACT CTACACTTAC TTTTTCTTAC    4857

TGGACTTAAA TAAGTTGGAA ATAAAGAGTT AAACTGAATG TTTAAGTGCA ACAGACTTTT    4917

ATTGGTTTTG GCTCACAACA AATTACAACA GCATAGACAA GTCATACCGG TCAAACAACA    4977

CAGGCTCTCG AAAACGGGCT AACCGCTCCA AGAATCTGTC ACGCAGACGA GCAAGTCCTA    5037

AATGTTTTTT CACTCTCTTC GGGGCCAAGT TCAGCATGTA TCGGATTTTC TGCTTACACC    5097

TTT                                                                  5100
```

( 2 ) INFORMATION FOR SEQ ID NO:22:

( i ) SEQUENCE CHARACTERISTICS:
        ( A ) LENGTH: 154 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

```
Pro  Pro  Ser  Val  His  Arg  Phe  Tyr  Pro  Val  Pro  Glu  Ser  Leu  Ser  Gln
 1              5                        10                       15

Pro  Ala  Phe  Gly  Val  Pro  Ser  Pro  Ile  Pro  Pro  Ser  Thr  Asn  Ser  Pro
              20                        25                       30

Pro  Met  Glu  Pro  Asp  Gly  Val  His  Ala  Glu  Gln  Gln  Phe  Ile  Leu  Asn
              35                        40                       45

Gln  Ile  Ser  Cys  Ala  Asn  Thr  Ala  Leu  Gln  Arg  Gln  Arg  Glu  Glu  Leu
              50                        55                       60

Ala  Ser  Leu  Val  Met  Leu  His  Ala  Cys  Lys  Arg  Gly  Leu  Phe  Cys  Pro
 65                       70                       75                       80

Val  Lys  Thr  Tyr  Lys  Leu  Ser  Leu  Asn  Ala  Ser  Ala  Ser  Glu  His  Ser
              85                        90                       95

Leu  His  Phe  Glu  Lys  Ser  Pro  Ser  Arg  Phe  Thr  Leu  Val  Asn  Thr  His
              100                      105                      110

Ala  Gly  Ala  Ser  Val  Arg  Val  Ala  Leu  His  His  Gln  Gly  Ala  Ser  Gly
              115                      120                      125

Ser  Ile  Arg  Cys  Ser  Cys  Ser  His  Ala  Glu  Cys  Leu  Pro  Val  Leu  Leu
              130                      135                      140

Lys  Thr  Leu  Cys  Ala  Phe  Asn  Phe  Leu  Asp
145                       150
```

( 2 ) INFORMATION FOR SEQ ID NO:23:

( i ) SEQUENCE CHARACTERISTICS:
        ( A ) LENGTH: 5100 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1439..1702

( x i ) SEQUENCE DESCRIPTION: SEQ ID NO:23:

| | | | | | | |
|---|---|---|---|---|---|---|
| CCTCATCAAA | CAACCCGTGG | TGGGCACCAC | CCACGTGGAA | ATGCCTCGCA | ACGAAGTCCT | 60 |
| AGAACAACAT | CTGACCTCAC | ATGGCGCTCA | AATCGCGGGC | GGAGGCGCTG | CGGGCGATTA | 120 |
| CTTTAAAAGC | CCCACTTCAG | CTCGAACCCT | TATCCCGCTC | ACCGCCTCCT | GCTTAAGACC | 180 |
| AGATGGAGTC | TTTCAACTAG | GAGGAGGCTC | GCGTTCATCT | TTCAACCCCC | TGCAAACAGA | 240 |
| TTTTGCCTTC | CACGCCCTGC | CCTCCAGACC | GCGCCACGGG | GGCATAGGAT | CCAGGCAGTT | 300 |
| TGTAGAGGAA | TTTGTGCCCG | CCGTCTACCT | CAACCCCTAC | TCGGGACCGC | CGGACTCTTA | 360 |
| TCCGGACCAG | TTTATACGCC | ACTACAACGT | GTACAGCAAC | TCTGTGAGCG | GTTATAGCTG | 420 |
| AGATTGTAAG | ACTCTCCTAT | CTGTCTCTGT | GCTGCTTTTC | CGCTTCAAGC | CCCACAAGCA | 480 |
| TGAAGGGGTT | TCTGCTCATC | TTCAGCCTGC | TTGTGCATTG | TCCCCTAATT | CATGTTGGGA | 540 |
| CCATTAGCTT | CTATGCTGCA | AGGCCCGGGT | CTGAGCCTAA | CGCGACTTAT | GTTTGTGACT | 600 |
| ATGGAAGCGA | GTCAGATTAC | AACCCCACCA | CGGTTCTGTG | GTTGGCTCGA | GAGACCGATG | 660 |
| GCTCCTGGAT | CTCTGTTCTT | TTCCGTCACA | ACGGCTCCTC | AACTGCAGCC | CCCGGGGTCG | 720 |
| TCGCGCACTT | TACTGACCAC | AACAGCAGCA | TTGTGGTGCC | CCAGTATTAC | CTCCTCAACA | 780 |
| ACTCACTCTC | TAAGCTCTGC | TGCTCATACC | GGCACAACGA | GCGTTCTCAG | TTTACCTGCA | 840 |
| AACAAGCTGA | CGTCCCTACC | TGTCACGAGC | CCGGCAAGCC | GCTCACCCTC | CGCGTCTCCC | 900 |
| CCGCGCTGGG | AACTGCCCAC | CAAGCAGTCA | CTTGGTTTTT | TCAAAATGTA | CCCATAGCTA | 960 |
| CTGTTTACCG | ACCTTGGGGC | AATGTAACTT | GGTTTTGTCC | TCCCTTCATG | TGTACCTTTA | 1020 |
| ATGTCAGCCT | GAACTCCCTA | CTTATTTACA | ACTTTTCTGA | CAAAACCGGG | GGGCAATACA | 1080 |
| CAGCTCTCAT | GCACTCCGGA | CCTGCTTCCC | TCTTTCAGCT | CTTTAAGCCA | ACGACTTGTG | 1140 |
| TCACCAAGGT | GGAGGACCCG | CCGTATGCCA | ACGACCCGGC | CTCGCCTGTG | TGGCGCCCAC | 1200 |
| TGCTTTTTGC | CTTCGTCCTC | TGCACCGGCT | GCGCGGTGTT | GTTAACCGCC | TTCGGTCCAT | 1260 |
| CGATTCTATC | CGGTACCCGA | AAGCTTATCT | CAGCCCGCTT | TTGGAGTCCC | GAGCCCTATA | 1320 |
| CCACCCTCCA | CTAACAGTCC | CCCCATGGAG | CCAGACGGAG | TTCATGCCGA | GCAGCAGTTT | 1380 |
| ATCCTCAATC | AGATTTCCTG | CGCCAACACT | GCCCTCCAGC | GTCAAAGGGA | GGAACTAG | 1438 |

| | | | | | | | | | | | | | | | | |
|---|---|---|---|---|---|---|---|---|---|---|---|---|---|---|---|---|
| CTT | CCC | TTG | TCA | TGT | TGC | ATG | CCT | GTA | AGC | GTG | GCC | TCT | TTT | GTC | CAG | 1486 |
| Leu | Pro | Leu | Ser | Cys | Cys | Met | Pro | Val | Ser | Val | Ala | Ser | Phe | Val | Gln | |
| 155 | | | | | 160 | | | | | 165 | | | | | 170 | |
| TCA | AAA | CTT | ACA | AGC | TCA | GCC | TCA | ACG | CCT | CGG | CCA | GCG | AGC | ACA | GCC | 1534 |
| Ser | Lys | Leu | Thr | Ser | Ser | Ala | Ser | Thr | Pro | Arg | Pro | Ala | Ser | Thr | Ala | |
| | | | | 175 | | | | | 180 | | | | | 185 | | |
| TGC | ACT | TTG | AAA | AAA | GTC | CCT | CCC | GAT | TCA | CCC | TGG | TCA | ACA | CTC | ACG | 1582 |
| Cys | Thr | Leu | Lys | Lys | Val | Pro | Pro | Asp | Ser | Pro | Trp | Ser | Thr | Leu | Thr | |
| | | | 190 | | | | | 195 | | | | | 200 | | | |
| CCG | GAG | CTT | CTG | TGC | GAG | TGG | CCC | TAC | ACC | ACC | AGG | GAG | CTT | CCG | GCA | 1630 |
| Pro | Glu | Leu | Leu | Cys | Glu | Trp | Pro | Tyr | Thr | Thr | Arg | Glu | Leu | Pro | Ala | |
| | | 205 | | | | | 210 | | | | | 215 | | | | |
| GCA | TCC | GCT | GTT | CCT | GTT | CCC | ACG | CCG | AGT | GCC | TCC | CCG | TCC | TCC | TCA | 1678 |
| Ala | Ser | Ala | Val | Pro | Val | Pro | Thr | Pro | Ser | Ala | Ser | Pro | Ser | Ser | Ser | |
| | | 220 | | | | | 225 | | | | | 230 | | | | |
| AGA | CCC | TCT | GTG | CCT | TTA | ACT | TTT | TAGATTAGCT | | GAAAGCAAAT | | ATAAAATGGT | | | | 1732 |
| Arg | Pro | Ser | Val | Pro | Leu | Thr | Phe | | | | | | | | | |
| 235 | | | | | 240 | | | | | | | | | | | |

| | | | | | | |
|---|---|---|---|---|---|---|
| GTGCTTACCG | TAATTCTGTT | TTGACTTGTG | TGCTTGATTT | CTCCCCCTGC | GCCGTAATCC | 1792 |
| AGTGCCCCTC | TTCAAAACTC | TCGTACCCTA | TGCGATTCGC | ATAGGCATAT | TTCTAAAAG | 1852 |
| CTCTGAAGTC | AACATCACTC | TCAAACACTT | CTCCGTTGTA | GGTTACTTTC | ATCTACAGAT | 1912 |

```
AAAGTCATCC  ACCGGTTAAC  ATCATGAAGA  GAAGTGTGCC  CCAGGACTTT  AATCTTGTGT   1972
ATCCGTACAA  GGCTAAGAGG  CCCAACATCA  TGCCGCCCTT  TTTTGACCGC  AATGGCTTTG   2032
TTGAAAACCA  AGAAGCCACG  CTAGCCATGC  TTGTGGAAAA  GCCGCTCACG  TTCGACAAGG   2092
AAGGTGCGCT  GACCCTGGGC  GTCGGACGCG  GCATCCGCAT  TAACCCCGCG  GGGCTTCTGG   2152
AGACAAACGA  CCTCGCGTCC  GCTGTCTTCC  CACCGCTGGC  CTCCGATGAG  GCCGGCAACG   2212
TCACGCTCAA  CATGTCTGAC  GGGCTATATA  CTAAGGACAA  CAAGCTAGCT  GTCAAAGTAG   2272
GTCCGGGCT   GTCCCTCGAC  TCCAATAATG  CTCTCCAGGT  CCACACAGGC  GACGGGCTCA   2332
CGGTAACCGA  TGACAAGGTG  TCTCTAAATA  CCCAAGCTCC  CCTCTCGACC  ACCAGCGCGG   2392
GCCTCTCCCT  ACTTCTGGGT  CCCAGCCTCC  ACTTAGGTGA  GGAGGAACGA  CTAACAGTAA   2452
ACACCGGAGC  GGGCCTCCAA  ATTAGCAATA  ACGCTCTGGC  CGTAAAAGTA  GGTTCAGGTA   2512
TCACCGTAGA  TGCTCAAAAC  CAGCTCGCTG  CATCCCTGGG  GGACGGTCTA  GAAAGCAGAG   2572
ATAATAAAAC  TGTCGTTAAG  GCTGGGCCCG  GACTTACAAT  AACTAATCAA  GCTCTTACTG   2632
TTGCTACCGG  GAACGGCCTT  CAGGTCAACC  CGGAAGGGCA  ACTGCAGCTA  ACATTACTG    2692
CCGGTCAGGG  CCTCAACTTT  GCAAACAACA  GCCTCGCCGT  GGAGCTGGGC  TCGGGCCTGC   2752
ATTTTCCCCC  TGGCCAAAAC  CAAGTAAGCC  TTTATCCCGG  AGATGGAATA  GACATCCGAG   2812
ATAATAGGGT  GACTGTGCCC  GCTGGGCCAG  GCCTGAGAAT  GCTCAACCAC  CAACTTGCCG   2872
TAGCTTCCGG  AGACGGTTTA  GAAGTCCACA  GCGACACCCT  CCGGTTAAAG  CTCTCCCACG   2932
GCCTGACATT  TGAAAATGGC  GCCGTACGAG  CAAAACTAGG  ACCAGGACTT  GGCACAGACG   2992
ACTCTGGTCG  GTCCGTGGTT  CGCACAGGTC  GAGGACTTAG  AGTTGCAAAC  GGCCAAGTCC   3052
AGATCTTCAG  CGGAAGAGGC  ACCGCCATCG  GCACTGATAG  CAGCCTCACT  CTCAACATCC   3112
GGGCGCCCCT  ACAATTTTCT  GGACCCGCCT  TGACTGCTAG  TTTGCAAGGC  AGTGGTCCGA   3172
TTACTTACAA  CAGCAACAAT  GGCACTTTCG  GTCTCTCTAT  AGGCCCCGGA  ATGTGGGTAG   3232
ACCAAAACAG  ACTTCAGGTA  AACCCAGGCG  CTGGTTTAGT  CTTCCAAGGA  AACAACCTTG   3292
TCCCAAACCT  TGCGGATCCG  CTGGCTATTT  CCGACAGCAA  AATTAGTCTC  AGTCTCGGTC   3352
CCGGCCTGAC  CCAAGCTTCC  AACGCCCTGA  CTTTAAGTTT  AGGAAACGGG  CTTGAATTCT   3412
CCAATCAAGC  CGTTGCTATA  AAAGCGGGCC  GGGGCTTACG  CTTTGAGTCT  TCCTCACAAG   3472
CTTTAGAGAG  CAGCCTCACA  GTCGGAAATG  GCTTAACGCT  TACCGATACT  GTGATCCGCC   3532
CCAACCTAGG  GGACGGCCTA  GAGGTCAGAG  ACAATAAAAT  CATTGTTAAG  CTGGGCGCGA   3592
ATCTTCGTTT  TGAAAACGGA  GCCGTAACCG  CCGGCACCGT  TAACCCTTCT  GCGCCCGAGG   3652
CACCACCAAC  TCTCACTGCA  GAACCACCCC  TCCGAGCCTC  CAACTCCCAT  CTTCAACTGT   3712
CCCTATCGGA  GGGCTTGGTT  GTGCATAACA  ACGCCCTTGC  TCTCCAACTG  GGAGACGGCA   3772
TGGAAGTAAA  TCAGCACGGA  CTTACTTTAA  GAGTAGGCTC  GGGTTTGCAA  ATGCGTGACG   3832
GCATTTTAAC  AGTTACACCC  AGCGGCACTC  CTATTGAGCC  CAGACTGACT  GCCCCACTGA   3892
CTCAGACAGA  GAATGGAATC  GGGCTCGCTC  TCGGCGCCGG  CTTGGAATTA  GACGAGAGCG   3952
CGCTCCAAGT  AAAAGTTGGG  CCCGGCATGC  GCCTGAACCC  TGTAGAAAAG  TATGTAACCC   4012
TGCTCCTGGG  TCCTGGCCTT  AGTTTGGGC   AGCCGGCCAA  CAGGACAAAT  TATGATGTGC   4072
GCGTTTCTGT  GGAGCCCCCC  ATGGTTTTCG  GACAGCGTGG  TCAGCTCACA  TTTTTAGTGG   4132
GTCACGGACT  ACACATTCAA  AATTCCAAAC  TTCAGCTCAA  TTTGGGACAA  GGCCTCAGAA   4192
CTGACCCCGT  CACCAACCAG  CTGGAAGTGC  CCCTCGGTCA  AGGTTTGGAA  ATTGCAGACG   4252
AATCCCAGGT  TAGGGTTAAA  TTGGGCGATG  GCCTGCAGTT  TGATTCACAA  GCTCGCATCA   4312
```

| | | | | | | |
|---|---|---|---|---|---|---|
|CTACCGCTCC|TAACATGGTC|ACTGAAACTC|TGTGGACCGG|AACAGGCAGT|AATGCTAATG|4372|
|TTACATGGCG|GGGCTACACT|GCCCCCGGCA|GCAAACTCTT|TTTGAGTCTC|ACTCGGTTCA|4432|
|GCACTGGTCT|AGTTTTAGGA|AACATGACTA|TTGACAGCAA|TGCATCCTTT|GGGCAATACA|4492|
|TTAACGCGGG|ACACGAACAG|ATCGAATGCT|TTATATTGTT|GGACAATCAG|GGTAACCTAA|4552|
|AAGAAGGATC|TAACTTGCAA|GGCACTTGGG|AAGTGAAGAA|CAACCCCTCT|GCTTCCAAAG|4612|
|CTGCTTTTTT|GCCTTCCACC|GCCCTATACC|CCATCCTCAA|CGAAAGCCGA|GGGAGTCTTC|4672|
|CTGGAAAAAA|TCTTGTGGGC|ATGCAAGCCA|TACTGGGAGG|CGGGGGCACT|TGCACTGTGA|4732|
|TAGCCACCCT|CAATGGCAGA|CGCAGCAACA|ACTATCCCGC|GGGCCAGTCC|ATAATTTTCG|4792|
|TGTGGCAAGA|ATTCAACACC|ATAGCCCGCC|AACCTCTGAA|CCACTCTACA|CTTACTTTTT|4852|
|CTTACTGGAC|TTAAATAAGT|TGGAAATAAA|GAGTTAAACT|GAATGTTTAA|GTGCAACAGA|4912|
|CTTTTATTGG|TTTTGGCTCA|CAACAAATTA|CAACAGCATA|GACAAGTCAT|ACCGGTCAAA|4972|
|CAACACAGGC|TCTCGAAAAC|GGGCTAACCG|CTCCAAGAAT|CTGTCACGCA|GACGAGCAAG|5032|
|TCCTAAATGT|TTTTTCACTC|TCTTCGGGGC|CAAGTTCAGC|ATGTATCGGA|TTTTCTGCTT|5092|
|ACACCTTT| | | | | |5100|

( 2 ) INFORMATION FOR SEQ ID NO:24:

( i ) SEQUENCE CHARACTERISTICS:
        ( A ) LENGTH: 88 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

Leu Pro Leu Ser Cys Cys Met Pro Val Ser Val Ala Ser Phe Val Gln
 1               5                  10                  15

Ser Lys Leu Thr Ser Ser Ala Ser Thr Pro Arg Pro Ala Ser Thr Ala
            20                  25                  30

Cys Thr Leu Lys Lys Val Pro Pro Asp Ser Pro Trp Ser Thr Leu Thr
            35                  40                  45

Pro Glu Leu Leu Cys Glu Trp Pro Tyr Thr Thr Arg Glu Leu Pro Ala
        50                  55                  60

Ala Ser Ala Val Pro Val Pro Thr Pro Ser Ala Ser Pro Ser Ser Ser
65                  70                  75                  80

Arg Pro Ser Val Pro Leu Thr Phe
                85

( 2 ) INFORMATION FOR SEQ ID NO:25:

( i ) SEQUENCE CHARACTERISTICS:
        ( A ) LENGTH: 5100 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1915..4863

( x i ) SEQUENCE DESCRIPTION: SEQ ID NO:25:

| | | | | | | |
|---|---|---|---|---|---|---|
|CCTCATCAAA|CAACCCGTGG|TGGGCACCAC|CCACGTGGAA|ATGCCTCGCA|ACGAAGTCCT|60|
|AGAACAACAT|CTGACCTCAC|ATGGCGCTCA|AATCGCGGGC|GGAGGCGCTG|CGGGCGATTA|120|

-continued

```
CTTTAAAAGC  CCCACTTCAG  CTCGAACCCT  TATCCCGCTC  ACCGCCTCCT  GCTTAAGACC   180
AGATGGAGTC  TTTCAACTAG  GAGGAGGCTC  GCGTTCATCT  TTCAACCCCC  TGCAAACAGA   240
TTTTGCCTTC  CACGCCCTGC  CCTCCAGACC  GCGCCACGGG  GGCATAGGAT  CCAGGCAGTT   300
TGTAGAGGAA  TTTGTGCCCG  CCGTCTACCT  CAACCCCTAC  TCGGGACCGC  CGGACTCTTA   360
TCCGGACCAG  TTTATACGCC  ACTACAACGT  GTACAGCAAC  TCTGTGAGCG  GTTATAGCTG   420
AGATTGTAAG  ACTCTCCTAT  CTGTCTCTGT  GCTGCTTTTC  CGCTTCAAGC  CCCACAAGCA   480
TGAAGGGGTT  TCTGCTCATC  TTCAGCCTGC  TTGTGCATTG  TCCCCTAATT  CATGTTGGGA   540
CCATTAGCTT  CTATGCTGCA  AGGCCCGGGT  CTGAGCCTAA  CGCGACTTAT  GTTTGTGACT   600
ATGGAAGCGA  GTCAGATTAC  AACCCCACCA  CGGTTCTGTG  GTTGGCTCGA  GAGACCGATG   660
GCTCCTGGAT  CTCTGTTCTT  TTCCGTCACA  ACGGCTCCTC  AACTGCAGCC  CCCGGGGTCG   720
TCGCGCACTT  TACTGACCAC  AACAGCAGCA  TTGTGGTGCC  CCAGTATTAC  CTCCTCAACA   780
ACTCACTCTC  TAAGCTCTGC  TGCTCATACC  GGCACAACGA  GCGTTCTCAG  TTTACCTGCA   840
AACAAGCTGA  CGTCCCTACC  TGTCACGAGC  CCGGCAAGCC  GCTCACCCTC  CGCGTCTCCC   900
CCGCGCTGGG  AACTGCCCAC  CAAGCAGTCA  CTTGGTTTTT  TCAAAATGTA  CCCATAGCTA   960
CTGTTTACCG  ACCTTGGGGC  AATGTAACTT  GGTTTTGTCC  TCCCTTCATG  TGTACCTTTA  1020
ATGTCAGCCT  GAACTCCCTA  CTTATTTACA  ACTTTTCTGA  CAAAACCGGG  GGGCAATACA  1080
CAGCTCTCAT  GCACTCCGGA  CCTGCTTCCC  TCTTTCAGCT  CTTTAAGCCA  ACGACTTGTG  1140
TCACCAAGGT  GGAGGACCCG  CCGTATGCCA  ACGACCCGGC  CTCGCCTGTG  TGGCGCCCAC  1200
TGCTTTTTGC  CTTCGTCCTC  TGCACCGGCT  GCGCGGTGTT  GTTAACCGCC  TTCGGTCCAT  1260
CGATTCTATC  CGGTACCCGA  AAGCTTATCT  CAGCCCGCTT  TTGGAGTCCC  GAGCCCTATA  1320
CCACCCTCCA  CTAACAGTCC  CCCCATGGAG  CCAGACGGAG  TTCATGCCGA  GCAGCAGTTT  1380
ATCCTCAATC  AGATTTCCTG  CGCCAACACT  GCCCTCCAGC  GTCAAAGGGA  GGAACTAGCT  1440
TCCCTTGTCA  TGTTGCATGC  CTGTAAGCGT  GGCCTCTTTT  GTCCAGTCAA  AACTTACAAG  1500
CTCAGCCTCA  ACGCCTCGGC  CAGCGAGCAC  AGCCTGCACT  TGAAAAAAG   TCCCTCCCGA  1560
TTCACCCTGG  TCAACACTCA  CGCCGGAGCT  TCTGTGCGAG  TGGCCCTACA  CCACCAGGGA  1620
GCTTCCGGCA  GCATCCGCTG  TTCCTGTTCC  CACGCCGAGT  GCCTCCCCGT  CCTCCTCAAG  1680
ACCCTCTGTG  CCTTTAACTT  TTTAGATTAG  CTGAAAGCAA  ATATAAAATG  GTGTGCTTAC  1740
CGTAATTCTG  TTTTGACTTG  TGTGCTTGAT  TTCTCCCCCT  GCGCCGTAAT  CCAGTGCCCC  1800
TCTTCAAAAC  TCTCGTACCC  TATGCGATTC  GCATAGGCAT  ATTTTCTAAA  AGCTCTGAAG  1860
TCAACATCAC  TCTCAAACAC  TTCTCCGTTG  TAGGTTACTT  TCATCTACAG  ATAA AGT    1917
                                                              Ser
CAT CCA CCG GTT AAC ATC ATG AAG AGA AGT GTG CCC CAG GAC TTT AAT         1965
His Pro Pro Val Asn Ile Met Lys Arg Ser Val Pro Gln Asp Phe Asn
 90              95                  100                 105
CTT GTG TAT CCG TAC AAG GCT AAG AGG CCC AAC ATC ATG CCG CCC TTT         2013
Leu Val Tyr Pro Tyr Lys Ala Lys Arg Pro Asn Ile Met Pro Pro Phe
                 110                 115                 120
TTT GAC CGC AAT GGC TTT GTT GAA AAC CAA GAA GCC ACG CTA GCC ATG         2061
Phe Asp Arg Asn Gly Phe Val Glu Asn Gln Glu Ala Thr Leu Ala Met
             125                 130                 135
CTT GTG GAA AAG CCG CTC ACG TTC GAC AAG GAA GGT GCG CTG ACC CTG         2109
Leu Val Glu Lys Pro Leu Thr Phe Asp Lys Glu Gly Ala Leu Thr Leu
         140                 145                 150
GGC GTC GGA CGC GGC ATC CGC ATT AAC CCC GCG GGG CTT CTG GAG ACA         2157
Gly Val Gly Arg Gly Ile Arg Ile Asn Pro Ala Gly Leu Leu Glu Thr
     155                 160                 165
```

| | | | | | | | | | | | | | | | | |
|---|---|---|---|---|---|---|---|---|---|---|---|---|---|---|---|---|
| AAC | GAC | CTC | GCG | TCC | GCT | GTC | TTC | CCA | CCG | CTG | GCC | TCC | GAT | GAG | GCC | 2205 |
| Asn | Asp | Leu | Ala | Ser | Ala | Val | Phe | Pro | Pro | Leu | Ala | Ser | Asp | Glu | Ala | |
| 170 | | | | 175 | | | | | 180 | | | | | | 185 | |
| GGC | AAC | GTC | ACG | CTC | AAC | ATG | TCT | GAC | GGG | CTA | TAT | ACT | AAG | GAC | AAC | 2253 |
| Gly | Asn | Val | Thr | Leu | Asn | Met | Ser | Asp | Gly | Leu | Tyr | Thr | Lys | Asp | Asn | |
| | | | | 190 | | | | | 195 | | | | | 200 | | |
| AAG | CTA | GCT | GTC | AAA | GTA | GGT | CCC | GGG | CTG | TCC | CTC | GAC | TCC | AAT | AAT | 2301 |
| Lys | Leu | Ala | Val | Lys | Val | Gly | Pro | Gly | Leu | Ser | Leu | Asp | Ser | Asn | Asn | |
| | | | 205 | | | | | 210 | | | | | 215 | | | |
| GCT | CTC | CAG | GTC | CAC | ACA | GGC | GAC | GGG | CTC | ACG | GTA | ACC | GAT | GAC | AAG | 2349 |
| Ala | Leu | Gln | Val | His | Thr | Gly | Asp | Gly | Leu | Thr | Val | Thr | Asp | Asp | Lys | |
| | | 220 | | | | | 225 | | | | | 230 | | | | |
| GTG | TCT | CTA | AAT | ACC | CAA | GCT | CCC | CTC | TCG | ACC | ACC | AGC | GCG | GGC | CTC | 2397 |
| Val | Ser | Leu | Asn | Thr | Gln | Ala | Pro | Leu | Ser | Thr | Thr | Ser | Ala | Gly | Leu | |
| | 235 | | | | | 240 | | | | | 245 | | | | | |
| TCC | CTA | CTT | CTG | GGT | CCC | AGC | CTC | CAC | TTA | GGT | GAG | GAG | GAA | CGA | CTA | 2445 |
| Ser | Leu | Leu | Leu | Gly | Pro | Ser | Leu | His | Leu | Gly | Glu | Glu | Glu | Arg | Leu | |
| 250 | | | | | 255 | | | | | 260 | | | | | 265 | |
| ACA | GTA | AAC | ACC | GGA | GCG | GGC | CTC | CAA | ATT | AGC | AAT | AAC | GCT | CTG | GCC | 2493 |
| Thr | Val | Asn | Thr | Gly | Ala | Gly | Leu | Gln | Ile | Ser | Asn | Asn | Ala | Leu | Ala | |
| | | | | 270 | | | | | 275 | | | | | 280 | | |
| GTA | AAA | GTA | GGT | TCA | GGT | ATC | ACC | GTA | GAT | GCT | CAA | AAC | CAG | CTC | GCT | 2541 |
| Val | Lys | Val | Gly | Ser | Gly | Ile | Thr | Val | Asp | Ala | Gln | Asn | Gln | Leu | Ala | |
| | | | 285 | | | | | 290 | | | | | 295 | | | |
| GCA | TCC | CTG | GGG | GAC | GGT | CTA | GAA | AGC | AGA | GAT | AAT | AAA | ACT | GTC | GTT | 2589 |
| Ala | Ser | Leu | Gly | Asp | Gly | Leu | Glu | Ser | Arg | Asp | Asn | Lys | Thr | Val | Val | |
| | | 300 | | | | | 305 | | | | | 310 | | | | |
| AAG | GCT | GGG | CCC | GGA | CTT | ACA | ATA | ACT | AAT | CAA | GCT | CTT | ACT | GTT | GCT | 2637 |
| Lys | Ala | Gly | Pro | Gly | Leu | Thr | Ile | Thr | Asn | Gln | Ala | Leu | Thr | Val | Ala | |
| | 315 | | | | | 320 | | | | | 325 | | | | | |
| ACC | GGG | AAC | GGC | CTT | CAG | GTC | AAC | CCG | GAA | GGG | CAA | CTG | CAG | CTA | AAC | 2685 |
| Thr | Gly | Asn | Gly | Leu | Gln | Val | Asn | Pro | Glu | Gly | Gln | Leu | Gln | Leu | Asn | |
| 330 | | | | | 335 | | | | | 340 | | | | | 345 | |
| ATT | ACT | GCC | GGT | CAG | GGC | CTC | AAC | TTT | GCA | AAC | AAC | AGC | CTC | GCC | GTG | 2733 |
| Ile | Thr | Ala | Gly | Gln | Gly | Leu | Asn | Phe | Ala | Asn | Asn | Ser | Leu | Ala | Val | |
| | | | | 350 | | | | | 355 | | | | | 360 | | |
| GAG | CTG | GGC | TCG | GGC | CTG | CAT | TTT | CCC | CCT | GGC | CAA | AAC | CAA | GTA | AGC | 2781 |
| Glu | Leu | Gly | Ser | Gly | Leu | His | Phe | Pro | Pro | Gly | Gln | Asn | Gln | Val | Ser | |
| | | | 365 | | | | | 370 | | | | | 375 | | | |
| CTT | TAT | CCC | GGA | GAT | GGA | ATA | GAC | ATC | CGA | GAT | AAT | AGG | GTG | ACT | GTG | 2829 |
| Leu | Tyr | Pro | Gly | Asp | Gly | Ile | Asp | Ile | Arg | Asp | Asn | Arg | Val | Thr | Val | |
| | | 380 | | | | | 385 | | | | | 390 | | | | |
| CCC | GCT | GGG | CCA | GGC | CTG | AGA | ATG | CTC | AAC | CAC | CAA | CTT | GCC | GTA | GCT | 2877 |
| Pro | Ala | Gly | Pro | Gly | Leu | Arg | Met | Leu | Asn | His | Gln | Leu | Ala | Val | Ala | |
| | 395 | | | | | 400 | | | | | 405 | | | | | |
| TCC | GGA | GAC | GGT | TTA | GAA | GTC | CAC | AGC | GAC | ACC | CTC | CGG | TTA | AAG | CTC | 2925 |
| Ser | Gly | Asp | Gly | Leu | Glu | Val | His | Ser | Asp | Thr | Leu | Arg | Leu | Lys | Leu | |
| 410 | | | | | 415 | | | | | 420 | | | | | 425 | |
| TCC | CAC | GGC | CTG | ACA | TTT | GAA | AAT | GGC | GCC | GTA | CGA | GCA | AAA | CTA | GGA | 2973 |
| Ser | His | Gly | Leu | Thr | Phe | Glu | Asn | Gly | Ala | Val | Arg | Ala | Lys | Leu | Gly | |
| | | | | 430 | | | | | 435 | | | | | 440 | | |
| CCA | GGA | CTT | GGC | ACA | GAC | GAC | TCT | GGT | CGG | TCC | GTG | GTT | CGC | ACA | GGT | 3021 |
| Pro | Gly | Leu | Gly | Thr | Asp | Asp | Ser | Gly | Arg | Ser | Val | Val | Arg | Thr | Gly | |
| | | | 445 | | | | | 450 | | | | | 455 | | | |
| CGA | GGA | CTT | AGA | GTT | GCA | AAC | GGC | CAA | GTC | CAG | ATC | TTC | AGC | GGA | AGA | 3069 |
| Arg | Gly | Leu | Arg | Val | Ala | Asn | Gly | Gln | Val | Gln | Ile | Phe | Ser | Gly | Arg | |
| | | 460 | | | | | 465 | | | | | 470 | | | | |
| GGC | ACC | GCC | ATC | GGC | ACT | GAT | AGC | AGC | CTC | ACT | CTC | AAC | ATC | CGG | GCG | 3117 |
| Gly | Thr | Ala | Ile | Gly | Thr | Asp | Ser | Ser | Leu | Thr | Leu | Asn | Ile | Arg | Ala | |
| | 475 | | | | | 480 | | | | | 485 | | | | | |

| | | | | | | | | | | | | | | | | |
|---|---|---|---|---|---|---|---|---|---|---|---|---|---|---|---|---|
| CCC | CTA | CAA | TTT | TCT | GGA | CCC | GCC | TTG | ACT | GCT | AGT | TTG | CAA | GGC | AGT | 3165 |
| Pro | Leu | Gln | Phe | Ser | Gly | Pro | Ala | Leu | Thr | Ala | Ser | Leu | Gln | Gly | Ser | |
| 490 | | | | | 495 | | | | 500 | | | | | | 505 | |
| GGT | CCG | ATT | ACT | TAC | AAC | AGC | AAC | AAT | GGC | ACT | TTC | GGT | CTC | TCT | ATA | 3213 |
| Gly | Pro | Ile | Thr | Tyr | Asn | Ser | Asn | Asn | Gly | Thr | Phe | Gly | Leu | Ser | Ile | |
| | | | | 510 | | | | | 515 | | | | | 520 | | |
| GGC | CCC | GGA | ATG | TGG | GTA | GAC | CAA | AAC | AGA | CTT | CAG | GTA | AAC | CCA | GGC | 3261 |
| Gly | Pro | Gly | Met | Trp | Val | Asp | Gln | Asn | Arg | Leu | Gln | Val | Asn | Pro | Gly | |
| | | | | 525 | | | | | 530 | | | | | 535 | | |
| GCT | GGT | TTA | GTC | TTC | CAA | GGA | AAC | AAC | CTT | GTC | CCA | AAC | CTT | GCG | GAT | 3309 |
| Ala | Gly | Leu | Val | Phe | Gln | Gly | Asn | Asn | Leu | Val | Pro | Asn | Leu | Ala | Asp | |
| | | | | 540 | | | | | 545 | | | | | 550 | | |
| CCG | CTG | GCT | ATT | TCC | GAC | AGC | AAA | ATT | AGT | CTC | AGT | CTC | GGT | CCC | GGC | 3357 |
| Pro | Leu | Ala | Ile | Ser | Asp | Ser | Lys | Ile | Ser | Leu | Ser | Leu | Gly | Pro | Gly | |
| | | | | 555 | | | | | 560 | | | | | 565 | | |
| CTG | ACC | CAA | GCT | TCC | AAC | GCC | CTG | ACT | TTA | AGT | TTA | GGA | AAC | GGG | CTT | 3405 |
| Leu | Thr | Gln | Ala | Ser | Asn | Ala | Leu | Thr | Leu | Ser | Leu | Gly | Asn | Gly | Leu | |
| 570 | | | | | 575 | | | | 580 | | | | | | 585 | |
| GAA | TTC | TCC | AAT | CAA | GCC | GTT | GCT | ATA | AAA | GCG | GGC | CGG | GGC | TTA | CGC | 3453 |
| Glu | Phe | Ser | Asn | Gln | Ala | Val | Ala | Ile | Lys | Ala | Gly | Arg | Gly | Leu | Arg | |
| | | | | 590 | | | | | 595 | | | | | 600 | | |
| TTT | GAG | TCT | TCC | TCA | CAA | GCT | TTA | GAG | AGC | AGC | CTC | ACA | GTC | GGA | AAT | 3501 |
| Phe | Glu | Ser | Ser | Ser | Gln | Ala | Leu | Glu | Ser | Ser | Leu | Thr | Val | Gly | Asn | |
| | | | 605 | | | | | 610 | | | | | 615 | | | |
| GGC | TTA | ACG | CTT | ACC | GAT | ACT | GTG | ATC | CGC | CCC | AAC | CTA | GGG | GAC | GGC | 3549 |
| Gly | Leu | Thr | Leu | Thr | Asp | Thr | Val | Ile | Arg | Pro | Asn | Leu | Gly | Asp | Gly | |
| | | 620 | | | | | 625 | | | | | 630 | | | | |
| CTA | GAG | GTC | AGA | GAC | AAT | AAA | ATC | ATT | GTT | AAG | CTG | GGC | GCG | AAT | CTT | 3597 |
| Leu | Glu | Val | Arg | Asp | Asn | Lys | Ile | Ile | Val | Lys | Leu | Gly | Ala | Asn | Leu | |
| 635 | | | | | 640 | | | | | 645 | | | | | | |
| CGT | TTT | GAA | AAC | GGA | GCC | GTA | ACC | GCC | GGC | ACC | GTT | AAC | CCT | TCT | GCG | 3645 |
| Arg | Phe | Glu | Asn | Gly | Ala | Val | Thr | Ala | Gly | Thr | Val | Asn | Pro | Ser | Ala | |
| 650 | | | | | 655 | | | | | 660 | | | | | 665 | |
| CCC | GAG | GCA | CCA | CCA | ACT | CTC | ACT | GCA | GAA | CCA | CCC | CTC | CGA | GCC | TCC | 3693 |
| Pro | Glu | Ala | Pro | Pro | Thr | Leu | Thr | Ala | Glu | Pro | Pro | Leu | Arg | Ala | Ser | |
| | | | | 670 | | | | | 675 | | | | | 680 | | |
| AAC | TCC | CAT | CTT | CAA | CTG | TCC | CTA | TCG | GAG | GGC | TTG | GTT | GTG | CAT | AAC | 3741 |
| Asn | Ser | His | Leu | Gln | Leu | Ser | Leu | Ser | Glu | Gly | Leu | Val | Val | His | Asn | |
| | | | 685 | | | | | 690 | | | | | 695 | | | |
| AAC | GCC | CTT | GCT | CTC | CAA | CTG | GGA | GAC | GGC | ATG | GAA | GTA | AAT | CAG | CAC | 3789 |
| Asn | Ala | Leu | Ala | Leu | Gln | Leu | Gly | Asp | Gly | Met | Glu | Val | Asn | Gln | His | |
| | | 700 | | | | | 705 | | | | | 710 | | | | |
| GGA | CTT | ACT | TTA | AGA | GTA | GGC | TCG | GGT | TTG | CAA | ATG | CGT | GAC | GGC | ATT | 3837 |
| Gly | Leu | Thr | Leu | Arg | Val | Gly | Ser | Gly | Leu | Gln | Met | Arg | Asp | Gly | Ile | |
| | | 715 | | | | | 720 | | | | | 725 | | | | |
| TTA | ACA | GTT | ACA | CCC | AGC | GGC | ACT | CCT | ATT | GAG | CCC | AGA | CTG | ACT | GCC | 3885 |
| Leu | Thr | Val | Thr | Pro | Ser | Gly | Thr | Pro | Ile | Glu | Pro | Arg | Leu | Thr | Ala | |
| 730 | | | | | 735 | | | | | 740 | | | | | 745 | |
| CCA | CTG | ACT | CAG | ACA | GAG | AAT | GGA | ATC | GGG | CTC | GCT | CTC | GGC | GCC | GGC | 3933 |
| Pro | Leu | Thr | Gln | Thr | Glu | Asn | Gly | Ile | Gly | Leu | Ala | Leu | Gly | Ala | Gly | |
| | | | | 750 | | | | | 755 | | | | | 760 | | |
| TTG | GAA | TTA | GAC | GAG | AGC | GCG | CTC | CAA | GTA | AAA | GTT | GGG | CCC | GGC | ATG | 3981 |
| Leu | Glu | Leu | Asp | Glu | Ser | Ala | Leu | Gln | Val | Lys | Val | Gly | Pro | Gly | Met | |
| | | | 765 | | | | | 770 | | | | | 775 | | | |
| CGC | CTG | AAC | CCT | GTA | GAA | AAG | TAT | GTA | ACC | CTG | CTC | CTG | GGT | CCT | GGC | 4029 |
| Arg | Leu | Asn | Pro | Val | Glu | Lys | Tyr | Val | Thr | Leu | Leu | Leu | Gly | Pro | Gly | |
| | | 780 | | | | | 785 | | | | | 790 | | | | |
| CTT | AGT | TTT | GGG | CAG | CCG | GCC | AAC | AGG | ACA | AAT | TAT | GAT | GTG | CGC | GTT | 4077 |
| Leu | Ser | Phe | Gly | Gln | Pro | Ala | Asn | Arg | Thr | Asn | Tyr | Asp | Val | Arg | Val | |
| | | 795 | | | | | 800 | | | | | 805 | | | | |

```
TCT  GTG  GAG  CCC  CCC  ATG  GTT  TTC  GGA  CAG  CGT  GGT  CAG  CTC  ACA  TTT    4125
Ser  Val  Glu  Pro  Pro  Met  Val  Phe  Gly  Gln  Arg  Gly  Gln  Leu  Thr  Phe
810            815                      820                      825

TTA  GTG  GGT  CAC  GGA  CTA  CAC  ATT  CAA  AAT  TCC  AAA  CTT  CAG  CTC  AAT    4173
Leu  Val  Gly  His  Gly  Leu  His  Ile  Gln  Asn  Ser  Lys  Leu  Gln  Leu  Asn
               830                      835                      840

TTG  GGA  CAA  GGC  CTC  AGA  ACT  GAC  CCC  GTC  ACC  AAC  CAG  CTG  GAA  GTG    4221
Leu  Gly  Gln  Gly  Leu  Arg  Thr  Asp  Pro  Val  Thr  Asn  Gln  Leu  Glu  Val
               845                      850                      855

CCC  CTC  GGT  CAA  GGT  TTG  GAA  ATT  GCA  GAC  GAA  TCC  CAG  GTT  AGG  GTT    4269
Pro  Leu  Gly  Gln  Gly  Leu  Glu  Ile  Ala  Asp  Glu  Ser  Gln  Val  Arg  Val
               860                      865                      870

AAA  TTG  GGC  GAT  GGC  CTG  CAG  TTT  GAT  TCA  CAA  GCT  CGC  ATC  ACT  ACC    4317
Lys  Leu  Gly  Asp  Gly  Leu  Gln  Phe  Asp  Ser  Gln  Ala  Arg  Ile  Thr  Thr
875                      880                      885

GCT  CCT  AAC  ATG  GTC  ACT  GAA  ACT  CTG  TGG  ACC  GGA  ACA  GGC  AGT  AAT    4365
Ala  Pro  Asn  Met  Val  Thr  Glu  Thr  Leu  Trp  Thr  Gly  Thr  Gly  Ser  Asn
890                      895                      900                      905

GCT  AAT  GTT  ACA  TGG  CGG  GGC  TAC  ACT  GCC  CCC  GGC  AGC  AAA  CTC  TTT    4413
Ala  Asn  Val  Thr  Trp  Arg  Gly  Tyr  Thr  Ala  Pro  Gly  Ser  Lys  Leu  Phe
               910                      915                      920

TTG  AGT  CTC  ACT  CGG  TTC  AGC  ACT  GGT  CTA  GTT  TTA  GGA  AAC  ATG  ACT    4461
Leu  Ser  Leu  Thr  Arg  Phe  Ser  Thr  Gly  Leu  Val  Leu  Gly  Asn  Met  Thr
               925                      930                      935

ATT  GAC  AGC  AAT  GCA  TCC  TTT  GGG  CAA  TAC  ATT  AAC  GCG  GGA  CAC  GAA    4509
Ile  Asp  Ser  Asn  Ala  Ser  Phe  Gly  Gln  Tyr  Ile  Asn  Ala  Gly  His  Glu
               940                      945                      950

CAG  ATC  GAA  TGC  TTT  ATA  TTG  TTG  GAC  AAT  CAG  GGT  AAC  CTA  AAA  GAA    4557
Gln  Ile  Glu  Cys  Phe  Ile  Leu  Leu  Asp  Asn  Gln  Gly  Asn  Leu  Lys  Glu
955                      960                      965

GGA  TCT  AAC  TTG  CAA  GGC  ACT  TGG  GAA  GTG  AAG  AAC  AAC  CCC  TCT  GCT    4605
Gly  Ser  Asn  Leu  Gln  Gly  Thr  Trp  Glu  Val  Lys  Asn  Asn  Pro  Ser  Ala
970                      975                      980                      985

TCC  AAA  GCT  GCT  TTT  TTG  CCT  TCC  ACC  GCC  CTA  TAC  CCC  ATC  CTC  AAC    4653
Ser  Lys  Ala  Ala  Phe  Leu  Pro  Ser  Thr  Ala  Leu  Tyr  Pro  Ile  Leu  Asn
               990                      995                      1000

GAA  AGC  CGA  GGG  AGT  CTT  CCT  GGA  AAA  AAT  CTT  GTG  GGC  ATG  CAA  GCC    4701
Glu  Ser  Arg  Gly  Ser  Leu  Pro  Gly  Lys  Asn  Leu  Val  Gly  Met  Gln  Ala
               1005                     1010                     1015

ATA  CTG  GGA  GGC  GGG  GGC  ACT  TGC  ACT  GTG  ATA  GCC  ACC  CTC  AAT  GGC    4749
Ile  Leu  Gly  Gly  Gly  Gly  Thr  Cys  Thr  Val  Ile  Ala  Thr  Leu  Asn  Gly
               1020                     1025                     1030

AGA  CGC  AGC  AAC  AAC  TAT  CCC  GCG  GGC  CAG  TCC  ATA  ATT  TTC  GTG  TGG    4797
Arg  Arg  Ser  Asn  Asn  Tyr  Pro  Ala  Gly  Gln  Ser  Ile  Ile  Phe  Val  Trp
               1035                     1040                     1045

CAA  GAA  TTC  AAC  ACC  ATA  GCC  CGC  CAA  CCT  CTG  AAC  CAC  TCT  ACA  CTT    4845
Gln  Glu  Phe  Asn  Thr  Ile  Ala  Arg  Gln  Pro  Leu  Asn  His  Ser  Thr  Leu
1050                     1055                     1060                     1065

ACT  TTT  TCT  TAC  TGG  ACT  TAAATAAGTT  GGAAATAAAG  AGTTAAACTG                   4893
Thr  Phe  Ser  Tyr  Trp  Thr
               1070

AATGTTTAAG  TGCAACAGAC  TTTTATTGGT  TTTGGCTCAC  AACAAATTAC  AACAGCATAG             4953

ACAAGTCATA  CCGGTCAAAC  AACACAGGCT  CTCGAAAACG  GGCTAACCGC  TCCAAGAATC             5013

TGTCACGCAG  ACGAGCAAGT  CCTAAATGTT  TTTTCACTCT  CTTCGGGGCC  AAGTTCAGCA             5073

TGTATCGGAT  TTTCTGCTTA  CACCTTT                                                    5100
```

( 2 ) INFORMATION FOR SEQ ID NO:26:

(i) SEQUENCE CHARACTERISTICS:
    (A) LENGTH: 983 amino acids
    (B) TYPE: amino acid
    (D) TOPOLOGY: linear (ii) MOLECULE TYPE: protein (xi) SEQUENCE DESCRIPTION: SEQ ID NO:26:

```
Ser  His  Pro  Pro  Val  Asn  Ile  Met  Lys  Arg  Ser  Val  Pro  Gln  Asp  Phe
 1                    5                   10                           15

Asn  Leu  Val  Tyr  Pro  Tyr  Lys  Ala  Lys  Arg  Pro  Asn  Ile  Met  Pro  Pro
              20                   25                        30

Phe  Phe  Asp  Arg  Asn  Gly  Phe  Val  Glu  Asn  Gln  Glu  Ala  Thr  Leu  Ala
          35                        40                   45

Met  Leu  Val  Glu  Lys  Pro  Leu  Thr  Phe  Asp  Lys  Glu  Gly  Ala  Leu  Thr
 50                             55                        60

Leu  Gly  Val  Gly  Arg  Gly  Ile  Arg  Ile  Asn  Pro  Ala  Gly  Leu  Leu  Glu
 65                        70                        75                       80

Thr  Asn  Asp  Leu  Ala  Ser  Ala  Val  Phe  Pro  Pro  Leu  Ala  Ser  Asp  Glu
                    85                        90                        95

Ala  Gly  Asn  Val  Thr  Leu  Asn  Met  Ser  Asp  Gly  Leu  Tyr  Thr  Lys  Asp
               100                       105                      110

Asn  Lys  Leu  Ala  Val  Lys  Val  Gly  Pro  Gly  Leu  Ser  Leu  Asp  Ser  Asn
               115                       120                      125

Asn  Ala  Leu  Gln  Val  His  Thr  Gly  Asp  Gly  Leu  Thr  Val  Thr  Asp  Asp
     130                        135                      140

Lys  Val  Ser  Leu  Asn  Thr  Gln  Ala  Pro  Leu  Ser  Thr  Thr  Ser  Ala  Gly
145                        150                      155                      160

Leu  Ser  Leu  Leu  Leu  Gly  Pro  Ser  Leu  His  Leu  Gly  Glu  Glu  Glu  Arg
                    165                       170                      175

Leu  Thr  Val  Asn  Thr  Gly  Ala  Gly  Leu  Gln  Ile  Ser  Asn  Asn  Ala  Leu
               180                       185                      190

Ala  Val  Lys  Val  Gly  Ser  Gly  Ile  Thr  Val  Asp  Ala  Gln  Asn  Gln  Leu
          195                       200                      205

Ala  Ala  Ser  Leu  Gly  Asp  Gly  Leu  Glu  Ser  Arg  Asp  Asn  Lys  Thr  Val
     210                       215                      220

Val  Lys  Ala  Gly  Pro  Gly  Leu  Thr  Ile  Thr  Asn  Gln  Ala  Leu  Thr  Val
225                       230                      235                      240

Ala  Thr  Gly  Asn  Gly  Leu  Gln  Val  Asn  Pro  Glu  Gly  Gln  Leu  Gln  Leu
                    245                       250                      255

Asn  Ile  Thr  Ala  Gly  Gln  Gly  Leu  Asn  Phe  Ala  Asn  Asn  Ser  Leu  Ala
               260                       265                      270

Val  Glu  Leu  Gly  Ser  Gly  Leu  His  Phe  Pro  Pro  Gly  Gln  Asn  Gln  Val
          275                       280                      285

Ser  Leu  Tyr  Pro  Gly  Asp  Gly  Ile  Asp  Ile  Arg  Asp  Asn  Arg  Val  Thr
     290                       295                      300

Val  Pro  Ala  Gly  Pro  Gly  Leu  Arg  Met  Leu  Asn  His  Gln  Leu  Ala  Val
305                       310                      315                      320

Ala  Ser  Gly  Asp  Gly  Leu  Glu  Val  His  Ser  Asp  Thr  Leu  Arg  Leu  Lys
                    325                       330                      335

Leu  Ser  His  Gly  Leu  Thr  Phe  Glu  Asn  Gly  Ala  Val  Arg  Ala  Lys  Leu
               340                       345                      350

Gly  Pro  Gly  Leu  Gly  Thr  Asp  Asp  Ser  Gly  Arg  Ser  Val  Val  Arg  Thr
          355                       360                      365

Gly  Arg  Gly  Leu  Arg  Val  Ala  Asn  Gly  Gln  Val  Gln  Ile  Phe  Ser  Gly
     370                       375                      380
```

```
Arg Gly Thr Ala Ile Gly Thr Asp Ser Ser Leu Thr Leu Asn Ile Arg
385             390                 395                 400

Ala Pro Leu Gln Phe Ser Gly Pro Ala Leu Thr Ala Ser Leu Gln Gly
                405             410              415

Ser Gly Pro Ile Thr Tyr Asn Ser Asn Asn Gly Thr Phe Gly Leu Ser
            420             425             430

Ile Gly Pro Gly Met Trp Val Asp Gln Asn Arg Leu Gln Val Asn Pro
            435             440             445

Gly Ala Gly Leu Val Phe Gln Gly Asn Asn Leu Val Pro Asn Leu Ala
    450             455             460

Asp Pro Leu Ala Ile Ser Asp Ser Lys Ile Ser Leu Ser Leu Gly Pro
465             470             475                 480

Gly Leu Thr Gln Ala Ser Asn Ala Leu Thr Leu Ser Leu Gly Asn Gly
                485             490             495

Leu Glu Phe Ser Asn Gln Ala Val Ala Ile Lys Ala Gly Arg Gly Leu
            500             505             510

Arg Phe Glu Ser Ser Ser Gln Ala Leu Glu Ser Ser Leu Thr Val Gly
        515             520             525

Asn Gly Leu Thr Leu Thr Asp Thr Val Ile Arg Pro Asn Leu Gly Asp
    530             535             540

Gly Leu Glu Val Arg Asp Asn Lys Ile Ile Val Lys Leu Gly Ala Asn
545             550             555                 560

Leu Arg Phe Glu Asn Gly Ala Val Thr Ala Gly Thr Val Asn Pro Ser
            565             570             575

Ala Pro Glu Ala Pro Pro Thr Leu Thr Ala Glu Pro Pro Leu Arg Ala
        580             585             590

Ser Asn Ser His Leu Gln Leu Ser Leu Ser Glu Gly Leu Val Val His
        595             600             605

Asn Asn Ala Leu Ala Leu Gln Leu Gly Asp Gly Met Glu Val Asn Gln
    610             615             620

His Gly Leu Thr Leu Arg Val Gly Ser Gly Leu Gln Met Arg Asp Gly
625             630             635                 640

Ile Leu Thr Val Thr Pro Ser Gly Thr Pro Ile Glu Pro Arg Leu Thr
            645             650             655

Ala Pro Leu Thr Gln Thr Glu Asn Gly Ile Gly Leu Ala Leu Gly Ala
            660             665             670

Gly Leu Glu Leu Asp Glu Ser Ala Leu Gln Val Lys Val Gly Pro Gly
        675             680             685

Met Arg Leu Asn Pro Val Glu Lys Tyr Val Thr Leu Leu Leu Gly Pro
        690             695             700

Gly Leu Ser Phe Gly Gln Pro Ala Asn Arg Thr Asn Tyr Asp Val Arg
705             710             715                 720

Val Ser Val Glu Pro Pro Met Val Phe Gly Gln Arg Gly Gln Leu Thr
            725             730             735

Phe Leu Val Gly His Gly Leu His Ile Gln Asn Ser Lys Leu Gln Leu
            740             745             750

Asn Leu Gly Gln Gly Leu Arg Thr Asp Pro Val Thr Asn Gln Leu Glu
        755             760             765

Val Pro Leu Gly Gln Gly Leu Glu Ile Ala Asp Glu Ser Gln Val Arg
    770             775             780

Val Lys Leu Gly Asp Gly Leu Gln Phe Asp Ser Gln Ala Arg Ile Thr
785             790             795             800
```

```
Thr Ala Pro Asn Met Val Thr Glu Thr Leu Trp Thr Gly Thr Gly Ser
            805             810                 815

Asn Ala Asn Val Thr Trp Arg Gly Tyr Thr Ala Pro Gly Ser Lys Leu
            820             825             830

Phe Leu Ser Leu Thr Arg Phe Ser Thr Gly Leu Val Leu Gly Asn Met
        835             840              845

Thr Ile Asp Ser Asn Ala Ser Phe Gly Gln Tyr Ile Asn Ala Gly His
    850             855             860

Glu Gln Ile Glu Cys Phe Ile Leu Leu Asp Asn Gln Gly Asn Leu Lys
865             870              875              880

Glu Gly Ser Asn Leu Gln Gly Thr Trp Glu Val Lys Asn Asn Pro Ser
            885             890              895

Ala Ser Lys Ala Ala Phe Leu Pro Ser Thr Ala Leu Tyr Pro Ile Leu
            900             905             910

Asn Glu Ser Arg Gly Ser Leu Pro Gly Lys Asn Leu Val Gly Met Gln
        915             920             925

Ala Ile Leu Gly Gly Gly Gly Thr Cys Thr Val Ile Ala Thr Leu Asn
    930             935             940

Gly Arg Arg Ser Asn Asn Tyr Pro Ala Gly Gln Ser Ile Ile Phe Val
945             950             955             960

Trp Gln Glu Phe Asn Thr Ile Ala Arg Gln Pro Leu Asn His Ser Thr
            965             970              975

Leu Thr Phe Ser Tyr Trp Thr
            980
```

( 2 ) INFORMATION FOR SEQ ID NO:27:

( i ) SEQUENCE CHARACTERISTICS:
        ( A ) LENGTH: 227 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:27:

```
Met Ser Lys Glu Ile Pro Thr Pro Tyr Met Trp Ser Tyr Gln Pro Gln
1               5               10                  15

Met Gly Leu Ala Ala Gly Ala Ala Gln Asp Tyr Ser Thr Arg Ile Asn
            20              25              30

Tyr Met Ser Ala Gly Pro His Met Ile Ser Arg Val Asn Gly Ile Arg
        35              40              45

Ala His Arg Asn Arg Ile Leu Leu Glu Gln Ala Ala Ile Thr Thr Thr
    50              55              60

Pro Arg Asn Asn Leu Asn Pro Arg Ser Trp Pro Ala Ala Leu Val Tyr
65              70              75              80

Gln Glu Ser Pro Ala Pro Thr Thr Val Val Leu Pro Arg Asp Ala Gln
            85              90              95

Ala Glu Val Gln Met Thr Asn Ser Gly Ala Gln Leu Ala Gly Gly Phe
            100             105             110

Arg His Arg Val Arg Ser Pro Gly Gln Gly Ile Thr His Leu Lys Ile
        115             120             125

Arg Gly Arg Gly Ile Gln Leu Asn Asp Glu Ser Val Ser Ser Ser Leu
    130             135             140

Gly Leu Arg Pro Asp Gly Thr Phe Gln Ile Gly Gly Ala Gly Arg Ser
145             150             155             160
```

-continued

```
Ser  Phe  Thr  Pro  Arg  Gln  Ala  Ile  Leu  Thr  Leu  Gln  Thr  Ser  Ser  Ser
               165                      170                      175

Glu  Pro  Arg  Ser  Gly  Gly  Ile  Gly  Thr  Leu  Gln  Phe  Ile  Glu  Glu  Phe
               180                      185                      190

Val  Pro  Ser  Val  Tyr  Phe  Asn  Pro  Phe  Ser  Gly  Pro  Gly  His  Tyr
               195                      200                 205

Pro  Asp  Gln  Phe  Ile  Pro  Asn  Phe  Asp  Ala  Val  Lys  Asp  Ser  Ala  Asp
               210                      215                 220

Gly  Tyr  Asp
225
```

( 2 ) INFORMATION FOR SEQ ID NO:28:

( i ) SEQUENCE CHARACTERISTICS:
  ( A ) LENGTH: 128 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:28:

```
Met  Thr  Asp  Thr  Leu  Asp  Leu  Glu  Met  Asp  Gly  Ile  Ile  Thr  Glu  Gln
1                   5                   10                      15

Arg  Leu  Leu  Glu  Arg  Arg  Ala  Ala  Ala  Glu  Gln  Gln  Arg  Met  Asn
               20                      25                      30

Gln  Glu  Leu  Gln  Asp  Met  Val  Asn  Leu  His  Gln  Cys  Lys  Arg  Gly  Ile
               35                      40                      45

Phe  Cys  Leu  Val  Lys  Gln  Ala  Lys  Val  Thr  Tyr  Asp  Ser  Asn  Thr  Thr
     50                       55                      60

Gly  His  Arg  Leu  Ser  Tyr  Lys  Leu  Pro  Thr  Lys  Arg  Gln  Lys  Leu  Val
65                            70                      75                      80

Val  Met  Val  Gly  Glu  Lys  Pro  Ile  Thr  Ile  Thr  Gln  His  Ser  Val  Glu
                    85                      90                      95

Thr  Glu  Gly  Cys  Ile  His  Ser  Pro  Cys  Gln  Gly  Pro  Glu  Asp  Leu  Cys
                    100                     105                     110

Thr  Leu  Ile  Lys  Thr  Leu  Cys  Gly  Leu  Lys  Asp  Leu  Ile  Pro  Phe  Asn
               115                     120                     125
```

( 2 ) INFORMATION FOR SEQ ID NO:29:

( i ) SEQUENCE CHARACTERISTICS:
  ( A ) LENGTH: 582 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:29:

```
Met  Lys  Arg  Ala  Arg  Pro  Ser  Glu  Asp  Thr  Phe  Asn  Pro  Val  Tyr  Pro
1                   5                   10                      15

Tyr  Asp  Thr  Glu  Thr  Gly  Pro  Pro  Thr  Val  Pro  Phe  Leu  Thr  Pro  Pro
               20                      25                      30

Phe  Val  Ser  Pro  Asn  Gly  Phe  Gln  Glu  Ser  Pro  Pro  Gly  Val  Leu  Ser
               35                      40                      45

Leu  Arg  Val  Ser  Glu  Pro  Leu  Asp  Thr  Ser  His  Gly  Met  Leu  Ala  Leu
     50                       55                      60

Lys  Met  Gly  Ser  Gly  Leu  Thr  Leu  Asp  Lys  Ala  Gly  Asn  Leu  Thr  Ser
65                       70                      75                      80
```

-continued

| | | | | | | | | | | | | | | |
|---|---|---|---|---|---|---|---|---|---|---|---|---|---|---|
| Gln | Asn | Val | Thr | Thr<br>85 | Val | Thr | Gln | Pro<br>90 | Leu | Lys | Lys | Thr | Lys<br>95 | Ser | Asn |
| Ile | Ser | Leu | Asp<br>100 | Thr | Ser | Ala | Pro | Leu<br>105 | Thr | Ile | Thr | Ser | Gly<br>110 | Ala | Leu |
| Thr | Val | Ala<br>115 | Thr | Thr | Ala | Pro | Leu<br>120 | Ile | Val | Thr | Ser | Gly<br>125 | Ala | Leu | Ser |
| Val | Gln<br>130 | Ser | Gln | Ala | Pro | Leu<br>135 | Thr | Val | Gln | Asp | Ser<br>140 | Lys | Leu | Ser | Ile |
| Ala<br>145 | Thr | Lys | Gly | Pro | Ile<br>150 | Thr | Val | Ser | Asp | Gly<br>155 | Lys | Leu | Ala | Leu | Gln<br>160 |
| Thr | Ser | Ala | Pro | Leu<br>165 | Ser | Gly | Ser | Asp | Ser<br>170 | Asp | Thr | Leu | Thr | Val<br>175 | Thr |
| Ala | Ser | Pro | Pro<br>180 | Leu | Thr | Thr | Ala | Thr<br>185 | Gly | Ser | Leu | Gly | Ile<br>190 | Asn | Met |
| Glu | Asp | Pro<br>195 | Ile | Tyr | Val | Asn | Asn<br>200 | Gly | Lys | Ile | Gly | Ile<br>205 | Lys | Ile | Ser |
| Gly | Pro<br>210 | Leu | Gln | Val | Ala | Gln<br>215 | Asn | Ser | Asp | Thr | Leu<br>220 | Thr | Val | Val | Thr |
| Gly<br>225 | Pro | Gly | Val | Thr | Val<br>230 | Glu | Gln | Asn | Ser | Leu<br>235 | Arg | Thr | Lys | Val | Ala<br>240 |
| Gly | Ala | Ile | Gly | Tyr<br>245 | Asp | Ser | Ser | Asn | Asn<br>250 | Met | Glu | Ile | Lys | Thr<br>255 | Gly |
| Gly | Gly | Met | Arg<br>260 | Ile | Asn | Asn | Asn | Leu<br>265 | Leu | Ile | Leu | Asp | Val<br>270 | Asp | Tyr |
| Pro | Phe | Asp<br>275 | Ala | Gln | Thr | Lys | Leu<br>280 | Arg | Leu | Lys | Leu | Gly<br>285 | Gln | Gly | Pro |
| Leu | Tyr<br>290 | Ile | Asn | Ala | Ser | His<br>295 | Asn | Leu | Asp | Ile | Asn<br>300 | Tyr | Asn | Arg | Gly |
| Leu<br>305 | Tyr | Leu | Phe | Asn | Ala<br>310 | Ser | Asn | Asn | Thr | Lys<br>315 | Lys | Leu | Glu | Val | Ser<br>320 |
| Ile | Lys | Lys | Ser | Ser<br>325 | Gly | Leu | Asn | Phe | Asp<br>330 | Asn | Thr | Ala | Ile | Ala<br>335 | Ile |
| Asn | Ala | Gly | Lys<br>340 | Gly | Leu | Glu | Phe | Asp<br>345 | Thr | Asn | Thr | Ser | Glu<br>350 | Ser | Pro |
| Asp | Ile | Asn<br>355 | Pro | Ile | Lys | Thr | Lys<br>360 | Ile | Gly | Ser | Gly | Ile<br>365 | Asp | Tyr | Asn |
| Glu | Asn<br>370 | Gly | Ala | Met | Ile | Thr<br>375 | Lys | Leu | Gly | Ala | Gly<br>380 | Leu | Ser | Phe | Asp |
| Asn<br>385 | Ser | Gly | Ala | Ile | Thr<br>390 | Ile | Gly | Asn | Lys | Asn<br>395 | Asp | Asp | Lys | Leu | Thr<br>400 |
| Leu | Trp | Thr | Thr | Pro<br>405 | Asp | Pro | Ser | Pro | Asn<br>410 | Cys | Arg | Ile | His | Ser<br>415 | Asp |
| Asn | Asp | Cys | Lys<br>420 | Phe | Thr | Leu | Val | Leu<br>425 | Thr | Lys | Cys | Gly | Ser<br>430 | Gln | Val |
| Leu | Ala | Thr<br>435 | Val | Ala | Ala | Leu | Ala<br>440 | Val | Ser | Gly | Asp | Leu<br>445 | Ser | Ser | Met |
| Thr | Gly<br>450 | Thr | Val | Ala | Ser | Val<br>455 | Ser | Ile | Phe | Leu | Arg<br>460 | Phe | Asp | Gln | Asn |
| Gly<br>465 | Val | Leu | Met | Glu | Asn<br>470 | Ser | Ser | Leu | Lys | Lys<br>475 | His | Tyr | Trp | Asn | Phe<br>480 |
| Arg | Asn | Gly | Asn | Ser<br>485 | Thr | Asn | Ala | Asn | Pro<br>490 | Tyr | Thr | Asn | Ala | Val<br>495 | Gly |
| Phe | Met | Pro | Asn<br>500 | Leu | Leu | Ala | Tyr | Pro<br>505 | Lys | Thr | Gln | Ser | Gln<br>510 | Thr | Ala |

| | | | | | | | | | | | | | | |
|---|---|---|---|---|---|---|---|---|---|---|---|---|---|---|
| Lys | Asn | Asn | Ile | Val | Ser | Gln | Val | Tyr | Leu | His | Gly | Asp | Lys | Thr | Lys |
| | | 515 | | | | | 520 | | | | | 525 | | | |
| Pro | Met | Ile | Leu | Thr | Ile | Thr | Leu | Asn | Gly | Thr | Ser | Glu | Ser | Thr | Glu |
| | 530 | | | | | 535 | | | | | 540 | | | | |
| Thr | Ser | Glu | Val | Ser | Thr | Tyr | Ser | Met | Ser | Phe | Thr | Trp | Ser | Trp | Glu |
| 545 | | | | | 550 | | | | | 555 | | | | | 560 |
| Ser | Gly | Lys | Tyr | Thr | Thr | Glu | Thr | Phe | Ala | Thr | Asn | Ser | Tyr | Thr | Phe |
| | | | | 565 | | | | | 570 | | | | | 575 | |
| Ser | Tyr | Ile | Ala | Gln | Glu | | | | | | | | | | |
| | | | 580 | | | | | | | | | | | | |

( 2 ) INFORMATION FOR SEQ ID NO:30:

( i ) SEQUENCE CHARACTERISTICS:
      ( A ) LENGTH: 21 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:30:

| Cys | Xaa | Xaa | Cys | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|---|
| 1 | | | | 5 | | | | | 10 | | | | | 15 | |
| Xaa | Cys | Xaa | Xaa | Cys | | | | | | | | | | | |
| | | | 20 | | | | | | | | | | | | |

( 2 ) INFORMATION FOR SEQ ID NO:31:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:31:

| Gln | Ser | Ser | Xaa | Ser | Thr | Ser |
|---|---|---|---|---|---|---|
| 1 | | | | 5 | | |

( 2 ) INFORMATION FOR SEQ ID NO:32:

( i ) SEQUENCE CHARACTERISTICS:
      ( A ) LENGTH: 27 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:32:

| Pro | Leu | Leu | Phe | Ala | Phe | Val | Leu | Cys | Thr | Gly | Cys | Ala | Val | Leu | Leu |
|---|---|---|---|---|---|---|---|---|---|---|---|---|---|---|---|
| 1 | | | | 5 | | | | | 10 | | | | | 15 | |
| Thr | Ala | Phe | Gly | Pro | Ser | Ile | Leu | Ser | Gly | Thr | | | | | |
| | | | 20 | | | | | 25 | | | | | | | |

( 2 ) INFORMATION FOR SEQ ID NO:33:

( i ) SEQUENCE CHARACTERISTICS:
      ( A ) LENGTH: 57 amino acids
      ( B ) TYPE: amino acid
      ( C ) STRANDEDNESS: single
      ( D ) TOPOLOGY: linear ( x i ) SEQUENCE DESCRIPTION: SEQ ID NO:33:

```
Glu  Glu  Val  Thr  Ser  His  Phe  Phe  Leu  Asp  Cys  Pro  Glu  Asp  Pro  Ser
1              5                        10                       15

Arg  Glu  Cys  Ser  Ser  Cys  Gly  Phe  His  Gln  Ala  Gln  Ser  Gly  Ile  Pro
              20                        25                       30

Gly  Ile  Met  Cys  Ser  Leu  Cys  Tyr  Met  Arg  Gln  Thr  Tyr  His  Cys  Ile
              35                   40                       45

Tyr  Ser  Pro  Val  Ser  Glu  Glu  Met
     50                   55
```

( 2 ) INFORMATION FOR SEQ ID NO:34:

( i ) SEQUENCE CHARACTERISTICS:
       ( A ) LENGTH: 12 amino acids
       ( B ) TYPE: amino acid
       ( C ) STRANDEDNESS: single
       ( D ) TOPOLOGY: linear ( x i ) SEQUENCE DESCRIPTION: SEQ ID NO:34:

```
Val  Asp  Leu  Glu  Cys  His  Glu  Val  Leu  Pro  Pro  Ser
1              5                        10
```